US007763244B2

(12) United States Patent
Rosen

(10) Patent No.: US 7,763,244 B2
(45) Date of Patent: Jul. 27, 2010

(54) ANTIBODIES THAT SPECIFICALLY BIND TO REG IV

(75) Inventor: Craig A. Rosen, Laytonsville, MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 11/583,101

(22) Filed: Oct. 19, 2006

(65) Prior Publication Data

US 2007/0036792 A1 Feb. 15, 2007

Related U.S. Application Data

(63) Continuation of application No. 11/017,030, filed on Dec. 21, 2004, now abandoned, which is a continuation-in-part of application No. PCT/US03/19908, filed on Jun. 26, 2003.

(60) Provisional application No. 60/392,382, filed on Jul. 1, 2002.

(51) Int. Cl.
*A61K 39/395* (2006.01)
*C07K 16/18* (2006.01)

(52) U.S. Cl. .................................................. 424/133.1

(58) Field of Classification Search ............. 424/133.8, 424/145.1; 530/388.25

See application file for complete search history.

(56) References Cited

U.S. PATENT DOCUMENTS 4,584,268 A 4/1986 Ceriani et al.
4,683,202 A 7/1987 Mullis
5,380,645 A 1/1995 Vogelstein
5,436,169 A 7/1995 Iovanna et al.
5,837,841 A 11/1998 Bandman et al.
6,342,220 B1 1/2002 Adams et al.
6,342,369 B1 1/2002 Ashkenazi
6,696,245 B2 2/2004 Winter et al.
6,737,249 B1 5/2004 Adams et al.
7,138,501 B2 11/2006 Ruben et al.
2002/0193571 A1 12/2002 Carter et al.
2003/0059862 A1 3/2003 Ruben et al.
2003/0157109 A1* 8/2003 Corvalan et al. ......... 424/146.1
2003/0161809 A1 8/2003 Houston et al.
2003/0175274 A1 9/2003 Rosen et al.
2003/0180296 A1 9/2003 Salcedo et al.
2003/0223996 A1 12/2003 Ruben et al.
2004/0001822 A1 1/2004 Levanon et al.
2004/0058393 A1 3/2004 Fukishima et al.
2004/0063632 A1 4/2004 Light et al.
2004/0071696 A1 4/2004 Adams et al.
2004/0073011 A1 4/2004 Hagay et al.
2004/0091475 A1 5/2004 Tsuchiya et al.
2004/0091973 A1 5/2004 Giovannoni
2004/0141969 A1* 7/2004 Floege et al. ............. 424/145.1
2004/0166544 A1 8/2004 Morton et al.
2004/0202665 A1 10/2004 Lazarovits et al.
2004/0219542 A1 11/2004 Houston et al.
2004/0219643 A1 11/2004 Winter et al.
2004/0242847 A1 12/2004 Fukushima et al.
2005/0129614 A1 6/2005 Rosen et al.
2005/0255109 A1 11/2005 Felding-Habermann et al.
2005/0266423 A1 12/2005 Tang et al.
2005/0271663 A1 12/2005 Ignatovich et al.
2006/0024308 A1 2/2006 Crea et al.
2006/0024667 A1 2/2006 Manucharyan et al.
2006/0034831 A1 2/2006 Tobin
2006/0099150 A1 5/2006 Houston et al.
2006/0099205 A1 5/2006 Adams et al.
2006/0104971 A1 5/2006 Garber et al.
2006/0115477 A1 6/2006 Unger et al.
2006/0121580 A1 6/2006 Ter Meulen et al.
2006/0134102 A1 6/2006 LePage et al.
2006/0134103 A1 6/2006 Hawley et al.
2006/0140960 A1 6/2006 Wang et al.
2006/0257397 A1 11/2006 Throsby et al.
2006/0257406 A1 11/2006 Winter et al.
2006/0257859 A1 11/2006 Chang et al.
2006/0269542 A1 11/2006 Hjortsvang et al.
2006/0269554 A1 11/2006 Adams (Continued)

FOREIGN PATENT DOCUMENTS

DE 4321944 3/1995

(Continued)

OTHER PUBLICATIONS

Rudikoff et al (Proc Natl Acad Sci USA 1982 vol. 79 p. 1979).*

(Continued)

*Primary Examiner*—Lynn Bristol

(57) ABSTRACT

The present invention relates to antibodies and related molecules that specifically bind to Reg IV. Such antibodies have uses, for example, in the prevention and treatment of gastrointestinal tract cancers, inflammatory bowel disorders, and diabetes. The invention also relates to nucleic acid molecules encoding anti-Reg IV antibodies, vectors and host cells containing these nucleic acids, and methods for producing the same. The present invention relates to methods and compositions for preventing, detecting, diagnosing, treating or ameliorating a disease or disorder, especially gastrointestinal tract cancers, inflammatory bowel disorders, and diabetes, comprising administering to an animal, preferably a human, an effective amount of one or more antibodies or fragments or variants thereof, or related molecules, that specifically bind to Reg IV.

19 Claims, No Drawings

U.S. PATENT DOCUMENTS

| | | | | |
|---|---|---|---|---|
| 2006/0275210 | A1 | 12/2006 | Rosen et al. | |
| 2006/0281072 | A1 | 12/2006 | Bakker et al. | |
| 2007/0004910 | A1* | 1/2007 | Sexton et al. | 530/388.26 |
| 2007/0179086 | A1* | 8/2007 | Gliniak et al. | 514/12 |
| 2007/0217997 | A1* | 9/2007 | Devy et al. | 424/1.49 |

FOREIGN PATENT DOCUMENTS

| | | |
|---|---|---|
| EP | 0934953 | 8/1999 |
| EP | 1051620 | 11/2000 |
| EP | 1382615 | 1/2004 |
| EP | 1439192 | 7/2004 |
| EP | 1479771 | 11/2004 |
| JP | 2001511653 | 8/2001 |
| JP | 2001520397 | 10/2001 |
| JP | 2002524024 | 8/2002 |
| JP | 2004512010 | 4/2004 |
| JP | 2006512895 | 4/2006 |
| WO | WO-95/00851 | 1/1995 |
| WO | WO-96/39541 | 12/1996 |
| WO | WO-98/03653 | 1/1998 |
| WO | WO-98/51793 | 11/1998 |
| WO | WO-99/55367 | 11/1999 |
| WO | WO-99/57266 | 11/1999 |
| WO | WO-00/73430 | 12/2000 |
| WO | WO-01/58956 | 8/2001 |
| WO | WO-01/72771 | 10/2001 |
| WO | WO-02/33072 | 4/2002 |
| WO | WO-02046455 | 7/2002 |
| WO | WO-03/002609 | 1/2003 |
| WO | WO-03/093313 | 11/2003 |
| WO | WO-2004/002528 | 1/2004 |
| WO | WO-2004/003019 | 1/2004 |
| WO | WO-2004/007550 | 1/2004 |
| WO | WO-2004/007717 | 1/2004 |
| WO | WO-2004/037861 | 5/2004 |
| WO | WO-2004/046189 | 6/2004 |
| WO | WO-2004/067569 | 8/2004 |
| WO | WO-2004/097041 | 11/2004 |
| WO | WO-2004/106380 | 12/2004 |
| WO | WO-2005/039613 | 5/2005 |
| WO | WO-2005/049652 | 6/2005 |
| WO | WO-2005/061546 | 7/2005 |
| WO | WO-2005/063819 | 7/2005 |
| WO | WO-2005/111623 | 11/2005 |
| WO | WO-2005/118644 | 12/2005 |
| WO | WO-2006/003388 | 1/2006 |
| WO | WO-2006/018650 | 2/2006 |
| WO | WO-2006/040322 | 4/2006 |
| WO | WO-2007/006665 | 1/2007 |

OTHER PUBLICATIONS

Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Casset et al. ((2003) BBRC 307, 198-205).*
Holm et al (Molec. Immunol. (2007) 44, 1075-1084).*
MacCallum et al. (J. Mol. Biol. (1996) 262, 732-745).*
Li et al., Prot. Expression and Purification 31:197-206 (2003).*
Heiskala et al., Virchows Arch. 448:295-300 (2006).*
Barbas et al. PNAS 91:3809-3813 (1994).*
Deng et al. JBC 269:9533-9538 (1994).*
Deng et al. PNAS 92:492-4996 (1995).*
Schier et al. JMB 263:551-567 (1996).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Alberts, et al., *Molecular Biology of the Cell*, 3rd Edition, p. 465 (1994).
Bartoli, et al., "A gene homologous to the *reg* gene is expressed in the human pancreas," *FEBS Letters*, 327:289-293 (Aug. 1993).
Brennan, et al., "Cytokine production in culture by cells isolated from the synovial membrane," *J. Autoimmunity*, 2 suppl.:177-186 (1989).
Bork, P., "Powers and pitfalls in sequence analysis: the 70% hurdle," *Genome Research*, 10:398-400 (2000).
Bowie, et al., "Deciphering the message in protein sequences; tolerance to amino acid substitutions," *Science*, 247:1306-1310 (1990).
Burgess, et al., "Possible dissociation of the heparin-binding and mitogenic activities of heparin-binding (acid fibroblast) growth factor-1 from its receptor-binding activities by site-directed mutagenesis of a single lysine residue," *J. of Cell Biol*., 111:2129-2138 (1990).
Carrere, et al., "Immunoreactive pancreatic Reg protein in sera from cystic fibrosis patients with and without pancreatic insufficiency," *Gut*, 44:545-551 (1999).
Eriksson, et al., "Insulin resistance in Type 2 (non-insulin-dependent) diabetic patients and their relatives is not associated with a defect in the expression of the insulin-responsive glucose transporter (GLUT-4) gene in human skeletal muscle," *Diabetologia*, 35:143-147 (1992).
Fu, et al., "Translational regulation of human p53 gene expression," *EMBO Journal*, 15:4392-4401 (1996).
Gelboin, *Pharmacological Review*, 45:413-453 (1993).
Geneseq Database, W37866 (Aug. 21, 1998).
Geneseq Database, W37929 (Aug. 21, 1998).
Guo, et al., "Induction profile of rat organic anion transporting polypeptide 2 (oatp2) by prototypical drug-metabolizing enzyme inducers that activate gene expression through ligand-activated transcription factor pathways," *J. Pharmacology and Experimental Therapeutics*, 300:206-212 (2002).
Hell, et al., "Hodgkin cells accumulate mRNA for *bcl*-2," *Lab. Investigation*, 73(4):492-496 (1995).
Jang, et al., "An examination of the effects of hypoxia, acidosis, and glucose starvation on the expression of metastasis-associated genes in murine tumor cells," *Clin. Exp. Metastasis*, 15:469-483 (1997).
Lazar, et al., "Transforming growth factor $\alpha$: mutation of aspartic acid 47 and leucine 48 results in different biological activities," *Molecular and Cellular Biology*, 8:1247-1252 (1988).
McClean, et al., "Evidence of post-translational regulation of P-glycoprotein associated with the expression of a distinctive multiple drug-resistant phenotype in Chinese hamster ovary cells," *Eur. J. of Cancer*, 29A:2243-2248 (1993).
Mount, et al., "Chimeric (mouse/human) anti-colon cancer antibody c30.6 inhibits the growth of human colorectal cancer xenografts in scid/scid mice," *Cancer Research*, 54(23):6160-6166 (Dec. 1, 1994).
The New England Biolabs Catalog 1993-94 Edition, pp. 92-95.
Nicolaides, et al., "Mutations of two PMS homologues in hereditary nonpolyposis colon cancer," *Nature*, 371:75-80 (Sep. 1, 1994).
O'Connell, et al., "Current status of adjuvant chemotherapy for colorectal cancer," *Cancer Supplement*, 70(6):1732-1739 (Sep. 15, 1992).
PCT International Search Report for PCT/US95/07169 (Nov. 3, 1995).
Powell, et al., "Expression of cytochrome P4502D1 in human liver: assessment by mRNA, genotype and phenotype," *Pharmacogenesis*, 8:411-421 (1998).
Shantz, et al., "Translational regulation of ornithine decarboxylase and other enzymes of the polyamine pathway," *Int. J. of Biochem and Cell Biol*., 31:107-122 (1999).
Singh, et al., "Modulation of azoxymethane-induced mutational activation of ras protooncogenes by chemopreventive agents in colon carcinogenesis," *Carcinogenesis*, 15(7):1317-1323 (Jul. 1994).
Ueda, et al., *Gastroenterology*, 104(4):911-917 (Apr. 1993).
Vallejo, et al., "Evidence of tissue-specific, post-transcriptional regulation of NRF-2 expression," *Biochimie*, 82:1129-1133 (2000).
Zimmer, "Examination of the calcium-modulated protein S100-alpha and its target proteins in adult and developing skeletal muscle," *Cell Motility and the Cytoskeleton*, 20:325-337 (1991).
Ikeda et al., "Epitope Mapping of Anti-recA Protein IgGs by Region Specified Polymerase Chain Reaction Mutagenesis" *J. Biol. Chem*. 267:6291-6296 (1992).
Stuurman, et al., "Interphase phosphorylation of the *Drosophila* nuclear lamin: site-mapping using a monoclonal antibody" *J. Cell Sci*. 108:3137-3144 (1995).

Munro and Pelham, "Use of peptide tagging to detect proteins expressed from cloned genes: deletion mapping functional domains of *Drosophila* hsp70" *EMBO J.* 3:3087-3093 (1984).
Pollard, et al., "Truncated variants of gp120 bind CD4 with high affinity and suggest a minimum CD4 binding region" *EMBO J.* 11:585-591 (1992).
Sugiyama, et al., "Membrane topology analysis of *Escherichla coli* mannitol permease by using a nested-deletion method to create mtlA-phoA fusions" *PNAS* 88:9603-9607 (1991).

* cited by examiner

SEQUENCE LISTING

```
<160> NUMBER OF SEQ ID NOS: 176

<210> SEQ ID NO 1
<211> LENGTH: 254
<212> TYPE: PRT
<213> ORGANISM: Artificial Sequence
<220> FEATURE:
<223> OTHER INFORMATION: scFv protein RGB0101
```

<400> SEQUENCE: 1

```
Glu Val Gln Leu Val Glu Thr Gly Gly Gly Val Val Gln Pro Gly Arg
1               5                   10                  15

Ser Gln Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Arg Tyr Tyr Tyr Asp Ser Ser Gly Tyr Tyr Asp Gly
            100                 105                 110

Tyr Tyr Tyr Tyr Gly Met Asp Val Trp Gly Gln Gly Thr Thr Val Thr
        115                 120                 125

Val Ser Ser Gly Gly Gly Gly Ser Gly Gly Gly Gly Ser Gly Gly Gly
    130                 135                 140

Gly Ser Ser Glu Leu Thr Gln Asp Pro Ala Val Ser Val Ala Leu Gly
145                 150                 155                 160

Gln Thr Val Arg Ile Thr Cys Gln Gly Asp Ser Leu Arg Ser Tyr Tyr
                165                 170                 175

Thr Asn Trp Phe Gln Gln Arg Pro Gly Gln Ala Pro Leu Leu Val Val
            180                 185                 190

Tyr Ala Lys Asn Lys Arg Pro Ser Gly Ile Pro Asp Arg Phe Ser Gly
        195                 200                 205

Ser Ser Ser Gly Asn Thr Ala Ser Leu Thr Ile Thr Gly Ala Gln Ala
    210                 215                 220

Glu Asp Glu Ala Asp Tyr Tyr Cys His Ser Arg Asp Ser Ser Gly Asn
225                 230                 235                 240

His Val Leu Phe Gly Gly Gly Thr Lys Leu Thr Val Leu Gly
                245                 250
```

<210> SEQ ID NO 2
<211> LENGTH: 251
<212> TYPE: PRT
<213> ORGANISM: Artificial Sequence
<220> FEATURE:
<223> OTHER INFORMATION: scFv protein RGB0102

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Met Ala Arg Asp Thr Ser Met Ser Thr Ala Ser
65                  70                  75                  80

Val Glu Leu Arg Arg Leu Thr Ser Asp Asp Thr Ala Val Tyr Tyr Cys
                85                  90                  95

Ala Arg Asn Ser Phe Asp Phe Gly Ser Gly Tyr Gly Leu Phe Tyr Gln
```

-continued

```
            100                 105                 110

Tyr Ile Met Asp Val Trp Gly Gln Gly Thr Leu Val Thr Val Ser Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Phe Leu Ser Ala Ser Val Gly Asp
145                 150                 155                 160

Arg Val Thr Ile Thr Cys Arg Ala Ser Gln Gly Ile Asn Asn Tyr Leu
                165                 170                 175

Ala Trp Tyr Gln Gln Lys Pro Gly Arg Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Leu Gln Asp Ser Asp Tyr Pro Leu Thr
225                 230                 235                 240

Phe Gly Gly Gly Thr Lys Leu Glu Ile Lys Arg
                245                 250


<210> SEQ ID NO 3
<211> LENGTH: 255
<212> TYPE: PRT
<213> ORGANISM: Artificial Sequence
<220> FEATURE:
<223> OTHER INFORMATION: scFv protein RGB0103

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Gln Ser Gly Gly Tyr Val Tyr Ile Thr Phe Tyr Tyr
            100                 105                 110

Pro Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Ala Leu
    130                 135                 140

Asn Phe Met Leu Thr Gln Pro His Ser Val Ser Glu Ser Pro Gly Lys
145                 150                 155                 160

Thr Val Thr Leu Ser Cys Thr Arg Ser Ser Gly Ser Ile Ser Phe Asp
                165                 170                 175

Tyr Val Gln Trp Tyr Gln Gln Arg Pro Gly Ser Ser Pro Ile Leu Val
            180                 185                 190

Ile Phe Glu Asp Asp Gln Arg Pro Ser Gly Val Pro Asp Arg Phe Ser
        195                 200                 205

Gly Ser Ile Asp Ser Thr Ser Asn Ser Ala Ser Leu Thr Ile Ser Gly
```

-continued

```
    210                 215                 220

Leu Gln Ser Glu Asp Glu Gly Asp Tyr Tyr Cys Gln Thr Tyr Asp Asp
225                 230                 235                 240

Asn Arg Gln Val Phe Gly Gly Gly Thr Lys Leu Thr Val Leu Gly
                245                 250                 255


<210> SEQ ID NO 4
<211> LENGTH: 248
<212> TYPE: PRT
<213> ORGANISM: Artificial Sequence
<220> FEATURE:
<223> OTHER INFORMATION: scFv protein RGB0104

<400> SEQUENCE: 4

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Arg Met Arg Thr Gln Leu Asp Ser Trp Gly Arg Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Gln Ser Val Leu Thr Gln Pro Pro Ser
    130                 135                 140

Val Ser Gly Ala Pro Gly Gln Arg Val Thr Ile Ser Cys Thr Gly Ser
145                 150                 155                 160

Ser Ser Asn Ile Gly Ala Asp Tyr Asp Val His Trp Tyr Gln His His
                165                 170                 175

Pro Gly Thr Ala Pro Arg Leu Leu Ile Tyr Asp Asn Thr Asn Arg Pro
            180                 185                 190

Ser Gly Val Pro Asp Arg Phe Ser Gly Ser Lys Ser Gly Thr Ser Ala
        195                 200                 205

Ser Leu Thr Ile Thr Gly Leu Gln Ala Glu Asp Glu Ala Asp Tyr Tyr
    210                 215                 220

Cys Gln Ser Tyr Asp Ala Ser Leu Ser Gly Tyr Val Val Phe Gly Gly
225                 230                 235                 240

Gly Thr Lys Leu Thr Val Leu Gly
                245


<210> SEQ ID NO 5
<211> LENGTH: 248
<212> TYPE: PRT
<213> ORGANISM: Artificial Sequence
<220> FEATURE:
<223> OTHER INFORMATION: scFv protein RGB0106

<400> SEQUENCE: 5

Lys Val Gln Leu Val Gln Ser Gly Ala Glu Val Lys Lys Pro Gly Ser
1               5                   10                  15
```

-continued

```
Ser Val Arg Val Ser Cys Lys Val Ser Gly Asp Thr Ser Thr Ser Tyr
            20                  25                  30

Ile Ile Asn Trp Val Arg Gln Ala Pro Gly Gln Gly Leu Glu Trp Met
        35                  40                  45

Gly Val Ile Ile Pro Met Phe Gly Thr Thr Asn Tyr Ala Gln Lys Phe
    50                  55                  60

Glu Asp Arg Val Thr Ile Ser Ala Asp Gly Ser Thr Ser Thr Val Tyr
65                  70                  75                  80

Met Glu Leu Ser Gly Leu Lys Ser Glu Asp Thr Ala Val Tyr Tyr Cys
                85                  90                  95

Ala Gly Ser Asp Phe Trp Ser Gly Tyr Asp Gly Glu Pro Asp Val Phe
            100                 105                 110

Asp Leu Trp Gly Gln Gly Thr Leu Val Thr Val Ser Ser Gly Gly Gly
        115                 120                 125

Gly Ser Gly Gly Gly Gly Ser Gly Gly Gly Gly Ser Ser Glu Leu Thr
    130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Thr Asn Trp Phe Gln Gln
                165                 170                 175

Lys Pro Gly Gln Ala Pro Leu Leu Val Val Tyr Ala Lys Asn Lys Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asp Glu Ala Asp Tyr
    210                 215                 220

Tyr Cys His Ser Arg Asp Ser Ser Gly Asn His Val Leu Phe Gly Gly
225                 230                 235                 240

Gly Thr Lys Leu Thr Val Leu Gly
                245


<210> SEQ ID NO 6
<211> LENGTH: 243
<212> TYPE: PRT
<213> ORGANISM: Artificial Sequence
<220> FEATURE:
<223> OTHER INFORMATION: scFv protein RGB0110

<400> SEQUENCE: 6

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ser Thr Tyr Tyr Asp Phe Trp Phe Asp Ile Trp Gly Gln
            100                 105                 110

Gly Thr Met Val Thr Val Ser Ser Gly Gly Gly Gly Ser Gly Gly Gly
        115                 120                 125
```

-continued

```
Gly Ser Gly Gly Gly Gly Ser Asp Ile Gln Met Thr Gln Ser Pro Ser
    130                 135                 140

Phe Leu Ser Ala Ser Val Gly Asp Arg Val Thr Ile Thr Cys Arg Ala
145                 150                 155                 160

Ser Gln Gly Ile Asn Asn Tyr Leu Ala Trp Tyr Gln Gln Lys Pro Gly
                165                 170                 175

Arg Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Asp Ser Asp Tyr Pro Leu Thr Phe Gly Gly Gly Thr Lys Leu Glu
225                 230                 235                 240

Ile Lys Arg


<210> SEQ ID NO 7
<211> LENGTH: 248
<212> TYPE: PRT
<213> ORGANISM: Artificial Sequence
<220> FEATURE:
<223> OTHER INFORMATION: scFv protein RGB0113

<400> SEQUENCE: 7

Gly Val Gln Leu Val Gln Ser Gly Ala Glu Gly Lys Lys Pro Gly Ala
1               5                   10                  15

Ser Val Lys Val Ser Cys Lys Ala Ser Gly Gly Asn Ile Ser Arg Phe
            20                  25                  30

Gly Ile Asn Trp Val Arg Gln Ala Pro Gly Gln Gly Leu Glu Trp Met
        35                  40                  45

Gly Val Ile Ile Pro Met Phe Gly Thr Thr Asn Tyr Ala Gln Lys Phe
    50                  55                  60

Glu Asp Arg Val Thr Ile Ser Ala Asp Gly Ser Thr Ser Thr Val Tyr
65                  70                  75                  80

Met Glu Leu Ser Gly Leu Lys Ser Glu Asp Thr Ala Val Tyr Tyr Cys
                85                  90                  95

Ala Gly Ser Asp Phe Trp Ser Gly Tyr Asp Gly Glu Pro Asp Val Phe
            100                 105                 110

Asp Leu Trp Gly Arg Gly Thr Leu Val Thr Val Ser Ser Gly Gly Gly
        115                 120                 125

Gly Ser Gly Gly Gly Gly Ser Gly Gly Gly Gly Ser Ser Glu Leu Thr
    130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Thr Asn Trp Phe Gln Gln
                165                 170                 175

Lys Pro Gly Gln Ala Pro Leu Leu Val Val Tyr Ala Lys Asn Lys Arg
            180                 185                 190

Pro Ser Glu Ile Pro Asp Arg Phe Ser Gly Ser Ser Ser Gly Asn Thr
        195                 200                 205

Ala Ser Leu Thr Ile Thr Gly Ala Gln Ala Glu Asp Glu Ala Asp Tyr
    210                 215                 220

Tyr Cys His Ser Arg Asp Ser Ser Gly Asn His Val Leu Phe Gly Gly
225                 230                 235                 240

Gly Thr Lys Leu Thr Val Leu Gly
```

```
                245


<210> SEQ ID NO 8

<400> SEQUENCE: 8

000


<210> SEQ ID NO 9
<211> LENGTH: 249
<212> TYPE: PRT
<213> ORGANISM: Artificial Sequence
<220> FEATURE:
<223> OTHER INFORMATION: scFv protein RGB0115

<400> SEQUENCE: 9

Gln Leu Gln Leu Gln Glu Ser Gly Pro Gly Leu Val Lys Pro Ser Gly
1               5                   10                  15

Thr Leu Ser Leu Asn Cys Ala Val Ser Gly Asp Ser Ile Ser Ser Gly
            20                  25                  30

Asn Trp Trp Ser Trp Val Arg Gln Pro Pro Gly Lys Gly Leu Glu Trp
        35                  40                  45

Thr Gly Glu Ile Tyr His Ser Gly Thr Ala Asn Tyr Asn Pro Ser Leu
    50                  55                  60

Lys Ser Arg Val Thr Val Ser Val Asp Lys Ser Thr Asn Gln Phe Ser
65                  70                  75                  80

Leu Arg Met Ser Ser Val Thr Ala Ala Asp Thr Ala Val Tyr Tyr Cys
                85                  90                  95

Ala Arg Ala Gly Tyr Tyr Asp Val Gly Leu Pro Phe Asp Tyr Trp Gly
            100                 105                 110

Lys Gly Thr Leu Val Thr Val Ser Ser Gly Gly Gly Gly Ser Gly Gly
        115                 120                 125

Gly Gly Ser Gly Gly Gly Gly Ser Ala Gln Ala Val Leu Thr Gln Pro
    130                 135                 140

Ser Ser Val Ser Gly Ala Pro Gly Gln Arg Val Thr Leu Ser Cys Thr
145                 150                 155                 160

Gly Ser Ser Ser Asn Ile Gly Ala Gly Ser Glu Phe His Trp Tyr Gln
                165                 170                 175

Gln Val Pro Gly Thr Ala Pro Lys Leu Leu Ile Phe Gly Asn Thr Asn
            180                 185                 190

Arg Pro Trp Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Ala Tyr Val Phe Gly
225                 230                 235                 240

Thr Gly Thr Lys Val Thr Val Leu Gly
                245


<210> SEQ ID NO 10
<211> LENGTH: 247
<212> TYPE: PRT
<213> ORGANISM: Artificial Sequence
<220> FEATURE:
<223> OTHER INFORMATION: scFv protein RGB0118

<400> SEQUENCE: 10

Glu Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Asp Leu Leu Ser Tyr Phe Tyr Asp Ser Ser Gly Tyr Leu Asp
            100                 105                 110

Asn Trp Gly Gln Gly Thr Met Val Thr Val Ser Ser Gly Gly Gly Gly
        115                 120                 125

Ser Gly Gly Gly Gly Ser Gly Gly Gly Gly Ser Ser Glu Leu Thr Gln
    130                 135                 140

Asp Thr Ala Val Ser Val Ala Leu Gly Gln Thr Val Arg Ile Thr Cys
145                 150                 155                 160

Gln Gly Asp Ser Leu Arg Ser Tyr Tyr Thr Asn Trp Phe Gln Gln Lys
                165                 170                 175

Pro Gly Gln Ala Pro Leu Leu Val Val Tyr Ala Lys Asn Lys Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Gly Asn His Val Val Phe Gly Gly Gly
225                 230                 235                 240

Thr Lys Leu Thr Val Leu Gly
                245


<210> SEQ ID NO 11
<211> LENGTH: 248
<212> TYPE: PRT
<213> ORGANISM: Artificial Sequence
<220> FEATURE:
<223> OTHER INFORMATION: scFv protein RGB0128

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Trp Ser Asp Ala Phe Asp Leu Trp Gly Arg Gly
            100                 105                 110

Thr Leu Val Thr Val Ser Ser Gly Gly Gly Gly Ser Gly Gly Gly Gly
        115                 120                 125
```

```
Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Gly
145                 150                 155                 160

Ser Ser Gly Ser Ile Ala Ser Asn Tyr Val Gln Trp Tyr Gln Gln Arg
                165                 170                 175

Pro Gly Ser Ala Pro Ala Thr Val Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Asp Leu Lys Thr Glu Asp Glu Ala Asp
    210                 215                 220

Tyr Tyr Cys Gln Ser Phe Asp Asn Ser Lys Tyr Val Val Phe Gly Gly
225                 230                 235                 240

Gly Thr Lys Leu Thr Val Leu Gly
                245


<210> SEQ ID NO 12
<211> LENGTH: 252
<212> TYPE: PRT
<213> ORGANISM: Artificial Sequence
<220> FEATURE:
<223> OTHER INFORMATION: scFv protein RGB0129

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Asp Cys Thr Asn Gly Val Cys Tyr Leu Pro Phe Asp
            100                 105                 110

Tyr Trp Gly Arg Gly Thr Leu Val Thr Val Ser Ser Gly Gly Gly Gly
        115                 120                 125

Ser Gly Gly Gly Gly Ser Gly Gly Gly Gly Ser Ala Leu Asn Phe Met
    130                 135                 140

Leu Thr Gln Pro His Ser Val Ser Glu Ser Pro Gly Lys Thr Val Thr
145                 150                 155                 160

Leu Ser Cys Thr Arg Ser Ser Gly Ser Ile Ser Phe Asp Tyr Val Gln
                165                 170                 175

Trp Tyr Gln Gln Arg Pro Gly Ser Ser Pro Ile Leu Val Ile Phe Glu
            180                 185                 190

Asp Asp Gln Arg Pro Ser Gly Val Pro Asp Arg Phe Ser Gly Ser Ile
        195                 200                 205

Asp Ser Thr Ser Asn Ser Ala Ser Leu Thr Ile Ser Gly Leu Gln Ser
    210                 215                 220

Glu Asp Glu Gly Asp Tyr Tyr Cys Gln Thr Tyr Asp Asp Asn Arg Gln
225                 230                 235                 240
```

-continued

```
Val Phe Gly Gly Gly Thr Lys Leu Thr Val Leu Gly
                245                 250


<210> SEQ ID NO 13
<211> LENGTH: 246
<212> TYPE: PRT
<213> ORGANISM: Artificial Sequence
<220> FEATURE:
<223> OTHER INFORMATION: scFv protein RGB0137

<400> SEQUENCE: 13

Glu Val Gln Leu Val Gln Ser Gly Ala Glu Val Glu Lys Pro Gly Ala
1               5                   10                  15

Ser Val Lys Val Ser Cys Lys Val Ser Gly Tyr Thr Phe Thr Gly Asp
            20                  25                  30

Tyr Met His Trp Val Arg Gln Ala Pro Gly Gln Gly Leu Glu Trp Met
        35                  40                  45

Gly Arg Ile Asp Pro Lys Tyr Gly Asp Thr Asn Tyr Ala Gln Lys Phe
    50                  55                  60

Gln Gly Arg Val Thr Met Thr Arg Asp Thr Ser Ile Ser Thr Val Tyr
65                  70                  75                  80

Met Glu Leu Ser Arg Leu Arg Ser Asp Asp Thr Ala Leu Tyr Phe Cys
                85                  90                  95

Ala Thr Asp Asn Ser Gly Leu Tyr Asp Ala Phe Asp Lys Trp Gly Lys
            100                 105                 110

Gly Thr Thr Val Thr Val Ser Ser Gly Gly Gly Gly Ser Gly Gly Gly
        115                 120                 125

Gly Ser Gly Gly Gly Gly Ser Gln Ser Val Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Glu Gly Ser Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Arg Leu Gln Ala Glu Asp Glu Ala Asp Tyr Tyr
    210                 215                 220

Cys Ser Ser Tyr Thr Thr Arg Ser Thr Arg Val Phe Gly Gly Gly Thr
225                 230                 235                 240

Lys Leu Thr Val Leu Gly
                245


<210> SEQ ID NO 14
<211> LENGTH: 249
<212> TYPE: PRT
<213> ORGANISM: Artificial Sequence
<220> FEATURE:
<223> OTHER INFORMATION: scFv protein RGB0146

<400> SEQUENCE: 14

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Arg Gly
            20                  25                  30

Gly Tyr Tyr Trp Ser Trp Ile Arg Gln Leu Pro Gly Lys Gly Leu Glu
```

-continued

```
        35                  40                  45

Trp Ile Gly Tyr Ile Tyr His Ser Gly Ser Thr Tyr Tyr Asn Pro Pro
    50                  55                  60

Leu Lys Ser Arg Val Thr Met Ser Val Asp Thr Ser Lys Asn Gln Phe
65                  70                  75                  80

Ser Leu Asn Leu Ser Ser Val Thr Ala Ala Asp Thr Ala Val Tyr Tyr
                85                  90                  95

Cys Ala Arg Glu Lys Gly Gly Asp Trp Glu Gln Leu Val Phe Asp His
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Gly Ser Gln Ser Val Leu Thr Gln
    130                 135                 140

Pro Pro Ser Val Ser Ala Ala Pro Gly Gln Lys Val Thr Ile Ser Cys
145                 150                 155                 160

Ser Gly Ser Thr Ser Asn Ile Gly Asn Asn Tyr Val Ser Trp Tyr Gln
                165                 170                 175

Gln His Pro Gly Lys Ala Pro Lys Leu Met Ile Tyr Asp Val Ser Lys
            180                 185                 190

Arg Pro Ser Gly Val Pro Asp Arg Phe Ser Gly Ser Lys Ser Gly Asn
        195                 200                 205

Ser Ala Ser Leu Asp Ile Ser Gly Leu Gln Ser Glu Asp Glu Ala Asp
    210                 215                 220

Tyr Tyr Cys Ala Ala Trp Asp Asp Ser Leu Ser Glu Phe Leu Phe Gly
225                 230                 235                 240

Thr Gly Thr Lys Leu Thr Val Leu Gly
                245


<210> SEQ ID NO 15
<211> LENGTH: 249
<212> TYPE: PRT
<213> ORGANISM: Artificial Sequence
<220> FEATURE:
<223> OTHER INFORMATION: scFv protein RGB0153

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Ala Thr Pro Phe Asn Ala Phe Asp Ile Trp Gly
            100                 105                 110

Arg Gly Thr Thr Val Thr Val Ser Ser Gly Gly Gly Gly Ser Gly Gly
        115                 120                 125

Gly Gly Ser Gly Gly Gly Gly Ser Ala Leu Asn Phe Met Leu Thr Gln
    130                 135                 140

Pro His Ser Val Ser Glu Ser Pro Gly Lys Thr Val Thr Leu Ser Cys
```

-continued

```
145                 150                 155                 160

Thr Arg Ser Ser Gly Ser Ile Ser Phe Asp Tyr Val Gln Trp Tyr Gln
                165                 170                 175

Gln Arg Pro Gly Ser Ser Pro Ile Leu Val Ile Phe Glu Asp Asp Gln
            180                 185                 190

Arg Pro Ser Gly Val Pro Asp Arg Phe Ser Gly Ser Ile Asp Ser Thr
        195                 200                 205

Ser Asn Ser Ala Ser Leu Thr Ile Ser Gly Leu Gln Ser Glu Asp Glu
    210                 215                 220

Gly Asp Tyr Tyr Cys Gln Thr Tyr Asp Asp Asn Arg Gln Val Phe Gly
225                 230                 235                 240

Gly Gly Thr Lys Val Thr Val Leu Gly
                245


<210> SEQ ID NO 16
<211> LENGTH: 247
<212> TYPE: PRT
<213> ORGANISM: Artificial Sequence
<220> FEATURE:
<223> OTHER INFORMATION: scFv protein RGB0163

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Pro Tyr Tyr Asp Ser Ser Gly Tyr Tyr Pro Phe Ser Tyr
            100                 105                 110

Trp Gly Arg Gly Thr Thr Val Thr Val Ser Ser Gly Gly Gly Gly Ser
        115                 120                 125

Gly Gly Gly Gly Ser Gly Gly Gly Gly Ser Ala Gln Ser Val Leu Thr
    130                 135                 140

Gln Pro Pro Ser Val Ser Val Ala Pro Gly Lys Thr Ala Thr Ile Thr
145                 150                 155                 160

Cys Gly Gly Asp Phe Ala Thr Lys Asn Val Asn Trp Tyr Gln Arg Lys
                165                 170                 175

Pro Gly Gln Ala Pro Val Thr Val Ile Tyr Tyr Asp Thr Glu Arg Pro
            180                 185                 190

Ser Ala Ile Pro Glu Arg Phe Ser Gly Ser Asn Thr Gly Ser Thr Ala
        195                 200                 205

Thr Leu Thr Ile Ser Arg Val Glu Ala Gly Asp Glu Ala Asp Tyr Tyr
    210                 215                 220

Cys Gln Val Trp Asp Ser Phe Thr Asp His Arg Leu Phe Gly Gly Gly
225                 230                 235                 240

Thr Lys Leu Thr Val Leu Gly
                245
```

-continued

```
<210> SEQ ID NO 17
<211> LENGTH: 253
<212> TYPE: PRT
<213> ORGANISM: Artificial Sequence
<220> FEATURE:
<223> OTHER INFORMATION: scFv protein RGB0165

<400> SEQUENCE: 17

Glu Val Gln Leu Leu Glu Ser Gly Gly Gly Leu Val Gln Pro Gly Gly
1               5                   10                  15

Ser Leu Gly Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Ser Gly Ser Pro Val Tyr Tyr Tyr Tyr His Tyr Leu
            100                 105                 110

Asp Val Trp Gly Arg Gly Thr Leu Val Thr Val Ser Ser Gly Gly Gly
        115                 120                 125

Gly Ser Gly Gly Gly Gly Ser Gly Gly Gly Gly Ser Ala Leu Asn Phe
    130                 135                 140

Met Leu Thr Gln Pro His Ser Val Ser Glu Ser Pro Gly Lys Thr Val
145                 150                 155                 160

Thr Leu Ser Cys Thr Arg Ser Ser Gly Ser Ile Ser Phe Asp Tyr Val
                165                 170                 175

Gln Trp Tyr Gln Gln Arg Pro Gly Ser Ser Pro Ile Leu Val Ile Phe
            180                 185                 190

Glu Asp Asp Gln Arg Pro Ser Gly Val Pro Asp Arg Phe Ser Gly Ser
        195                 200                 205

Ile Asp Ser Thr Ser Asn Ser Ala Ser Leu Thr Ile Ser Gly Leu Gln
    210                 215                 220

Ser Glu Asp Glu Gly Asp Tyr Tyr Cys Gln Thr Tyr Asp Asp Asn Arg
225                 230                 235                 240

Gln Val Phe Gly Gly Gly Thr Lys Leu Thr Val Leu Gly
                245                 250


<210> SEQ ID NO 18
<211> LENGTH: 248
<212> TYPE: PRT
<213> ORGANISM: Artificial Sequence
<220> FEATURE:
<223> OTHER INFORMATION: scFv protein RGB0174

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Ser Asp Ser Ser Asp Tyr Tyr Tyr Phe Asp Ser Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Ala Gln Ser Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Ser Asn Ile Gly Phe Asn Asp Val Tyr Trp Tyr Gln Gln
                165                 170                 175

Leu Pro Gly Leu Ala Pro Lys Leu Leu Ile Tyr Ser Asn Asn Gln Arg
            180                 185                 190

Pro Ser Gly Val Pro Asp Arg Phe Ser Gly Ser Glu Ser Gly Thr Ser
        195                 200                 205

Ala Ser Leu Ala Ile Ser Gly Leu Arg Ser Glu Asp Glu Ala Asp Tyr
    210                 215                 220

Tyr Cys Ala Thr Trp Asp Asp Ser Leu Ser Ala Pro Val Phe Gly Gly
225                 230                 235                 240

Gly Thr Lys Val Thr Val Leu Gly
                245


<210> SEQ ID NO 19
<211> LENGTH: 251
<212> TYPE: PRT
<213> ORGANISM: Artificial Sequence
<220> FEATURE:
<223> OTHER INFORMATION: scFv protein RGB0185

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Met Ala Arg Asp Thr Ser Met Ser Thr Ala Ser
65                  70                  75                  80

Val Glu Leu Arg Arg Leu Thr Ser Asp Asp Thr Ala Val Tyr Tyr Cys
                85                  90                  95

Ala Arg Asn Ser Phe Asp Phe Gly Ser Gly Tyr Gly Leu Phe Tyr Gln
            100                 105                 110

Tyr Ile Met Asp Val Trp Gly Gln Gly Thr Leu Val Thr Val Ser Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Phe Leu Ser Ala Ser Val Gly Asp
145                 150                 155                 160

Arg Val Thr Ile Thr Cys Arg Ala Ser Gln Gly Ile Asn Asn Tyr Leu
                165                 170                 175
```

```
Ala Trp Tyr Gln Gln Lys Pro Gly Arg Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Leu Gln Asp Ser Asp Tyr Pro Leu Thr
225                 230                 235                 240

Phe Gly Gly Gly Thr Lys Leu Thr Val Leu Gly
                245                 250


<210> SEQ ID NO 20
<211> LENGTH: 253
<212> TYPE: PRT
<213> ORGANISM: Artificial Sequence
<220> FEATURE:
<223> OTHER INFORMATION: scFv protein RGB0187

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Cys Pro Tyr Cys Ser Thr Asn Ser Gly Ser Phe Asp
            100                 105                 110

Tyr Trp Gly Gln Gly Thr Met Val Thr Val Ser Ser Gly Gly Gly Gly
        115                 120                 125

Ser Gly Gly Gly Gly Ser Gly Gly Gly Gly Ser Ala Leu Asn Phe Met
    130                 135                 140

Leu Thr Gln Pro His Ser Val Ser Glu Ser Pro Gly Lys Thr Val Thr
145                 150                 155                 160

Ile Ser Cys Thr Arg Thr Ser Gly Asn Ile Ala Gly Tyr Phe Val Gln
                165                 170                 175

Trp Tyr Gln Gln Arg Pro Gly Ser Ser Pro Thr Thr Val Ile Tyr Glu
            180                 185                 190

Asp Tyr Gln Arg Pro Ser Gly Val Pro Asp Arg Phe Ser Gly Ser Ile
        195                 200                 205

Asp Arg Ser Ser Asn Ser Ala Ser Leu Thr Ile Ser Gly Leu Lys Pro
    210                 215                 220

Asp Asp Glu Ala Asp Tyr Tyr Cys Gln Ser Tyr Asp Asp Thr Ser Gln
225                 230                 235                 240

Gly Val Phe Gly Ala Gly Thr Lys Leu Thr Val Leu Gly
                245                 250


<210> SEQ ID NO 21
<211> LENGTH: 248
<212> TYPE: PRT
<213> ORGANISM: Artificial Sequence
<220> FEATURE:
```

<223> OTHER INFORMATION: scFv protein RGB0194

<400> SEQUENCE: 21

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Leu Ser Arg Phe
            20                  25                  30

Gly Ile Asn Trp Val Arg Gln Ala Pro Gly Gln Gly Leu Glu Trp Met
        35                  40                  45

Gly Val Ile Ile Pro Met Phe Gly Thr Thr Asn Tyr Ala Gln Lys Phe
    50                  55                  60

Glu Asp Arg Val Thr Ile Ser Ala Asp Gly Ser Thr Ser Thr Val Tyr
65                  70                  75                  80

Met Glu Leu Ser Gly Leu Lys Ser Glu Asp Thr Ala Val Tyr Tyr Cys
                85                  90                  95

Ala Gly Ser Asp Phe Trp Ser Gly Tyr Asp Gly Glu Pro Asp Val Phe
            100                 105                 110

Asp Leu Trp Gly Arg Gly Thr Leu Val Thr Val Ser Ser Gly Gly Gly
        115                 120                 125

Gly Ser Gly Gly Gly Gly Ser Gly Gly Gly Gly Ser Ser Glu Leu Thr
    130                 135                 140

Gln Asp Pro Ala Ala Ser Val Ala Leu Gly Gln Thr Val Arg Ile Thr
145                 150                 155                 160

Cys Gln Gly Asp Ser Leu Arg Ser Tyr Tyr Thr Asn Trp Phe Gln Gln
                165                 170                 175

Lys Pro Gly Gln Ala Pro Leu Leu Val Val Tyr Ala Lys Asn Lys Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asp Glu Ala Asp Tyr
    210                 215                 220

Tyr Cys His Ser Arg Asp Ser Ser Gly Asn His Val Leu Phe Gly Gly
225                 230                 235                 240

Gly Thr Lys Leu Thr Val Leu Gly
                245
```

<210> SEQ ID NO 22
<211> LENGTH: 250
<212> TYPE: PRT
<213> ORGANISM: Artificial Sequence
<220> FEATURE:
<223> OTHER INFORMATION: scFv protein RGC0102

<400> SEQUENCE: 22

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Tyr Trp Ser Trp Val Arg Gln Pro Pro Gly Lys Gly Leu Glu Trp
        35                  40                  45

Ile Gly Glu Ile Tyr His Asp Gly Ser Thr Asn Tyr Asn Pro Ser Leu
    50                  55                  60

Lys Ser Arg Val Thr Met Ser Ala Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Asp Ser Pro Ser Tyr Ser Ser Gly Trp Tyr Ser Asp Tyr Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Ala Gln Ser Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Ser Ser Asn Ile Gly Ser Asn Thr Val Asn Trp Tyr Gln
                165                 170                 175

Gln Leu Pro Gly Thr Ala Pro Lys Leu Leu Ile Phe Ser Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Val
    210                 215                 220

Tyr Tyr Cys Ala Ala Trp Asp Asp Ser Leu Thr Gly Phe Tyr Val Phe
225                 230                 235                 240

Gly Ala Gly Thr Lys Val Thr Val Leu Gly
                245                 250


<210> SEQ ID NO 23
<211> LENGTH: 242
<212> TYPE: PRT
<213> ORGANISM: Artificial Sequence
<220> FEATURE:
<223> OTHER INFORMATION: scFv protein RGC0104

<400> SEQUENCE: 23

Glu Val Gln Leu Val Gln Ser Gly Ala Glu Val Arg Lys Pro Gly Ser
1               5                   10                  15

Ser Val Lys Val Ser Cys Thr Thr Ser Glu Asn Thr Phe Arg Arg Ser
            20                  25                  30

Ser Phe Ser Trp Leu Arg Gln Ala Pro Gly Gln Gly Leu Glu Trp Met
        35                  40                  45

Gly Arg Ile Ile Pro Ile Ile His Ser Glu Thr Tyr Ala Gln Asn Phe
    50                  55                  60

Gln Gly Arg Val Thr Met Thr Ala Asp Glu Ser Thr Ser Thr Val Tyr
65                  70                  75                  80

Val Glu Val Arg Ser Leu Arg Ser Glu Asp Thr Ala Val Tyr Tyr Cys
                85                  90                  95

Ala Arg Asp Ser Pro Pro Tyr Asn Ala Asp Phe Asp Phe Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Gln Ser Val Leu Thr Gln Pro Pro
    130                 135                 140

Ser Val Ser Val Ser Pro Gly Gln Thr Ala Thr Ile Thr Cys Ser Gly
145                 150                 155                 160

Asp Lys Leu Gly Asp Lys Tyr Ala Ser Trp Tyr Gln Lys Lys Ala Gly
                165                 170                 175

Gln Ser Pro Val Leu Val Ile Tyr Gln Asp Asn Lys Arg Pro Ser Gly
            180                 185                 190

Ile Pro Glu Arg Phe Ser Gly Ser Asn Ser Gly Asn Thr Ala Thr Leu
        195                 200                 205
```

-continued

```
Thr Ile Ser Gly Thr Gln Ala Met Asp Glu Ala Asp Tyr Tyr Cys Gln
    210                 215                 220

Ala Trp Asp Ser Ser Val Val Phe Gly Gly Gly Thr Lys Val Thr Val
225                 230                 235                 240

Leu Gly


<210> SEQ ID NO 24
<211> LENGTH: 246
<212> TYPE: PRT
<213> ORGANISM: Artificial Sequence
<220> FEATURE:
<223> OTHER INFORMATION: scFv protein RGC0107

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Leu Ser Arg Ser
            20                  25                  30

Ser Tyr Tyr Trp Gly Trp Ile Arg Gln Pro Pro Gly Lys Gly Leu Glu
        35                  40                  45

Trp Ile Gly Ser Val Phe Tyr Ser Gly Ser Ala Asp Tyr Asn Pro Ser
    50                  55                  60

Leu Lys Ser Arg Ala Ser Ile Ser Val Asp Thr Tyr Gln Asn Gln Val
65                  70                  75                  80

Ser Leu Lys Leu Thr Ser Val Thr Ala Ala Asp Thr Ala Val Tyr Tyr
                85                  90                  95

Cys Ala Arg Asp Asp Gly Ser Thr Phe Asp Pro Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Tyr Val Leu Thr Gln Pro Pro Ser
    130                 135                 140

Ala Ser Glu Thr Pro Gly Gln Arg Val Thr Ile Ser Cys Ser Gly Ser
145                 150                 155                 160

Ser Ala Asn Ile Glu Tyr Asn Phe Val Tyr Trp Tyr Gln Gln Leu Pro
                165                 170                 175

Gly Thr Ala Pro Lys Leu Leu Ile Tyr Arg Asn Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Asn Gly Tyr Val Phe Gly Thr Gly Thr
225                 230                 235                 240

Lys Val Thr Val Leu Gly
                245


<210> SEQ ID NO 25
<211> LENGTH: 246
<212> TYPE: PRT
<213> ORGANISM: Artificial Sequence
<220> FEATURE:
<223> OTHER INFORMATION: scFv protein RGC0108

<400> SEQUENCE: 25

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Asp Ser Ile Asp Lys Ser
            20                  25                  30

Ser Tyr Tyr Trp Ala Trp Ile Arg Gln Pro Pro Gly Lys Gly Leu Glu
        35                  40                  45

Trp Ile Ala Ser Val Phe Tyr Asp Gly Thr Ala Asp Tyr Ser Pro Ser
    50                  55                  60

Leu Arg Ser Arg Val Ser Met Ser Val Asp Arg Ser Leu Asn His Val
65                  70                  75                  80

Ser Leu Arg Leu Thr Ser Leu Thr Ala Ala Asp Thr Ala Thr Tyr Tyr
                85                  90                  95

Cys Ala Arg Asp Asp Gly Ser Ser Phe Asp Pro Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Tyr Val Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Thr Gly Ser Asn Tyr Val Tyr Trp Tyr Gln Gln Leu Pro
                165                 170                 175

Gly Thr Ala Pro Lys Leu Leu Ile Tyr Arg Asn Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Ser Gly Tyr Val Phe Gly Thr Gly Thr
225                 230                 235                 240

Lys Val Thr Val Leu Gly
                245


<210> SEQ ID NO 26
<211> LENGTH: 246
<212> TYPE: PRT
<213> ORGANISM: Artificial Sequence
<220> FEATURE:
<223> OTHER INFORMATION: scFv protein RGC0110

<400> SEQUENCE: 26

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Asn Arg Tyr
            20                  25                  30

Tyr Ile His Trp Val Arg Gln Ala Pro Gly Gln Gly Leu Glu Trp Val
        35                  40                  45

Gly Ile Ile Asn Pro Arg Gly Asp Ser Ala Asn Tyr Ala Gln Lys Phe
    50                  55                  60

Gln Gly Arg Val Thr Leu Thr Arg Asp Thr Ser Ala Arg Thr Val Tyr
65                  70                  75                  80

Met Glu Met Asn Ser Leu Arg Pro Asp Asp Thr Ala Val Tyr Tyr Cys
                85                  90                  95

Ala Arg Glu Gly Val Gly Ala Thr Trp Val His Trp Gly Lys Gly Thr
            100                 105                 110

Leu Val Thr Val Ser Ser Gly Gly Gly Gly Ser Gly Gly Gly Gly Ser
        115                 120                 125
```

-continued

```
Gly Gly Gly Gly Ser Ala Leu Asn Phe Met Leu Thr Gln Pro His Ser
    130                 135                 140

Val Ser Gly Ser Pro Gly Lys Thr Val Thr Ile Ser Cys Thr Gly Ser
145                 150                 155                 160

Ser Gly Ser Ile Ala Ser Asn Tyr Val Gln Trp Tyr Gln Gln Arg Pro
                165                 170                 175

Gly Ser Ala Pro Thr Thr Val Ile Tyr Glu Asp Asn Gln Arg Pro Ser
            180                 185                 190

Gly Val Pro Asp Arg Phe Ser Gly Ser Ile Asp Arg Ser Ser Asn Ser
        195                 200                 205

Ala Ser Leu Thr Ile Ser Gly Leu Lys Thr Glu Asp Glu Ala Asp Tyr
    210                 215                 220

Tyr Cys Gln Ser Ser Asp Thr Met Phe Gln Val Phe Gly Gly Gly Thr
225                 230                 235                 240

Lys Leu Thr Val Leu Gly
                245
```

<210> SEQ ID NO 27
<211> LENGTH: 246
<212> TYPE: PRT
<213> ORGANISM: Artificial Sequence
<220> FEATURE:
<223> OTHER INFORMATION: scFv protein RGC0114

<400> SEQUENCE: 27

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Ser Ile Asn Trp Val Arg Gln Ala Pro Gly Gln Gly Leu Glu Trp Met
        35                  40                  45

Gly Val Ile Ile Ser Asn Leu Gly Thr Pro Tyr Tyr Ala Gln Ser Phe
    50                  55                  60

Gln Gly Arg Val Thr Ile Ser Ala Asp Lys Ser Thr Gly Thr Val Tyr
65                  70                  75                  80

Leu Asp Val Ser Ser Leu Arg Ser Asp Asp Ser Ala Thr Tyr Tyr Cys
                85                  90                  95

Ala Arg Ala Arg Arg Leu Trp Gln Thr Phe Asp Ile Trp Gly Lys Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Gln Ser Val Leu Thr Gln Pro Pro Ser
    130                 135                 140

Ala Ser Gly Ala Pro Gly Gln Arg Val Val Ile Ser Cys Ser Gly Ser
145                 150                 155                 160

Thr Ser Ser Ile Gly Ser Asn Thr Val Asn Trp Tyr Lys His Val Pro
                165                 170                 175

Gly Glu Ala Pro Lys Leu Leu Ile Tyr Ser Ser Thr Gln Arg Pro Ser
            180                 185                 190

Gly Val Pro Gly Arg Phe Ser Gly Ser Thr Ser Gly Thr Ser Gly Ser
        195                 200                 205

Leu Thr Ile Ser Gly Leu Gln Ser Gly Asp Glu Ala Asp Tyr Tyr Cys
    210                 215                 220

Ala Ala Phe Asp Asp Ser Leu Asn Gly Phe Val Phe Gly Thr Gly Thr
225                 230                 235                 240
```

```
Lys Leu Thr Val Leu Gly
                245


<210> SEQ ID NO 28
<211> LENGTH: 242
<212> TYPE: PRT
<213> ORGANISM: Artificial Sequence
<220> FEATURE:
<223> OTHER INFORMATION: scFv protein RGC0115

<400> SEQUENCE: 28

Gln Val Thr Leu Lys Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Tyr Ala Leu Asp Tyr Trp Gly Lys Gly Thr Leu Val
            100                 105                 110

Thr Val Ser Ser Gly Gly Gly Gly Ser Gly Gly Gly Gly Ser Gly Gly
        115                 120                 125

Gly Gly Ser Ala Leu Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Asn Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Val
            180                 185                 190

Arg Phe Ser Gly Ser Ser Ser Gly Asn Thr Ala Ser Leu Thr Ile Thr
        195                 200                 205

Gly Thr Gln Ala Glu Asp Gly Ala Asp Tyr Tyr Cys Asn Ser Arg Asp
    210                 215                 220

Ser Ser Gly Lys His Val Ile Phe Gly Gly Gly Thr Lys Val Thr Val
225                 230                 235                 240

Leu Gly


<210> SEQ ID NO 29
<211> LENGTH: 252
<212> TYPE: PRT
<213> ORGANISM: Artificial Sequence
<220> FEATURE:
<223> OTHER INFORMATION: scFv protein RGC0128

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Ser Phe Ser Ser Tyr
            20                  25                  30

Gly Met Ser Trp Val Arg Gln Ala Pro Gly Lys Gly Leu Glu Trp Val
        35                  40                  45
```

```
Ser Ser Ile Thr Ser Arg Gly Arg Gly Gly Ser Thr Tyr His Ala Asp
    50                  55                  60

Tyr Val Glu Gly Arg Phe Thr Ile Ser Arg Asp Asp Ala Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Trp Ser Ala Tyr Asp Ser Val His Leu Phe Asp
            100                 105                 110

Tyr Trp Gly Arg Gly Thr Leu Val Thr Val Ser Ser Gly Gly Gly Gly
        115                 120                 125

Ser Gly Gly Gly Gly Ser Gly Gly Gly Gly Ser Ala Leu Asn Phe Met
    130                 135                 140

Leu Thr Gln Pro His Ser Val Ser Glu Ser Pro Gly Lys Thr Val Thr
145                 150                 155                 160

Ile Ser Cys Thr Arg Asn Thr Asp Asn Ile Ala Phe Asn Tyr Val Gln
                165                 170                 175

Trp Phe Gln Gln Arg Pro Gly Ser Ser Pro Thr Thr Val Ile Tyr Glu
            180                 185                 190

Asp Asn Gln Arg Pro Ser Gly Val Pro Asp Arg Phe Ser Gly Ser Ile
        195                 200                 205

Asp Ser Ser Ser Asn Ser Ala Ser Leu Thr Ile Ser Gly Leu Lys Thr
    210                 215                 220

Glu Asp Glu Ala Asp Tyr Tyr Cys Gln Ser Tyr Asp Gly Asn Asn Leu
225                 230                 235                 240

Val Phe Gly Gly Gly Thr Lys Leu Thr Val Leu Gly
                245                 250


<210> SEQ ID NO 30
<211> LENGTH: 249
<212> TYPE: PRT
<213> ORGANISM: Artificial Sequence
<220> FEATURE:
<223> OTHER INFORMATION: scFv protein RGC0130

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Arg Pro Arg Gly Ile Ala Ala Arg Pro Leu Leu Ser
            100                 105                 110

Tyr Trp Gly Arg Gly Thr Thr Val Thr Val Ser Ser Gly Gly Gly Gly
        115                 120                 125

Ser Gly Gly Gly Gly Ser Gly Gly Gly Gly Ser Gln Ser Val Leu Thr
    130                 135                 140

Gln Pro Pro Ser Val Ser Ala Ala Pro Gly Glu Lys Val Thr Ile Ser
145                 150                 155                 160
```

```
Cys Ser Gly Ser Thr Ser Asn Ile Gly Asn Asn Tyr Val Ser Trp Tyr
                165                 170                 175

Gln Gln His Pro Gly Lys Ala Pro Lys Leu Met Ile Tyr Asp Val Ser
            180                 185                 190

Lys Arg Pro Ser Gly Val Pro Asp Arg Phe Ser Gly Ser Lys Ser Gly
        195                 200                 205

Asn Thr Ala Ser Leu Thr Ile Ser Gly Val Gln Ala Glu Asp Glu Ala
    210                 215                 220

Asp Tyr Tyr Cys Ser Ser Tyr Thr Ser Ala Ser Thr Val Ile Phe Gly
225                 230                 235                 240

Gly Gly Thr Lys Leu Thr Val Leu Gly
                245


<210> SEQ ID NO 31
<211> LENGTH: 257
<212> TYPE: PRT
<213> ORGANISM: Artificial Sequence
<220> FEATURE:
<223> OTHER INFORMATION: scFv protein RGC0131

<400> SEQUENCE: 31

Gln Val Gln Leu Val Gln Ser Gly Ala Glu Val Arg Lys Pro Gly Ala
1               5                   10                  15

Ser Val Arg Val Ser Cys Arg Ala Ser Gly Tyr Ser Phe Thr Asn Tyr
            20                  25                  30

Asp Ile Asn Trp Val Arg Gln Ala Pro Gly Gln Gly Leu Glu Trp Met
        35                  40                  45

Gly Trp Met Asn Pro Asn Gly Gly His Thr Gly Ser Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Asp Asp Thr Ala Val Tyr Tyr Cys
                85                  90                  95

Ala Arg Gly Ser Gln Trp Cys Thr Gly Gly Asn Cys Tyr Gly Thr His
            100                 105                 110

Tyr Tyr Tyr Met Glu Asp Trp Gly Arg Gly Thr Leu Val Thr Val Ser
        115                 120                 125

Ser Gly Gly Gly Gly Ser Gly Gly Gly Gly Ser Gly Gly Gly Gly Ser
    130                 135                 140

Ala Leu Asn Phe Met Leu Thr Gln Pro His Ser Val Ser Glu Ser Pro
145                 150                 155                 160

Gly Lys Thr Val Thr Ile Ser Cys Thr Arg Asn Thr Asp Asn Ile Ala
                165                 170                 175

Phe Asn Tyr Val Gln Trp Phe Gln Gln Arg Pro Gly Ser Ser Pro Thr
            180                 185                 190

Thr Val Ile Tyr Glu Asp Asn Gln Arg Pro Ser Gly Val Pro Asp Arg
        195                 200                 205

Phe Ser Gly Ser Ile Asp Ser Ser Ser Asn Ser Ala Ser Leu Thr Ile
    210                 215                 220

Ser Gly Leu Lys Thr Glu Asp Glu Ala Asp Tyr Tyr Cys Gln Ser Tyr
225                 230                 235                 240

Asp Gly Asn Asn Leu Val Phe Gly Gly Gly Thr Lys Leu Thr Val Leu
                245                 250                 255

Gly
```

<210> SEQ ID NO 32
<211> LENGTH: 244
<212> TYPE: PRT
<213> ORGANISM: Artificial Sequence
<220> FEATURE:
<223> OTHER INFORMATION: scFv protein RGC0137

<400> SEQUENCE: 32

Glu Val Gln Leu Val Gln Ser Gly Ser Glu Val Lys Lys Pro Gly Ser
1 5 10 15

Ser Val Arg Val Ser Cys Lys Thr Ser Gly Asp Thr Phe Arg Arg Phe
20 25 30

Thr Val Ser Trp Val Arg Gln Ala Pro Gly Gln Gly Leu Glu Trp Met
35 40 45

Gly Arg Val Ile Pro Leu Tyr Asn Ser Pro Thr Tyr Ala Gln Lys Phe
50 55 60

Gln Asp Arg Val Thr Ile Thr Ala Asp Glu Ser Thr Thr Thr Val Tyr
65 70 75 80

Met Glu Val Thr Gly Leu Thr Ser Glu Asp Thr Ala Val Tyr Tyr Cys
85 90 95

Ala Arg Asp Ser Pro Pro Tyr Asn Ala Asp Phe Asp Ser Trp Gly Gln
100 105 110

Gly Thr Met Val Thr Val Ser Ser Gly Gly Gly Gly Ser Gly Gly Gly
115 120 125

Gly Ser Gly Gly Gly Gly Ser Ala Gln Ala Val Leu Thr Gln Pro Ser
130 135 140

Ser Met Ser Val Ser Pro Gly Gln Thr Ala Ile Ile Thr Cys Ser Gly
145 150 155 160

Asn Arg Leu Gly Asp Lys Tyr Val Ser Trp Tyr Gln Gln Arg Pro Gly
165 170 175

Gln Ser Pro Val Leu Val Ile Phe Gln Asp Asn Lys Arg Pro Ser Gly
180 185 190

Ile Ser Glu Arg Phe Ser Gly Ser Asn Ser Gly Asn Thr Ala Thr Leu
195 200 205

Thr Ile Ser Asp Val Glu Ala Met Asp Glu Ala Glu Tyr Phe Cys Gln
210 215 220

Ala Trp His Ser Ser Phe Tyr Tyr Ala Phe Gly Thr Gly Thr Lys Leu
225 230 235 240

Thr Val Leu Gly

<210> SEQ ID NO 33
<211> LENGTH: 248
<212> TYPE: PRT
<213> ORGANISM: Artificial Sequence
<220> FEATURE:
<223> OTHER INFORMATION: scFv protein RGC0139

<400> SEQUENCE: 33

Glu Val Gln Leu Val Gln Ser Gly Ala Glu Val Lys Glu Pro Gly Ala
1 5 10 15

Ser Met Lys Val Tyr Cys Lys Ala Ser Gly Tyr Arg Phe Thr Arg Tyr
20 25 30

Tyr Ile His Trp Val Arg Gln Ala Pro Gly Gln Gly Leu Glu Trp Met
35 40 45

Gly Thr Ile Asn Pro Ser Asp Gly Ser Thr Ser Tyr Ala Gln Lys Phe
50 55 60

-continued

```
Gln Asp Arg Val Thr Met Thr Arg Asp Thr Ser Thr Arg Thr Val Tyr
65                  70                  75                  80

Met Glu Leu Ser Ser Leu Arg Ser Glu Asp Thr Ala Met Tyr Tyr Cys
                85                  90                  95

Gly Arg Val Glu Asp Tyr Tyr Ser Glu Ser Asn Gly Pro Ala Asp Asn
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Gly Ser Ala Gln Ser Val Leu Thr
    130                 135                 140

Gln Pro Pro Ser Val Ser Val Ala Pro Gly Gln Thr Ala Ser Ile Thr
145                 150                 155                 160

Cys Gly Gly Asn Lys Ile Gly Thr Lys Gly Val His Trp Tyr Gln Gln
                165                 170                 175

Lys Pro Gly Arg Ala Pro Val Leu Val Val Tyr Asp Asp Gly Asp Arg
            180                 185                 190

Pro Ser Gly Ile Pro Asp Arg Phe Ser Gly Ser Asn Ser Asp Asn Thr
        195                 200                 205

Ala Thr Leu Thr Ile Ser Arg Val Glu Ala Gly Asp Glu Ala Asp Tyr
    210                 215                 220

Tyr Cys Gln Val Trp Asp Ser Asp Ser Asp Leu Gly Val Phe Gly Gly
225                 230                 235                 240

Gly Thr Lys Val Thr Val Leu Gly
                245


<210> SEQ ID NO 34
<211> LENGTH: 243
<212> TYPE: PRT
<213> ORGANISM: Artificial Sequence
<220> FEATURE:
<223> OTHER INFORMATION: scFv protein RGC0142

<400> SEQUENCE: 34

Glu Val Gln Leu Val Gln Ser Gly Ala Ala Val Lys Lys Pro Gly Ser
1               5                   10                  15

Ser Val Lys Ile Ser Cys Glu Val Ser Gly Gly Ile Phe Lys Asn Tyr
            20                  25                  30

Ala Ile Ser Trp Val Arg Gln Ala Pro Gly Gln Gly Leu Glu Trp Met
        35                  40                  45

Gly Gly Ser Ile Pro Met Tyr Gly Thr Pro Ser Tyr Ala Pro Lys Phe
    50                  55                  60

Gln Gly Arg Val Thr Ile Ile Ala Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Thr Thr Glu Val Asp Asp Ala Phe Asp Ile Trp Gly Arg
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Gln Ser Val Leu Thr Gln Pro Pro
    130                 135                 140

Ser Val Ser Ala Ala Pro Arg Gln Arg Val Thr Ile Ser Cys Ser Gly
145                 150                 155                 160

Ser Ser Ser Asn Ile Gly Asn Asn Val Val Asn Trp Tyr Gln His Phe
                165                 170                 175
```

-continued

```
Pro Gly Lys Ala Pro Arg Leu Leu Ile Phe Ser Asp Ser Leu Leu Ser
            180                 185                 190

Asp Arg Phe Ser Gly Ser Lys Ser Gly Thr Ser Ala Ser Leu Ala Ile
        195                 200                 205

Ser Gly Leu Gln Ser Asp Asp Glu Ala Glu Tyr Tyr Cys Ala Ser Trp
    210                 215                 220

Asp Asp Ser Leu Asn Gly Leu Val Phe Gly Gly Gly Thr Lys Leu Thr
225                 230                 235                 240

Val Leu Gly


<210> SEQ ID NO 35
<211> LENGTH: 243
<212> TYPE: PRT
<213> ORGANISM: Artificial Sequence
<220> FEATURE:
<223> OTHER INFORMATION: scFv protein RGC0145

<400> SEQUENCE: 35

Glu Val Gln Leu Val Gln Ser Gly Ala Glu Val Lys Lys Pro Gly Ser
1               5                   10                  15

Ser Val Lys Ile Ser Cys Glu Val Ser Gly Gly Ile Phe Lys Asn Tyr
            20                  25                  30

Ala Ile Ser Trp Val Arg Gln Ala Pro Gly Gln Gly Leu Glu Trp Met
        35                  40                  45

Gly Gly Ser Ile Pro Met Tyr Gly Thr Pro Ser Tyr Ala Pro Lys Phe
    50                  55                  60

Gln Gly Arg Val Thr Ile Ile Ala Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Thr Thr Glu Val Asp Asp Ala Phe Asn Ile Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Gln Ser Val Leu Thr Gln Pro Pro
    130                 135                 140

Ser Val Ser Ala Ala Pro Arg Gln Arg Val Thr Ile Ser Cys Ser Gly
145                 150                 155                 160

Ser Ser Ser Asn Ile Gly Asn Asn Val Val Asn Trp Tyr Gln His Phe
                165                 170                 175

Pro Gly Lys Ala Pro Arg Leu Leu Ile Phe Pro Asp Ser Leu Leu Ser
            180                 185                 190

Asp Arg Phe Ser Gly Ser Lys Ser Gly Thr Ser Ala Ser Leu Ala Ile
        195                 200                 205

Ser Gly Leu Gln Ser Asp Asp Glu Ala Glu Tyr Tyr Cys Ala Ser Trp
    210                 215                 220

Asp Asp Ser Leu Asn Gly Leu Val Phe Gly Gly Gly Thr Lys Leu Thr
225                 230                 235                 240

Val Leu Gly


<210> SEQ ID NO 36
<211> LENGTH: 249
<212> TYPE: PRT
<213> ORGANISM: Artificial Sequence
<220> FEATURE:
<223> OTHER INFORMATION: scFv protein RGC0150
```

<400> SEQUENCE: 36

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Tyr Trp Ser Trp Val Arg Gln Pro Pro Gly Lys Gly Leu Glu Trp
        35                  40                  45

Ile Gly Glu Ile Tyr His Asp Gly Ser Thr Asn Tyr Asn Pro Ser Leu
    50                  55                  60

Lys Ser Arg Val Thr Met Ser Ala Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Pro Ser Tyr Ser Ser Gly Trp Tyr Ser Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Ala Gln Ser Val Leu Thr Gln
    130                 135                 140

Pro Pro Ser Ala Ser Gly Thr Pro Gly Arg Arg Val Thr Ile Ser Cys
145                 150                 155                 160

Ser Gly Ser Ser Ser Asn Ile Gly Ser Asn Pro Val Asn Trp Tyr Gln
                165                 170                 175

Gln Leu Pro Gly Thr Ala Pro Lys Ile Val Met Tyr Ser Thr Asp Gln
            180                 185                 190

Arg Thr Ser Gly Ala Pro Asp Arg Phe Ser Gly Ser Lys Ser Gly Thr
        195                 200                 205

Ser Ala Ser Leu Ala Ile Thr Gly Leu Gln Ser Glu Asp Glu Ala Asp
    210                 215                 220

Tyr Phe Cys Ala Thr Trp Asp Asp Ser Pro Asn Ala Val Val Phe Gly
225                 230                 235                 240

Gly Gly Thr Lys Leu Thr Val Leu Gly
                245
```

<210> SEQ ID NO 37
<211> LENGTH: 251
<212> TYPE: PRT
<213> ORGANISM: Artificial Sequence
<220> FEATURE:
<223> OTHER INFORMATION: scFv protein RGC0153

<400> SEQUENCE: 37

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Ala Arg Tyr Tyr Tyr Asp Ser Thr Ser Tyr Pro Phe Asp Tyr
```

-continued

```
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Ala Leu Asn Phe Met Leu
    130                 135                 140

Thr Gln Pro His Ser Val Ser Glu Ser Pro Gly Lys Thr Val Thr Leu
145                 150                 155                 160

Ser Cys Thr Arg Ser Ser Gly Ser Ile Ser Phe Asp Tyr Val Gln Trp
                165                 170                 175

Tyr Gln Gln Arg Pro Gly Ser Ser Pro Ile Leu Val Ile Phe Glu Asp
            180                 185                 190

Asp Gln Arg Pro Ser Gly Val Pro Asp Arg Phe Ser Gly Ser Ile Asp
        195                 200                 205

Ser Thr Ser Asn Ser Ala Ser Leu Thr Ile Ser Gly Leu Gln Ser Glu
    210                 215                 220

Asp Glu Gly Asp Tyr Tyr Cys Gln Thr Tyr Asp Asp Asn Arg Gln Val
225                 230                 235                 240

Phe Gly Gly Gly Thr Lys Val Thr Val Leu Gly
                245                 250


<210> SEQ ID NO 38
<211> LENGTH: 245
<212> TYPE: PRT
<213> ORGANISM: Artificial Sequence
<220> FEATURE:
<223> OTHER INFORMATION: scFv protein RGC0154

<400> SEQUENCE: 38

Gln Val Gln Leu Val Gln Ser Gly Ala Glu Val Arg Lys Pro Gly Ser
1               5                   10                  15

Ser Val Lys Val Ser Cys Thr Thr Ser Glu Asn Thr Phe Arg Arg Ser
            20                  25                  30

Ser Phe Ser Trp Leu Arg Gln Ala Pro Gly Gln Gly Leu Glu Trp Met
        35                  40                  45

Gly Arg Ile Ile Pro Ile Ile His Ser Glu Thr Tyr Ala Gln Asn Phe
    50                  55                  60

Gln Gly Arg Val Thr Met Thr Ala Asp Glu Ser Thr Ser Thr Val Tyr
65                  70                  75                  80

Val Glu Val Arg Ser Leu Arg Ser Glu Asp Thr Ala Val Tyr Tyr Cys
                85                  90                  95

Ala Arg Asp Ser Pro Pro Tyr Asn Ala Asp Phe Asp Phe Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Leu Ser Tyr Glu Leu Thr Gln Pro
    130                 135                 140

Pro Ser Val Ser Val Ser Pro Gly Gln Thr Ala Ser Ile Thr Cys Ser
145                 150                 155                 160

Gly Asp Asn Leu Gly Asp Lys Tyr Val Ser Trp Tyr Gln Gln Arg Pro
                165                 170                 175

Gly Gln Ser Pro Val Leu Val Ile Tyr Gln Asp Val Lys Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Gly Thr Gln Ala Met Asp Glu Ala Asp Tyr Tyr Cys
```

-continued

```
    210                 215                 220

Gln Ala Trp Asp Ser Asn Thr Ser Tyr Val Phe Gly Thr Gly Thr Gln
225                 230                 235                 240

Leu Thr Val Leu Ser
                245


<210> SEQ ID NO 39
<211> LENGTH: 253
<212> TYPE: PRT
<213> ORGANISM: Artificial Sequence
<220> FEATURE:
<223> OTHER INFORMATION: scFv protein RGC0157

<400> SEQUENCE: 39

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Asn Ser Ser
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Asn Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Asp Tyr Val Asp Pro Asp Met Leu Thr Ala Gly Tyr Tyr Phe
            100                 105                 110

Asp Gln Trp Gly Gln Gly Thr Leu Val Thr Val Ser Ser Gly Gly Gly
        115                 120                 125

Gly Ser Gly Gly Gly Gly Ser Gly Gly Gly Gly Ser Ala Leu Asn Phe
    130                 135                 140

Met Leu Thr Gln Pro His Ser Val Ser Glu Ser Pro Gly Lys Thr Val
145                 150                 155                 160

Thr Ile Ser Cys Thr Arg Asn Thr Asp Asn Ile Ala Phe Asn Tyr Val
                165                 170                 175

Gln Trp Phe Gln Gln Arg Pro Gly Ser Ser Pro Thr Thr Val Ile Tyr
            180                 185                 190

Glu Asp Asn Gln Arg Pro Ser Gly Val Pro Asp Arg Phe Ser Gly Ser
        195                 200                 205

Ile Asp Ser Ser Ser Asn Ser Ala Ser Leu Thr Ile Ser Gly Leu Lys
    210                 215                 220

Thr Glu Asp Glu Ala Asp Tyr Tyr Cys Gln Ser Tyr Asp Gly Asn Asn
225                 230                 235                 240

Leu Val Phe Gly Gly Gly Thr Lys Leu Thr Val Leu Gly
                245                 250


<210> SEQ ID NO 40
<211> LENGTH: 247
<212> TYPE: PRT
<213> ORGANISM: Artificial Sequence
<220> FEATURE:
<223> OTHER INFORMATION: scFv protein RGC0162

<400> SEQUENCE: 40

Gln Val Gln Leu Val Gln Ser Gly Ala Glu Val Lys Lys Pro Gly Ala
1               5                   10                  15
```

```
Ser Val Lys Val Ser Cys Lys Ala Ala Gly Phe Arg Phe Ser Gly Asp
            20                  25                  30

Tyr Leu His Trp Leu Arg Gln Val Pro Gly Gln Gly Pro Glu Trp Met
        35                  40                  45

Gly Trp Ile Asn Leu Ser Ser Gly Gly Thr Asn Tyr Gly Glu Lys Phe
    50                  55                  60

Gln Gly Arg Val Thr Met Thr Arg Asp Arg Pro Ser Ser Thr Ala Tyr
65                  70                  75                  80

Met Glu Ile Lys Ser Leu Arg Val Asp Asp Thr Ala Val Tyr Tyr Cys
                85                  90                  95

Ala Arg Glu Ser Pro Val Val Glu Ala Met Asp Val Trp Gly Arg Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Arg
145                 150                 155                 160

Ser Ser Asp Asn Ile Ala Phe Asn Tyr Val Gln Trp Tyr Gln Gln Arg
                165                 170                 175

Pro Gly Ser Ala Pro Thr Thr Leu Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Asn Leu Lys Thr Glu Asp Glu Ala Asp
    210                 215                 220

Tyr Tyr Cys Gln Ser Tyr Asp Gly Ser Asn Tyr Val Phe Gly Thr Gly
225                 230                 235                 240

Thr Lys Leu Thr Val Leu Gly
                245


<210> SEQ ID NO 41
<211> LENGTH: 245
<212> TYPE: PRT
<213> ORGANISM: Artificial Sequence
<220> FEATURE:
<223> OTHER INFORMATION: scFv protein RGC0164

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Asn Tyr Pro Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Thr Gly Asp Phe Phe Asp Tyr Trp Gly Arg Gly Thr
            100                 105                 110

Leu Val Thr Val Ser Ser Gly Gly Gly Gly Ser Gly Gly Gly Gly Ser
        115                 120                 125
```

-continued

```
Gly Gly Gly Gly Ser Ala Gln Pro Val Leu Thr Gln Pro Pro Ser Ala
    130                 135                 140

Ser Gly Ser Pro Gly Gln Ser Val Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Val Ser Lys Arg Pro Ser
            180                 185                 190

Gly Val Pro Asp Arg Phe Ser Ala Ser Lys Ser Gly Asn Thr Ala Ser
        195                 200                 205

Leu Thr Val Ser Gly Leu Gln Ala Glu Asp Glu Ala Tyr Tyr Tyr Cys
    210                 215                 220

Ser Ser Tyr Ala Gly Ser Asn Asn Ser Val Phe Gly Gly Gly Thr Lys
225                 230                 235                 240

Leu Thr Val Leu Gly
                245


<210> SEQ ID NO 42
<211> LENGTH: 246
<212> TYPE: PRT
<213> ORGANISM: Artificial Sequence
<220> FEATURE:
<223> OTHER INFORMATION: scFv protein RGC0169

<400> SEQUENCE: 42

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Asn Ile Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Arg Gln Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Gly Val Tyr Tyr Cys
                85                  90                  95

Ala Arg Asp Pro Ser Leu Ala Pro Val Tyr Gln Phe Asp Tyr Trp Gly
            100                 105                 110

Arg Gly Thr Met Val Thr Val Ser Ser Gly Gly Gly Gly Ser Gly Gly
        115                 120                 125

Gly Gly Ser Gly Gly Gly Gly Ser Ala Leu Asp Val Val Met Thr Gln
    130                 135                 140

Ser Pro Ser Ser Leu Ser Ala Ser Val Gly Glu Arg Val Thr Ile Thr
145                 150                 155                 160

Cys Arg Ala Ser Gln Asn Ile Phe Asn Asn Leu Asn Trp Tyr Gln Gln
                165                 170                 175

Lys Pro Gly Asn Ala Pro Ser Leu Leu Ile Ser Asp Ala Ser Ser Leu
            180                 185                 190

Gln Ser Gly Ala Pro Ser Arg Phe Ser Gly Ser Gly Ser Gly Thr Asp
        195                 200                 205

Tyr Thr Leu Thr Ile Ser Ser Leu Gln Pro Glu Asp Leu Gly Thr Tyr
    210                 215                 220

Tyr Cys Gln Gln Ser Tyr Thr Ile Pro Pro Thr Phe Gly Gln Gly Thr
225                 230                 235                 240
```

-continued

```
Arg Leu Glu Ile Lys Arg
                245


<210> SEQ ID NO 43
<211> LENGTH: 248
<212> TYPE: PRT
<213> ORGANISM: Artificial Sequence
<220> FEATURE:
<223> OTHER INFORMATION: scFv protein RGC0175

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Pro Tyr Asn Tyr Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Thr Gly Ser Tyr His Gly Phe Asp Tyr Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Leu Asn Phe Met Leu Thr Gln Pro
    130                 135                 140

His Ser Val Ser Glu Ser Pro Gly Lys Thr Val Thr Ile Ser Cys Thr
145                 150                 155                 160

Ala Ser Ser Gly Asn Ile Ala Phe Asn Tyr Val Gln Trp Tyr Gln Gln
                165                 170                 175

Arg Pro Gly Ser Ala Pro Thr Ile Val Ile Gln Glu Asp Asn Gln Arg
            180                 185                 190

Pro Ser Gly Val Pro Asp Arg Phe Ser Gly Ser Ile Asp Arg Ser Ser
        195                 200                 205

Asn Ser Ala Ser Leu Thr Ile Ser Gly Leu Lys Ala Glu Asp Glu Gly
    210                 215                 220

Asp Tyr Tyr Cys Gln Ser Tyr Asp Lys Tyr Tyr Arg Ile Phe Gly Gly
225                 230                 235                 240

Gly Thr Lys Leu Thr Val Leu Gly
                245


<210> SEQ ID NO 44
<211> LENGTH: 243
<212> TYPE: PRT
<213> ORGANISM: Artificial Sequence
<220> FEATURE:
<223> OTHER INFORMATION: scFv protein RGD0102

<400> SEQUENCE: 44

Glu Val Gln Leu Val Gln Ser Gly Gly Glu Val Lys Lys Pro Gly Asp
1               5                   10                  15

Ser Val Lys Val Ser Cys Lys Ala Ser Gly Tyr Thr Phe Ser His Tyr
            20                  25                  30

Gly Ile Ser Trp Val Arg Gln Ala Pro Gly Gln Gly Leu Glu Trp Met
        35                  40                  45
```

```
Gly Trp Thr Ser Ala Tyr Ser Gly Ser Thr Asn Tyr Ala Gln Lys Phe
    50                  55                  60

Arg Gly Arg Val Thr Met Thr Thr Asp Thr Ser Thr Gly Thr Ala Tyr
65                  70                  75                  80

Met Glu Leu Arg Ser Leu Arg Pro Asp Asp Thr Ala Val Tyr Tyr Cys
                85                  90                  95

Gly Arg Gly Asp Ser Tyr Gly Ser Ile Pro Ala Asp Tyr Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Ser
    130                 135                 140

Ser Leu Ser Ala Ser Leu Gly Asp Arg Val Thr Ile Thr Cys Arg Ala
145                 150                 155                 160

Ser Gln Asp Ile Thr Asn Asp Leu Ala Trp Tyr Gln Gln Lys Pro Gly
                165                 170                 175

Lys Ala Pro Lys Leu Leu Ile Tyr Gly Ala Ser Thr Leu Gln Tyr Gly
            180                 185                 190

Val Pro Thr Arg Phe Ser Gly Ser Gly Ser Gly Thr Asn Phe Ser Leu
        195                 200                 205

Thr Ile Ser Ser Leu Gln Pro Glu Asp Phe Ala Thr Tyr Phe Cys Gln
    210                 215                 220

Gln Ser His Ser Phe Pro Pro Thr Phe Gly Gly Gly Thr Lys Leu Glu
225                 230                 235                 240

Ile Lys Arg
```

<210> SEQ ID NO 45
<211> LENGTH: 254
<212> TYPE: PRT
<213> ORGANISM: Artificial Sequence
<220> FEATURE:
<223> OTHER INFORMATION: scFv protein RGD0108

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Tyr Asp Phe Trp Arg Gly Tyr Gln Ser Gln Pro Asn
            100                 105                 110

Tyr Met Asp Val Trp Gly Gln Gly Thr Met Val Thr Val Ser Ser Gly
        115                 120                 125

Gly Gly Gly Ser Gly Gly Gly Gly Ser Gly Gly Gly Gly Ser Ala Gln
    130                 135                 140

Ser Val Leu Thr Gln Pro Pro Ser Ala Ser Gly Thr Pro Glu Gln Arg
145                 150                 155                 160
```

-continued

```
Val Thr Ile Ser Cys Ser Gly Ser Ser Ser Asn Ile Gly Tyr Asn Tyr
                165                 170                 175

Val Tyr Trp Phe Gln His Leu Pro Gly Thr Ala Pro Lys Leu Leu Ile
            180                 185                 190

Tyr Thr Asn Asn Leu Arg Pro Ser Gly Val Pro Asp Gln Phe Ser Gly
        195                 200                 205

Ser Lys Ser Gly Thr Ser Ala Ser Leu Ala Ile Ser Gly Leu Arg Ser
    210                 215                 220

Glu Asp Glu Gly Asp Tyr Tyr Cys Ala Ala Trp Asp Asp Ser Leu Ser
225                 230                 235                 240

Gly Arg Val Phe Gly Gly Gly Thr Lys Val Thr Val Leu Gly
                245                 250


<210> SEQ ID NO 46
<211> LENGTH: 248
<212> TYPE: PRT
<213> ORGANISM: Artificial Sequence
<220> FEATURE:
<223> OTHER INFORMATION: scFv protein RGD0112

<400> SEQUENCE: 46

Glu Val Gln Leu Leu Glu Ser Gly Gly Ser Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Trp Ser Asp Ala Phe Asp Leu Trp Gly Arg Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Gly
145                 150                 155                 160

Ser Ser Gly Ser Ile Ala Ser Asn Tyr Val Gln Trp Tyr Gln Gln Arg
                165                 170                 175

Pro Gly Ser Ala Pro Thr Thr Val Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Gly Leu Lys Thr Glu Asp Glu Ala Asp
    210                 215                 220

Tyr Tyr Cys Gln Ser Tyr Asp Ser Ser Asn His Trp Val Phe Gly Gly
225                 230                 235                 240

Gly Thr Lys Leu Thr Val Leu Gly
                245


<210> SEQ ID NO 47
<211> LENGTH: 248
```

<212> TYPE: PRT
<213> ORGANISM: Artificial Sequence
<220> FEATURE:
<223> OTHER INFORMATION: scFv protein RGD0117

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Pro Asp Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Gly
145                 150                 155                 160

Ser Ser Gly Ser Ile Ala Ser Asn Tyr Val Gln Trp Tyr Gln Gln Arg
                165                 170                 175

Pro Gly Ser Ala Pro Thr Thr Val Ile Tyr Glu Tyr Ser Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Gly Leu Lys Thr Glu Asp Glu Ala Asp
    210                 215                 220

Tyr Tyr Cys Gln Ser Phe Asp Thr Asn Asn Gln Gly Val Phe Gly Gly
225                 230                 235                 240

Gly Thr Lys Leu Thr Val Leu Gly
                245
```

<210> SEQ ID NO 48
<211> LENGTH: 245
<212> TYPE: PRT
<213> ORGANISM: Artificial Sequence
<220> FEATURE:
<223> OTHER INFORMATION: scFv protein RGD0119

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Gly Ile Ser Ser Ser Trp Thr Leu Phe Asp Tyr Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Leu Glu Thr Thr Leu Thr Gln Ser
    130                 135                 140

Pro Ala Thr Leu Ser Leu Ser Pro Gly Glu Ser Ala Thr Leu Ser Cys
145                 150                 155                 160

Arg Ala Ser Gln Ser Ile Gly Ser Leu Leu Ala Trp Tyr Gln Gln Arg
                165                 170                 175

Pro Gly Gln Ala Pro Arg Leu Val Ile Ser Asp Ala Ser Asn Arg Ala
            180                 185                 190

Ser Gly Ile Pro Ala Arg Phe Arg Gly Ser Gly Ser Gly Thr Asp Phe
        195                 200                 205

Thr Leu Thr Ile Ser Ser Leu Ala Pro Glu Asp Phe Ala Val Tyr Tyr
    210                 215                 220

Cys His Gln Arg Ser Met Trp Pro Leu Ser Phe Gly Gly Gly Thr Lys
225                 230                 235                 240

Val Glu Ile Lys Arg
                245


<210> SEQ ID NO 49
<211> LENGTH: 244
<212> TYPE: PRT
<213> ORGANISM: Artificial Sequence
<220> FEATURE:
<223> OTHER INFORMATION: scFv protein RGD0121

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His Asn Trp Asn Asp Met Phe Asp Tyr Trp Gly Arg Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asp Ile Gln Leu Thr Gln Ser Pro
    130                 135                 140

Ser Ser Leu Ser Ala Ser Val Gly Asp Lys Val Thr Ile Ala Cys Arg
145                 150                 155                 160

Pro Ser Gln Gly Ile Ser Ser Ala Leu Ala Trp Tyr Gln Gln Lys Pro
                165                 170                 175

Gly Lys Pro Pro Arg Leu Leu Ile Tyr Asp Val Ser Thr Leu Glu Ser
            180                 185                 190
```

```
Gly Val Pro Ser Arg Phe Ser Gly Ser Gly Ser Gly Thr Tyr Phe Thr
        195                 200                 205

Leu Thr Ile Ser Ser Leu Gln Pro Glu Asp Phe Ala Thr Tyr Tyr Cys
    210                 215                 220

Gln Gln Phe Asp Asn Tyr Pro Val Thr Phe Gly Gln Gly Thr Arg Leu
225                 230                 235                 240

Glu Ile Lys Arg


<210> SEQ ID NO 50
<211> LENGTH: 247
<212> TYPE: PRT
<213> ORGANISM: Artificial Sequence
<220> FEATURE:
<223> OTHER INFORMATION: scFv protein RGD0122

<400> SEQUENCE: 50

Glu Val Gln Leu Leu Glu Ser Gly Glu Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Pro Tyr Tyr Asp Ser Ser Gly Tyr Tyr Pro Phe Ser Tyr
            100                 105                 110

Trp Gly Lys Gly Thr Thr Val Thr Val Ser Ser Gly Gly Gly Gly Ser
        115                 120                 125

Gly Gly Gly Gly Ser Gly Gly Gly Gly Ser Ala Gln Ser Val Leu Thr
    130                 135                 140

Gln Pro Pro Ser Val Ser Val Ala Pro Gly Gln Thr Ala Thr Ile Thr
145                 150                 155                 160

Cys Gly Gly Asp Phe Ala Thr Lys Ser Val Asn Trp Tyr Gln Arg Lys
                165                 170                 175

Pro Gly Gln Ala Pro Val Thr Val Ile Tyr Tyr Ser Thr Glu Arg Pro
            180                 185                 190

Pro Ala Ile Pro Glu Arg Phe Ser Gly Ser Asn Thr Gly Ser Thr Ala
        195                 200                 205

Thr Leu Thr Ile Ser Arg Val Glu Ala Gly Asp Glu Ala Asp Tyr Tyr
    210                 215                 220

Cys Gln Val Trp Asp Ser Phe Thr Asp His Arg Leu Phe Gly Gly Gly
225                 230                 235                 240

Thr Lys Leu Thr Val Leu Gly
                245


<210> SEQ ID NO 51
<211> LENGTH: 248
<212> TYPE: PRT
<213> ORGANISM: Artificial Sequence
<220> FEATURE:
<223> OTHER INFORMATION: scFv protein RGD0123

<400> SEQUENCE: 51
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Ser Gly Leu Leu Asp Ala Phe Asp Ile Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Ala Gln Ser Val Leu Thr Gln Pro Pro
    130                 135                 140

Ser Val Ser Gly Ala Pro Gly Gln Arg Val Thr Ile Ser Cys Thr Gly
145                 150                 155                 160

Ser Ser Ser Asn Ile Gly Ala Gly Asn Asp Val Asn Trp Tyr Gln Gln
                165                 170                 175

Val Pro Gly Arg Ala Pro Lys Leu Leu Ile Tyr Gly Thr Thr Tyr Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Phe Cys Gln Ser Asp Asp Ser Ser Leu Ser Gly Ser Val Phe Gly Gly
225                 230                 235                 240

Gly Thr Lys Leu Thr Val Leu Gly
                245
```

<210> SEQ ID NO 52
<211> LENGTH: 254
<212> TYPE: PRT
<213> ORGANISM: Artificial Sequence
<220> FEATURE:
<223> OTHER INFORMATION: scFv protein RGD0124

<400> SEQUENCE: 52

```
Glu Val Gln Leu Leu Glu Ser Gly Gly Gly Leu Val Gln Pro Gly Gly
1               5                   10                  15

Pro Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Thr Glu Phe Tyr Tyr Asp Phe Trp Ser Asn Asp Gly Gly
            100                 105                 110
```

-continued

```
Trp Phe Asp Thr Trp Gly Arg Gly Thr Met Val Thr Val Ser Ser Gly
        115                 120                 125

Gly Gly Gly Ser Gly Gly Gly Gly Ser Gly Gly Gly Gly Ser Ala Gln
    130                 135                 140

Ala Val Leu Thr Gln Pro Ser Ser Thr Ser Gly Ser Pro Gly Gln Arg
145                 150                 155                 160

Val Thr Ile Ser Cys Ser Gly Ser Asn Ser Asn Ile Gly Ser Asn Tyr
                165                 170                 175

Val Tyr Trp Tyr Gln Gln Leu Pro Gly Thr Ala Pro Lys Leu Leu Ile
            180                 185                 190

Tyr Arg Asn Asn Gln Arg Pro Ser Gly Val Pro Asp Arg Phe Ser Gly
        195                 200                 205

Ser Lys Ser Gly Thr Ser Ala Ser Leu Ala Ile Ser Gly Leu Arg Ser
    210                 215                 220

Gly Asp Glu Gly Asp Tyr His Cys Ala Thr Trp Asp Asp Arg Leu Tyr
225                 230                 235                 240

Gly Trp Val Phe Gly Gly Gly Thr Lys Val Thr Val Leu Gly
                245                 250


<210> SEQ ID NO 53
<211> LENGTH: 245
<212> TYPE: PRT
<213> ORGANISM: Artificial Sequence
<220> FEATURE:
<223> OTHER INFORMATION: scFv protein RGD0130

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Ser Ser Ser Trp Thr Leu Phe Asp Tyr Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Leu Glu Thr Thr Leu Thr Gln Ser
    130                 135                 140

Pro Ala Thr Leu Ser Leu Ser Pro Gly Glu Ser Ala Thr Leu Ser Cys
145                 150                 155                 160

Arg Ala Ser Gln Ser Ile Gly Ser Leu Leu Ala Trp Tyr Gln Gln Arg
                165                 170                 175

Pro Gly Gln Ala Pro Arg Leu Val Ile Ser Asp Ala Ser Asn Arg Ala
            180                 185                 190

Ser Gly Ile Pro Ala Arg Phe Arg Gly Ser Gly Ser Gly Thr Asp Phe
        195                 200                 205

Thr Leu Thr Ile Ser Ser Leu Ala Pro Glu Asp Phe Ala Val Tyr Tyr
    210                 215                 220
```

-continued

```
Cys Gln Gln Arg Ser Met Trp Pro Leu Ser Phe Gly Gly Gly Thr Lys
225                 230                 235                 240

Val Glu Ile Lys Arg
                245


<210> SEQ ID NO 54
<211> LENGTH: 249
<212> TYPE: PRT
<213> ORGANISM: Artificial Sequence
<220> FEATURE:
<223> OTHER INFORMATION: scFv protein RGD0135

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Ser Gly Leu Val Asp Ala Phe Asp Met Trp Gly Arg
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Gln Ala Val Leu Thr Gln Pro Ser
    130                 135                 140

Ser Val Ser Gly Ala Pro Gly Gln Arg Val Thr Ile Ser Cys Thr Gly
145                 150                 155                 160

Arg Ser Ser Asn Ile Gly Ala Gly Tyr Asp Val Asn Trp Tyr Gln Gln
                165                 170                 175

Leu Pro Gly Ala Ala Pro Lys Leu Leu Ile Tyr Asp Asn Asn Tyr Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Asp Asp Glu Ala Val Tyr
    210                 215                 220

Tyr Cys Gln Ser Tyr Asp Ser Ser Leu Ser Gly Ser Glu Val Phe Gly
225                 230                 235                 240

Gly Gly Thr Lys Val Thr Val Leu Gly
                245


<210> SEQ ID NO 55
<211> LENGTH: 251
<212> TYPE: PRT
<213> ORGANISM: Artificial Sequence
<220> FEATURE:
<223> OTHER INFORMATION: scFv protein RGD0136

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Asp Ser Leu Gly Leu Trp Phe Gly Leu Gly His Phe Glu Asn
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Ala Leu Asn Phe Met Leu
    130                 135                 140

Thr Gln Pro His Ser Val Ser Glu Ser Pro Gly Lys Thr Val Thr Leu
145                 150                 155                 160

Ser Cys Thr Arg Ser Ser Gly Ser Ile Ser Phe Asp Tyr Val Gln Trp
                165                 170                 175

Tyr Gln Gln Arg Pro Gly Ser Ser Pro Ile Leu Val Ile Phe Glu Asp
            180                 185                 190

Asp Gln Arg Pro Ser Gly Val Pro Asp Arg Phe Ser Gly Ser Ile Asp
        195                 200                 205

Ser Thr Ser Asn Ser Ala Ser Leu Thr Ile Ser Gly Leu Gln Ser Glu
    210                 215                 220

Asp Glu Gly Asp Tyr Tyr Cys Gln Thr Tyr Asp Asp Asn Arg Gln Val
225                 230                 235                 240

Phe Gly Gly Gly Thr Lys Leu Thr Val Leu Gly
                245                 250


<210> SEQ ID NO 56
<211> LENGTH: 248
<212> TYPE: PRT
<213> ORGANISM: Artificial Sequence
<220> FEATURE:
<223> OTHER INFORMATION: scFv protein RGD0141

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Tyr Gly Asp Leu Glu Tyr Phe Gln His Trp Gly
            100                 105                 110

Arg Gly Thr Thr Val Thr Val Ser Ser Gly Gly Gly Gly Ser Gly Gly
        115                 120                 125

Gly Gly Ser Gly Gly Gly Gly Ser Ala Gln Ser Val Leu Thr Gln Pro
```

-continued

```
    130                 135                 140

Ser Ser Ala Ser Gly Asn Pro Gly Gln Arg Val Thr Ile Ser Cys Ser
145                 150                 155                 160

Gly Ser Ser Ser Asn Ile Gly Asp Asn Pro Val Asp Trp Tyr Gln His
                165                 170                 175

Val Pro Gly Arg Ala Pro Lys Leu Leu Ile Phe Arg Asp Asn Gln Arg
            180                 185                 190

Pro Ser Gly Val Pro Asp Arg Phe Ser Gly Thr Lys Ser Gly Thr Ser
        195                 200                 205

Ala Ser Leu Ala Ile Ser Gly Leu Gln Ser Glu Asp Glu Ala Asp Tyr
    210                 215                 220

Tyr Cys Glu Ala Trp Asp Asp Ser Leu Asp Ser Pro Val Phe Gly Gly
225                 230                 235                 240

Gly Thr Lys Leu Thr Val Leu Gly
                245


<210> SEQ ID NO 57
<211> LENGTH: 253
<212> TYPE: PRT
<213> ORGANISM: Artificial Sequence
<220> FEATURE:
<223> OTHER INFORMATION: scFv protein RGD0143

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ala Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Ile Thr Met Tyr Gly Val Leu Arg Pro Gly Asp
            100                 105                 110

Met Asp Val Trp Gly Arg Gly Thr Leu Val Thr Val Ser Ser Gly Gly
        115                 120                 125

Gly Gly Ser Gly Gly Gly Gly Ser Gly Gly Gly Gly Ser Ala Gln Ala
    130                 135                 140

Val Leu Thr Gln Pro Ser Ser Ala Ser Ala Thr Pro Gly Gln Arg Val
145                 150                 155                 160

Thr Ile Ser Cys Ser Gly Ser Ser Ser Asn Ile Gly Ser Asn Ser Val
                165                 170                 175

Asn Trp Tyr Gln His Leu Pro Gly Thr Ala Pro Lys Leu Leu Ile Tyr
            180                 185                 190

Thr Asn Asp Gln Arg Pro Ser Gly Val Pro Asp Arg Phe Ser Gly Ser
        195                 200                 205

Lys Ser Gly Thr Ser Ala Ser Leu Ala Ile Ser Gly Leu Gln Ser Glu
    210                 215                 220

Asp Glu Ala Asp Tyr Tyr Cys Ala Ala Trp Asp Asp Thr Leu Thr Gly
225                 230                 235                 240

Pro Val Phe Gly Gly Gly Thr Lys Leu Thr Val Leu Gly
```

```
                245                 250


<210> SEQ ID NO 58
<211> LENGTH: 242
<212> TYPE: PRT
<213> ORGANISM: Artificial Sequence
<220> FEATURE:
<223> OTHER INFORMATION: scFv protein RGD0145

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Arg Tyr Phe Asp Asn Trp Gly Gln Gly Thr Met Val
            100                 105                 110

Thr Val Ser Ser Gly Gly Gly Gly Ser Gly Gly Gly Gly Ser Gly Gly
        115                 120                 125

Gly Gly Ser Ala Leu Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Thr Tyr Tyr Ala Ser Trp Tyr Gln Gln Lys Pro Gly Gln Ala Pro
                165                 170                 175

Val Leu Val Phe Tyr Gly Lys Lys Asn Arg Pro Ser Gly Ile Pro Asp
            180                 185                 190

Arg Phe Ser Gly Ser Ser Ser Gly Asn Thr Ser Ser Leu Thr Ile Thr
        195                 200                 205

Gly Ala Gln Ala Glu Asp Asp Ala Asp Tyr Tyr Cys Asn Ser Arg Asp
    210                 215                 220

Ser Ser Gly Asn His Leu Val Phe Gly Gly Gly Thr Lys Leu Thr Val
225                 230                 235                 240

Leu Gly


<210> SEQ ID NO 59
<211> LENGTH: 251
<212> TYPE: PRT
<213> ORGANISM: Artificial Sequence
<220> FEATURE:
<223> OTHER INFORMATION: scFv protein RGD0153

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Thr Tyr Tyr Ala Asp Ser Val
```

-continued

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Arg Gly Ser Thr Arg Trp Glu Asp Phe Tyr Tyr Phe Asp
            100                 105                 110

Tyr Trp Gly Lys Gly Thr Met Val Thr Val Ser Ser Gly Gly Gly Gly
        115                 120                 125

Ser Gly Gly Gly Gly Ser Gly Gly Gly Gly Ser Ala Gln Thr Val Val
    130                 135                 140

Ile Gln Glu Pro Ser Phe Ser Val Ser Pro Gly Gly Thr Val Thr Leu
145                 150                 155                 160

Thr Cys Gly Leu Ser Ser Gly Ser Val Ser Thr Thr Tyr Tyr Pro Ser
                165                 170                 175

Trp Tyr Gln Gln Thr Pro Gly Gln Ala Pro Arg Thr Leu Ile Tyr Asn
            180                 185                 190

Thr Asn Thr Arg Ser Ser Gly Val Pro Asp Arg Phe Ser Gly Ser Ile
        195                 200                 205

Leu Gly Asn Lys Ala Ala Leu Thr Ile Thr Gly Ala Gln Ala Asp Asp
    210                 215                 220

Glu Ser Asp Tyr Tyr Cys Val Leu Tyr Leu Gly Ser Gly Ile Trp Val
225                 230                 235                 240

Phe Gly Gly Gly Thr Lys Leu Thr Val Leu Gly
                245                 250


<210> SEQ ID NO 60
<211> LENGTH: 247
<212> TYPE: PRT
<213> ORGANISM: Artificial Sequence
<220> FEATURE:
<223> OTHER INFORMATION: scFv protein RGD0154

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Pro Tyr Tyr Asp Ser Ser Gly Tyr Tyr Pro Phe Ser Tyr
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Gly Ser Ala Gln Ser Val Val Thr
    130                 135                 140

Gln Pro Pro Ser Val Ser Val Ala Pro Gly Lys Thr Ala Thr Ile Thr
145                 150                 155                 160

Cys Gly Gly Asp Phe Ala Thr Lys Ser Val Asn Trp Tyr Gln Arg Lys
```

-continued

```
                165                 170                 175

Pro Gly Gln Ala Pro Val Thr Val Ile Tyr Tyr Asn Thr Glu Arg Pro
            180                 185                 190

Pro Ala Ile Pro Glu Arg Phe Ser Gly Ser Asn Thr Gly Ser Thr Ala
        195                 200                 205

Thr Leu Thr Ile Ser Arg Val Glu Ala Gly Asp Glu Ala Asp Tyr Tyr
    210                 215                 220

Cys Gln Val Trp Asp Ser Phe Thr Asp His Arg Leu Phe Gly Gly Gly
225                 230                 235                 240

Thr Lys Val Thr Val Leu Gly
                245


<210> SEQ ID NO 61
<211> LENGTH: 251
<212> TYPE: PRT
<213> ORGANISM: Artificial Sequence
<220> FEATURE:
<223> OTHER INFORMATION: scFv protein RGD0169

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Arg Arg Val Pro Phe Gly Ser Gly Ser Tyr Leu
            100                 105                 110

Asn Pro Phe Asp Trp Gly Gln Gly Thr Met Val Thr Val Ser Ser Gly
        115                 120                 125

Gly Gly Gly Ser Gly Gly Gly Gly Ser Gly Gly Gly Gly Ser Ala Leu
    130                 135                 140

Ser Tyr Glu Leu Thr Gln Pro Pro Ser Val Ser Val Ser Pro Gly Gln
145                 150                 155                 160

Thr Ala Ser Ile Thr Cys Thr Gly Asp Lys Leu Ala Glu Lys Tyr Val
                165                 170                 175

Ser Trp Tyr Gln Gln Lys Thr Gly Arg Ser Pro Val Leu Val Ile Tyr
            180                 185                 190

Gln Asp Asp Arg Arg Pro Ser Glu Ile Pro Glu Arg Phe Ser Gly Ser
        195                 200                 205

Asn Ser Gly Asn Thr Ala Thr Leu Thr Val Ser Gly Ala Gln Ser Met
    210                 215                 220

Asp Glu Ala Asp Tyr Tyr Cys Gln Val Trp Asp Ser Asn Thr Val Ile
225                 230                 235                 240

Phe Gly Gly Gly Thr Lys Val Thr Val Leu Gly
                245                 250


<210> SEQ ID NO 62
<211> LENGTH: 249
<212> TYPE: PRT
```

-continued

<213> ORGANISM: Artificial Sequence
<220> FEATURE:
<223> OTHER INFORMATION: scFv protein RGD0170

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gln Gln Pro Phe Thr Asp Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Gly
145                 150                 155                 160

Ser Ser Gly Asn Ile Ala Asn Asn Tyr Val Gln Trp Phe Gln Gln Arg
                165                 170                 175

Pro Gly Ser Ala Pro Thr Thr Val Ile Tyr Glu Asp Asn Gln Arg Pro
            180                 185                 190

Ser Gly Val Pro Asp Arg Phe Ser Gly Ser Ile Asp Ser Ser Ser Asn
        195                 200                 205

Ser Ala Ser Leu Thr Ile Ser Gly Leu Lys Thr Glu Asp Glu Ala Asp
    210                 215                 220

Tyr Tyr Cys Gln Ser Tyr Asp Ser Ser Asn Leu Tyr Val Val Phe Gly
225                 230                 235                 240

Gly Gly Thr Lys Val Thr Val Leu Gly
                245
```

<210> SEQ ID NO 63
<211> LENGTH: 248
<212> TYPE: PRT
<213> ORGANISM: Artificial Sequence
<220> FEATURE:
<223> OTHER INFORMATION: scFv protein RGD0180

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Gly Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Leu Gly Asn Trp Asn Asp Val Phe Asp Tyr Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Arg
145                 150                 155                 160

Ser Ser Gly Ser Ile Ala Asn Asn Tyr Val Gln Trp Tyr Gln Gln Arg
                165                 170                 175

Pro Gly Ser Ala Pro Thr Thr Val Ile Phe Glu Asp Asp Gln Arg Pro
            180                 185                 190

Ser Gly Val Pro Asp Arg Phe Ser Gly Ser Ile Asp Arg Ser Ser Asn
        195                 200                 205

Ser Ala Ser Leu Thr Ile Ser Gly Leu Lys Thr Asp Asp Glu Ala Asp
    210                 215                 220

Tyr Tyr Cys Gln Ser Asn Asp Gly Thr Asn Pro Trp Val Phe Gly Gly
225                 230                 235                 240

Gly Thr Lys Leu Thr Val Leu Gly
                245


<210> SEQ ID NO 64
<211> LENGTH: 248
<212> TYPE: PRT
<213> ORGANISM: Artificial Sequence
<220> FEATURE:
<223> OTHER INFORMATION: scFv protein RGD0182

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Trp Ser Asp Ala Phe Asp Leu Trp Gly Lys Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Leu Asn Phe Met Leu Thr Gln Pro His
    130                 135                 140

Ser Val Ser Glu Ser Pro Gly Lys Thr Val Thr Ile Ser Cys Thr Gly
145                 150                 155                 160

Ser Ser Gly Ser Ile Ala Asn Asn Tyr Val Gln Trp Tyr Gln Gln Arg
                165                 170                 175

Pro Gly Ser Ala Pro Thr Thr Val Ile Tyr Glu Asp Asn Gln Arg Pro
            180                 185                 190
```

-continued

```
Ser Gly Val Pro Asp Arg Phe Ser Ala Ser Ile Asp Arg Ser Ser Asn
        195                 200                 205

Ser Ala Ser Leu Thr Ile Ser Gly Leu Met Thr Glu Asp Glu Ala Asp
    210                 215                 220

Tyr Tyr Cys Gln Ser Tyr Asp Ser Asn Asn His Trp Val Phe Gly Gly
225                 230                 235                 240

Gly Thr Lys Leu Thr Val Leu Gly
                245


<210> SEQ ID NO 65
<211> LENGTH: 245
<212> TYPE: PRT
<213> ORGANISM: Artificial Sequence
<220> FEATURE:
<223> OTHER INFORMATION: scFv protein RGD0183

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Asp Ser Ser Asn Trp Phe Phe Asp Tyr Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Ala Leu Asp Val Val Met Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Phe Leu Ala Trp Tyr Gln Gln Lys
                165                 170                 175

Pro Gly Gln Ala Pro Arg Leu Leu Met Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Arg Ser Asn Trp Pro Ile Thr Phe Gly Gln Gly Thr Arg
225                 230                 235                 240

Leu Glu Ile Lys Arg
                245


<210> SEQ ID NO 66
<211> LENGTH: 242
<212> TYPE: PRT
<213> ORGANISM: Artificial Sequence
<220> FEATURE:
<223> OTHER INFORMATION: scFv protein RGD0193

<400> SEQUENCE: 66
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Tyr Ala Leu Asp Tyr Trp Gly Arg Gly Thr Leu Val
            100                 105                 110

Thr Val Ser Ser Gly Gly Gly Gly Ser Gly Gly Gly Gly Ser Gly Gly
        115                 120                 125

Gly Gly Ser Ala Leu Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Asn Tyr Tyr Pro Ser Trp Tyr Gln Gln Ser Pro Gly Gln Ala Pro
                165                 170                 175

Val Leu Val Ile Tyr Gly Lys Asn Lys Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Arg Asp
    210                 215                 220

Ser Ser Gly Asn His Leu Leu Phe Gly Gly Gly Thr Lys Leu Thr Val
225                 230                 235                 240

Leu Gly


<210> SEQ ID NO 67
<211> LENGTH: 247
<212> TYPE: PRT
<213> ORGANISM: Artificial Sequence
<220> FEATURE:
<223> OTHER INFORMATION: scFv protein RGD0195

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Pro Tyr Tyr Asp Ser Ser Gly Tyr Tyr Pro Phe Ser Tyr
            100                 105                 110
```

-continued

```
Trp Gly Gln Gly Thr Met Val Thr Val Ser Ser Gly Gly Gly Gly Ser
        115                 120                 125

Gly Gly Gly Gly Ser Gly Gly Gly Gly Ser Ala Gln Ser Val Leu Thr
    130                 135                 140

Gln Pro Pro Ser Val Ser Val Ala Pro Gly Lys Thr Ala Thr Ile Thr
145                 150                 155                 160

Cys Gly Gly Asp Phe Ala Thr Lys Asn Val Asn Trp Tyr Gln Arg Lys
                165                 170                 175

Pro Gly Gln Ala Pro Val Thr Val Ile Tyr Tyr Asn Thr Glu Arg Pro
            180                 185                 190

Ser Ala Ile Pro Glu Arg Phe Ser Gly Ser Asn Thr Gly Ser Thr Ala
        195                 200                 205

Thr Leu Thr Ile Ser Arg Val Glu Ala Gly Asp Glu Ala Asp Tyr Tyr
    210                 215                 220

Cys Gln Val Trp Asp Ser Phe Thr Asp His Arg Leu Phe Gly Gly Gly
225                 230                 235                 240

Thr Lys Leu Thr Val Leu Gly
                245


<210> SEQ ID NO 68
<211> LENGTH: 762
<212> TYPE: DNA
<213> ORGANISM: Artificial Sequence
<220> FEATURE:
<221> NAME/KEY: CDS
<222> LOCATION: (1)..(762)
<223> OTHER INFORMATION: Polynucleotide encoding RGB0101 scFv protein

<400> SEQUENCE: 68

gag gtg cag ctg gtg gag act ggg gga ggc gtg gtc cag cct ggg agg       48
Glu Val Gln Leu Val Glu Thr Gly Gly Gly Val Val Gln Pro Gly Arg
1               5                   10                  15

tcc cag aga ctc tcc tgt gca gcc tct gga ttc acc ttt agc gac tat       96
Ser Gln Arg Leu Ser Cys Ala Ala Ser Gly Phe Thr Phe Ser Asp Tyr
            20                  25                  30

gct atg cac tgg gtc cgc cag gct cca ggg aag ggg ctg gag tgg gtc      144
Ala Met His Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gta tat tac tgt      288
Leu Gln Met Asn Ser Leu Arg Ala Glu Asp Thr Ala Val Tyr Tyr Cys
                85                  90                  95

gcg aaa gga atc agg tat tac tat gat agt agt ggt tat tac gat ggg      336
Ala Lys Gly Ile Arg Tyr Tyr Tyr Asp Ser Ser Gly Tyr Tyr Asp Gly
            100                 105                 110

tac tac tac tac ggt atg gac gtc tgg ggc caa ggg acc acg gtc acc      384
Tyr Tyr Tyr Tyr Gly Met Asp Val Trp Gly Gln Gly Thr Thr Val Thr
        115                 120                 125

gtc tcc tca ggt gga ggc ggt tca ggc gga ggt ggc agc ggc ggt ggc      432
Val Ser Ser Gly Gly Gly Gly Ser Gly Gly Gly Gly Ser Gly Gly Gly
    130                 135                 140

gga tcg tct gag ctg act cag gac cct gct gtg tct gtg gcc ttg gga      480
Gly Ser Ser Glu Leu Thr Gln Asp Pro Ala Val Ser Val Ala Leu Gly
145                 150                 155                 160
```

-continued

```
cag aca gtc agg atc act tgc caa gga gac agt ctc aga agc tat tac      528
Gln Thr Val Arg Ile Thr Cys Gln Gly Asp Ser Leu Arg Ser Tyr Tyr
                165                 170                 175

aca aac tgg ttc cag cag agg cca gga cag gcc cct cta ctt gtc gtc      576
Thr Asn Trp Phe Gln Gln Arg Pro Gly Gln Ala Pro Leu Leu Val Val
            180                 185                 190

tat gct aaa aat aag cgg ccc tca ggg atc cca gac cga ttc tct ggc      624
Tyr Ala Lys Asn Lys Arg Pro Ser Gly Ile Pro Asp Arg Phe Ser Gly
        195                 200                 205

tcc agc tca gga aac aca gct tcc ttg acc atc act ggg gct cag gcg      672
Ser Ser Ser Gly Asn Thr Ala Ser Leu Thr Ile Thr Gly Ala Gln Ala
    210                 215                 220

gaa gat gag gct gac tat tac tgt cat tcc cgg gac agc agt ggt aac      720
Glu Asp Glu Ala Asp Tyr Tyr Cys His Ser Arg Asp Ser Ser Gly Asn
225                 230                 235                 240

cat gtg ctt ttc ggc gga ggg acc aag ctg acc gtc cta ggt              762
His Val Leu Phe Gly Gly Gly Thr Lys Leu Thr Val Leu Gly
                245                 250


<210> SEQ ID NO 69
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGB0102 scFv protein

<400> SEQUENCE: 69

cag gtg cag ctg gta cag tct ggg gct gag gtg aag aag cct ggg gcc       48
Gln Val Gln Leu Val Gln Ser Gly Ala Glu Val Lys Lys Pro Gly Ala
1               5                   10                  15

tca gtg aag gtc tcc tgc aag gct tct gga tac acc ttc acc gac tac       96
Ser Val Lys Val Ser Cys Lys Ala Ser Gly Tyr Thr Phe Thr Asp Tyr
            20                  25                  30

tat ata cac tgg gtg cga cag gcc cct gga caa ggg ctt gag tgg atg      144
Tyr Ile His Trp Val Arg Gln Ala Pro Gly Gln Gly Leu Glu Trp Met
        35                  40                  45

gga tgg atc aac cct aaa agt ggt gac aca aac tat gca cag aag ttt      192
Gly Trp Ile Asn Pro Lys Ser Gly Asp Thr Asn Tyr Ala Gln Lys Phe
    50                  55                  60

cag ggc agg gtc acc atg gcc agg gac acg tcc atg agc acg gcc tcc      240
Gln Gly Arg Val Thr Met Ala Arg Asp Thr Ser Met Ser Thr Ala Ser
65                  70                  75                  80

gtg gaa ctg aga agg ttg aca tct gac gac acg gcc gtg tat tac tgt      288
Val Glu Leu Arg Arg Leu Thr Ser Asp Asp Thr Ala Val Tyr Tyr Cys
                85                  90                  95

gcg agg aac tcg ttc gac ttt ggg agt ggc tat ggg ctc ttc tac cag      336
Ala Arg Asn Ser Phe Asp Phe Gly Ser Gly Tyr Gly Leu Phe Tyr Gln
            100                 105                 110

tac att atg gac gtc tgg ggc caa gga acc ctg gtc acc gtc tcc tca      384
Tyr Ile Met Asp Val Trp Gly Gln Gly Thr Leu Val Thr Val Ser Ser
        115                 120                 125

ggt gga ggc ggt tca ggc gga ggt ggc agc ggc ggt ggc gga tcg gac      432
Gly Gly Gly Gly Ser Gly Gly Gly Gly Ser Gly Gly Gly Gly Ser Asp
    130                 135                 140

atc cag atg acc cag tct cca tcc ttc ctg tct gca tct gta gga gac      480
Ile Gln Met Thr Gln Ser Pro Ser Phe Leu Ser Ala Ser Val Gly Asp
145                 150                 155                 160

aga gtc acc atc act tgc cgg gcc agt cag ggc att aac aat tat tta      528
Arg Val Thr Ile Thr Cys Arg Ala Ser Gln Gly Ile Asn Asn Tyr Leu
                165                 170                 175
```

```
gcc tgg tat cag caa aaa cca ggg aga gcc cct aag ctc ctg atc tac      576
Ala Trp Tyr Gln Gln Lys Pro Gly Arg Ala Pro Lys Leu Leu Ile Tyr
            180                 185                 190

gct gca tcc agt tta caa agt ggg gtc cca tca agg ttc agc ggc agt      624
Ala Ala Ser Ser Leu Gln Ser Gly Val Pro Ser Arg Phe Ser Gly Ser
        195                 200                 205

gga tct ggc aca gat ttc act ctc acc atc agc agc ctg cag cct gaa      672
Gly Ser Gly Thr Asp Phe Thr Leu Thr Ile Ser Ser Leu Gln Pro Glu
    210                 215                 220

gat ttt gca act tat tac tgt ctc caa gat tcc gat tat ccc ctc act      720
Asp Phe Ala Thr Tyr Tyr Cys Leu Gln Asp Ser Asp Tyr Pro Leu Thr
225                 230                 235                 240

ttc ggc gga ggg acc aag ctg gag atc aaa cgt                          753
Phe Gly Gly Gly Thr Lys Leu Glu Ile Lys Arg
                245                 250


<210> SEQ ID NO 70
<211> LENGTH: 765
<212> TYPE: DNA
<213> ORGANISM: Artificial Sequence
<220> FEATURE:
<221> NAME/KEY: CDS
<222> LOCATION: (1)..(765)
<223> OTHER INFORMATION: Polynucleotide encoding RGB0103 scFv protein

<400> SEQUENCE: 70

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga cat tat cag agt ggt ggc tat gtc tac att acc ttc tat tac      336
Ala Arg His Tyr Gln Ser Gly Gly Tyr Val Tyr Ile Thr Phe Tyr Tyr
            100                 105                 110

cct atg gac gtc tgg ggc cag ggc acc ctg gtc acc gtc tcg agt gga      384
Pro Met Asp Val Trp Gly Gln Gly Thr Leu Val Thr Val Ser Ser Gly
        115                 120                 125

ggc ggc ggt tca ggc gga ggt ggc tct ggc ggt ggc gga agt gca ctt      432
Gly Gly Gly Ser Gly Gly Gly Gly Ser Gly Gly Gly Gly Ser Ala Leu
    130                 135                 140

aat ttt atg ctg act cag ccc cac tct gtg tcg gag tct ccg ggt aag      480
Asn Phe Met Leu Thr Gln Pro His Ser Val Ser Glu Ser Pro Gly Lys
145                 150                 155                 160

aca gta act ctc tcc tgc acc cgc tcc agt ggc agc att tca ttc gac      528
Thr Val Thr Leu Ser Cys Thr Arg Ser Ser Gly Ser Ile Ser Phe Asp
                165                 170                 175

tat gtg cag tgg tat caa cag cgg ccg ggc agc tcc ccc att ctt gtg      576
Tyr Val Gln Trp Tyr Gln Gln Arg Pro Gly Ser Ser Pro Ile Leu Val
```

```
            180                 185                 190

atc ttt gaa gat gac caa aga ccc tct ggg gtc cct gat cga ttc tct      624
Ile Phe Glu Asp Asp Gln Arg Pro Ser Gly Val Pro Asp Arg Phe Ser
        195                 200                 205

ggc tcc atc gac agt acc tcc aac tct gcc tcc ctc acc atc tct ggc      672
Gly Ser Ile Asp Ser Thr Ser Asn Ser Ala Ser Leu Thr Ile Ser Gly
    210                 215                 220

ctg cag agt gag gac gag ggt gac tac tat tgt cag act tat gat gac      720
Leu Gln Ser Glu Asp Glu Gly Asp Tyr Tyr Cys Gln Thr Tyr Asp Asp
225                 230                 235                 240

aac cgt cag gtg ttc ggc ggg ggg acc aag ctg acc gtc cta ggt          765
Asn Arg Gln Val Phe Gly Gly Gly Thr Lys Leu Thr Val Leu Gly
                245                 250                 255


<210> SEQ ID NO 71
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0104 scFv protein

<400> SEQUENCE: 71

gag gtg cag ctg ttg gag tct ggg gga gac ttg gta cag cct ggg ggg       48
Glu Val Gln Leu Leu Glu Ser Gly Gly Asp Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga gag gac aga atg aga act cag ctt gac tcc tgg ggc cgg ggc      336
Ala Arg Glu Asp Arg Met Arg Thr Gln Leu Asp Ser Trp Gly Arg Gly
            100                 105                 110

acc ctg gtc acc gtc tcg agt gga ggc ggc ggt tca ggc gga ggt ggc      384
Thr Leu Val Thr Val Ser Ser Gly Gly Gly Gly Ser Gly Gly Gly Gly
        115                 120                 125

tct ggc ggt ggc gga agt gca cag tct gtg ttg acg cag ccg ccc tca      432
Ser Gly Gly Gly Gly Ser Ala Gln Ser Val Leu Thr Gln Pro Pro Ser
    130                 135                 140

gtg tct ggg gcc cca ggg cag agg gtc acc atc tcc tgc act ggg agc      480
Val Ser Gly Ala Pro Gly Gln Arg Val Thr Ile Ser Cys Thr Gly Ser
145                 150                 155                 160

agc tcc aac atc ggg gcg gat tat gat gta cac tgg tac caa cac cat      528
Ser Ser Asn Ile Gly Ala Asp Tyr Asp Val His Trp Tyr Gln His His
                165                 170                 175

cca gga aca gcc ccc aga ctc ctc ata tat gat aac acc aat cgg ccc      576
Pro Gly Thr Ala Pro Arg Leu Leu Ile Tyr Asp Asn Thr Asn Arg Pro
            180                 185                 190

tca ggg gtc cct gac cga ttc tct ggc tcc aag tct ggc acc tca gcc      624
```

-continued

```
Ser Gly Val Pro Asp Arg Phe Ser Gly Ser Lys Ser Gly Thr Ser Ala
        195                 200                 205

tcc ctg acc atc act ggg ctc cag gct gag gat gag gct gat tat tac      672
Ser Leu Thr Ile Thr Gly Leu Gln Ala Glu Asp Glu Ala Asp Tyr Tyr
    210                 215                 220

tgc cag tcc tat gac gcc agt ctg agt ggt tat gtg gtc ttc ggc gga      720
Cys Gln Ser Tyr Asp Ala Ser Leu Ser Gly Tyr Val Val Phe Gly Gly
225                 230                 235                 240

ggg acc aag ctg acc gtc cta ggt                                      744
Gly Thr Lys Leu Thr Val Leu Gly
                245


<210> SEQ ID NO 72
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0106 scFv protein

<400> SEQUENCE: 72

aag gtg cag ctg gtg cag tct ggg gct gag gtg aag aag cct ggg tcg       48
Lys Val Gln Leu Val Gln Ser Gly Ala Glu Val Lys Lys Pro Gly Ser
1               5                   10                  15

tcg gtg agg gtc tcc tgc aag gtc tct gga gac acc tcc acc tcc tat       96
Ser Val Arg Val Ser Cys Lys Val Ser Gly Asp Thr Ser Thr Ser Tyr
            20                  25                  30

att atc aac tgg gtg cga cag gcc cct gga caa ggg ctt gag tgg atg      144
Ile Ile Asn Trp Val Arg Gln Ala Pro Gly Gln Gly Leu Glu Trp Met
        35                  40                  45

gga gtg atc atc cct atg ttt ggt aca aca aat tac gca cag aag ttc      192
Gly Val Ile Ile Pro Met Phe Gly Thr Thr Asn Tyr Ala Gln Lys Phe
    50                  55                  60

gaa gac aga gtc acg att agc gcg gac gga tcc acg agc aca gtg tac      240
Glu Asp Arg Val Thr Ile Ser Ala Asp Gly Ser Thr Ser Thr Val Tyr
65                  70                  75                  80

atg gaa ttg agt ggc ctg aaa tcc gag gac acg gcc gta tat tac tgt      288
Met Glu Leu Ser Gly Leu Lys Ser Glu Asp Thr Ala Val Tyr Tyr Cys
                85                  90                  95

gcg gga tcc gat ttt tgg agt ggt tat gat ggc gag ccc gac gtc ttt      336
Ala Gly Ser Asp Phe Trp Ser Gly Tyr Asp Gly Glu Pro Asp Val Phe
            100                 105                 110

gat ctc tgg ggc caa gga acc ctg gtc acc gtc tcc tca ggc gga ggc      384
Asp Leu Trp Gly Gln Gly Thr Leu Val Thr Val Ser Ser Gly Gly Gly
        115                 120                 125

ggt tca ggc gga ggt ggc agc ggc ggt ggt gga tcg tct gag ctg act      432
Gly Ser Gly Gly Gly Gly Ser Gly Gly Gly Gly Ser Ser Glu Leu Thr
    130                 135                 140

cag gac cct gct gtg tct gtg gcc ttg gga cag aca gtc agg atc act      480
Gln Asp Pro Ala Val Ser Val Ala Leu Gly Gln Thr Val Arg Ile Thr
145                 150                 155                 160

tgc caa gga gac agt ctc aga agc tat tac aca aac tgg ttc cag cag      528
Cys Gln Gly Asp Ser Leu Arg Ser Tyr Tyr Thr Asn Trp Phe Gln Gln
                165                 170                 175

aag cca gga cag gcc cct cta ctt gtc gtc tat gct aaa aat aag cgg      576
Lys Pro Gly Gln Ala Pro Leu Leu Val Val Tyr Ala Lys Asn Lys Arg
            180                 185                 190

ccc tca ggg atc cca gac cga ttc tct ggc tcc agc tca gga aac aca      624
Pro Ser Gly Ile Pro Asp Arg Phe Ser Gly Ser Ser Ser Gly Asn Thr
        195                 200                 205
```

-continued

```
gct tcc ttg acc atc act ggg gct cag gcg gaa gat gag gct gac tat      672
Ala Ser Leu Thr Ile Thr Gly Ala Gln Ala Glu Asp Glu Ala Asp Tyr
    210                 215                 220

tac tgt cat tcc cgg gac agc agt ggt aac cat gtg ctt ttc ggc gga      720
Tyr Cys His Ser Arg Asp Ser Ser Gly Asn His Val Leu Phe Gly Gly
225                 230                 235                 240

ggg acc aag ctg acc gtc cta ggt                                      744
Gly Thr Lys Leu Thr Val Leu Gly
                245


<210> SEQ ID NO 73
<211> LENGTH: 729
<212> TYPE: DNA
<213> ORGANISM: Artificial Sequence
<220> FEATURE:
<221> NAME/KEY: CDS
<222> LOCATION: (1)..(729)
<223> OTHER INFORMATION: Polynucleotide encoding RGB0110 scFv protein

<400> SEQUENCE: 73

gag gtg cag ctg gtg cag tct ggg gga ggc gtg gtc cag cct ggg agg       48
Glu Val Gln Leu Val Gln Ser Gly Gly Gly Val Val Gln Pro Gly Arg
1               5                   10                  15

tcc ctg aga ctc tcc tgc gca gcc tct gga ttc acc ttc agt agc tat       96
Ser Leu Arg Leu Ser Cys Ala Ala Ser Gly Phe Thr Phe Ser Ser Tyr
            20                  25                  30

ggc atg cac tgg gtc cgc cag gct cca ggc aag ggg ctg gag tgg gtg      144
Gly Met His Trp Val Arg Gln Ala Pro Gly Lys Gly Leu Glu Trp Val
        35                  40                  45

gca gtt ata tca tat gat gga agt aat aaa tac tat gca gac tcc gtg      192
Ala Val Ile Ser Tyr Asp Gly Ser Asn Lys Tyr Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95

gcg aaa gcc tcc acg tat tac gat ttt tgg ttt gat atc tgg ggc cag      336
Ala Lys Ala Ser Thr Tyr Tyr Asp Phe Trp Phe Asp Ile Trp Gly Gln
            100                 105                 110

ggg aca atg gtc act gtc tct tca ggt gga ggc ggt tca ggc gga ggt      384
Gly Thr Met Val Thr Val Ser Ser Gly Gly Gly Gly Ser Gly Gly Gly
        115                 120                 125

ggc agc ggc ggt ggc gga tcg gac atc cag atg acc cag tct cca tcc      432
Gly Ser Gly Gly Gly Gly Ser Asp Ile Gln Met Thr Gln Ser Pro Ser
    130                 135                 140

ttc ctg tct gca tct gta gga gac aga gtc acc atc act tgc cgg gcc      480
Phe Leu Ser Ala Ser Val Gly Asp Arg Val Thr Ile Thr Cys Arg Ala
145                 150                 155                 160

agt cag ggc att aac aat tat tta gcc tgg tat cag caa aaa cca ggg      528
Ser Gln Gly Ile Asn Asn Tyr Leu Ala Trp Tyr Gln Gln Lys Pro Gly
                165                 170                 175

aga gcc cct aag ctc ctg atc tac gct gca tcc agt tta caa agt ggg      576
Arg Ala Pro Lys Leu Leu Ile Tyr Ala Ala Ser Ser Leu Gln Ser Gly
            180                 185                 190

gtc cca tca agg ttc agc ggc agt gga tct ggc aca gat ttc act ctc      624
Val Pro Ser Arg Phe Ser Gly Ser Gly Ser Gly Thr Asp Phe Thr Leu
        195                 200                 205

acc atc agc agc ctg cag cct gaa gat ttt gca act tat tac tgt ctc      672
Thr Ile Ser Ser Leu Gln Pro Glu Asp Phe Ala Thr Tyr Tyr Cys Leu
    210                 215                 220
```

```
caa gat tcc gat tat ccc ctc act ttc ggc gga ggg acc aag ctg gag      720
Gln Asp Ser Asp Tyr Pro Leu Thr Phe Gly Gly Gly Thr Lys Leu Glu
225                 230                 235                 240

atc aaa cgt                                                          729
Ile Lys Arg


<210> SEQ ID NO 74
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0113 scFv protein

<400> SEQUENCE: 74

ggg gtc cag ctg gtg cag tct ggg gct gag ggg aag aag cct ggg gcc       48
Gly Val Gln Leu Val Gln Ser Gly Ala Glu Gly Lys Lys Pro Gly Ala
1               5                   10                  15

tca gtg aag gtc tcc tgc aag gct tct ggg ggc aac atc agc agg ttt       96
Ser Val Lys Val Ser Cys Lys Ala Ser Gly Gly Asn Ile Ser Arg Phe
            20                  25                  30

ggt atc aac tgg gtg cga cag gcc cct gga caa ggg ctt gag tgg atg      144
Gly Ile Asn Trp Val Arg Gln Ala Pro Gly Gln Gly Leu Glu Trp Met
        35                  40                  45

gga gtg atc atc cct atg ttt ggt aca aca aat tac gca cag aag ttc      192
Gly Val Ile Ile Pro Met Phe Gly Thr Thr Asn Tyr Ala Gln Lys Phe
    50                  55                  60

gaa gac aga gtc acg att agc gcg gac gga tcc acg agc aca gtg tac      240
Glu Asp Arg Val Thr Ile Ser Ala Asp Gly Ser Thr Ser Thr Val Tyr
65                  70                  75                  80

atg gaa ttg agt ggc ctg aaa tcc gag gac acg gcc gta tat tac tgt      288
Met Glu Leu Ser Gly Leu Lys Ser Glu Asp Thr Ala Val Tyr Tyr Cys
                85                  90                  95

gcg gga tcc gat ttt tgg agt ggt tat gat ggc gag ccc gac gtc ttt      336
Ala Gly Ser Asp Phe Trp Ser Gly Tyr Asp Gly Glu Pro Asp Val Phe
            100                 105                 110

gat ctc tgg ggc cgg gga acc ctg gtc acc gtc tct tca ggt gga ggc      384
Asp Leu Trp Gly Arg Gly Thr Leu Val Thr Val Ser Ser Gly Gly Gly
        115                 120                 125

ggt tca ggc gga ggt ggc agc ggc ggt ggc gga tcg tct gag ctg act      432
Gly Ser Gly Gly Gly Gly Ser Gly Gly Gly Gly Ser Ser Glu Leu Thr
    130                 135                 140

cag gac cct gct gtg tct gtg gcc ttg gga cag aca gtc agg atc act      480
Gln Asp Pro Ala Val Ser Val Ala Leu Gly Gln Thr Val Arg Ile Thr
145                 150                 155                 160

tgc caa gga gac agt ctc aga agc tat tac aca aac tgg ttc cag cag      528
Cys Gln Gly Asp Ser Leu Arg Ser Tyr Tyr Thr Asn Trp Phe Gln Gln
                165                 170                 175

aag cca gga cag gcc cct cta ctt gtc gtc tat gct aaa aat aag cgg      576
Lys Pro Gly Gln Ala Pro Leu Leu Val Val Tyr Ala Lys Asn Lys Arg
            180                 185                 190

ccc tca gag atc cca gac cga ttc tct ggc tcc agc tca gga aac aca      624
Pro Ser Glu Ile Pro Asp Arg Phe Ser Gly Ser Ser Ser Gly Asn Thr
        195                 200                 205

gct tcc ttg acc atc act ggg gct cag gcg gaa gat gag gct gac tat      672
Ala Ser Leu Thr Ile Thr Gly Ala Gln Ala Glu Asp Glu Ala Asp Tyr
    210                 215                 220

tac tgt cat tcc cgg gac agc agt ggt aac cat gtg ctt ttc ggc gga      720
Tyr Cys His Ser Arg Asp Ser Ser Gly Asn His Val Leu Phe Gly Gly
225                 230                 235                 240
```

```
ggg acc aag ctg acc gtc cta ggt                                    744
Gly Thr Lys Leu Thr Val Leu Gly
                245


<210> SEQ ID NO 75

<400> SEQUENCE: 75

000


<210> SEQ ID NO 76
<211> LENGTH: 747
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGB0115 scFv protein

<400> SEQUENCE: 76

cag ctg cag ctg cag gag tcg ggc cca gga ctg gtg aag cct tcg ggg     48
Gln Leu Gln Leu Gln Glu Ser Gly Pro Gly Leu Val Lys Pro Ser Gly
1               5                   10                  15

acc ctg tcc ctc aac tgc gct gta tct ggt gac tcc atc agc agt gga     96
Thr Leu Ser Leu Asn Cys Ala Val Ser Gly Asp Ser Ile Ser Ser Gly
            20                  25                  30

aat tgg tgg agt tgg gtc cgc cag ccc cca ggg aag ggg ctg gaa tgg    144
Asn Trp Trp Ser Trp Val Arg Gln Pro Pro Gly Lys Gly Leu Glu Trp
        35                  40                  45

act gga gaa atc tat cat agt ggg acc gcc aac tac aac ccg tcc ctc    192
Thr Gly Glu Ile Tyr His Ser Gly Thr Ala Asn Tyr Asn Pro Ser Leu
    50                  55                  60

aag agt cga gtc acc gtg tca gtg gac aag tcc acg aac cag ttt tcc    240
Lys Ser Arg Val Thr Val Ser Val Asp Lys Ser Thr Asn Gln Phe Ser
65                  70                  75                  80

ctg aga atg agc tct gtg acc gcc gcg gac acg gcc gtt tat tac tgt    288
Leu Arg Met Ser Ser Val Thr Ala Ala Asp Thr Ala Val Tyr Tyr Cys
                85                  90                  95

gcg agg gcc ggc tac tat gat gtg gga ctc cca ttc gac tac tgg ggc    336
Ala Arg Ala Gly Tyr Tyr Asp Val Gly Leu Pro Phe Asp Tyr Trp Gly
            100                 105                 110

aaa gga acc ctg gtc acc gtc tcg agt gga ggc ggc ggt tca ggc gga    384
Lys Gly Thr Leu Val Thr Val Ser Ser Gly Gly Gly Gly Ser Gly Gly
        115                 120                 125

ggt ggc tct ggc ggt ggc gga agt gca cag gct gtg ctg act cag ccg    432
Gly Gly Ser Gly Gly Gly Gly Ser Ala Gln Ala Val Leu Thr Gln Pro
    130                 135                 140

tcc tca gta tct ggg gcc cca ggg cag agg gtc acc ctc tcc tgc act    480
Ser Ser Val Ser Gly Ala Pro Gly Gln Arg Val Thr Leu Ser Cys Thr
145                 150                 155                 160

ggg agc agc tcc aac atc ggg gca ggt tct gag ttc cac tgg tac cag    528
Gly Ser Ser Ser Asn Ile Gly Ala Gly Ser Glu Phe His Trp Tyr Gln
                165                 170                 175

cag gtt cca gga aca gcc ccc aag ctc ctc atc ttt ggt aac acc aat    576
Gln Val Pro Gly Thr Ala Pro Lys Leu Leu Ile Phe Gly Asn Thr Asn
            180                 185                 190

cgg ccc tgg gga gtc cct gac cga ttc tct ggc tcc aag tct ggc acc    624
Arg Pro Trp Gly Val Pro Asp Arg Phe Ser Gly Ser Lys Ser Gly Thr
        195                 200                 205

tca gcc tcc ctg gcc atc act ggg ctc cag gct gag gat gag gct gat    672
Ser Ala Ser Leu Ala Ile Thr Gly Leu Gln Ala Glu Asp Glu Ala Asp
    210                 215                 220
```

```
tat tat tgc cag tcc tat gac agc agc ctg agt gct tat gtc ttc gga      720
Tyr Tyr Cys Gln Ser Tyr Asp Ser Ser Leu Ser Ala Tyr Val Phe Gly
225                 230                 235                 240

act ggg acc aag gtc acc gtc cta ggt                                  747
Thr Gly Thr Lys Val Thr Val Leu Gly
                245


<210> SEQ ID NO 77
<211> LENGTH: 741
<212> TYPE: DNA
<213> ORGANISM: Artificial Sequence
<220> FEATURE:
<221> NAME/KEY: CDS
<222> LOCATION: (1)..(741)
<223> OTHER INFORMATION: Polynucleotide encoding RGB0118 scFv protein

<400> SEQUENCE: 77

gag gtc cag ctg gtg cag tct ggg gct gag gtg aag aag cct ggg gcc       48
Glu Val Gln Leu Val Gln Ser Gly Ala Glu Val Lys Lys Pro Gly Ala
1               5                   10                  15

tca gtg aag gtc tcc tgc aag gct tct gga tac acc ttc acc gac tac       96
Ser Val Lys Val Ser Cys Lys Ala Ser Gly Tyr Thr Phe Thr Asp Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttt      192
Gly Trp Ile Asn Pro Asn Ser Gly Gly Thr Asn Tyr Ala Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gtg tat ttc tgt      288
Met Glu Leu Ser Arg Leu Arg Ser Asp Asp Thr Ala Val Tyr Phe Cys
                85                  90                  95

gcg aga gat ctt ctc tct tat ttc tat gat agt agt ggt tac ctc gac      336
Ala Arg Asp Leu Leu Ser Tyr Phe Tyr Asp Ser Ser Gly Tyr Leu Asp
            100                 105                 110

aac tgg ggc caa ggg aca atg gtc acc gtc tcg agt ggt gga ggc ggt      384
Asn Trp Gly Gln Gly Thr Met Val Thr Val Ser Ser Gly Gly Gly Gly
        115                 120                 125

tca ggc gga ggt ggc agc ggc ggt ggc gga tcg tct gag ctg act cag      432
Ser Gly Gly Gly Gly Ser Gly Gly Gly Gly Ser Ser Glu Leu Thr Gln
    130                 135                 140

gac act gct gtg tct gtg gcc ttg gga cag aca gtc agg atc act tgc      480
Asp Thr Ala Val Ser Val Ala Leu Gly Gln Thr Val Arg Ile Thr Cys
145                 150                 155                 160

caa gga gac agt ctc aga agc tat tac aca aac tgg ttc cag cag aag      528
Gln Gly Asp Ser Leu Arg Ser Tyr Tyr Thr Asn Trp Phe Gln Gln Lys
                165                 170                 175

cca gga cag gcc cct cta ctt gtc gtc tat gct aaa aat aag cgg ccc      576
Pro Gly Gln Ala Pro Leu Leu Val Val Tyr Ala Lys Asn Lys Arg Pro
            180                 185                 190

tca ggg atc cca gac cga ttc tct ggc tcc agc tca gga aac aca gct      624
Ser Gly Ile Pro Asp Arg Phe Ser Gly Ser Ser Ser Gly Asn Thr Ala
        195                 200                 205

tcc ttg acc atc act ggg gct cag gcg gaa gat gag gct gac tat tac      672
Ser Leu Thr Ile Thr Gly Ala Gln Ala Glu Asp Glu Ala Asp Tyr Tyr
    210                 215                 220

tgt aac tcc cgg gac agc agt ggt aac cat gtg gta ttc ggc gga ggg      720
Cys Asn Ser Arg Asp Ser Ser Gly Asn His Val Val Phe Gly Gly Gly
```

-continued

```
225                 230                 235                 240

acc aag ctg acc gtc cta ggt                                         741
Thr Lys Leu Thr Val Leu Gly
                245


<210> SEQ ID NO 78
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0128 scFv protein

<400> SEQUENCE: 78

gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95

gca aga gag gat cct tgg agt gac gct ttt gat ttg tgg ggc cgg gga     336
Ala Arg Glu Asp Pro Trp Ser Asp Ala Phe Asp Leu Trp Gly Arg Gly
            100                 105                 110

acc ctg gtc acc gtc tcg agt gga ggc ggc ggt tca ggc gga ggt ggc     384
Thr Leu Val Thr Val Ser Ser Gly Gly Gly Gly Ser Gly Gly Gly Gly
        115                 120                 125

tct ggc ggt ggc gga agt gca ctt aat ttt atg ctg act cag ccc cac     432
Ser Gly Gly Gly Gly Ser Ala Leu Asn Phe Met Leu Thr Gln Pro His
    130                 135                 140

tct gtg tcg gag tct ccg ggg aag acg gta acc att tcc tgc acc ggc     480
Ser Val Ser Glu Ser Pro Gly Lys Thr Val Thr Ile Ser Cys Thr Gly
145                 150                 155                 160

agc agt ggc agc att gcc agc aac tat gtg cag tgg tac cag cag cgc     528
Ser Ser Gly Ser Ile Ala Ser Asn Tyr Val Gln Trp Tyr Gln Gln Arg
                165                 170                 175

ccg ggc agt gcc ccc gcc act gtg atc tat gag gat aac caa aga ccc     576
Pro Gly Ser Ala Pro Ala Thr Val Ile Tyr Glu Asp Asn Gln Arg Pro
            180                 185                 190

tct ggg gtc cct gat cgg ttc tct ggc tcc atc gac agc tcc tcc aac     624
Ser Gly Val Pro Asp Arg Phe Ser Gly Ser Ile Asp Ser Ser Ser Asn
        195                 200                 205

tct gcc tcc ctc acc atc tct gac ctg aag act gag gac gag gct gac     672
Ser Ala Ser Leu Thr Ile Ser Asp Leu Lys Thr Glu Asp Glu Ala Asp
    210                 215                 220

tac tac tgt cag tct ttt gat aac agc aaa tat gtg gta ttc ggc gga     720
Tyr Tyr Cys Gln Ser Phe Asp Asn Ser Lys Tyr Val Val Phe Gly Gly
225                 230                 235                 240

ggg acc aag ctg acc gtc cta ggt                                     744
```

```
Gly Thr Lys Leu Thr Val Leu Gly
                245


<210> SEQ ID NO 79
<211> LENGTH: 756
<212> TYPE: DNA
<213> ORGANISM: Artificial Sequence
<220> FEATURE:
<221> NAME/KEY: CDS
<222> LOCATION: (1)..(756)
<223> OTHER INFORMATION: Polynucleotide encoding RGB0129 scFv protein

<400> SEQUENCE: 79

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aaa ggg cct gat tgt act aat ggt gta tgc tat ctc ccc ttt gac      336
Ala Lys Gly Pro Asp Cys Thr Asn Gly Val Cys Tyr Leu Pro Phe Asp
            100                 105                 110

tac tgg ggc agg ggc acc ctg gtc acc gtc tcg agt gga ggc ggc ggt      384
Tyr Trp Gly Arg Gly Thr Leu Val Thr Val Ser Ser Gly Gly Gly Gly
        115                 120                 125

tca ggc gga ggt ggc tct ggc ggt ggc gga agt gca ctt aat ttt atg      432
Ser Gly Gly Gly Gly Ser Gly Gly Gly Gly Ser Ala Leu Asn Phe Met
    130                 135                 140

ctg act cag ccc cac tct gtg tcg gag tct ccg ggt aag aca gta act      480
Leu Thr Gln Pro His Ser Val Ser Glu Ser Pro Gly Lys Thr Val Thr
145                 150                 155                 160

ctc tcc tgc acc cgc tcc agt ggc agc att tca ttc gac tat gtg cag      528
Leu Ser Cys Thr Arg Ser Ser Gly Ser Ile Ser Phe Asp Tyr Val Gln
                165                 170                 175

tgg tat caa cag cgg ccg ggc agc tcc ccc att ctt gtg atc ttt gaa      576
Trp Tyr Gln Gln Arg Pro Gly Ser Ser Pro Ile Leu Val Ile Phe Glu
            180                 185                 190

gat gac caa aga ccc tct ggg gtc cct gat cga ttc tct ggc tcc atc      624
Asp Asp Gln Arg Pro Ser Gly Val Pro Asp Arg Phe Ser Gly Ser Ile
        195                 200                 205

gac agt acc tcc aac tct gcc tcc ctc acc atc tct ggc ctg cag agt      672
Asp Ser Thr Ser Asn Ser Ala Ser Leu Thr Ile Ser Gly Leu Gln Ser
    210                 215                 220

gag gac gag ggt gac tac tat tgt cag act tat gat gac aac cgt cag      720
Glu Asp Glu Gly Asp Tyr Tyr Cys Gln Thr Tyr Asp Asp Asn Arg Gln
225                 230                 235                 240

gtg ttc ggc ggg ggg acc aag ctg acc gtc cta ggt                      756
Val Phe Gly Gly Gly Thr Lys Leu Thr Val Leu Gly
                245                 250
```

```
<210> SEQ ID NO 80
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGB0137 scFv protein

<400> SEQUENCE: 80

gag gtg cag ctg gtg cag tct ggg gct gag gtg gag aag cct ggg gcc       48
Glu Val Gln Leu Val Gln Ser Gly Ala Glu Val Glu Lys Pro Gly Ala
1               5                   10                  15

tca gtg aaa gtc tcc tgc aag gtt tct ggc tac acc ttc acc ggc gac       96
Ser Val Lys Val Ser Cys Lys Val Ser Gly Tyr Thr Phe Thr Gly Asp
            20                  25                  30

tat atg cac tgg gtg cga cag gcc cct gga caa gga ctt gag tgg atg      144
Tyr Met His Trp Val Arg Gln Ala Pro Gly Gln Gly Leu Glu Trp Met
        35                  40                  45

gga agg atc gac cct aag tat ggt gac aca aac tat gca cag aag ttt      192
Gly Arg Ile Asp Pro Lys Tyr Gly Asp Thr Asn Tyr Ala Gln Lys Phe
    50                  55                  60

cag ggc agg gtc acc atg acc agg gac acg tcc atc agc aca gtc tac      240
Gln Gly Arg Val Thr Met Thr Arg Asp Thr Ser Ile Ser Thr Val Tyr
65                  70                  75                  80

atg gag ctg agc agg ctg aga tct gac gac acg gcc cta tat ttc tgt      288
Met Glu Leu Ser Arg Leu Arg Ser Asp Asp Thr Ala Leu Tyr Phe Cys
                85                  90                  95

gcg aca gat aac agt ggg tta tat gat gct ttt gac aag tgg ggg aaa      336
Ala Thr Asp Asn Ser Gly Leu Tyr Asp Ala Phe Asp Lys Trp Gly Lys
            100                 105                 110

ggg acc acg gtc acc gtc tcg agt ggt gga ggc ggt tca ggc gga ggt      384
Gly Thr Thr Val Thr Val Ser Ser Gly Gly Gly Gly Ser Gly Gly Gly
        115                 120                 125

ggc agc ggc ggt ggc gga tcg cag tct gtg ctg act cag cct gcc tcc      432
Gly Ser Gly Gly Gly Gly Ser Gln Ser Val Leu Thr Gln Pro Ala Ser
    130                 135                 140

gtg tct ggg tct cct gga cag tcg atc acc atc tcc tgc act gga acc      480
Val Ser Gly Ser Pro Gly Gln Ser Ile Thr Ile Ser Cys Thr Gly Thr
145                 150                 155                 160

agc agt gac gtt ggt ggt tat aac tat gtc tcc tgg tac caa caa cac      528
Ser Ser Asp Val Gly Gly Tyr Asn Tyr Val Ser Trp Tyr Gln Gln His
                165                 170                 175

cca ggc aaa gcc ccc aaa ctc atg att tat gag ggc agt aag cgg ccc      576
Pro Gly Lys Ala Pro Lys Leu Met Ile Tyr Glu Gly Ser Lys Arg Pro
            180                 185                 190

tca ggg gtt tct aat cgc ttc tct ggc tcc aag tct ggc aac acg gcc      624
Ser Gly Val Ser Asn Arg Phe Ser Gly Ser Lys Ser Gly Asn Thr Ala
        195                 200                 205

tcc ctg aca atc tct agg ctc cag gct gag gac gag gct gat tat tac      672
Ser Leu Thr Ile Ser Arg Leu Gln Ala Glu Asp Glu Ala Asp Tyr Tyr
    210                 215                 220

tgc agc tca tat aca acc agg agc act cga gtt ttc ggc gga ggg acc      720
Cys Ser Ser Tyr Thr Thr Arg Ser Thr Arg Val Phe Gly Gly Gly Thr
225                 230                 235                 240

aag ctg acc gtc cta ggt                                              738
Lys Leu Thr Val Leu Gly
                245


<210> SEQ ID NO 81
<211> LENGTH: 747
```

```
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGB0146 scFv protein

<400> SEQUENCE: 81

cag gta cag ctg cag cag tca ggc cca aga cta gtg aag cct tca cag       48
Gln Val Gln Leu Gln Gln Ser Gly Pro Arg Leu Val Lys Pro Ser Gln
1               5                   10                  15

acc ctg tcc ctc acc tgc act gtc tct ggt ggc tcc atc agc aga ggg       96
Thr Leu Ser Leu Thr Cys Thr Val Ser Gly Gly Ser Ile Ser Arg Gly
            20                  25                  30

ggt tac tac tgg agc tgg atc cgc cag ctc cca ggg aag ggc ctg gag      144
Gly Tyr Tyr Trp Ser Trp Ile Arg Gln Leu Pro Gly Lys Gly Leu Glu
        35                  40                  45

tgg att ggg tac atc tat cac agt ggg agc acc tac tac aac ccg ccc      192
Trp Ile Gly Tyr Ile Tyr His Ser Gly Ser Thr Tyr Tyr Asn Pro Pro
    50                  55                  60

ctc aag agt cga gtt acc atg tca gta gac acg tct aag aat cag ttc      240
Leu Lys Ser Arg Val Thr Met Ser Val Asp Thr Ser Lys Asn Gln Phe
65                  70                  75                  80

tcc ctg aac ctg agc tct gtg act gcc gcg gac acg gcc gtt tat tac      288
Ser Leu Asn Leu Ser Ser Val Thr Ala Ala Asp Thr Ala Val Tyr Tyr
                85                  90                  95

tgt gcg aga gaa aag ggc ggc gac tgg gag caa ctg gtc ttt gac cac      336
Cys Ala Arg Glu Lys Gly Gly Asp Trp Glu Gln Leu Val Phe Asp His
            100                 105                 110

tgg ggc aga ggg aca atg gtc acc gtc tct tca ggt gga ggc ggt tca      384
Trp Gly Arg Gly Thr Met Val Thr Val Ser Ser Gly Gly Gly Gly Ser
        115                 120                 125

ggc gga ggt ggc agc ggc ggt ggc gga tcg cag tct gtg ttg acg cag      432
Gly Gly Gly Gly Ser Gly Gly Gly Gly Ser Gln Ser Val Leu Thr Gln
    130                 135                 140

ccg ccc tca gtg tct gcg gcc cca gga cag aag gtc acc att tcc tgc      480
Pro Pro Ser Val Ser Ala Ala Pro Gly Gln Lys Val Thr Ile Ser Cys
145                 150                 155                 160

tct gga agc acc tcc aac att ggg aat aat tat gtc tcc tgg tac caa      528
Ser Gly Ser Thr Ser Asn Ile Gly Asn Asn Tyr Val Ser Trp Tyr Gln
                165                 170                 175

cag cac cca ggc aaa gcc ccc aaa ctc atg att tat gat gtc agt aag      576
Gln His Pro Gly Lys Ala Pro Lys Leu Met Ile Tyr Asp Val Ser Lys
            180                 185                 190

cgg ccc tca ggg gtc cct gac cga ttc tct ggc tcc aag tct ggc aac      624
Arg Pro Ser Gly Val Pro Asp Arg Phe Ser Gly Ser Lys Ser Gly Asn
        195                 200                 205

tca gcc tcc ctg gac atc agt ggg ctc cag tct gag gat gag gct gat      672
Ser Ala Ser Leu Asp Ile Ser Gly Leu Gln Ser Glu Asp Glu Ala Asp
    210                 215                 220

tat tac tgt gca gca tgg gat gac agc ctg agt gaa ttt ctc ttc gga      720
Tyr Tyr Cys Ala Ala Trp Asp Asp Ser Leu Ser Glu Phe Leu Phe Gly
225                 230                 235                 240

act ggg acc aag ctg acc gtc cta ggt                                  747
Thr Gly Thr Lys Leu Thr Val Leu Gly
                245


<210> SEQ ID NO 82
<211> LENGTH: 747
<212> TYPE: DNA
<213> ORGANISM: Artificial Sequence
<220> FEATURE:
```

```
<221> NAME/KEY: CDS
<222> LOCATION: (1)..(747)
<223> OTHER INFORMATION: Polynucleotide encoding RGB0153 scFv protein

<400> SEQUENCE: 82

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga ggt gcg gga gct act cca ttt aat gct ttt gat atc tgg ggg      336
Ala Arg Gly Ala Gly Ala Thr Pro Phe Asn Ala Phe Asp Ile Trp Gly
            100                 105                 110

cgg ggg acc acg gtc acc gtc tcg agt gga ggc ggc ggt tca ggc gga      384
Arg Gly Thr Thr Val Thr Val Ser Ser Gly Gly Gly Gly Ser Gly Gly
        115                 120                 125

ggt ggc tct ggc ggt ggc gga agt gca ctt aat ttt atg ctg act cag      432
Gly Gly Ser Gly Gly Gly Gly Ser Ala Leu Asn Phe Met Leu Thr Gln
    130                 135                 140

ccc cac tct gtg tcg gag tct ccg ggt aag aca gta act ctc tcc tgc      480
Pro His Ser Val Ser Glu Ser Pro Gly Lys Thr Val Thr Leu Ser Cys
145                 150                 155                 160

acc cgc tcc agt ggc agt att tca ttc gac tat gtg cag tgg tat caa      528
Thr Arg Ser Ser Gly Ser Ile Ser Phe Asp Tyr Val Gln Trp Tyr Gln
                165                 170                 175

cag cgg ccg ggc agc tcc ccc att ctt gtg atc ttt gaa gat gac caa      576
Gln Arg Pro Gly Ser Ser Pro Ile Leu Val Ile Phe Glu Asp Asp Gln
            180                 185                 190

aga ccc tct ggg gtc cct gat cga ttc tct ggc tcc atc gac agt acc      624
Arg Pro Ser Gly Val Pro Asp Arg Phe Ser Gly Ser Ile Asp Ser Thr
        195                 200                 205

tcc aac tct gcc tcc ctc acc atc tct ggc ctg cag agt gag gac gag      672
Ser Asn Ser Ala Ser Leu Thr Ile Ser Gly Leu Gln Ser Glu Asp Glu
    210                 215                 220

ggt gac tac tat tgt cag act tat gat gac aac cgt cag gtg ttc ggc      720
Gly Asp Tyr Tyr Cys Gln Thr Tyr Asp Asp Asn Arg Gln Val Phe Gly
225                 230                 235                 240

ggg ggg acc aag gtc acc gtc cta ggt                                  747
Gly Gly Thr Lys Val Thr Val Leu Gly
                245


<210> SEQ ID NO 83
<211> LENGTH: 741
<212> TYPE: DNA
<213> ORGANISM: Artificial Sequence
<220> FEATURE:
<221> NAME/KEY: CDS
<222> LOCATION: (1)..(741)
<223> OTHER INFORMATION: Polynucleotide encoding RGB0163 scFv protein
```

```
<400> SEQUENCE: 83

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aca gat cct tac tat gat agt agt ggt tat tac ccc ttt agc tac      336
Ala Thr Asp Pro Tyr Tyr Asp Ser Ser Gly Tyr Tyr Pro Phe Ser Tyr
            100                 105                 110

tgg ggg cgg ggg acc acg gtc acc gtc tcg agt gga ggc ggc ggt tca      384
Trp Gly Arg Gly Thr Thr Val Thr Val Ser Ser Gly Gly Gly Gly Ser
        115                 120                 125

ggc gga ggt ggc tct ggc ggt ggc gga agt gca cag tct gtg ctg acg      432
Gly Gly Gly Gly Ser Gly Gly Gly Gly Ser Ala Gln Ser Val Leu Thr
    130                 135                 140

cag ccg ccc tca gtg tca gtg gcc cca gga aag acg gcc aca att acc      480
Gln Pro Pro Ser Val Ser Val Ala Pro Gly Lys Thr Ala Thr Ile Thr
145                 150                 155                 160

tgt ggg gga gac ttt gca act aaa aat gtg aat tgg tac caa cgg aag      528
Cys Gly Gly Asp Phe Ala Thr Lys Asn Val Asn Trp Tyr Gln Arg Lys
                165                 170                 175

ccg ggc cag gcc cct gtg acg gtc atc tat tat gac acc gag cgg ccc      576
Pro Gly Gln Ala Pro Val Thr Val Ile Tyr Tyr Asp Thr Glu Arg Pro
            180                 185                 190

tca gcg atc cct gag cgc ttc tct ggc tcc aac act ggg tcc acg gcc      624
Ser Ala Ile Pro Glu Arg Phe Ser Gly Ser Asn Thr Gly Ser Thr Ala
        195                 200                 205

acc ctg acc atc agc agg gtc gaa gcc ggg gat gag gcc gac tat tat      672
Thr Leu Thr Ile Ser Arg Val Glu Ala Gly Asp Glu Ala Asp Tyr Tyr
    210                 215                 220

tgt cag gtg tgg gat agt ttt act gat cat cgg ctg ttc ggc gga ggg      720
Cys Gln Val Trp Asp Ser Phe Thr Asp His Arg Leu Phe Gly Gly Gly
225                 230                 235                 240

acc aag ctg acc gtc cta ggt                                          741
Thr Lys Leu Thr Val Leu Gly
                245


<210> SEQ ID NO 84
<211> LENGTH: 759
<212> TYPE: DNA
<213> ORGANISM: Artificial Sequence
<220> FEATURE:
<221> NAME/KEY: CDS
<222> LOCATION: (1)..(759)
<223> OTHER INFORMATION: Polynucleotide encoding RGB0165 scFv protein

<400> SEQUENCE: 84
```

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg gga ctc tcc tgt gca gcc tct gga ttc acc ttt agc agc tat       96
Ser Leu Gly Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg acg ggg ggt agt ggt tcc ccc gta tac tac tat tac cac tac ttg      336
Ala Thr Gly Gly Ser Gly Ser Pro Val Tyr Tyr Tyr Tyr His Tyr Leu
            100                 105                 110

gac gtc tgg ggc cga ggc acc ctg gtc acc gtc tcg agt gga ggc ggc      384
Asp Val Trp Gly Arg Gly Thr Leu Val Thr Val Ser Ser Gly Gly Gly
        115                 120                 125

ggt tca ggc gga ggt ggc tct ggc ggt ggc gga agt gca ctt aat ttt      432
Gly Ser Gly Gly Gly Gly Ser Gly Gly Gly Gly Ser Ala Leu Asn Phe
    130                 135                 140

atg ctg act cag ccc cac tct gtg tcg gag tct ccg ggt aag aca gta      480
Met Leu Thr Gln Pro His Ser Val Ser Glu Ser Pro Gly Lys Thr Val
145                 150                 155                 160

act ctc tcc tgc acc cgc tcc agt ggc agc att tca ttc gac tat gtg      528
Thr Leu Ser Cys Thr Arg Ser Ser Gly Ser Ile Ser Phe Asp Tyr Val
                165                 170                 175

cag tgg tat caa cag cgg ccg ggc agc tcc ccc att ctt gtg atc ttt      576
Gln Trp Tyr Gln Gln Arg Pro Gly Ser Ser Pro Ile Leu Val Ile Phe
            180                 185                 190

gaa gat gac caa aga ccc tct ggg gtc cct gat cga ttc tct ggc tcc      624
Glu Asp Asp Gln Arg Pro Ser Gly Val Pro Asp Arg Phe Ser Gly Ser
        195                 200                 205

atc gac agt acc tcc aac tct gcc tcc ctc acc atc tct ggc ctg cag      672
Ile Asp Ser Thr Ser Asn Ser Ala Ser Leu Thr Ile Ser Gly Leu Gln
    210                 215                 220

agt gag gac gag ggt gac tac tat tgt cag act tat gat gac aac cgt      720
Ser Glu Asp Glu Gly Asp Tyr Tyr Cys Gln Thr Tyr Asp Asp Asn Arg
225                 230                 235                 240

cag gtg ttc ggc ggg ggg acc aag ctg acc gtc cta ggt                  759
Gln Val Phe Gly Gly Gly Thr Lys Leu Thr Val Leu Gly
                245                 250
```

<210> SEQ ID NO 85
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0174 scFv protein

<400> SEQUENCE: 85

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15
```

-continued

```
tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg agt gac tct gat agt agt gat tat tac tat ttt gac tct tgg ggc      336
Ala Ser Asp Ser Asp Ser Ser Asp Tyr Tyr Tyr Phe Asp Ser Trp Gly
            100                 105                 110

cag ggg aca atg gtc acc gtc tcg agt gga ggc ggc ggt tca ggc gga      384
Gln Gly Thr Met Val Thr Val Ser Ser Gly Gly Gly Gly Ser Gly Gly
        115                 120                 125

ggt ggc tct ggc ggt ggc gga agt gca cag tct gtg ctg act cag cca      432
Gly Gly Ser Gly Gly Gly Gly Ser Ala Gln Ser Val Leu Thr Gln Pro
    130                 135                 140

ccc tca gcg tct ggg acc ccc ggg cag agg gtc acc atc tct tgt tct      480
Pro Ser Ala Ser Gly Thr Pro Gly Gln Arg Val Thr Ile Ser Cys Ser
145                 150                 155                 160

gga agc agc tcc aat atc gga ttt aat gat gtg tac tgg tat cag cag      528
Gly Ser Ser Ser Asn Ile Gly Phe Asn Asp Val Tyr Trp Tyr Gln Gln
                165                 170                 175

ctc cca gga ttg gcc ccc aaa ctc ctc atc tat agt aat aat cag cgg      576
Leu Pro Gly Leu Ala Pro Lys Leu Leu Ile Tyr Ser Asn Asn Gln Arg
            180                 185                 190

ccc tca ggg gtc cct gac cga ttc tct ggc tcc gag tct ggc acc tca      624
Pro Ser Gly Val Pro Asp Arg Phe Ser Gly Ser Glu Ser Gly Thr Ser
        195                 200                 205

gcc tcc ctg gcc atc agt ggg ctc cgg tcc gag gat gag gct gat tat      672
Ala Ser Leu Ala Ile Ser Gly Leu Arg Ser Glu Asp Glu Ala Asp Tyr
    210                 215                 220

tac tgt gca aca tgg gat gac agc ctg agt gcc ccg gtg ttc ggc gga      720
Tyr Cys Ala Thr Trp Asp Asp Ser Leu Ser Ala Pro Val Phe Gly Gly
225                 230                 235                 240

ggg acc aag gtc acc gtc cta ggt                                      744
Gly Thr Lys Val Thr Val Leu Gly
                245
```

<210> SEQ ID NO 86
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGB0185 scFv protein

<400> SEQUENCE: 86

```
cag gtg cag ctg gta cag tct ggg gct gag gtg aag aag cct ggg gcc       48
Gln Val Gln Leu Val Gln Ser Gly Ala Glu Val Lys Lys Pro Gly Ala
1               5                   10                  15

tca gtg aag gtc tcc tgc aag gct tct gga tac acc ttc acc gac tac       96
Ser Val Lys Val Ser Cys Lys Ala Ser Gly Tyr Thr Phe Thr Asp Tyr
```

-continued

```
            20                  25                  30

tat ata cac tgg gtg cga cag gcc cct gga caa ggg ctt gag tgg atg      144
Tyr Ile His Trp Val Arg Gln Ala Pro Gly Gln Gly Leu Glu Trp Met
        35                  40                  45

gga tgg atc aac cct aaa agt ggt gac aca aac tat gca cag aag ttt      192
Gly Trp Ile Asn Pro Lys Ser Gly Asp Thr Asn Tyr Ala Gln Lys Phe
    50                  55                  60

cag ggc agg gtc acc atg gcc agg gac acg tcc atg agc acg gcc tcc      240
Gln Gly Arg Val Thr Met Ala Arg Asp Thr Ser Met Ser Thr Ala Ser
65                  70                  75                  80

gtg gaa ctg aga agg ttg aca tct gac gac acg gcc gtg tat tac tgt      288
Val Glu Leu Arg Arg Leu Thr Ser Asp Asp Thr Ala Val Tyr Tyr Cys
                85                  90                  95

gcg agg aac tcg ttc gac ttt ggg agt ggc tat ggg ctc ttc tac cag      336
Ala Arg Asn Ser Phe Asp Phe Gly Ser Gly Tyr Gly Leu Phe Tyr Gln
            100                 105                 110

tac att atg gac gtc tgg ggc caa gga acc ctg gtc acc gtc tcc tca      384
Tyr Ile Met Asp Val Trp Gly Gln Gly Thr Leu Val Thr Val Ser Ser
        115                 120                 125

ggt gga ggc ggt tca ggc gga ggt ggc agc ggc ggt ggc gga tcg gac      432
Gly Gly Gly Gly Ser Gly Gly Gly Gly Ser Gly Gly Gly Gly Ser Asp
    130                 135                 140

atc cag atg acc cag tct cca tcc ttc ctg tct gca tct gta gga gac      480
Ile Gln Met Thr Gln Ser Pro Ser Phe Leu Ser Ala Ser Val Gly Asp
145                 150                 155                 160

aga gtc acc atc act tgc cgg gcc agt cag ggc att aac aat tat tta      528
Arg Val Thr Ile Thr Cys Arg Ala Ser Gln Gly Ile Asn Asn Tyr Leu
                165                 170                 175

gcc tgg tat cag caa aaa cca ggg aga gcc cct aag ctc ctg atc tac      576
Ala Trp Tyr Gln Gln Lys Pro Gly Arg Ala Pro Lys Leu Leu Ile Tyr
            180                 185                 190

gct gca tcc agt tta caa agt ggg gtc cca tca agg ttc agc ggc agt      624
Ala Ala Ser Ser Leu Gln Ser Gly Val Pro Ser Arg Phe Ser Gly Ser
        195                 200                 205

gga tct ggc aca gat ttc act ctc acc atc agc agc ctg cag cct gaa      672
Gly Ser Gly Thr Asp Phe Thr Leu Thr Ile Ser Ser Leu Gln Pro Glu
    210                 215                 220

gat ttt gca act tat tac tgt ctc caa gat tcc gat tat ccc ctc act      720
Asp Phe Ala Thr Tyr Tyr Cys Leu Gln Asp Ser Asp Tyr Pro Leu Thr
225                 230                 235                 240

ttc ggc gga ggg acc aag ctg acc gtc cta ggt                          753
Phe Gly Gly Gly Thr Lys Leu Thr Val Leu Gly
                245                 250
```

<210> SEQ ID NO 87
<211> LENGTH: 759
<212> TYPE: DNA
<213> ORGANISM: Artificial Sequence
<220> FEATURE:
<221> NAME/KEY: CDS
<222> LOCATION: (1)..(759)
<223> OTHER INFORMATION: Polynucleotide encoding RGB0187 scFv protein

<400> SEQUENCE: 87

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
```

-continued

```
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga gat tcg tgt ccg tat tgt agt acc aac agc ggc tcc ttt gac      336
Ala Arg Asp Ser Cys Pro Tyr Cys Ser Thr Asn Ser Gly Ser Phe Asp
            100                 105                 110

tac tgg ggc caa ggg aca atg gtc acc gtc tcg agt gga ggc ggc ggt      384
Tyr Trp Gly Gln Gly Thr Met Val Thr Val Ser Ser Gly Gly Gly Gly
        115                 120                 125

tca ggc gga ggt ggc tct ggc ggt ggc gga agt gca ctt aat ttt atg      432
Ser Gly Gly Gly Gly Ser Gly Gly Gly Gly Ser Ala Leu Asn Phe Met
    130                 135                 140

ctg act cag ccc cac tct gtg tcg gag tct ccg ggg aag acg gtc acc      480
Leu Thr Gln Pro His Ser Val Ser Glu Ser Pro Gly Lys Thr Val Thr
145                 150                 155                 160

atc tcc tgc acc cgc acc agt ggg aac att gcc ggc tac ttt gtg cag      528
Ile Ser Cys Thr Arg Thr Ser Gly Asn Ile Ala Gly Tyr Phe Val Gln
                165                 170                 175

tgg tac cag cag cgc ccg ggc agt tcc ccc acc act gtg atc tat gag      576
Trp Tyr Gln Gln Arg Pro Gly Ser Ser Pro Thr Thr Val Ile Tyr Glu
            180                 185                 190

gat tac caa cga ccc tct ggg gtc cct gat cgg ttc tct ggc tcc atc      624
Asp Tyr Gln Arg Pro Ser Gly Val Pro Asp Arg Phe Ser Gly Ser Ile
        195                 200                 205

gac agg tcc tcc aac tct gcc tcc ctc acc atc tct gga ctg aag cct      672
Asp Arg Ser Ser Asn Ser Ala Ser Leu Thr Ile Ser Gly Leu Lys Pro
    210                 215                 220

gac gac gag gct gac tac tat tgt cag tct tat gat gac acc tct caa      720
Asp Asp Glu Ala Asp Tyr Tyr Cys Gln Ser Tyr Asp Asp Thr Ser Gln
225                 230                 235                 240

ggt gtg ttc ggc gca ggg acc aag ctg acc gtc cta ggt                  759
Gly Val Phe Gly Ala Gly Thr Lys Leu Thr Val Leu Gly
                245                 250


<210> SEQ ID NO 88
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGB0194 scFv protein

<400> SEQUENCE: 88

gag gtg cag ctg gtg gag tct ggg gct gaa gtg aag aag cct ggg tcc       48
Glu Val Gln Leu Val Glu Ser Gly Ala Glu Val Lys Lys Pro Gly Ser
1               5                   10                  15

tcg gtg aag gtc tcc tgc aag gct tct gga ggc acc ctc agc agg ttt       96
Ser Val Lys Val Ser Cys Lys Ala Ser Gly Gly Thr Leu Ser Arg Phe
            20                  25                  30

ggt atc aac tgg gtg cga cag gcc cct gga caa ggg ctt gag tgg atg      144
Gly Ile Asn Trp Val Arg Gln Ala Pro Gly Gln Gly Leu Glu Trp Met
        35                  40                  45
```

```
ggg gtg atc atc cct atg ttt ggt aca aca aat tac gca cag aag ttc      192
Gly Val Ile Ile Pro Met Phe Gly Thr Thr Asn Tyr Ala Gln Lys Phe
    50                  55                  60

gaa gac aga gtc acg att agc gcg gac gga tcc acg agc aca gtg tac      240
Glu Asp Arg Val Thr Ile Ser Ala Asp Gly Ser Thr Ser Thr Val Tyr
65                  70                  75                  80

atg gaa ttg agt ggc ctg aag tcc gag gac acg gcc gtt tat tac tgt      288
Met Glu Leu Ser Gly Leu Lys Ser Glu Asp Thr Ala Val Tyr Tyr Cys
                85                  90                  95

gcg gga tca gat ttt tgg agt ggt tat gat ggc gag ccc gac gtc ttt      336
Ala Gly Ser Asp Phe Trp Ser Gly Tyr Asp Gly Glu Pro Asp Val Phe
            100                 105                 110

gat ctc tgg ggc cga ggc acc ctg gtc acc gtc tcg agt ggt gga ggc      384
Asp Leu Trp Gly Arg Gly Thr Leu Val Thr Val Ser Ser Gly Gly Gly
        115                 120                 125

ggt tca ggc gga ggt ggc agc ggc ggt ggc gga tcg tct gag ctg act      432
Gly Ser Gly Gly Gly Gly Ser Gly Gly Gly Gly Ser Ser Glu Leu Thr
    130                 135                 140

cag gac cct gct gcg tct gtg gcc ttg gga cag aca gtc agg atc act      480
Gln Asp Pro Ala Ala Ser Val Ala Leu Gly Gln Thr Val Arg Ile Thr
145                 150                 155                 160

tgc caa gga gac agt ctc aga agc tat tac aca aac tgg ttc cag cag      528
Cys Gln Gly Asp Ser Leu Arg Ser Tyr Tyr Thr Asn Trp Phe Gln Gln
                165                 170                 175

aag cca gga cag gcc cct cta ctt gtc gtc tat gct aaa aat aag cgg      576
Lys Pro Gly Gln Ala Pro Leu Leu Val Val Tyr Ala Lys Asn Lys Arg
            180                 185                 190

ccc tca ggg atc cca gac cga ttc tct ggc tcc agc tca ggg aac aca      624
Pro Ser Gly Ile Pro Asp Arg Phe Ser Gly Ser Ser Ser Gly Asn Thr
        195                 200                 205

gct tcc ttg acc atc act ggg gct cag gcg gaa gat gag gct gac tat      672
Ala Ser Leu Thr Ile Thr Gly Ala Gln Ala Glu Asp Glu Ala Asp Tyr
    210                 215                 220

tac tgt cat tcc cgg gac agc agt ggt aac cat gtg ctt ttc ggc gga      720
Tyr Cys His Ser Arg Asp Ser Ser Gly Asn His Val Leu Phe Gly Gly
225                 230                 235                 240

ggg acc aag ctg acc gtc cta ggt                                      744
Gly Thr Lys Leu Thr Val Leu Gly
                245
```

<210> SEQ ID NO 89
<211> LENGTH: 750
<212> TYPE: DNA
<213> ORGANISM: Artificial Sequence
<220> FEATURE:
<221> NAME/KEY: CDS
<222> LOCATION: (1)..(750)
<223> OTHER INFORMATION: Polynucleotide encoding RGC0102 scFv protein

<400> SEQUENCE: 89

```
cag gtg cag ctg cag gag tcc ggc cca gga ctg gtg aag cct tcg ggg       48
Gln Val Gln Leu Gln Glu Ser Gly Pro Gly Leu Val Lys Pro Ser Gly
1               5                   10                  15

acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30

aac tac tgg agt tgg gtc cgc cag ccc cca ggg aag ggg ctg gag tgg      144
Asn Tyr Trp Ser Trp Val Arg Gln Pro Pro Gly Lys Gly Leu Glu Trp
        35                  40                  45

att ggg gag atc tat cat gat ggg agc acc aac tac aac ccg tcc ctc      192
Ile Gly Glu Ile Tyr His Asp Gly Ser Thr Asn Tyr Asn Pro Ser Leu
    50                  55                  60
```

```
aag agt cga gtc acc atg tca gca gac aag tcc aag aac cag ttc tcc      240
Lys Ser Arg Val Thr Met Ser Ala Asp Lys Ser Lys Asn Gln Phe Ser
65                  70                  75                  80

ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95

gcg aga gat tcc ccc tcg tat agc agt ggc tgg tac tct gac tac tgg      336
Ala Arg Asp Ser Pro Ser Tyr Ser Ser Gly Trp Tyr Ser Asp Tyr Trp
            100                 105                 110

ggc aga ggc acc ctg gtc acc gtc tcg agt gga ggc ggc ggt tca ggc      384
Gly Arg Gly Thr Leu Val Thr Val Ser Ser Gly Gly Gly Gly Ser Gly
        115                 120                 125

gga ggt ggc tct ggc ggt ggc gga agt gca cag tct gtg ctg act cag      432
Gly Gly Gly Ser Gly Gly Gly Gly Ser Ala Gln Ser Val Leu Thr Gln
    130                 135                 140

cca ccc tca gcg tct ggg acc ccc ggg cag agg gtc acc atc tct tgt      480
Pro Pro Ser Ala Ser Gly Thr Pro Gly Gln Arg Val Thr Ile Ser Cys
145                 150                 155                 160

tct gga agc agc tcc aac atc gga agt aat act gta aac tgg tac cag      528
Ser Gly Ser Ser Ser Asn Ile Gly Ser Asn Thr Val Asn Trp Tyr Gln
                165                 170                 175

caa ctc cca gga acg gcc ccc aaa ctc ctc atc ttt agt aat aat cag      576
Gln Leu Pro Gly Thr Ala Pro Lys Leu Leu Ile Phe Ser Asn Asn Gln
            180                 185                 190

cgg ccc tca ggg gtc cct gac cga ttc tct ggc tcc aag tct ggc acc      624
Arg Pro Ser Gly Val Pro Asp Arg Phe Ser Gly Ser Lys Ser Gly Thr
        195                 200                 205

tca gcc tcc ctg gcc atc agt ggg ctc cag tct gag gat gag gct gtt      672
Ser Ala Ser Leu Ala Ile Ser Gly Leu Gln Ser Glu Asp Glu Ala Val
    210                 215                 220

tat tac tgt gca gcg tgg gat gac agc ctg act ggt ttt tat gtc ttc      720
Tyr Tyr Cys Ala Ala Trp Asp Asp Ser Leu Thr Gly Phe Tyr Val Phe
225                 230                 235                 240

gga gct ggg acc aag gtc acc gtc cta ggt                              750
Gly Ala Gly Thr Lys Val Thr Val Leu Gly
                245                 250
```

<210> SEQ ID NO 90
<211> LENGTH: 726
<212> TYPE: DNA
<213> ORGANISM: Artificial Sequence
<220> FEATURE:
<221> NAME/KEY: CDS
<222> LOCATION: (1)..(726)
<223> OTHER INFORMATION: Polynucleotide encoding RGC0104 scFv protein

<400> SEQUENCE: 90

```
gag gtg cag ctg gtg cag tct ggg gct gag gtg agg aag cct ggg tcc       48
Glu Val Gln Leu Val Gln Ser Gly Ala Glu Val Arg Lys Pro Gly Ser
1               5                   10                  15

tca gtg aag gtc tcc tgc acg acc tct gaa aac acc ttt agg agg tct       96
Ser Val Lys Val Ser Cys Thr Thr Ser Glu Asn Thr Phe Arg Arg Ser
            20                  25                  30

agt ttc agt tgg cta cgc cag gcc cct gga caa ggt ctt gag tgg atg      144
Ser Phe Ser Trp Leu Arg Gln Ala Pro Gly Gln Gly Leu Glu Trp Met
        35                  40                  45

gga agg atc atc cct atc att cat tct gaa acc tac gca cag aac ttt      192
Gly Arg Ile Ile Pro Ile Ile His Ser Glu Thr Tyr Ala Gln Asn Phe
    50                  55                  60

cag ggc aga gtc acc atg acc gcg gac gaa tct acg agt aca gtc tat      240
Gln Gly Arg Val Thr Met Thr Ala Asp Glu Ser Thr Ser Thr Val Tyr
```

-continued

```
65                  70                  75                  80

gtg gag gtg aga agc ctg aga tct gaa gac acg gcc gtc tat tac tgt      288
Val Glu Val Arg Ser Leu Arg Ser Glu Asp Thr Ala Val Tyr Tyr Cys
                85                  90                  95

gcg aga gac tcc ccc ccc tac aat gca gac ttt gat ttc tgg ggc aga      336
Ala Arg Asp Ser Pro Pro Tyr Asn Ala Asp Phe Asp Phe Trp Gly Arg
            100                 105                 110

ggc acc ctg gtc acc gtc tcg agt gga ggc ggc ggt tca ggc gga ggt      384
Gly Thr Leu Val Thr Val Ser Ser Gly Gly Gly Gly Ser Gly Gly Gly
        115                 120                 125

ggc tct ggc ggt ggc gga agt gca cag tct gtg ctg act cag cca ccc      432
Gly Ser Gly Gly Gly Gly Ser Ala Gln Ser Val Leu Thr Gln Pro Pro
    130                 135                 140

tca gtg tcc gtg tct cca gga cag aca gcc acc atc acc tgc tct gga      480
Ser Val Ser Val Ser Pro Gly Gln Thr Ala Thr Ile Thr Cys Ser Gly
145                 150                 155                 160

gac aaa ttg ggg gat aaa tat gct tcc tgg tat cag aag aag gca gga      528
Asp Lys Leu Gly Asp Lys Tyr Ala Ser Trp Tyr Gln Lys Lys Ala Gly
                165                 170                 175

cag tcc cct gtg ctg gtc atc tat caa gat aac aag cgg ccg tca ggg      576
Gln Ser Pro Val Leu Val Ile Tyr Gln Asp Asn Lys Arg Pro Ser Gly
            180                 185                 190

atc cct gag cga ttc tct ggc tcc aac tct ggg aac aca gcc act ctg      624
Ile Pro Glu Arg Phe Ser Gly Ser Asn Ser Gly Asn Thr Ala Thr Leu
        195                 200                 205

acc atc agc ggg acc cag gct atg gat gag gct gac tat tac tgt cag      672
Thr Ile Ser Gly Thr Gln Ala Met Asp Glu Ala Asp Tyr Tyr Cys Gln
    210                 215                 220

gcg tgg gac agc agt gtg gtt ttc ggc gga ggg acc aag gtc acg gtc      720
Ala Trp Asp Ser Ser Val Val Phe Gly Gly Gly Thr Lys Val Thr Val
225                 230                 235                 240

cta ggt                                                              726
Leu Gly


<210> SEQ ID NO 91
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGC0107 scFv protein

<400> SEQUENCE: 91

cag gtg cag ctg cag gag tcg ggc cca gga ctg gtg aag ccg tcg gag       48
Gln Val Gln Leu Gln Glu Ser Gly Pro Gly Leu Val Lys Pro Ser Glu
1               5                   10                  15

act ctg tcc ctc acc tgc acc gtc tcc ggt gac tca ctt agt agg agt       96
Thr Leu Ser Leu Thr Cys Thr Val Ser Gly Asp Ser Leu Ser Arg Ser
            20                  25                  30

agt tac tac tgg ggc tgg atc cgc cag ccc cca ggg aag ggg ctg gag      144
Ser Tyr Tyr Trp Gly Trp Ile Arg Gln Pro Pro Gly Lys Gly Leu Glu
        35                  40                  45

tgg att gga agt gtc ttt tat agt ggg agc gcc gac tac aac ccg tcc      192
Trp Ile Gly Ser Val Phe Tyr Ser Gly Ser Ala Asp Tyr Asn Pro Ser
    50                  55                  60

ctc aag agt cgc gcc tcc ata tca gtg gac acg tac caa aac caa gtc      240
Leu Lys Ser Arg Ala Ser Ile Ser Val Asp Thr Tyr Gln Asn Gln Val
65                  70                  75                  80

tcc ctg aag ttg acc tct gtg acc gcc gcg gac acg gcc gtg tat tac      288
Ser Leu Lys Leu Thr Ser Val Thr Ala Ala Asp Thr Ala Val Tyr Tyr
```

```
              85                  90                  95

tgt gcg agg gat gac ggg agc acc ttc gac ccc tgg ggc cga gga acc      336
Cys Ala Arg Asp Asp Gly Ser Thr Phe Asp Pro Trp Gly Arg Gly Thr
            100                 105                 110

ctg gtc acc gtc tcg agt gga ggc ggc ggt tca ggc gga ggt ggc tct      384
Leu Val Thr Val Ser Ser Gly Gly Gly Gly Ser Gly Gly Gly Gly Ser
        115                 120                 125

ggc ggt ggc gga agt gca ctt tcc tat gtg ctg act cag cca ccc tca      432
Gly Gly Gly Gly Ser Ala Leu Ser Tyr Val Leu Thr Gln Pro Pro Ser
    130                 135                 140

gcg tct gag acc ccc ggg cag agg gtc acc atc tct tgt tct gga agc      480
Ala Ser Glu Thr Pro Gly Gln Arg Val Thr Ile Ser Cys Ser Gly Ser
145                 150                 155                 160

agc gcc aac atc gaa tat aat ttt gta tac tgg tac cag caa ctc cca      528
Ser Ala Asn Ile Glu Tyr Asn Phe Val Tyr Trp Tyr Gln Gln Leu Pro
                165                 170                 175

gga acg gcc ccc aaa ctc ctc atc tat agg aat aat cag cgg ccc tca      576
Gly Thr Ala Pro Lys Leu Leu Ile Tyr Arg Asn Asn Gln Arg Pro Ser
            180                 185                 190

ggg gtc cct gat cga ttc tct ggc tcc aag tct ggc acc tca gcc tcc      624
Gly Val Pro Asp Arg Phe Ser Gly Ser Lys Ser Gly Thr Ser Ala Ser
        195                 200                 205

ctg gcc atc agt ggg ctc cgg tcc gag gat gag gcc gat tat tac tgt      672
Leu Ala Ile Ser Gly Leu Arg Ser Glu Asp Glu Ala Asp Tyr Tyr Cys
    210                 215                 220

gca gca tgg gat gac agt ctg aat ggt tat gtc ttc gga act ggg acc      720
Ala Ala Trp Asp Asp Ser Leu Asn Gly Tyr Val Phe Gly Thr Gly Thr
225                 230                 235                 240

aag gtc acc gtc cta ggt                                              738
Lys Val Thr Val Leu Gly
                245


<210> SEQ ID NO 92
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGC0108 scFv protein

<400> SEQUENCE: 92

cag gtg cag ctg cag gag tcg ggc cca gga ctg gtg aag ccg tcg gag       48
Gln Val Gln Leu Gln Glu Ser Gly Pro Gly Leu Val Lys Pro Ser Glu
1               5                   10                  15

acc ctg tcc ctc acc tgc act gtc tct ggg gac tcc atc gac aag agt       96
Thr Leu Ser Leu Thr Cys Thr Val Ser Gly Asp Ser Ile Asp Lys Ser
            20                  25                  30

tct tac tac tgg gcc tgg atc cgt cag ccc cca ggg aag ggc ctg gag      144
Ser Tyr Tyr Trp Ala Trp Ile Arg Gln Pro Pro Gly Lys Gly Leu Glu
        35                  40                  45

tgg att gcg agt gtc ttt tac gat ggg acc gcc gac tac agt ccg tcc      192
Trp Ile Ala Ser Val Phe Tyr Asp Gly Thr Ala Asp Tyr Ser Pro Ser
    50                  55                  60

ctc agg agt cga gtc tcc atg tcg gta gac agg tcc cta aac cac gtc      240
Leu Arg Ser Arg Val Ser Met Ser Val Asp Arg Ser Leu Asn His Val
65                  70                  75                  80

tcc ctg agg ctg acc tct ctg acc gcc gcg gac acg gcc act tat tac      288
Ser Leu Arg Leu Thr Ser Leu Thr Ala Ala Asp Thr Ala Thr Tyr Tyr
                85                  90                  95

tgt gcg aga gat gac ggg agt tcg ttc gac ccc tgg ggc cga ggc acc      336
```

```
Cys Ala Arg Asp Asp Gly Ser Ser Phe Asp Pro Trp Gly Arg Gly Thr
            100                 105                 110

ctg gtc acc gtc tcg agt gga ggc ggc ggt tca ggc gga ggt ggc tct      384
Leu Val Thr Val Ser Ser Gly Gly Gly Gly Ser Gly Gly Gly Gly Ser
        115                 120                 125

ggc ggt ggc gga agt gca ctt tcc tat gtg ctg act cag cca ccc tca      432
Gly Gly Gly Gly Ser Ala Leu Ser Tyr Val Leu Thr Gln Pro Pro Ser
    130                 135                 140

gcg tct ggg acc ccc ggg cag agg gtc acc atc tct tgt tct gga agc      480
Ala Ser Gly Thr Pro Gly Gln Arg Val Thr Ile Ser Cys Ser Gly Ser
145                 150                 155                 160

agc tcc aac acc gga agt aat tat gta tac tgg tac cag cag ctc cca      528
Ser Ser Asn Thr Gly Ser Asn Tyr Val Tyr Trp Tyr Gln Gln Leu Pro
                165                 170                 175

gga acg gcc ccc aaa ctc ctc atc tat agg aat aat cag cgg ccc tca      576
Gly Thr Ala Pro Lys Leu Leu Ile Tyr Arg Asn Asn Gln Arg Pro Ser
            180                 185                 190

ggg gtc cct gac cga ttc tct ggc tcc aag tct ggc acc tca gcc tcc      624
Gly Val Pro Asp Arg Phe Ser Gly Ser Lys Ser Gly Thr Ser Ala Ser
        195                 200                 205

ctg gcc atc agt ggg ctc cgg tcc gag gat gag gct gat tat tac tgt      672
Leu Ala Ile Ser Gly Leu Arg Ser Glu Asp Glu Ala Asp Tyr Tyr Cys
    210                 215                 220

gca gca tgg gat gac agc ctg agt ggt tat gtc ttc gga act ggg acc      720
Ala Ala Trp Asp Asp Ser Leu Ser Gly Tyr Val Phe Gly Thr Gly Thr
225                 230                 235                 240

aag gtc acc gtc cta ggt                                              738
Lys Val Thr Val Leu Gly
                245


<210> SEQ ID NO 93
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGC0110 scFv protein

<400> SEQUENCE: 93

cag gtc cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15

tca gtg aag att tcc tgc aag gca tct gga tac acc ttc aac aga tat       96
Ser Val Lys Ile Ser Cys Lys Ala Ser Gly Tyr Thr Phe Asn Arg Tyr
            20                  25                  30

tac atc cac tgg gtg cga cag gcc cct gga caa gga ctt gag tgg gtg      144
Tyr Ile His Trp Val Arg Gln Ala Pro Gly Gln Gly Leu Glu Trp Val
        35                  40                  45

gga att atc aac cct cgt gga gat agc gca aat tac gca cag aag ttc      192
Gly Ile Ile Asn Pro Arg Gly Asp Ser Ala Asn Tyr Ala Gln Lys Phe
    50                  55                  60

cag ggc aga gtc acc ctg acc agg gac acg tcc gcg cgc aca gtt tac      240
Gln Gly Arg Val Thr Leu Thr Arg Asp Thr Ser Ala Arg Thr Val Tyr
65                  70                  75                  80

atg gaa atg aac agc ctg aga cct gac gac acg gcc gta tat tat tgt      288
Met Glu Met Asn Ser Leu Arg Pro Asp Asp Thr Ala Val Tyr Tyr Cys
                85                  90                  95

gcg aga gag ggg gtg gga gct act tgg gtc cac tgg ggc aaa gga acc      336
Ala Arg Glu Gly Val Gly Ala Thr Trp Val His Trp Gly Lys Gly Thr
            100                 105                 110
```

```
ctg gtc acc gtc tcg agt gga ggc ggc ggt tca ggc gga ggt ggc tct      384
Leu Val Thr Val Ser Ser Gly Gly Gly Gly Ser Gly Gly Gly Gly Ser
        115                 120                 125

ggc ggt ggc gga agt gca ctt aat ttt atg ctg act cag ccc cac tct      432
Gly Gly Gly Gly Ser Ala Leu Asn Phe Met Leu Thr Gln Pro His Ser
    130                 135                 140

gtg tcg ggg tct ccg ggg aag acg gta acc atc tcc tgc acc ggc agc      480
Val Ser Gly Ser Pro Gly Lys Thr Val Thr Ile Ser Cys Thr Gly Ser
145                 150                 155                 160

agt ggc agc att gcc agc aac tat gtg cag tgg tac cag cag cgc ccg      528
Ser Gly Ser Ile Ala Ser Asn Tyr Val Gln Trp Tyr Gln Gln Arg Pro
                165                 170                 175

ggc agt gcc ccc acc act gtg atc tat gag gat aac caa aga ccc tct      576
Gly Ser Ala Pro Thr Thr Val Ile Tyr Glu Asp Asn Gln Arg Pro Ser
            180                 185                 190

ggg gtc cct gat cgg ttc tct ggc tcc atc gac cgc tcc tcc aac tct      624
Gly Val Pro Asp Arg Phe Ser Gly Ser Ile Asp Arg Ser Ser Asn Ser
        195                 200                 205

gcc tcc ctc acc atc tct gga ctg aag act gag gac gag gct gac tac      672
Ala Ser Leu Thr Ile Ser Gly Leu Lys Thr Glu Asp Glu Ala Asp Tyr
    210                 215                 220

tac tgt cag tct tct gat acc atg ttc cag gtg ttc ggc gga ggg acc      720
Tyr Cys Gln Ser Ser Asp Thr Met Phe Gln Val Phe Gly Gly Gly Thr
225                 230                 235                 240

aag ctg acc gtc cta ggt                                              738
Lys Leu Thr Val Leu Gly
                245
```

```
<210> SEQ ID NO 94
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGC0114 scFv protein

<400> SEQUENCE: 94
```

```
cag atg cag ctg gtg cag tct ggg gct gag gtg aag aag cct ggg tcc       48
Gln Met Gln Leu Val Gln Ser Gly Ala Glu Val Lys Lys Pro Gly Ser
1               5                   10                  15

tcg gtg aag gtc tcc tgc aag gct tct gga gga acc ttc agc agc tct       96
Ser Val Lys Val Ser Cys Lys Ala Ser Gly Gly Thr Phe Ser Ser Ser
            20                  25                  30

tca atc aat tgg gtg cga cag gcc cct gga caa gga ctt gag tgg atg      144
Ser Ile Asn Trp Val Arg Gln Ala Pro Gly Gln Gly Leu Glu Trp Met
        35                  40                  45

gga gtg atc atc tct aat ctt ggt aca cca tat tat gca cag agt ttc      192
Gly Val Ile Ile Ser Asn Leu Gly Thr Pro Tyr Tyr Ala Gln Ser Phe
    50                  55                  60

cag ggc aga gtc acg ata tcc gcg gac aaa tct acg ggg act gtc tac      240
Gln Gly Arg Val Thr Ile Ser Ala Asp Lys Ser Thr Gly Thr Val Tyr
65                  70                  75                  80

ctg gac gtg agt agc ctg aga tct gac gac tcg gcc acg tat tac tgt      288
Leu Asp Val Ser Ser Leu Arg Ser Asp Asp Ser Ala Thr Tyr Tyr Cys
                85                  90                  95

gcg aga gct cgc cgg ctg tgg cag act ttt gac atc tgg ggc aag gga      336
Ala Arg Ala Arg Arg Leu Trp Gln Thr Phe Asp Ile Trp Gly Lys Gly
            100                 105                 110

acc ctg gtc acc gtc tcg agt gga ggc ggc ggt tca ggc gga ggt ggc      384
Thr Leu Val Thr Val Ser Ser Gly Gly Gly Gly Ser Gly Gly Gly Gly
        115                 120                 125
```

```
tct ggc ggt ggc gga agt gca cag tct gtg ctg acg cag ccg ccc tca      432
Ser Gly Gly Gly Gly Ser Ala Gln Ser Val Leu Thr Gln Pro Pro Ser
    130                 135                 140

gcg tct ggg gcc ccc ggg cag agg gtc gtc atc tca tgt tct gga agc      480
Ala Ser Gly Ala Pro Gly Gln Arg Val Val Ile Ser Cys Ser Gly Ser
145                 150                 155                 160

acg tcc agc att gga agt aat act gtg aac tgg tac aaa cac gtc cca      528
Thr Ser Ser Ile Gly Ser Asn Thr Val Asn Trp Tyr Lys His Val Pro
                165                 170                 175

gga gag gcc ccc aaa ctc ctc atc tac agt tcc act cag cgg ccc tca      576
Gly Glu Ala Pro Lys Leu Leu Ile Tyr Ser Ser Thr Gln Arg Pro Ser
            180                 185                 190

ggg gtc cct ggc cgc ttc tct ggc tcc acg tct ggc acc tca ggc tcc      624
Gly Val Pro Gly Arg Phe Ser Gly Ser Thr Ser Gly Thr Ser Gly Ser
        195                 200                 205

ctg acc atc agt ggg ctc cag tct ggg gat gag gct gat tac tac tgt      672
Leu Thr Ile Ser Gly Leu Gln Ser Gly Asp Glu Ala Asp Tyr Tyr Cys
    210                 215                 220

gca gca ttt gat gac agc ctg aat ggt ttt gtc ttc gga act ggg acc      720
Ala Ala Phe Asp Asp Ser Leu Asn Gly Phe Val Phe Gly Thr Gly Thr
225                 230                 235                 240

aag ctg acc gtc cta ggt                                              738
Lys Leu Thr Val Leu Gly
                245


<210> SEQ ID NO 95
<211> LENGTH: 726
<212> TYPE: DNA
<213> ORGANISM: Artificial Sequence
<220> FEATURE:
<221> NAME/KEY: CDS
<222> LOCATION: (1)..(726)
<223> OTHER INFORMATION: Polynucleotide encoding RGC0115 scFv protein

<400> SEQUENCE: 95

cag gtc acc ttg aag gag tct ggg gga ggt gtg gta cgg cct ggg ggg       48
Gln Val Thr Leu Lys Glu Ser Gly Gly Gly Val Val Arg Pro Gly Gly
1               5                   10                  15

tcc ctg aga ctc tcc tgt gca gcc tct gga ttc acc ttt gat gat tat       96
Ser Leu Arg Leu Ser Cys Ala Ala Ser Gly Phe Thr Phe Asp Asp Tyr
            20                  25                  30

ggc atg agc tgg gtc cgc caa gct cca ggg aag ggg ctg gag tgg gtc      144
Gly Met Ser Trp Val Arg Gln Ala Pro Gly Lys Gly Leu Glu Trp Val
        35                  40                  45

tct ggt att aat tgg aat ggt ggt agc aca ggt tat gca gac tct gtg      192
Ser Gly Ile Asn Trp Asn Gly Gly Ser Thr Gly Tyr Ala Asp Ser Val
    50                  55                  60

aag ggc cga ttc acc atc tcc aga gac aac gcc aag aac tcc ctg tat      240
Lys Gly Arg Phe Thr Ile Ser Arg Asp Asn Ala Lys Asn Ser Leu Tyr
65                  70                  75                  80

ctg caa atg aac agt ctg aga gcc gag gac aca gcc gtg tat tac tgt      288
Leu Gln Met Asn Ser Leu Arg Ala Glu Asp Thr Ala Val Tyr Tyr Cys
                85                  90                  95

gca aga agg cgg tat gcg ttg gat tat tgg ggc aag gga acc ctg gtc      336
Ala Arg Arg Arg Tyr Ala Leu Asp Tyr Trp Gly Lys Gly Thr Leu Val
            100                 105                 110

acc gtc tcg agt gga ggc ggc ggt tca ggc gga ggt ggc tct ggc ggt      384
Thr Val Ser Ser Gly Gly Gly Gly Ser Gly Gly Gly Gly Ser Gly Gly
        115                 120                 125

ggc gga agt gca ctt tct tct gag ctg act cag gac cct gct gtg tct      432
Gly Gly Ser Ala Leu Ser Ser Glu Leu Thr Gln Asp Pro Ala Val Ser
```

```
    130                 135                 140

gtg gcc ttg gga cag aca gtc agg atc aca tgc caa gga gac agc ctc      480
Val Ala Leu Gly Gln Thr Val Arg Ile Thr Cys Gln Gly Asp Ser Leu
145                 150                 155                 160

aga aac tat tat gca agc tgg tac cag cag aag cca gga cag gcc cct      528
Arg Asn Tyr Tyr Ala Ser Trp Tyr Gln Gln Lys Pro Gly Gln Ala Pro
                165                 170                 175

gta ctt gtc atc tat ggt aaa aac aat cgg ccc tca ggg atc cca gtc      576
Val Leu Val Ile Tyr Gly Lys Asn Asn Arg Pro Ser Gly Ile Pro Val
            180                 185                 190

cga ttc tct ggc tcc agc tca gga aac aca gct tcc ttg acc atc act      624
Arg Phe Ser Gly Ser Ser Ser Gly Asn Thr Ala Ser Leu Thr Ile Thr
        195                 200                 205

ggg act cag gcg gaa gat gga gct gac tat tac tgt aac tcc cgg gac      672
Gly Thr Gln Ala Glu Asp Gly Ala Asp Tyr Tyr Cys Asn Ser Arg Asp
    210                 215                 220

agc agt ggt aag cat gtg ata ttc ggc gga ggg acc aag gtc acc gtc      720
Ser Ser Gly Lys His Val Ile Phe Gly Gly Gly Thr Lys Val Thr Val
225                 230                 235                 240

cta ggt                                                              726
Leu Gly


<210> SEQ ID NO 96
<211> LENGTH: 756
<212> TYPE: DNA
<213> ORGANISM: Artificial Sequence
<220> FEATURE:
<221> NAME/KEY: CDS
<222> LOCATION: (1)..(756)
<223> OTHER INFORMATION: Polynucleotide encoding RGC0128 scFv protein

<400> SEQUENCE: 96

gag gtg cag ctg gtg gag tct ggg gga ggc ttg gta cag cct ggg ggg       48
Glu Val Gln Leu Val Glu Ser Gly Gly Gly Leu Val Gln Pro Gly Gly
1               5                   10                  15

tcc ctc aga ctc tcc tgt gaa gcc tct gga ttc agc ttt agt agt tat       96
Ser Leu Arg Leu Ser Cys Glu Ala Ser Gly Phe Ser Phe Ser Ser Tyr
            20                  25                  30

ggc atg agc tgg gtc cgc cag gct cca ggg aag ggg ctg gag tgg gtc      144
Gly Met Ser Trp Val Arg Gln Ala Pro Gly Lys Gly Leu Glu Trp Val
        35                  40                  45

tct agt atc act agt cgt ggt cgt ggt gga agt aca tac cac gca gat      192
Ser Ser Ile Thr Ser Arg Gly Arg Gly Gly Ser Thr Tyr His Ala Asp
    50                  55                  60

tac gtg gag ggc cgg ttc acc atc tcc aga gac gat gcc aag aac acg      240
Tyr Val Glu Gly Arg Phe Thr Ile Ser Arg Asp Asp Ala Lys Asn Thr
65                  70                  75                  80

ctg tat ctg caa atg aac agc ctg cga gcc gag gac acg gcc gta tat      288
Leu Tyr Leu Gln Met Asn Ser Leu Arg Ala Glu Asp Thr Ala Val Tyr
                85                  90                  95

tat tgt gca aaa gat tgg agt gcc tac gat agc gtc cac ctc ttt gac      336
Tyr Cys Ala Lys Asp Trp Ser Ala Tyr Asp Ser Val His Leu Phe Asp
            100                 105                 110

tac tgg ggc cga gga acc ctg gtc acc gtc tcg agt gga ggc ggc ggt      384
Tyr Trp Gly Arg Gly Thr Leu Val Thr Val Ser Ser Gly Gly Gly Gly
        115                 120                 125

tca ggc gga ggt ggc tct ggc ggt ggc gga agt gca ctt aat ttt atg      432
Ser Gly Gly Gly Gly Ser Gly Gly Gly Gly Ser Ala Leu Asn Phe Met
    130                 135                 140

ctg act cag ccc cac tct gtg tcg gag tct ccg ggg aag acg gta acc      480
Leu Thr Gln Pro His Ser Val Ser Glu Ser Pro Gly Lys Thr Val Thr
```

-continued

```
145                 150                 155                 160

atc tcc tgc acc cgc aac act gac aac att gcc ttc aac tat gtg cag      528
Ile Ser Cys Thr Arg Asn Thr Asp Asn Ile Ala Phe Asn Tyr Val Gln
                165                 170                 175

tgg ttc cag cag cgc ccg ggc agt tcc ccc acc act gtg atc tat gag      576
Trp Phe Gln Gln Arg Pro Gly Ser Ser Pro Thr Thr Val Ile Tyr Glu
            180                 185                 190

gat aac caa aga ccc tct ggg gtc cct gat cgg ttc tct ggc tcc atc      624
Asp Asn Gln Arg Pro Ser Gly Val Pro Asp Arg Phe Ser Gly Ser Ile
        195                 200                 205

gac agc tcc tcc aac tct gcc tcc ctc acc atc tct gga ctg aag act      672
Asp Ser Ser Ser Asn Ser Ala Ser Leu Thr Ile Ser Gly Leu Lys Thr
    210                 215                 220

gag gac gag gct gac tac tac tgt cag tct tat gat ggc aac aat ctg      720
Glu Asp Glu Ala Asp Tyr Tyr Cys Gln Ser Tyr Asp Gly Asn Asn Leu
225                 230                 235                 240

gtg ttc ggc gga ggg acc aag ctg acc gtc cta ggt                      756
Val Phe Gly Gly Gly Thr Lys Leu Thr Val Leu Gly
                245                 250


<210> SEQ ID NO 97
<211> LENGTH: 747
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGC0130 scFv protein

<400> SEQUENCE: 97

gaa gtg cag ctg gtg cag tct gga gct gag gtg aag aag cct ggg gcc       48
Glu Val Gln Leu Val Gln Ser Gly Ala Glu Val Lys Lys Pro Gly Ala
1               5                   10                  15

tca gtg aag gtc tcc tgc aag gct tct ggt tac acc ttt acc agc tat       96
Ser Val Lys Val Ser Cys Lys Ala Ser Gly Tyr Thr Phe Thr Ser Tyr
            20                  25                  30

ggt atc agc tgg gtg cga cag gcc cct gga caa ggg ctt gag tgg atg      144
Gly Ile Ser Trp Val Arg Gln Ala Pro Gly Gln Gly Leu Glu Trp Met
        35                  40                  45

gga tgg atc agc gct tac aat ggt aac aca aac tat gca cag aag ctc      192
Gly Trp Ile Ser Ala Tyr Asn Gly Asn Thr Asn Tyr Ala Gln Lys Leu
    50                  55                  60

cag ggc aga gtc acc atg acc aca gac aca tcc acg agc aca gcc tac      240
Gln Gly Arg Val Thr Met Thr Thr Asp Thr Ser Thr Ser Thr Ala Tyr
65                  70                  75                  80

atg gag ctg agg agc ctg aga tct gac gac acg gcc gtg tat tac tgt      288
Met Glu Leu Arg Ser Leu Arg Ser Asp Asp Thr Ala Val Tyr Tyr Cys
                85                  90                  95

gcg aga gat gcc cga cct cgg ggt ata gca gct cgt cca tta ctt agc      336
Ala Arg Asp Ala Arg Pro Arg Gly Ile Ala Ala Arg Pro Leu Leu Ser
            100                 105                 110

tac tgg ggg agg ggg acc acg gtc acc gtc tct tca ggt gga ggc ggt      384
Tyr Trp Gly Arg Gly Thr Thr Val Thr Val Ser Ser Gly Gly Gly Gly
        115                 120                 125

tca ggc gga ggt ggc agc ggc ggt ggc gga tcg cag tct gtg ttg acg      432
Ser Gly Gly Gly Gly Ser Gly Gly Gly Gly Ser Gln Ser Val Leu Thr
    130                 135                 140

cag ccg ccc tca gtg tct gcg gcc cca gga gag aag gtc acc att tcc      480
Gln Pro Pro Ser Val Ser Ala Ala Pro Gly Glu Lys Val Thr Ile Ser
145                 150                 155                 160

tgc tct gga agc acc tcc aac att ggg aat aat tat gtc tcc tgg tac      528
```

-continued

```
Cys Ser Gly Ser Thr Ser Asn Ile Gly Asn Asn Tyr Val Ser Trp Tyr
                165                 170                 175

caa cag cac cca ggc aaa gcc ccc aaa ctc atg att tat gat gtc agt      576
Gln Gln His Pro Gly Lys Ala Pro Lys Leu Met Ile Tyr Asp Val Ser
            180                 185                 190

aag cgg ccc tca ggg gtc cct gac cga ttc tct ggc tcc aag tct ggc      624
Lys Arg Pro Ser Gly Val Pro Asp Arg Phe Ser Gly Ser Lys Ser Gly
        195                 200                 205

aac acg gcg tcc ctg acc atc tct ggg gtc cag gct gag gac gag gct      672
Asn Thr Ala Ser Leu Thr Ile Ser Gly Val Gln Ala Glu Asp Glu Ala
    210                 215                 220

gat tat tac tgc agc tca tat aca agc gcc agc act gtg ata ttc ggc      720
Asp Tyr Tyr Cys Ser Ser Tyr Thr Ser Ala Ser Thr Val Ile Phe Gly
225                 230                 235                 240

gga ggg acc aag ctg acc gtc cta ggt                                  747
Gly Gly Thr Lys Leu Thr Val Leu Gly
                245


<210> SEQ ID NO 98
<211> LENGTH: 771
<212> TYPE: DNA
<213> ORGANISM: Artificial Sequence
<220> FEATURE:
<221> NAME/KEY: CDS
<222> LOCATION: (1)..(771)
<223> OTHER INFORMATION: Polynucleotide encoding RGC0131 scFv protein

<400> SEQUENCE: 98

cag gtg cag ctg gtg cag tct ggg gct gaa gtg agg aag cct ggg gcc       48
Gln Val Gln Leu Val Gln Ser Gly Ala Glu Val Arg Lys Pro Gly Ala
1               5                   10                  15

tca gtg agg gtc tcc tgc agg gct tct gga tac agc ttc acg aat tat       96
Ser Val Arg Val Ser Cys Arg Ala Ser Gly Tyr Ser Phe Thr Asn Tyr
            20                  25                  30

gat atc aac tgg gtg cga cag gcc cct ggg caa ggg ctt gag tgg atg      144
Asp Ile Asn Trp Val Arg Gln Ala Pro Gly Gln Gly Leu Glu Trp Met
        35                  40                  45

ggc tgg atg aac cct aac ggc ggt cac aca ggc tct gca cag aag ttc      192
Gly Trp Met Asn Pro Asn Gly Gly His Thr Gly Ser Ala Gln Lys Phe
    50                  55                  60

cag ggc aga gtc acc atg acc agg gac acc tcc ata aac act gcc tac      240
Gln Gly Arg Val Thr Met Thr Arg Asp Thr Ser Ile Asn Thr Ala Tyr
65                  70                  75                  80

atg gag ctg agc agc ctg aca tct gac gac acg gcc gtc tat tac tgt      288
Met Glu Leu Ser Ser Leu Thr Ser Asp Asp Thr Ala Val Tyr Tyr Cys
                85                  90                  95

gcg aga ggg tct cag tgg tgt act ggt ggt aac tgc tac gga aca cac      336
Ala Arg Gly Ser Gln Trp Cys Thr Gly Gly Asn Cys Tyr Gly Thr His
            100                 105                 110

tac tac tac atg gag gac tgg ggc cga gga acc ctg gtc acc gtc tcg      384
Tyr Tyr Tyr Met Glu Asp Trp Gly Arg Gly Thr Leu Val Thr Val Ser
        115                 120                 125

agt gga ggc ggc ggt tca ggc gga ggt ggc tct ggc ggt ggc gga agt      432
Ser Gly Gly Gly Gly Ser Gly Gly Gly Gly Ser Gly Gly Gly Gly Ser
    130                 135                 140

gca ctt aat ttt atg ctg act cag ccc cac tct gtg tcg gag tct ccg      480
Ala Leu Asn Phe Met Leu Thr Gln Pro His Ser Val Ser Glu Ser Pro
145                 150                 155                 160

ggg aag acg gta acc atc tcc tgc acc cgc aac act gac aac att gcc      528
Gly Lys Thr Val Thr Ile Ser Cys Thr Arg Asn Thr Asp Asn Ile Ala
                165                 170                 175
```

```
ttc aac tat gtg cag tgg ttc cag cag cgc ccg ggc agt tcc ccc acc      576
Phe Asn Tyr Val Gln Trp Phe Gln Gln Arg Pro Gly Ser Ser Pro Thr
            180                 185                 190

act gtg atc tat gag gat aac caa aga ccc tct ggg gtc cct gat cgg      624
Thr Val Ile Tyr Glu Asp Asn Gln Arg Pro Ser Gly Val Pro Asp Arg
        195                 200                 205

ttc tct ggc tcc atc gac agc tcc tcc aac tct gcc tcc ctc acc atc      672
Phe Ser Gly Ser Ile Asp Ser Ser Ser Asn Ser Ala Ser Leu Thr Ile
    210                 215                 220

tct gga ctg aag act gag gac gag gct gac tac tac tgt cag tct tat      720
Ser Gly Leu Lys Thr Glu Asp Glu Ala Asp Tyr Tyr Cys Gln Ser Tyr
225                 230                 235                 240

gat ggc aac aat ctg gtg ttc ggc gga ggg acc aag ctg acc gtc cta      768
Asp Gly Asn Asn Leu Val Phe Gly Gly Gly Thr Lys Leu Thr Val Leu
                245                 250                 255

ggt                                                                  771
Gly


<210> SEQ ID NO 99
<211> LENGTH: 732
<212> TYPE: DNA
<213> ORGANISM: Artificial Sequence
<220> FEATURE:
<221> NAME/KEY: CDS
<222> LOCATION: (1)..(732)
<223> OTHER INFORMATION: Polynucleotide encoding RGC0137 scFv protein

<400> SEQUENCE: 99

gag gtg cag ctg gtg cag tct ggg tct gag gtg aag aag cct ggg tcg       48
Glu Val Gln Leu Val Gln Ser Gly Ser Glu Val Lys Lys Pro Gly Ser
1               5                   10                  15

tca gtg aga gtc tcc tgc aag act tct gga gac acc ttc agg agg ttt       96
Ser Val Arg Val Ser Cys Lys Thr Ser Gly Asp Thr Phe Arg Arg Phe
            20                  25                  30

act gtc agt tgg gtg cga cag gcc cct gga cag ggg ctt gag tgg atg      144
Thr Val Ser Trp Val Arg Gln Ala Pro Gly Gln Gly Leu Glu Trp Met
        35                  40                  45

gga agg gtc atc cct ctc tac aat tct cca acc tac gcc cag aag ttc      192
Gly Arg Val Ile Pro Leu Tyr Asn Ser Pro Thr Tyr Ala Gln Lys Phe
    50                  55                  60

cag gac aga gtc acg att acc gcg gac gaa tcc acg acc aca gtc tac      240
Gln Asp Arg Val Thr Ile Thr Ala Asp Glu Ser Thr Thr Thr Val Tyr
65                  70                  75                  80

atg gag gtg acc ggc ctg aca tct gaa gac acc gcc gtc tat tac tgt      288
Met Glu Val Thr Gly Leu Thr Ser Glu Asp Thr Ala Val Tyr Tyr Cys
                85                  90                  95

gcg aga gac tcc ccc ccc tac aat gca gac ttt gat tca tgg ggc caa      336
Ala Arg Asp Ser Pro Pro Tyr Asn Ala Asp Phe Asp Ser Trp Gly Gln
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca cag gct gtg ctg act cag ccg tcg      432
Gly Ser Gly Gly Gly Gly Ser Ala Gln Ala Val Leu Thr Gln Pro Ser
    130                 135                 140

tca atg tct gtg tcc ccg gga cag acg gcc atc atc acc tgc tct gga      480
Ser Met Ser Val Ser Pro Gly Gln Thr Ala Ile Ile Thr Cys Ser Gly
145                 150                 155                 160

aat aga ttg ggg gac aaa tat gtt tcg tgg tat cag cag agg cca ggc      528
Asn Arg Leu Gly Asp Lys Tyr Val Ser Trp Tyr Gln Gln Arg Pro Gly
                165                 170                 175
```

-continued

```
cag tcc cct gtc ctg gtc ata ttt caa gat aac aag agg ccc tca gga      576
Gln Ser Pro Val Leu Val Ile Phe Gln Asp Asn Lys Arg Pro Ser Gly
            180                 185                 190

att tct gag cga ttc tct ggc tcc aac tct ggc aac aca gcc act ctg      624
Ile Ser Glu Arg Phe Ser Gly Ser Asn Ser Gly Asn Thr Ala Thr Leu
        195                 200                 205

acc atc agc gac gtc gag gcc atg gat gag gct gaa tat ttc tgt cag      672
Thr Ile Ser Asp Val Glu Ala Met Asp Glu Ala Glu Tyr Phe Cys Gln
    210                 215                 220

gcg tgg cac agt agt ttt tat tat gcc ttc gga act ggg acc aag ctg      720
Ala Trp His Ser Ser Phe Tyr Tyr Ala Phe Gly Thr Gly Thr Lys Leu
225                 230                 235                 240

acc gtc cta ggt                                                      732
Thr Val Leu Gly


<210> SEQ ID NO 100
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGC0139 scFv protein

<400> SEQUENCE: 100

gag gtg cag ctg gtg cag tct ggg gct gaa gtg aag gag ccg ggg gcc       48
Glu Val Gln Leu Val Gln Ser Gly Ala Glu Val Lys Glu Pro Gly Ala
1               5                   10                  15

tca atg aag gtt tac tgc aag gca tct gga tac agg ttc acc agg tat       96
Ser Met Lys Val Tyr Cys Lys Ala Ser Gly Tyr Arg Phe Thr Arg Tyr
            20                  25                  30

tat ata cat tgg gta cga cag gcc cct gga caa ggg ctt gag tgg atg      144
Tyr Ile His Trp Val Arg Gln Ala Pro Gly Gln Gly Leu Glu Trp Met
        35                  40                  45

gga aca atc aac cct agt gat ggt agc aca agt tac gca cag aag ttc      192
Gly Thr Ile Asn Pro Ser Asp Gly Ser Thr Ser Tyr Ala Gln Lys Phe
    50                  55                  60

cag gac aga gtc act atg acc agg gac acg tcc acg aga aca gtc tac      240
Gln Asp Arg Val Thr Met Thr Arg Asp Thr Ser Thr Arg Thr Val Tyr
65                  70                  75                  80

atg gag ttg agc agc ctg aga tct gag gac acg gcc atg tat tac tgt      288
Met Glu Leu Ser Ser Leu Arg Ser Glu Asp Thr Ala Met Tyr Tyr Cys
                85                  90                  95

ggg aga gtg gag gac tat tac tct gaa agt aat ggt cca gct gat aac      336
Gly Arg Val Glu Asp Tyr Tyr Ser Glu Ser Asn Gly Pro Ala Asp Asn
            100                 105                 110

tgg ggc cgg ggg aca atg gtc acc gtc tcg agt gga ggc ggc ggt tca      384
Trp Gly Arg Gly Thr Met Val Thr Val Ser Ser Gly Gly Gly Gly Ser
        115                 120                 125

ggc gga ggt ggc tct ggc ggt ggc gga agt gca cag tct gtg ctg acg      432
Gly Gly Gly Gly Ser Gly Gly Gly Gly Ser Ala Gln Ser Val Leu Thr
    130                 135                 140

cag ccg ccc tcg gtg tca gtg gcc cca gga cag acg gcc agc att acc      480
Gln Pro Pro Ser Val Ser Val Ala Pro Gly Gln Thr Ala Ser Ile Thr
145                 150                 155                 160

tgt ggg gga aac aag att ggg act aaa ggt gtg cac tgg tac cag cag      528
Cys Gly Gly Asn Lys Ile Gly Thr Lys Gly Val His Trp Tyr Gln Gln
                165                 170                 175

aag cca ggc cgg gcc cct gtg ctg gtc gtc tat gat gat ggc gac cgg      576
Lys Pro Gly Arg Ala Pro Val Leu Val Val Tyr Asp Asp Gly Asp Arg
            180                 185                 190
```

-continued

```
ccc tca ggg atc cct gac cga ttc tct ggc tcc aac tct gac aac acg      624
Pro Ser Gly Ile Pro Asp Arg Phe Ser Gly Ser Asn Ser Asp Asn Thr
        195                 200                 205

gcc acc ctg acc atc agc agg gtc gaa gcc ggg gat gag gcc gac tat      672
Ala Thr Leu Thr Ile Ser Arg Val Glu Ala Gly Asp Glu Ala Asp Tyr
    210                 215                 220

tac tgt cag gtg tgg gat agt gat agt gat cta ggg gta ttc ggc gga      720
Tyr Cys Gln Val Trp Asp Ser Asp Ser Asp Leu Gly Val Phe Gly Gly
225                 230                 235                 240

ggg acc aag gtc acc gtc cta ggt                                      744
Gly Thr Lys Val Thr Val Leu Gly
                245


<210> SEQ ID NO 101
<211> LENGTH: 729
<212> TYPE: DNA
<213> ORGANISM: Artificial Sequence
<220> FEATURE:
<221> NAME/KEY: CDS
<222> LOCATION: (1)..(729)
<223> OTHER INFORMATION: Polynucleotide encoding RGC0142 scFv protein

<400> SEQUENCE: 101

gaa gtg cag ctg gtg cag tct ggg gct gcg gtg aag aag cct ggg tcg       48
Glu Val Gln Leu Val Gln Ser Gly Ala Ala Val Lys Lys Pro Gly Ser
1               5                   10                  15

tcg gtg aag att tcg tgc gag gtt tct ggg ggc atc ttc aag aac tat       96
Ser Val Lys Ile Ser Cys Glu Val Ser Gly Gly Ile Phe Lys Asn Tyr
            20                  25                  30

gct atc agc tgg gtg cga cag gcc cct gga caa gga ctt gag tgg atg      144
Ala Ile Ser Trp Val Arg Gln Ala Pro Gly Gln Gly Leu Glu Trp Met
        35                  40                  45

gga gga agc atc cct atg tat ggg aca cca agt tac gct ccg aag ttc      192
Gly Gly Ser Ile Pro Met Tyr Gly Thr Pro Ser Tyr Ala Pro Lys Phe
    50                  55                  60

cag ggc aga gtc act att atc gcg gac gaa tct acg agc aca gcc tac      240
Gln Gly Arg Val Thr Ile Ile Ala Asp Glu Ser Thr Ser Thr Ala Tyr
65                  70                  75                  80

atg gag ctg agc agc ctg aga tct gag gac acg gcc atg tac tac tgt      288
Met Glu Leu Ser Ser Leu Arg Ser Glu Asp Thr Ala Met Tyr Tyr Cys
                85                  90                  95

gcg cgg gag aca act gaa gtc gat gac gct ttt gat atc tgg ggc aga      336
Ala Arg Glu Thr Thr Glu Val Asp Asp Ala Phe Asp Ile Trp Gly Arg
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca cag tct gtg ttg acg cag ccg ccc      432
Gly Ser Gly Gly Gly Gly Ser Ala Gln Ser Val Leu Thr Gln Pro Pro
    130                 135                 140

tcg gtg tct gca gcc ccc agg cag agg gtc acc atc tcc tgt tct gga      480
Ser Val Ser Ala Ala Pro Arg Gln Arg Val Thr Ile Ser Cys Ser Gly
145                 150                 155                 160

agc agt tcc aac atc gga aat aat gtt gtg aac tgg tac cag cac ttc      528
Ser Ser Ser Asn Ile Gly Asn Asn Val Val Asn Trp Tyr Gln His Phe
                165                 170                 175

ccg gga aag gct ccc agg ctc ctc atc ttc tct gat agt ctc ctg tcc      576
Pro Gly Lys Ala Pro Arg Leu Leu Ile Phe Ser Asp Ser Leu Leu Ser
            180                 185                 190

gac cga ttc tct ggc tcc aag tcc ggc acc tca gcc tcc ctg gcc atc      624
Asp Arg Phe Ser Gly Ser Lys Ser Gly Thr Ser Ala Ser Leu Ala Ile
        195                 200                 205
```

```
agt gga ctg cag tct gac gat gag gct gaa tat tac tgt gcg tca tgg      672
Ser Gly Leu Gln Ser Asp Asp Glu Ala Glu Tyr Tyr Cys Ala Ser Trp
    210                 215                 220

gat gac agc ctg aat ggt ttg gtt ttc ggc gga ggg acc aag ctg acc      720
Asp Asp Ser Leu Asn Gly Leu Val Phe Gly Gly Gly Thr Lys Leu Thr
225                 230                 235                 240

gtc cta ggt                                                          729
Val Leu Gly


<210> SEQ ID NO 102
<211> LENGTH: 729
<212> TYPE: DNA
<213> ORGANISM: Artificial Sequence
<220> FEATURE:
<221> NAME/KEY: CDS
<222> LOCATION: (1)..(729)
<223> OTHER INFORMATION: Polynucleotide encoding RGC0145 scFv protein

<400> SEQUENCE: 102

gag gtc cag ctg gtg cag tct ggg gct gag gtg aag aag cct ggg tcg       48
Glu Val Gln Leu Val Gln Ser Gly Ala Glu Val Lys Lys Pro Gly Ser
1               5                   10                  15

tcg gtg aag att tcc tgc gag gtt tct ggg ggc atc ttc aag aac tat       96
Ser Val Lys Ile Ser Cys Glu Val Ser Gly Gly Ile Phe Lys Asn Tyr
            20                  25                  30

gct atc agc tgg gtg cga cag gcc cct gga caa gga ctt gag tgg atg      144
Ala Ile Ser Trp Val Arg Gln Ala Pro Gly Gln Gly Leu Glu Trp Met
        35                  40                  45

gga gga agc atc cct atg tat ggg aca cca agt tac gct ccg aag ttc      192
Gly Gly Ser Ile Pro Met Tyr Gly Thr Pro Ser Tyr Ala Pro Lys Phe
    50                  55                  60

cag ggc aga gtc act att atc gcg gac gaa tct acg agc aca gcc tac      240
Gln Gly Arg Val Thr Ile Ile Ala Asp Glu Ser Thr Ser Thr Ala Tyr
65                  70                  75                  80

atg gag ctg agc agc ctg aga tct gag gac acg gcc atg tac tac tgt      288
Met Glu Leu Ser Ser Leu Arg Ser Glu Asp Thr Ala Met Tyr Tyr Cys
                85                  90                  95

gcg cgg gag aca act gaa gtc gat gac gct ttt aat atc tgg ggc aga      336
Ala Arg Glu Thr Thr Glu Val Asp Asp Ala Phe Asn Ile Trp Gly Arg
            100                 105                 110

ggc acc ctg gtc acc gtc tcg agt gga ggc ggc ggt tca ggc gga ggt      384
Gly Thr Leu Val Thr Val Ser Ser Gly Gly Gly Gly Ser Gly Gly Gly
        115                 120                 125

ggc tct ggc ggt ggc gga agt gca cag tct gtg ctg acg cag ccg ccc      432
Gly Ser Gly Gly Gly Gly Ser Ala Gln Ser Val Leu Thr Gln Pro Pro
    130                 135                 140

tcg gtg tct gca gcc ccc agg cag agg gtc acc atc tcc tgt tct gga      480
Ser Val Ser Ala Ala Pro Arg Gln Arg Val Thr Ile Ser Cys Ser Gly
145                 150                 155                 160

agc agt tcc aac atc gga aat aat gtt gtg aac tgg tac cag cac ttc      528
Ser Ser Ser Asn Ile Gly Asn Asn Val Val Asn Trp Tyr Gln His Phe
                165                 170                 175

ccg gga aag gct ccc agg ctc ctc atc ttt cct gat agt ctc ctg tcc      576
Pro Gly Lys Ala Pro Arg Leu Leu Ile Phe Pro Asp Ser Leu Leu Ser
            180                 185                 190

gac cga ttc tct ggc tcc aag tcc ggc acc tca gcc tcc ctg gcc atc      624
Asp Arg Phe Ser Gly Ser Lys Ser Gly Thr Ser Ala Ser Leu Ala Ile
        195                 200                 205

agt ggg ctg cag tct gac gat gag gct gaa tat tac tgt gcg tca tgg      672
Ser Gly Leu Gln Ser Asp Asp Glu Ala Glu Tyr Tyr Cys Ala Ser Trp
    210                 215                 220
```

```
gat gac agc ctg aat ggt ttg gtt ttc ggc gga ggg acc aag ctg acc      720
Asp Asp Ser Leu Asn Gly Leu Val Phe Gly Gly Gly Thr Lys Leu Thr
225                 230                 235                 240

gtc cta ggt                                                          729
Val Leu Gly


<210> SEQ ID NO 103
<211> LENGTH: 747
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGC0150 scFv protein

<400> SEQUENCE: 103

cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15

acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30

aac tac tgg agt tgg gtc cgc cag ccc cca ggg aag ggg ctg gag tgg      144
Asn Tyr Trp Ser Trp Val Arg Gln Pro Pro Gly Lys Gly Leu Glu Trp
        35                  40                  45

att ggg gag atc tat cat gat ggg agc acc aac tac aac ccg tcc ctc      192
Ile Gly Glu Ile Tyr His Asp Gly Ser Thr Asn Tyr Asn Pro Ser Leu
    50                  55                  60

aag agt cga gtc acc atg tca gca gac aag tcc aag aac cag ttc tcc      240
Lys Ser Arg Val Thr Met Ser Ala Asp Lys Ser Lys Asn Gln Phe Ser
65                  70                  75                  80

ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95

gcg aga gat tcc ccc tcg tat agc agt ggc tgg tac tct gac tac tgg      336
Ala Arg Asp Ser Pro Ser Tyr Ser Ser Gly Trp Tyr Ser Asp Tyr Trp
            100                 105                 110

ggc caa ggc acc ctg gtc acc gtc tcg agt gga ggc ggc ggt tca ggc      384
Gly Gln Gly Thr Leu Val Thr Val Ser Ser Gly Gly Gly Gly Ser Gly
        115                 120                 125

gga ggt ggc tct ggc ggt ggc gga agt gca cag tct gtg ttg acg cag      432
Gly Gly Gly Ser Gly Gly Gly Gly Ser Ala Gln Ser Val Leu Thr Gln
    130                 135                 140

ccg ccc tca gcg tct ggg acc ccc ggg cgg agg gtc acc atc tct tgt      480
Pro Pro Ser Ala Ser Gly Thr Pro Gly Arg Arg Val Thr Ile Ser Cys
145                 150                 155                 160

tcc ggg agc agc tcc aac atc gga agt aac cct gta aac tgg tac cag      528
Ser Gly Ser Ser Ser Asn Ile Gly Ser Asn Pro Val Asn Trp Tyr Gln
                165                 170                 175

caa ctc cca gga acg gcc ccc aaa atc gtc atg tat agt act gat cag      576
Gln Leu Pro Gly Thr Ala Pro Lys Ile Val Met Tyr Ser Thr Asp Gln
            180                 185                 190

cgg acc tca ggg gcc cct gac cga ttc tct ggc tcc aag tct ggc acc      624
Arg Thr Ser Gly Ala Pro Asp Arg Phe Ser Gly Ser Lys Ser Gly Thr
        195                 200                 205

tca gcc tcc ctg gcc atc act ggg ctc cag tct gag gat gag gct gat      672
Ser Ala Ser Leu Ala Ile Thr Gly Leu Gln Ser Glu Asp Glu Ala Asp
    210                 215                 220

tat ttc tgt gca aca tgg gat gac agc ccg aat gcc gtg gta ttc ggc      720
Tyr Phe Cys Ala Thr Trp Asp Asp Ser Pro Asn Ala Val Val Phe Gly
225                 230                 235                 240
```

```
gga ggg acc aag ctg acc gtc cta ggt                              747
Gly Gly Thr Lys Leu Thr Val Leu Gly
                245


<210> SEQ ID NO 104
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGC0153 scFv protein

<400> SEQUENCE: 104

gaa gtg cag ctg gtg cag tct ggg gct gag gtg aag aag cct ggg gcc       48
Glu Val Gln Leu Val Gln Ser Gly Ala Glu Val Lys Lys Pro Gly Ala
1               5                   10                  15

tca gtg aag gtc tcc tgc aag gct tct ggc tac acc ttc acc ggc gac       96
Ser Val Lys Val Ser Cys Lys Ala Ser Gly Tyr Thr Phe Thr Gly Asp
            20                  25                  30

tat ttg cac tgg gtg cga cag gcc cct gga caa ggg ctt gag tgg atg      144
Tyr Leu His Trp Val Arg Gln Ala Pro Gly Gln Gly Leu Glu Trp Met
        35                  40                  45

gga tgg atc aac cct aac act ggt ggc aca aac tat gca cag aag ttt      192
Gly Trp Ile Asn Pro Asn Thr Gly Gly Thr Asn Tyr Ala Gln Lys Phe
    50                  55                  60

cag ggc agg gtc acc atg acc agg gac acg tcc atc agc aca gcg tac      240
Gln Gly Arg Val Thr Met Thr Arg Asp Thr Ser Ile Ser Thr Ala Tyr
65                  70                  75                  80

atg gag ttg agc agg ctg aga tct gac gac acg gcc atc tat tac tgt      288
Met Glu Leu Ser Arg Leu Arg Ser Asp Asp Thr Ala Ile Tyr Tyr Cys
                85                  90                  95

gcg aga gcg cga tat tac tat gac agt act agt tac ccc ttt gac tac      336
Ala Arg Ala Arg Tyr Tyr Tyr Asp Ser Thr Ser Tyr Pro Phe Asp Tyr
            100                 105                 110

tgg ggc cgg gga acc ctg gtc acc gtc tcg agt gga ggc ggc ggt tca      384
Trp Gly Arg Gly Thr Leu Val Thr Val Ser Ser Gly Gly Gly Gly Ser
        115                 120                 125

ggc gga ggt ggc tct ggc ggt ggc gga agt gca ctt aat ttt atg ctg      432
Gly Gly Gly Gly Ser Gly Gly Gly Gly Ser Ala Leu Asn Phe Met Leu
    130                 135                 140

act cag ccc cac tct gtg tcg gag tct ccg ggt aag aca gta act ctc      480
Thr Gln Pro His Ser Val Ser Glu Ser Pro Gly Lys Thr Val Thr Leu
145                 150                 155                 160

tcc tgc acc cgc tcc agt ggc agc att tca ttc gac tat gtg cag tgg      528
Ser Cys Thr Arg Ser Ser Gly Ser Ile Ser Phe Asp Tyr Val Gln Trp
                165                 170                 175

tat caa cag cgg ccg ggc agc tcc ccc att ctt gtg atc ttt gaa gat      576
Tyr Gln Gln Arg Pro Gly Ser Ser Pro Ile Leu Val Ile Phe Glu Asp
            180                 185                 190

gac caa aga ccc tct ggg gtc cct gat cga ttc tct ggc tcc atc gac      624
Asp Gln Arg Pro Ser Gly Val Pro Asp Arg Phe Ser Gly Ser Ile Asp
        195                 200                 205

agt acc tcc aac tct gcc tcc ctc acc atc tct ggc ctg cag agt gag      672
Ser Thr Ser Asn Ser Ala Ser Leu Thr Ile Ser Gly Leu Gln Ser Glu
    210                 215                 220

gac gag ggt gac tac tat tgt cag act tat gat gac aac cgt cag gtg      720
Asp Glu Gly Asp Tyr Tyr Cys Gln Thr Tyr Asp Asp Asn Arg Gln Val
225                 230                 235                 240

ttc ggc ggg ggg acc aag gtc acc gtc cta ggt                          753
Phe Gly Gly Gly Thr Lys Val Thr Val Leu Gly
```

```
                245                 250


<210> SEQ ID NO 105
<211> LENGTH: 735
<212> TYPE: DNA
<213> ORGANISM: Artificial Sequence
<220> FEATURE:
<221> NAME/KEY: CDS
<222> LOCATION: (1)..(735)
<223> OTHER INFORMATION: Polynucleotide encoding RGC0154 scFv protein

<400> SEQUENCE: 105

cag gtc cag ctg gtg cag tct ggg gct gag gtg agg aag cct ggg tcc       48
Gln Val Gln Leu Val Gln Ser Gly Ala Glu Val Arg Lys Pro Gly Ser
1               5                   10                  15

tca gtg aag gtc tcc tgc acg acc tct gaa aac acc ttt agg agg tct       96
Ser Val Lys Val Ser Cys Thr Thr Ser Glu Asn Thr Phe Arg Arg Ser
            20                  25                  30

agt ttc agt tgg cta cgc cag gcc cct gga caa ggt ctt gag tgg atg      144
Ser Phe Ser Trp Leu Arg Gln Ala Pro Gly Gln Gly Leu Glu Trp Met
        35                  40                  45

gga agg atc atc cct atc att cat tct gaa acc tac gca cag aac ttt      192
Gly Arg Ile Ile Pro Ile Ile His Ser Glu Thr Tyr Ala Gln Asn Phe
    50                  55                  60

cag ggc agg gtc acc atg acc gcg gac gaa tct acg agt aca gtc tat      240
Gln Gly Arg Val Thr Met Thr Ala Asp Glu Ser Thr Ser Thr Val Tyr
65                  70                  75                  80

gtg gag gtg aga agc ctg aga tct gaa gac acg gcc gtc tat tac tgt      288
Val Glu Val Arg Ser Leu Arg Ser Glu Asp Thr Ala Val Tyr Tyr Cys
                85                  90                  95

gcg aga gac tcc ccc ccc tac aat gca gac ttt gat ttc tgg ggc caa      336
Ala Arg Asp Ser Pro Pro Tyr Asn Ala Asp Phe Asp Phe Trp Gly Gln
            100                 105                 110

gga acc ctg gtc acc gtc tcg agt gga ggc ggc ggt tca ggc gga ggt      384
Gly Thr Leu Val Thr Val Ser Ser Gly Gly Gly Gly Ser Gly Gly Gly
        115                 120                 125

ggc tct ggc ggt ggc gga agt gca ctt tcc tat gag ctg act cag cca      432
Gly Ser Gly Gly Gly Gly Ser Ala Leu Ser Tyr Glu Leu Thr Gln Pro
    130                 135                 140

ccc tca gtg tcc gtg tcc cca gga cag aca gcc agc atc acc tgt tct      480
Pro Ser Val Ser Val Ser Pro Gly Gln Thr Ala Ser Ile Thr Cys Ser
145                 150                 155                 160

gga gat aac tta ggg gat aag tat gtt agt tgg tat cag cag agg cca      528
Gly Asp Asn Leu Gly Asp Lys Tyr Val Ser Trp Tyr Gln Gln Arg Pro
                165                 170                 175

ggc cag tcc cct gtt ctg gtc atc tat caa gat gtc aag cgg ccc tct      576
Gly Gln Ser Pro Val Leu Val Ile Tyr Gln Asp Val Lys Arg Pro Ser
            180                 185                 190

ggg att cct gag cga ttc tct ggc tcc aac tct ggg aac aca gcc act      624
Gly Ile Pro Glu Arg Phe Ser Gly Ser Asn Ser Gly Asn Thr Ala Thr
        195                 200                 205

ctg acc atc agc ggg acc cag gct atg gat gag gct gac tac tac tgt      672
Leu Thr Ile Ser Gly Thr Gln Ala Met Asp Glu Ala Asp Tyr Tyr Cys
    210                 215                 220

cag gcg tgg gac agt aac act tct tat gtc ttc gga act ggg acc cag      720
Gln Ala Trp Asp Ser Asn Thr Ser Tyr Val Phe Gly Thr Gly Thr Gln
225                 230                 235                 240

ctc acc gtt tta agt                                                  735
Leu Thr Val Leu Ser
                245
```

```
<210> SEQ ID NO 106
<211> LENGTH: 759
<212> TYPE: DNA
<213> ORGANISM: Artificial Sequence
<220> FEATURE:
<221> NAME/KEY: CDS
<222> LOCATION: (1)..(759)
<223> OTHER INFORMATION: Polynucleotide encoding RGC0157 scFv protein

<400> SEQUENCE: 106

cag gta cag ctg cag cag tcg ggg gct gag gtg aag aag cct ggg tcc       48
Gln Val Gln Leu Gln Gln Ser Gly Ala Glu Val Lys Lys Pro Gly Ser
1               5                   10                  15

tcg gtg aag gtc tcc tgc aag gct tct gga ggc acc ttc aac agt tct       96
Ser Val Lys Val Ser Cys Lys Ala Ser Gly Gly Thr Phe Asn Ser Ser
            20                  25                  30

gct atc agt tgg gtg cga cag gcc cct gga caa ggg ctt gag tgg atg      144
Ala Ile Ser Trp Val Arg Gln Ala Pro Gly Gln Gly Leu Glu Trp Met
        35                  40                  45

gga agg atc atc cct atc ctt ggt ata gca aac tac gca cag aat ttc      192
Gly Arg Ile Ile Pro Ile Leu Gly Ile Ala Asn Tyr Ala Gln Asn Phe
    50                  55                  60

cag gac aga gtc acg att acc gcg gac aaa tcc acg agc aca gcc tac      240
Gln Asp Arg Val Thr Ile Thr Ala Asp Lys Ser Thr Ser Thr Ala Tyr
65                  70                  75                  80

atg gag ctg agc agc ctg aca tct gag gac acg gcc gtt tat tac tgt      288
Met Glu Leu Ser Ser Leu Thr Ser Glu Asp Thr Ala Val Tyr Tyr Cys
                85                  90                  95

acg aga gat tac gtg gat cca gat atg ctt acg gcc gga tac tac ttt      336
Thr Arg Asp Tyr Val Asp Pro Asp Met Leu Thr Ala Gly Tyr Tyr Phe
            100                 105                 110

gac cag tgg ggc cag gga acc ctg gtc acc gtc tcg agt gga ggc ggc      384
Asp Gln Trp Gly Gln Gly Thr Leu Val Thr Val Ser Ser Gly Gly Gly
        115                 120                 125

ggt tca ggc gga ggt ggc tct ggc ggt ggc gga agt gca ctt aat ttt      432
Gly Ser Gly Gly Gly Gly Ser Gly Gly Gly Gly Ser Ala Leu Asn Phe
    130                 135                 140

atg ctg act cag ccc cac tct gtg tcg gag tct ccg ggg aag acg gta      480
Met Leu Thr Gln Pro His Ser Val Ser Glu Ser Pro Gly Lys Thr Val
145                 150                 155                 160

acc atc tcc tgc acc cgc aac act gac aac att gcc ttc aac tat gtg      528
Thr Ile Ser Cys Thr Arg Asn Thr Asp Asn Ile Ala Phe Asn Tyr Val
                165                 170                 175

cag tgg ttc cag cag cgc ccg ggc agt tcc ccc acc act gtg atc tat      576
Gln Trp Phe Gln Gln Arg Pro Gly Ser Ser Pro Thr Thr Val Ile Tyr
            180                 185                 190

gag gat aac caa aga ccc tct ggg gtc cct gat cgg ttc tct ggc tcc      624
Glu Asp Asn Gln Arg Pro Ser Gly Val Pro Asp Arg Phe Ser Gly Ser
        195                 200                 205

atc gac agc tcc tcc aac tct gcc tcc ctc acc atc tct gga ctg aag      672
Ile Asp Ser Ser Ser Asn Ser Ala Ser Leu Thr Ile Ser Gly Leu Lys
    210                 215                 220

act gag gac gag gct gac tac tac tgt cag tct tat gat ggc aac aat      720
Thr Glu Asp Glu Ala Asp Tyr Tyr Cys Gln Ser Tyr Asp Gly Asn Asn
225                 230                 235                 240

ctg gtg ttc ggc gga ggg acc aag ctg acc gtc cta ggt                  759
Leu Val Phe Gly Gly Gly Thr Lys Leu Thr Val Leu Gly
                245                 250


<210> SEQ ID NO 107
<211> LENGTH: 741
<212> TYPE: DNA
```

```
<213> ORGANISM: Artificial Sequence
<220> FEATURE:
<221> NAME/KEY: CDS
<222> LOCATION: (1)..(741)
<223> OTHER INFORMATION: Polynucleotide encoding RGC0162 scFv protein

<400> SEQUENCE: 107

cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15

tca gtg aag gtc tct tgc aag gct gct ggg ttc agg ttc agc ggc gac      96
Ser Val Lys Val Ser Cys Lys Ala Ala Gly Phe Arg Phe Ser Gly Asp
            20                  25                  30

tat ttg cac tgg ctg cga caa gtt cct gga caa ggg cct gag tgg atg     144
Tyr Leu His Trp Leu Arg Gln Val Pro Gly Gln Gly Pro Glu Trp Met
        35                  40                  45

gga tgg atc aat ctc agc agt ggt ggc aca aat tat gga gag aag ttt     192
Gly Trp Ile Asn Leu Ser Ser Gly Gly Thr Asn Tyr Gly Glu Lys Phe
    50                  55                  60

cag ggc cgg gtc acc atg acc agg gac agg ccc agt agc aca gcc tac     240
Gln Gly Arg Val Thr Met Thr Arg Asp Arg Pro Ser Ser Thr Ala Tyr
65                  70                  75                  80

atg gaa ata aaa agt ctg aga gtt gac gac acg gcc gta tat tat tgt     288
Met Glu Ile Lys Ser Leu Arg Val Asp Asp Thr Ala Val Tyr Tyr Cys
                85                  90                  95

gcg aga gag agc ccc gta gta gag gcc atg gac gtc tgg ggc cgg gga     336
Ala Arg Glu Ser Pro Val Val Glu Ala Met Asp Val Trp Gly Arg Gly
            100                 105                 110

acc ctg gtc acc gtc tcg agt gga ggc ggc ggt tca ggc gga ggt ggc     384
Thr Leu Val Thr Val Ser Ser Gly Gly Gly Gly Ser Gly Gly Gly Gly
        115                 120                 125

tct ggc ggt ggc gga agt gca ctt aat ttt atg ctg act cag ccc cac     432
Ser Gly Gly Gly Gly Ser Ala Leu Asn Phe Met Leu Thr Gln Pro His
    130                 135                 140

tct gtg tca gag tct ccg ggg aag acg gta acc atc tcc tgc acc cgc     480
Ser Val Ser Glu Ser Pro Gly Lys Thr Val Thr Ile Ser Cys Thr Arg
145                 150                 155                 160

agc agt gac aac att gcc ttc aat tat gtg cag tgg tac cag cag cgc     528
Ser Ser Asp Asn Ile Ala Phe Asn Tyr Val Gln Trp Tyr Gln Gln Arg
                165                 170                 175

ccg ggc agt gcc ccc acc act ttg att tat gag gat aac caa aga cct     576
Pro Gly Ser Ala Pro Thr Thr Leu Ile Tyr Glu Asp Asn Gln Arg Pro
            180                 185                 190

tct ggg gtc cct gat cgg ttc tct ggc tcc atc gac agc tcc tcc aac     624
Ser Gly Val Pro Asp Arg Phe Ser Gly Ser Ile Asp Ser Ser Ser Asn
        195                 200                 205

tct gcc tcc ctc acc atc tct aat ctg aag act gag gac gaa gct gac     672
Ser Ala Ser Leu Thr Ile Ser Asn Leu Lys Thr Glu Asp Glu Ala Asp
    210                 215                 220

tac tac tgt cag tct tat gat ggc agt aat tat gtc ttc gga act ggg     720
Tyr Tyr Cys Gln Ser Tyr Asp Gly Ser Asn Tyr Val Phe Gly Thr Gly
225                 230                 235                 240

acc aag ctg acc gtc cta ggt                                         741
Thr Lys Leu Thr Val Leu Gly
                245


<210> SEQ ID NO 108
<211> LENGTH: 735
<212> TYPE: DNA
<213> ORGANISM: Artificial Sequence
<220> FEATURE:
<221> NAME/KEY: CDS
```

```
<222> LOCATION: (1)..(735)
<223> OTHER INFORMATION: Polynucleotide encoding RGC0164 scFv protein

<400> SEQUENCE: 108

gag gtc cag ctg gtg cag tct ggg gct gag gtg aag aag cct ggg gcc       48
Glu Val Gln Leu Val Gln Ser Gly Ala Glu Val Lys Lys Pro Gly Ala
1               5                   10                  15

tca gtg aag gtc tcc tgc aag gcc tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aat cct aaa agc ggt ggc aca aac tat cca cag aag ttt      192
Gly Trp Ile Asn Pro Lys Ser Gly Gly Thr Asn Tyr Pro Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gta tat tac tgt      288
Met Glu Leu Ser Arg Leu Arg Ser Asp Asp Thr Ala Val Tyr Tyr Cys
                85                  90                  95

gcg aga gag gga act ggg gac ttc ttt gac tac tgg ggc cgg gga acc      336
Ala Arg Glu Gly Thr Gly Asp Phe Phe Asp Tyr Trp Gly Arg Gly Thr
            100                 105                 110

ctg gtc acc gtc tcg agt gga ggc ggc ggt tca ggc gga ggt ggc tct      384
Leu Val Thr Val Ser Ser Gly Gly Gly Gly Ser Gly Gly Gly Gly Ser
        115                 120                 125

ggc ggt ggc gga agt gca cag cct gtg ctg act cag ccc ccc tcc gcg      432
Gly Gly Gly Gly Ser Ala Gln Pro Val Leu Thr Gln Pro Pro Ser Ala
    130                 135                 140

tcc ggg tct cct gga cag tca gtc acc atc tcc tgc act gga acc agc      480
Ser Gly Ser Pro Gly Gln Ser Val Thr Ile Ser Cys Thr Gly Thr Ser
145                 150                 155                 160

agt gac gtt ggt ggt tat aac tat gtc tcc tgg tac caa cag cac cca      528
Ser Asp Val Gly Gly Tyr Asn Tyr Val Ser Trp Tyr Gln Gln His Pro
                165                 170                 175

ggc aaa gcc ccc aaa ctc atg att tat gag gtc agt aag cgg ccc tca      576
Gly Lys Ala Pro Lys Leu Met Ile Tyr Glu Val Ser Lys Arg Pro Ser
            180                 185                 190

ggg gtc cct gat cgc ttc tct gcc tcc aag tct ggc aac acg gcc tcc      624
Gly Val Pro Asp Arg Phe Ser Ala Ser Lys Ser Gly Asn Thr Ala Ser
        195                 200                 205

ctg acc gtc tct ggg ctc cag gct gag gat gag gct tat tat tac tgc      672
Leu Thr Val Ser Gly Leu Gln Ala Glu Asp Glu Ala Tyr Tyr Tyr Cys
    210                 215                 220

agc tca tat gca ggc agc aac aat tcg gta ttc ggc gga ggg acc aag      720
Ser Ser Tyr Ala Gly Ser Asn Asn Ser Val Phe Gly Gly Gly Thr Lys
225                 230                 235                 240

ctg acc gtc cta ggt                                                  735
Leu Thr Val Leu Gly
                245


<210> SEQ ID NO 109
<211> LENGTH: 738
<212> TYPE: DNA
<213> ORGANISM: Artificial Sequence
<220> FEATURE:
<221> NAME/KEY: CDS
<222> LOCATION: (1)..(738)
<223> OTHER INFORMATION: Polynucleotide encoding RGC0169 scFv protein
```

```
<400> SEQUENCE: 109

cag gtg cag ctg cag gag tcg ggt gga ggc gtg gtc cag cct ggg ggg       48
Gln Val Gln Leu Gln Glu Ser Gly Gly Gly Val Val Gln Pro Gly Gly
1               5                   10                  15

tcc ctg aga ctc tcc tgt gca gcg tct gga ttc acc ttt aat att tat       96
Ser Leu Arg Leu Ser Cys Ala Ala Ser Gly Phe Thr Phe Asn Ile Tyr
            20                  25                  30

ggc atg cac tgg gtc cgc cag gct cca ggc aag ggg ccg gag tgg gtg      144
Gly Met His Trp Val Arg Gln Ala Pro Gly Lys Gly Pro Glu Trp Val
        35                  40                  45

gca gtt att tgg tat gat gga agc aga caa tat tat gga gac tcc gtg      192
Ala Val Ile Trp Tyr Asp Gly Ser Arg Gln Tyr Tyr Gly Asp Ser Val
    50                  55                  60

aag ggc cga ttc acc atc tcc aga gac aac tcc aag aac aca gtg tat      240
Lys Gly Arg Phe Thr Ile Ser Arg Asp Asn Ser Lys Asn Thr Val Tyr
65                  70                  75                  80

ctg caa atg aac agc ctg aga gcc gag gac acg ggt gta tat tac tgt      288
Leu Gln Met Asn Ser Leu Arg Ala Glu Asp Thr Gly Val Tyr Tyr Cys
                85                  90                  95

gcg aga gac cct agt ctg gca cct gtg tac cag ttt gac tac tgg ggc      336
Ala Arg Asp Pro Ser Leu Ala Pro Val Tyr Gln Phe Asp Tyr Trp Gly
            100                 105                 110

cgg ggg aca atg gtc acc gtc tcg agt gga ggc ggc ggt tca ggc gga      384
Arg Gly Thr Met Val Thr Val Ser Ser Gly Gly Gly Gly Ser Gly Gly
        115                 120                 125

ggt ggc tct ggc ggt ggc gga agt gca ctt gat gtt gtg atg act cag      432
Gly Gly Ser Gly Gly Gly Gly Ser Ala Leu Asp Val Val Met Thr Gln
    130                 135                 140

tct cct tcc tcc ctg tct gca tct gtg gga gag aga gtc acc atc aca      480
Ser Pro Ser Ser Leu Ser Ala Ser Val Gly Glu Arg Val Thr Ile Thr
145                 150                 155                 160

tgc cgg gca agt cag aac att ttc aac aat tta aat tgg tat caa cag      528
Cys Arg Ala Ser Gln Asn Ile Phe Asn Asn Leu Asn Trp Tyr Gln Gln
                165                 170                 175

aaa cca ggg aat gcc cct agc ctc ctg atc tct gat gca tcc agt ttg      576
Lys Pro Gly Asn Ala Pro Ser Leu Leu Ile Ser Asp Ala Ser Ser Leu
            180                 185                 190

caa agt ggg gcc cca tca agg ttc agt ggc agt gga tct ggg aca gat      624
Gln Ser Gly Ala Pro Ser Arg Phe Ser Gly Ser Gly Ser Gly Thr Asp
        195                 200                 205

tat act ctc acc atc agc agt ctg cag cct gaa gat ctt gga act tac      672
Tyr Thr Leu Thr Ile Ser Ser Leu Gln Pro Glu Asp Leu Gly Thr Tyr
    210                 215                 220

tac tgt caa cag agt tac acc atc cct ccg acc ttc ggc caa ggg aca      720
Tyr Cys Gln Gln Ser Tyr Thr Ile Pro Pro Thr Phe Gly Gln Gly Thr
225                 230                 235                 240

cga ctg gag att aaa cgt                                              738
Arg Leu Glu Ile Lys Arg
                245


<210> SEQ ID NO 110
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGC0175 scFv protein

<400> SEQUENCE: 110

gag gtg cag ctg gtg cag tct ggg gct gag gtg aag aag cct ggg gcc       48
```

-continued

```
Glu Val Gln Leu Val Gln Ser Gly Ala Glu Val Lys Lys Pro Gly Ala
1               5                   10                  15

tca gtg aag gtc tcc tgc aag gct tct ggt tac acc ttt acc agc tat       96
Ser Val Lys Val Ser Cys Lys Ala Ser Gly Tyr Thr Phe Thr Ser Tyr
            20                  25                  30

ggt atc aac tgg gtg cga cag gcc cct gga cag ggg ctt gag tgg atg      144
Gly Ile Asn Trp Val Arg Gln Ala Pro Gly Gln Gly Leu Glu Trp Met
        35                  40                  45

ggg tgg atc agc cct tac aat tat aac aca aac tat gca cag aag ttg      192
Gly Trp Ile Ser Pro Tyr Asn Tyr Asn Thr Asn Tyr Ala Gln Lys Leu
    50                  55                  60

cag ggc aga gtc acc atg acc aca gac aca tcc acg agc aca gcc tac      240
Gln Gly Arg Val Thr Met Thr Thr Asp Thr Ser Thr Ser Thr Ala Tyr
65                  70                  75                  80

atg gag ctg agg agc ctg aga tct gac gac acg gcc gtg tat tat tgt      288
Met Glu Leu Arg Ser Leu Arg Ser Asp Asp Thr Ala Val Tyr Tyr Cys
                85                  90                  95

gcg aga gag gaa acg ggg agt tat cat ggg ttt gac tac tgg ggc agg      336
Ala Arg Glu Glu Thr Gly Ser Tyr His Gly Phe Asp Tyr Trp Gly Arg
            100                 105                 110

gga acc ctg gtc acc gtc tcg agt gga ggc ggc ggt tca ggc gga ggt      384
Gly Thr Leu Val Thr Val Ser Ser Gly Gly Gly Gly Ser Gly Gly Gly
        115                 120                 125

ggc tct ggc ggt ggc gga agt gca ctt aat ttt atg ctg act cag ccc      432
Gly Ser Gly Gly Gly Gly Ser Ala Leu Asn Phe Met Leu Thr Gln Pro
    130                 135                 140

cac tct gtg tcg gag tct ccg ggg aag acg gta acc atc tcc tgc acc      480
His Ser Val Ser Glu Ser Pro Gly Lys Thr Val Thr Ile Ser Cys Thr
145                 150                 155                 160

gcc agc agt ggc aat att gcc ttc aac tat gtg cag tgg tac cag cag      528
Ala Ser Ser Gly Asn Ile Ala Phe Asn Tyr Val Gln Trp Tyr Gln Gln
                165                 170                 175

cgc ccg ggc agt gcc ccc acc att gtg atc caa gag gat aac caa aga      576
Arg Pro Gly Ser Ala Pro Thr Ile Val Ile Gln Glu Asp Asn Gln Arg
            180                 185                 190

ccc tct ggg gtc cct gat cgg ttc tct ggc tcc atc gac agg tcc tcc      624
Pro Ser Gly Val Pro Asp Arg Phe Ser Gly Ser Ile Asp Arg Ser Ser
        195                 200                 205

aac tct gcc tcc ctc acc atc tct gga ctg aag gct gag gac gaa ggt      672
Asn Ser Ala Ser Leu Thr Ile Ser Gly Leu Lys Ala Glu Asp Glu Gly
    210                 215                 220

gac tat tac tgt cag tct tat gat aag tac tac cgg atc ttc ggc ggc      720
Asp Tyr Tyr Cys Gln Ser Tyr Asp Lys Tyr Tyr Arg Ile Phe Gly Gly
225                 230                 235                 240

ggg acc aag ctg acc gtc cta ggt                                      744
Gly Thr Lys Leu Thr Val Leu Gly
                245


<210> SEQ ID NO 111
<211> LENGTH: 729
<212> TYPE: DNA
<213> ORGANISM: Artificial Sequence
<220> FEATURE:
<221> NAME/KEY: CDS
<222> LOCATION: (1)..(729)
<223> OTHER INFORMATION: Polynucleotide encoding RGD0102 scFv protein

<400> SEQUENCE: 111

gag gtc cag ctg gta cag tct gga ggt gag gtg aag aag cct ggg gac       48
Glu Val Gln Leu Val Gln Ser Gly Gly Glu Val Lys Lys Pro Gly Asp
1               5                   10                  15
```

-continued

```
tca gtg aag gtc tcc tgc aag gct tct ggt tac acc ttt tct cac tat        96
Ser Val Lys Val Ser Cys Lys Ala Ser Gly Tyr Thr Phe Ser His Tyr
            20                  25                  30

ggt ata agt tgg gtg cga cag gcc cct gga caa ggg ctt gag tgg atg       144
Gly Ile Ser Trp Val Arg Gln Ala Pro Gly Gln Gly Leu Glu Trp Met
        35                  40                  45

gga tgg acc agc gct tac agt ggt agc aca aac tat gca cag aag ttc       192
Gly Trp Thr Ser Ala Tyr Ser Gly Ser Thr Asn Tyr Ala Gln Lys Phe
    50                  55                  60

cgg ggc aga gtc acc atg acc aca gac aca tcc acg ggc aca gca tac       240
Arg Gly Arg Val Thr Met Thr Thr Asp Thr Ser Thr Gly Thr Ala Tyr
65                  70                  75                  80

atg gaa ctg agg agc ctg aga cct gac gac acg gcc gtc tat tac tgt       288
Met Glu Leu Arg Ser Leu Arg Pro Asp Asp Thr Ala Val Tyr Tyr Cys
                85                  90                  95

ggg aga gga gac agt tat ggt tcg ata ccc gct gat tac tgg ggc cgg       336
Gly Arg Gly Asp Ser Tyr Gly Ser Ile Pro Ala Asp Tyr Trp Gly Arg
            100                 105                 110

gga acc ctg gtc acc gtc tcg agt ggt gga ggc ggt tca ggc gga ggt       384
Gly Thr Leu Val Thr Val Ser Ser Gly Gly Gly Gly Ser Gly Gly Gly
        115                 120                 125

ggc agc ggc ggt ggc gga tcg gat gtt gtg atg act cag tct cca tcc       432
Gly Ser Gly Gly Gly Gly Ser Asp Val Val Met Thr Gln Ser Pro Ser
    130                 135                 140

tcc ctg tct gca tct cta gga gac aga gtc acc atc act tgc cgg gca       480
Ser Leu Ser Ala Ser Leu Gly Asp Arg Val Thr Ile Thr Cys Arg Ala
145                 150                 155                 160

agt cag gac att aca aat gac tta gcc tgg tat cag cag aaa cca ggg       528
Ser Gln Asp Ile Thr Asn Asp Leu Ala Trp Tyr Gln Gln Lys Pro Gly
                165                 170                 175

aaa gcc cct aaa ctc ctg atc tat ggt gca tcc act ttg caa tat ggg       576
Lys Ala Pro Lys Leu Leu Ile Tyr Gly Ala Ser Thr Leu Gln Tyr Gly
            180                 185                 190

gtc cca acc agg ttc agc ggc agt ggg tct ggg aca aac ttc tct ctc       624
Val Pro Thr Arg Phe Ser Gly Ser Gly Ser Gly Thr Asn Phe Ser Leu
        195                 200                 205

act atc agc agc ctg cag cct gag gat ttt gcg act tac ttt tgt caa       672
Thr Ile Ser Ser Leu Gln Pro Glu Asp Phe Ala Thr Tyr Phe Cys Gln
    210                 215                 220

cag tct cac agt ttc cct ccc act ttc ggc gga ggg acc aag ctg gag       720
Gln Ser His Ser Phe Pro Pro Thr Phe Gly Gly Gly Thr Lys Leu Glu
225                 230                 235                 240

atc aaa cgt                                                           729
Ile Lys Arg


<210> SEQ ID NO 112
<211> LENGTH: 762
<212> TYPE: DNA
<213> ORGANISM: Artificial Sequence
<220> FEATURE:
<221> NAME/KEY: CDS
<222> LOCATION: (1)..(762)
<223> OTHER INFORMATION: Polynucleotide encoding RGD0108 scFv protein

<400> SEQUENCE: 112

gag gtg cag ctg ttg gag tct ggg gga ggc ttg gta cag cct ggg ggg        48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
            20                  25                  30
```

-continued

```
gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga aat tat tac gat ttt tgg cgt ggt tat caa tca cag ccc aac      336
Ala Arg Asn Tyr Tyr Asp Phe Trp Arg Gly Tyr Gln Ser Gln Pro Asn
            100                 105                 110

tac atg gac gtc tgg ggc caa ggg aca atg gtc acc gtc tcg agt gga      384
Tyr Met Asp Val Trp Gly Gln Gly Thr Met Val Thr Val Ser Ser Gly
        115                 120                 125

ggc ggc ggt tca ggc gga ggt ggc tct ggc ggt ggc gga agt gca cag      432
Gly Gly Gly Ser Gly Gly Gly Gly Ser Gly Gly Gly Gly Ser Ala Gln
    130                 135                 140

tct gtg ctg acg cag ccg ccc tca gcg tct ggg acc ccc gag cag agg      480
Ser Val Leu Thr Gln Pro Pro Ser Ala Ser Gly Thr Pro Glu Gln Arg
145                 150                 155                 160

gtc acc atc tcc tgt tct gga agc agc tcc aac atc gga tat aat tat      528
Val Thr Ile Ser Cys Ser Gly Ser Ser Ser Asn Ile Gly Tyr Asn Tyr
                165                 170                 175

gta tac tgg ttc cag cac ctc ccc gga acg gcc ccc aag ctc ctc atc      576
Val Tyr Trp Phe Gln His Leu Pro Gly Thr Ala Pro Lys Leu Leu Ile
            180                 185                 190

tat acg aat aat ctg cgg ccc tcg ggg gtc cct gac caa ttc tct ggc      624
Tyr Thr Asn Asn Leu Arg Pro Ser Gly Val Pro Asp Gln Phe Ser Gly
        195                 200                 205

tcc aag tct ggc acc tca gcc tcc ctg gcc atc agt ggg ctc cgg tcc      672
Ser Lys Ser Gly Thr Ser Ala Ser Leu Ala Ile Ser Gly Leu Arg Ser
    210                 215                 220

gag gat gag ggt gat tat tac tgt gca gct tgg gat gac agc ctg agt      720
Glu Asp Glu Gly Asp Tyr Tyr Cys Ala Ala Trp Asp Asp Ser Leu Ser
225                 230                 235                 240

ggt cgg gtg ttc ggc gga ggg acc aag gtc acc gtc cta ggt              762
Gly Arg Val Phe Gly Gly Gly Thr Lys Val Thr Val Leu Gly
                245                 250


<210> SEQ ID NO 113
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0112 scFv protein

<400> SEQUENCE: 113

gag gtg cag ctg ttg gag tct ggg gga agc ttg gta cag cct ggg ggg       48
Glu Val Gln Leu Leu Glu Ser Gly Gly Ser Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45
```

```
tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gca aga gag gat cct tgg agc gac gct ttt gat ttg tgg ggc cga gga      336
Ala Arg Glu Asp Pro Trp Ser Asp Ala Phe Asp Leu Trp Gly Arg Gly
            100                 105                 110

acc ctg gtc acc gtc tcg agt gga ggc ggc ggt tca ggc gga ggt ggc      384
Thr Leu Val Thr Val Ser Ser Gly Gly Gly Gly Ser Gly Gly Gly Gly
        115                 120                 125

tct ggc ggt ggc gga agt gca ctt aat ttt atg ctg act cag ccc cac      432
Ser Gly Gly Gly Gly Ser Ala Leu Asn Phe Met Leu Thr Gln Pro His
    130                 135                 140

tct gtg tcg gag tct ccg ggg aag acg gta acc atc tcc tgc acc ggc      480
Ser Val Ser Glu Ser Pro Gly Lys Thr Val Thr Ile Ser Cys Thr Gly
145                 150                 155                 160

agc agt ggc agc att gcc agc aac tat gtg cag tgg tac cag cag cgc      528
Ser Ser Gly Ser Ile Ala Ser Asn Tyr Val Gln Trp Tyr Gln Gln Arg
                165                 170                 175

ccg ggc agt gcc ccc acc act gtg atc tat gag gat aac caa aga ccc      576
Pro Gly Ser Ala Pro Thr Thr Val Ile Tyr Glu Asp Asn Gln Arg Pro
            180                 185                 190

tct ggg gtc cct gat cgc ttc tct ggc tcc atc gac agc tcc tcc aac      624
Ser Gly Val Pro Asp Arg Phe Ser Gly Ser Ile Asp Ser Ser Ser Asn
        195                 200                 205

tct gcc tcc ctc acc atc tct gga ctg aag act gag gac gag gct gac      672
Ser Ala Ser Leu Thr Ile Ser Gly Leu Lys Thr Glu Asp Glu Ala Asp
    210                 215                 220

tac tac tgt cag tct tat gat agc agc aat cat tgg gtg ttc ggc gga      720
Tyr Tyr Cys Gln Ser Tyr Asp Ser Ser Asn His Trp Val Phe Gly Gly
225                 230                 235                 240

ggg acc aag ctg acc gtc cta ggt                                      744
Gly Thr Lys Leu Thr Val Leu Gly
                245
```

```
<210> SEQ ID NO 114
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0117 scFv protein

<400> SEQUENCE: 114

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gcc cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
```

-continued

```
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gca aga gat agg ggg tcc cct gat gct ttt gat atc tgg ggc cag ggg      336
Ala Arg Asp Arg Gly Ser Pro Asp Ala Phe Asp Ile Trp Gly Gln Gly
            100                 105                 110

aca atg gtc acc gtc tcg agt gga ggc ggc ggt tca ggc gga ggt ggc      384
Thr Met Val Thr Val Ser Ser Gly Gly Gly Gly Ser Gly Gly Gly Gly
        115                 120                 125

tct ggc ggt ggc gga agt gca ctt aat ttt atg ctg act cag ccc cac      432
Ser Gly Gly Gly Gly Ser Ala Leu Asn Phe Met Leu Thr Gln Pro His
    130                 135                 140

tct gtg tcg gag tct ccg ggg aag acg gtg acc atc tcc tgc acc ggc      480
Ser Val Ser Glu Ser Pro Gly Lys Thr Val Thr Ile Ser Cys Thr Gly
145                 150                 155                 160

agc agt ggc agc att gcc agc aac tat gtg cag tgg tac cag cag cgc      528
Ser Ser Gly Ser Ile Ala Ser Asn Tyr Val Gln Trp Tyr Gln Gln Arg
                165                 170                 175

ccg ggc agt gcc ccc acc act gtg atc tat gag tat agt caa aga ccc      576
Pro Gly Ser Ala Pro Thr Thr Val Ile Tyr Glu Tyr Ser Gln Arg Pro
            180                 185                 190

tct ggg gtc cct gat cgg ttc tct ggc tcc atc gac agc tcc tcc aac      624
Ser Gly Val Pro Asp Arg Phe Ser Gly Ser Ile Asp Ser Ser Ser Asn
        195                 200                 205

tct gcc tcc ctc acc atc tct ggg ctg aag act gag gac gag gct gac      672
Ser Ala Ser Leu Thr Ile Ser Gly Leu Lys Thr Glu Asp Glu Ala Asp
    210                 215                 220

tac tac tgt cag tct ttt gat acc aac aat cag ggg gtg ttc ggc gga      720
Tyr Tyr Cys Gln Ser Phe Asp Thr Asn Asn Gln Gly Val Phe Gly Gly
225                 230                 235                 240

ggg acc aag ctg acc gtc cta ggt                                      744
Gly Thr Lys Leu Thr Val Leu Gly
                245


<210> SEQ ID NO 115
<211> LENGTH: 735
<212> TYPE: DNA
<213> ORGANISM: Artificial Sequence
<220> FEATURE:
<221> NAME/KEY: CDS
<222> LOCATION: (1)..(735)
<223> OTHER INFORMATION: Polynucleotide encoding RGD0119 scFv protein

<400> SEQUENCE: 115

gag gtg cag ctg ttg gag tct ggg gga ggc ttg gta cag cca ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
```

-continued

```
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aaa ggc atc agc agc agc tgg acg tta ttt gac tac tgg ggc caa      336
Ala Lys Gly Ile Ser Ser Ser Trp Thr Leu Phe Asp Tyr Trp Gly Gln
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca ctt gaa acg aca ctc acg cag tct      432
Gly Ser Gly Gly Gly Gly Ser Ala Leu Glu Thr Thr Leu Thr Gln Ser
    130                 135                 140

cca gcc acc ctg tcc ttg tct cca ggg gaa agc gcc acc ctc tcc tgc      480
Pro Ala Thr Leu Ser Leu Ser Pro Gly Glu Ser Ala Thr Leu Ser Cys
145                 150                 155                 160

agg gcc agt cag agt att gga agt ctc tta gcc tgg tac caa cag aga      528
Arg Ala Ser Gln Ser Ile Gly Ser Leu Leu Ala Trp Tyr Gln Gln Arg
                165                 170                 175

cct ggc cag gct ccc agg ctc gtg atc tcc gat gca tcc aat agg gcc      576
Pro Gly Gln Ala Pro Arg Leu Val Ile Ser Asp Ala Ser Asn Arg Ala
            180                 185                 190

tct ggc atc cca gcc agg ttc aga ggc agt ggg tct gga aca gac ttc      624
Ser Gly Ile Pro Ala Arg Phe Arg Gly Ser Gly Ser Gly Thr Asp Phe
        195                 200                 205

act ctc acc atc agc agc cta gcg cct gaa gat ttt gca gtt tat tac      672
Thr Leu Thr Ile Ser Ser Leu Ala Pro Glu Asp Phe Ala Val Tyr Tyr
    210                 215                 220

tgt cat caa cgt agc atg tgg cct ctc agt ttc ggc gga ggg acc aag      720
Cys His Gln Arg Ser Met Trp Pro Leu Ser Phe Gly Gly Gly Thr Lys
225                 230                 235                 240

gtg gaa atc aaa cgt                                                  735
Val Glu Ile Lys Arg
                245


<210> SEQ ID NO 116
<211> LENGTH: 732
<212> TYPE: DNA
<213> ORGANISM: Artificial Sequence
<220> FEATURE:
<221> NAME/KEY: CDS
<222> LOCATION: (1)..(732)
<223> OTHER INFORMATION: Polynucleotide encoding RGD0121 scFv protein

<400> SEQUENCE: 116

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80
```

```
ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga atc cac aac tgg aac gac atg ttt gac tac tgg ggc cga ggg      336
Ala Arg Ile His Asn Trp Asn Asp Met Phe Asp Tyr Trp Gly Arg Gly
            100                 105                 110

aca atg gtc acc gtc tcg agt gga ggc ggc ggt tca ggc gga ggt ggc      384
Thr Met Val Thr Val Ser Ser Gly Gly Gly Gly Ser Gly Gly Gly Gly
        115                 120                 125

tct ggc ggt ggc gga agt gca ctt gac atc cag ttg acc cag tct cct      432
Ser Gly Gly Gly Gly Ser Ala Leu Asp Ile Gln Leu Thr Gln Ser Pro
    130                 135                 140

tcc tcc ctg tct gca tct gtt gga gac aaa gtt acc atc gct tgc cgc      480
Ser Ser Leu Ser Ala Ser Val Gly Asp Lys Val Thr Ile Ala Cys Arg
145                 150                 155                 160

cca agt cag ggc att agc agt gct tta gcc tgg tat caa cag aaa ccg      528
Pro Ser Gln Gly Ile Ser Ser Ala Leu Ala Trp Tyr Gln Gln Lys Pro
                165                 170                 175

gga aaa cct cct aga ctc ctt atc tat gat gtc tcc act ttg gaa agt      576
Gly Lys Pro Pro Arg Leu Leu Ile Tyr Asp Val Ser Thr Leu Glu Ser
            180                 185                 190

ggg gtc cca tca agg ttc agc ggc agt gga tct ggg aca tat ttc act      624
Gly Val Pro Ser Arg Phe Ser Gly Ser Gly Ser Gly Thr Tyr Phe Thr
        195                 200                 205

ctc acc atc agc agt ctg cag cct gag gat ttt gca act tat tac tgt      672
Leu Thr Ile Ser Ser Leu Gln Pro Glu Asp Phe Ala Thr Tyr Tyr Cys
    210                 215                 220

caa caa ttt gat aac tac ccg gtc acc ttc ggc caa ggg aca cga ctg      720
Gln Gln Phe Asp Asn Tyr Pro Val Thr Phe Gly Gln Gly Thr Arg Leu
225                 230                 235                 240

gag att aaa cgt                                                      732
Glu Ile Lys Arg
```

```
<210> SEQ ID NO 117
<211> LENGTH: 741
<212> TYPE: DNA
<213> ORGANISM: Artificial Sequence
<220> FEATURE:
<221> NAME/KEY: CDS
<222> LOCATION: (1)..(741)
<223> OTHER INFORMATION: Polynucleotide encoding RGD0122 scFv protein

<400> SEQUENCE: 117

gag gtg cag ctg ttg gag tct ggg gaa ggc ttg gta cag cct ggg ggg       48
Glu Val Gln Leu Leu Glu Ser Gly Glu Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95
```

-continued

```
gcg aca gat cct tac tat gat agt agt ggt tat tac ccc ttt agc tac      336
Ala Thr Asp Pro Tyr Tyr Asp Ser Ser Gly Tyr Tyr Pro Phe Ser Tyr
            100                 105                 110

tgg ggg aag ggg acc acg gtc acc gtc tcg agt gga ggc ggc ggt tca      384
Trp Gly Lys Gly Thr Thr Val Thr Val Ser Ser Gly Gly Gly Gly Ser
        115                 120                 125

ggc gga ggt ggc tct ggc ggt ggc gga agt gca cag tct gtg ctg act      432
Gly Gly Gly Gly Ser Gly Gly Gly Gly Ser Ala Gln Ser Val Leu Thr
    130                 135                 140

cag cca ccc tca gtg tca gtg gcc cca gga cag acg gcc acg att acc      480
Gln Pro Pro Ser Val Ser Val Ala Pro Gly Gln Thr Ala Thr Ile Thr
145                 150                 155                 160

tgt ggg gga gac ttt gca act aaa agt gtg aat tgg tac caa cgg aag      528
Cys Gly Gly Asp Phe Ala Thr Lys Ser Val Asn Trp Tyr Gln Arg Lys
                165                 170                 175

ccg ggc cag gcc cct gtg acg gtc atc tat tat tct acc gag cgg ccc      576
Pro Gly Gln Ala Pro Val Thr Val Ile Tyr Tyr Ser Thr Glu Arg Pro
            180                 185                 190

ccc gcg atc cct gag cgc ttc tct ggc tcc aac act ggg tcc acg gcc      624
Pro Ala Ile Pro Glu Arg Phe Ser Gly Ser Asn Thr Gly Ser Thr Ala
        195                 200                 205

acc ctg acc atc agc agg gtc gaa gcc ggg gat gag gcc gac tat tat      672
Thr Leu Thr Ile Ser Arg Val Glu Ala Gly Asp Glu Ala Asp Tyr Tyr
    210                 215                 220

tgt cag gtg tgg gac agt ttt act gat cat cgg ctg ttc ggc gga ggg      720
Cys Gln Val Trp Asp Ser Phe Thr Asp His Arg Leu Phe Gly Gly Gly
225                 230                 235                 240

acc aag ctg acc gtc cta ggt                                          741
Thr Lys Leu Thr Val Leu Gly
                245


<210> SEQ ID NO 118
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0123 scFv protein

<400> SEQUENCE: 118

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga tat gct agt ggc ttg ctt gat gct ttt gac ata tgg ggg cag      336
Ala Arg Tyr Ala Ser Gly Leu Leu Asp Ala Phe Asp Ile Trp Gly Gln
            100                 105                 110
```

-continued

```
ggg acc acg gtc acc gtc tcg agt gga ggc ggc ggt tca ggc gga ggt      384
Gly Thr Thr Val Thr Val Ser Ser Gly Gly Gly Gly Ser Gly Gly Gly
        115                 120                 125

ggc tct ggc ggt ggc gga agt gca cag tct gtg ctg acg cag ccg ccc      432
Gly Ser Gly Gly Gly Gly Ser Ala Gln Ser Val Leu Thr Gln Pro Pro
    130                 135                 140

tca gtg tct ggg gcc cca ggg cag agg gtc acc atc tcc tgc act ggg      480
Ser Val Ser Gly Ala Pro Gly Gln Arg Val Thr Ile Ser Cys Thr Gly
145                 150                 155                 160

agc agc tcc aac atc ggg gca ggt aat gat gta aat tgg tac caa caa      528
Ser Ser Ser Asn Ile Gly Ala Gly Asn Asp Val Asn Trp Tyr Gln Gln
                165                 170                 175

gtt cca gga aga gcc ccc aaa ctc ctc atc tat ggt acc acc tat cgg      576
Val Pro Gly Arg Ala Pro Lys Leu Leu Ile Tyr Gly Thr Thr Tyr Arg
            180                 185                 190

ccc tca ggg gtc cct gac cga ttc tct ggc tcc aag tct ggc acc tca      624
Pro Ser Gly Val Pro Asp Arg Phe Ser Gly Ser Lys Ser Gly Thr Ser
        195                 200                 205

gcc tcc ctg gcc atc act ggg ctc cag gct gaa gat gag gct gat tat      672
Ala Ser Leu Ala Ile Thr Gly Leu Gln Ala Glu Asp Glu Ala Asp Tyr
    210                 215                 220

ttc tgc cag tcc gat gac agc agc ctg agt ggt tcg gtc ttc ggc gga      720
Phe Cys Gln Ser Asp Asp Ser Ser Leu Ser Gly Ser Val Phe Gly Gly
225                 230                 235                 240

ggg acc aag ctg acc gtc cta ggt                                      744
Gly Thr Lys Leu Thr Val Leu Gly
                245
```

```
<210> SEQ ID NO 119
<211> LENGTH: 762
<212> TYPE: DNA
<213> ORGANISM: Artificial Sequence
<220> FEATURE:
<221> NAME/KEY: CDS
<222> LOCATION: (1)..(762)
<223> OTHER INFORMATION: Polynucleotide encoding RGD0124 scFv protein

<400> SEQUENCE: 119

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

ccc ctg aga ctc tcc tgt gca gcc tct gga ttc acc ttt agc agc tat       96
Pro Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gtg aaa gat acg gag ttt tat tac gat ttt tgg agt aat gac ggg ggc      336
Val Lys Asp Thr Glu Phe Tyr Tyr Asp Phe Trp Ser Asn Asp Gly Gly
            100                 105                 110

tgg ttc gac acc tgg ggc cgg ggg aca atg gtc acc gtc tcg agt gga      384
Trp Phe Asp Thr Trp Gly Arg Gly Thr Met Val Thr Val Ser Ser Gly
```

-continued

```
        115                 120                 125

ggc ggc ggt tca ggc gga ggt ggc tct ggc ggt ggc gga agt gca cag      432
Gly Gly Gly Ser Gly Gly Gly Gly Ser Gly Gly Gly Gly Ser Ala Gln
    130                 135                 140

gct gtg ctg act cag ccg tcc tca acg tct ggg tcc ccc ggg cag agg      480
Ala Val Leu Thr Gln Pro Ser Ser Thr Ser Gly Ser Pro Gly Gln Arg
145                 150                 155                 160

gtc acc atc tct tgt tct gga agc aac tcc aac atc gga agt aat tat      528
Val Thr Ile Ser Cys Ser Gly Ser Asn Ser Asn Ile Gly Ser Asn Tyr
                165                 170                 175

gtc tac tgg tac cag caa ctc ccg gga acg gcc ccc aaa ctc ctc att      576
Val Tyr Trp Tyr Gln Gln Leu Pro Gly Thr Ala Pro Lys Leu Leu Ile
            180                 185                 190

tat agg aat aat cag cgg ccc tca ggg gtc cct gac cga ttc tct ggc      624
Tyr Arg Asn Asn Gln Arg Pro Ser Gly Val Pro Asp Arg Phe Ser Gly
        195                 200                 205

tcc aag tct ggc acc tca gcc tcc ctg gcc atc agt ggg ctc cgg tcc      672
Ser Lys Ser Gly Thr Ser Ala Ser Leu Ala Ile Ser Gly Leu Arg Ser
    210                 215                 220

ggc gat gag ggt gat tat cac tgt gca acg tgg gat gac agg ctg tat      720
Gly Asp Glu Gly Asp Tyr His Cys Ala Thr Trp Asp Asp Arg Leu Tyr
225                 230                 235                 240

ggt tgg gtg ttc ggc gga ggg acc aag gtc acc gtc cta ggt              762
Gly Trp Val Phe Gly Gly Gly Thr Lys Val Thr Val Leu Gly
                245                 250


<210> SEQ ID NO 120
<211> LENGTH: 735
<212> TYPE: DNA
<213> ORGANISM: Artificial Sequence
<220> FEATURE:
<221> NAME/KEY: CDS
<222> LOCATION: (1)..(735)
<223> OTHER INFORMATION: Polynucleotide encoding RGD0130 scFv protein

<400> SEQUENCE: 120

gag gtg cag ctg ttg gag tct ggg gga ggc ttg gta cag cca ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aaa ggc atc agc agc agc tgg acg tta ttt gac tac tgg ggc caa      336
Ala Lys Gly Ile Ser Ser Ser Trp Thr Leu Phe Asp Tyr Trp Gly Gln
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca ctt gaa acg aca ctc acg cag tct      432
```

```
Gly Ser Gly Gly Gly Gly Ser Ala Leu Glu Thr Thr Leu Thr Gln Ser
    130                 135                 140

cca gcc acc ctg tcc ttg tct cca ggg gaa agc gcc acc ctc tcc tgc      480
Pro Ala Thr Leu Ser Leu Ser Pro Gly Glu Ser Ala Thr Leu Ser Cys
145                 150                 155                 160

agg gcc agt cag agt att gga agt ctc tta gcc tgg tac caa cag aga      528
Arg Ala Ser Gln Ser Ile Gly Ser Leu Leu Ala Trp Tyr Gln Gln Arg
                165                 170                 175

cct ggc cag gct ccc agg ctc gtg atc tcc gat gca tcc aat agg gcc      576
Pro Gly Gln Ala Pro Arg Leu Val Ile Ser Asp Ala Ser Asn Arg Ala
            180                 185                 190

tct ggc atc cca gcc agg ttc aga ggc agt ggg tct gga aca gac ttc      624
Ser Gly Ile Pro Ala Arg Phe Arg Gly Ser Gly Ser Gly Thr Asp Phe
        195                 200                 205

act ctc acc atc agc agc cta gcg cct gaa gat ttt gca gtt tat tac      672
Thr Leu Thr Ile Ser Ser Leu Ala Pro Glu Asp Phe Ala Val Tyr Tyr
    210                 215                 220

tgt caa caa cgt agc atg tgg cct ctc agt ttc ggc gga ggg acc aag      720
Cys Gln Gln Arg Ser Met Trp Pro Leu Ser Phe Gly Gly Gly Thr Lys
225                 230                 235                 240

gtg gaa atc aaa cgt                                                  735
Val Glu Ile Lys Arg
                245


<210> SEQ ID NO 121
<211> LENGTH: 747
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGD0135 scFv protein

<400> SEQUENCE: 121

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga tat gct agt ggc ttg gtt gat gct ttt gac atg tgg ggc cgg      336
Ala Arg Tyr Ala Ser Gly Leu Val Asp Ala Phe Asp Met Trp Gly Arg
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca cag gct gtg ctg act cag ccg tcc      432
Gly Ser Gly Gly Gly Gly Ser Ala Gln Ala Val Leu Thr Gln Pro Ser
    130                 135                 140
```

-continued

```
tca gtg tcc ggg gcc cca ggg cag agg gtc acc atc tcc tgc act ggg      480
Ser Val Ser Gly Ala Pro Gly Gln Arg Val Thr Ile Ser Cys Thr Gly
145                 150                 155                 160

cgc agc tcc aac atc ggg gca ggt tat gat gtt aat tgg tac cag cag      528
Arg Ser Ser Asn Ile Gly Ala Gly Tyr Asp Val Asn Trp Tyr Gln Gln
                165                 170                 175

ctt cca gga gca gcc ccc aaa ctc ctc atc tat gat aac aac tat cgg      576
Leu Pro Gly Ala Ala Pro Lys Leu Leu Ile Tyr Asp Asn Asn Tyr Arg
            180                 185                 190

ccc tcg ggg gtc cct gac cga ttc tct ggc tcc aag tct ggc acc tca      624
Pro Ser Gly Val Pro Asp Arg Phe Ser Gly Ser Lys Ser Gly Thr Ser
        195                 200                 205

gcc tcc ctg gcc ata act ggg ctc cag gct gac gat gag gct gtt tat      672
Ala Ser Leu Ala Ile Thr Gly Leu Gln Ala Asp Asp Glu Ala Val Tyr
    210                 215                 220

tac tgc cag tct tat gac agc agc ctg agt ggt tca gag gtc ttc ggc      720
Tyr Cys Gln Ser Tyr Asp Ser Ser Leu Ser Gly Ser Glu Val Phe Gly
225                 230                 235                 240

gga ggg acc aag gtc acc gtc cta ggt                                  747
Gly Gly Thr Lys Val Thr Val Leu Gly
                245
```

<210> SEQ ID NO 122
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGD0136 scFv protein

<400> SEQUENCE: 122

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac gcg gcc gtg tat tac tgt      288
Leu Gln Met Asn Ser Leu Arg Ala Glu Asp Ala Ala Val Tyr Tyr Cys
                85                  90                  95

gcg aaa gat tcc ctg gga cta tgg ttc gga ctc gga cac ttt gag aac      336
Ala Lys Asp Ser Leu Gly Leu Trp Phe Gly Leu Gly His Phe Glu Asn
            100                 105                 110

tgg ggc cgg ggc acc ctg gtc acc gtc tcg agt gga ggc ggc ggt tca      384
Trp Gly Arg Gly Thr Leu Val Thr Val Ser Ser Gly Gly Gly Gly Ser
        115                 120                 125

ggc gga ggt ggc tct ggc ggt ggc gga agt gca ctt aat ttt atg ctg      432
Gly Gly Gly Gly Ser Gly Gly Gly Gly Ser Ala Leu Asn Phe Met Leu
    130                 135                 140

act cag ccc cac tct gtg tcg gag tct ccg ggt aag aca gta act ctc      480
Thr Gln Pro His Ser Val Ser Glu Ser Pro Gly Lys Thr Val Thr Leu
145                 150                 155                 160
```

```
tcc tgc acc cgc tcc agt ggc agc att tca ttc gac tat gtg cag tgg      528
Ser Cys Thr Arg Ser Ser Gly Ser Ile Ser Phe Asp Tyr Val Gln Trp
                165                 170                 175

tat caa cag cgg ccg ggc agc tcc ccc att ctt gtg atc ttt gaa gat      576
Tyr Gln Gln Arg Pro Gly Ser Ser Pro Ile Leu Val Ile Phe Glu Asp
            180                 185                 190

gac caa aga ccc tct ggg gtc cct gat cga ttc tct ggc tcc atc gac      624
Asp Gln Arg Pro Ser Gly Val Pro Asp Arg Phe Ser Gly Ser Ile Asp
        195                 200                 205

agt acc tcc aac tct gcc tcc ctc acc atc tct ggc ctg cag agt gag      672
Ser Thr Ser Asn Ser Ala Ser Leu Thr Ile Ser Gly Leu Gln Ser Glu
    210                 215                 220

gac gag ggt gac tac tat tgt cag act tat gat gac aac cgt cag gtg      720
Asp Glu Gly Asp Tyr Tyr Cys Gln Thr Tyr Asp Asp Asn Arg Gln Val
225                 230                 235                 240

ttc ggc gga ggg acc aag ctg acc gtc cta ggt                          753
Phe Gly Gly Gly Thr Lys Leu Thr Val Leu Gly
                245                 250


<210> SEQ ID NO 123
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0141 scFv protein

<400> SEQUENCE: 123

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga gac tcc ctc tac ggt gac ctc gaa tac ttc cag cac tgg ggg      336
Ala Arg Asp Ser Leu Tyr Gly Asp Leu Glu Tyr Phe Gln His Trp Gly
            100                 105                 110

cga ggg acc acg gtc acc gtc tcg agt gga ggc ggc ggt tca ggc gga      384
Arg Gly Thr Thr Val Thr Val Ser Ser Gly Gly Gly Gly Ser Gly Gly
        115                 120                 125

ggt ggc tct ggc ggt ggc gga agt gca cag tct gtg ctg act cag cca      432
Gly Gly Ser Gly Gly Gly Gly Ser Ala Gln Ser Val Leu Thr Gln Pro
    130                 135                 140

tcc tca gcg tct ggg aac ccc gga cag agg gtc acc att tct tgt tct      480
Ser Ser Ala Ser Gly Asn Pro Gly Gln Arg Val Thr Ile Ser Cys Ser
145                 150                 155                 160

gga agc agc tcc aac atc ggg gat aat cct gtg gac tgg tat cag cat      528
Gly Ser Ser Ser Asn Ile Gly Asp Asn Pro Val Asp Trp Tyr Gln His
```

-continued

```
                165                 170                 175

gtc cca gga agg gcc ccc aaa ctc ctc atc ttt agg gat aat cag cgg      576
Val Pro Gly Arg Ala Pro Lys Leu Leu Ile Phe Arg Asp Asn Gln Arg
            180                 185                 190

ccc tca ggg gtc cct gac cga ttc tct ggc acc aag tct ggc acc tca      624
Pro Ser Gly Val Pro Asp Arg Phe Ser Gly Thr Lys Ser Gly Thr Ser
        195                 200                 205

gcc tcc ctg gcc atc agt ggc ctc cag tct gag gat gag gct gat tat      672
Ala Ser Leu Ala Ile Ser Gly Leu Gln Ser Glu Asp Glu Ala Asp Tyr
    210                 215                 220

tac tgt gaa gca tgg gat gac agc ctg gat agt ccg gtg ttc ggc gga      720
Tyr Cys Glu Ala Trp Asp Asp Ser Leu Asp Ser Pro Val Phe Gly Gly
225                 230                 235                 240

ggg acc aag ctg acc gtc cta ggt                                      744
Gly Thr Lys Leu Thr Val Leu Gly
                245


<210> SEQ ID NO 124
<211> LENGTH: 759
<212> TYPE: DNA
<213> ORGANISM: Artificial Sequence
<220> FEATURE:
<221> NAME/KEY: CDS
<222> LOCATION: (1)..(759)
<223> OTHER INFORMATION: Polynucleotide encoding RGD0143 scFv protein

<400> SEQUENCE: 124

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gcc cgc cag gct cca ggg aag ggg ctg gag tgg gtc      144
Ala Met Ser Trp Ala Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga cat cgg ggg att aca atg tat gga gtg ctc cgt cct ggc gat      336
Ala Arg His Arg Gly Ile Thr Met Tyr Gly Val Leu Arg Pro Gly Asp
            100                 105                 110

atg gac gtc tgg ggc cga gga acc ctg gtc acc gtc tcg agt gga ggc      384
Met Asp Val Trp Gly Arg Gly Thr Leu Val Thr Val Ser Ser Gly Gly
        115                 120                 125

ggc ggt tca ggc gga ggt ggc tct ggc ggt ggc gga agt gca cag gct      432
Gly Gly Ser Gly Gly Gly Gly Ser Gly Gly Gly Gly Ser Ala Gln Ala
    130                 135                 140

gtg ctg act cag ccg tcc tca gcg tct gcg acc ccc ggg cag agg gtc      480
Val Leu Thr Gln Pro Ser Ser Ala Ser Ala Thr Pro Gly Gln Arg Val
145                 150                 155                 160

acc atc tct tgt tct gga agc agc tcc aac atc gga agt aat agt gta      528
Thr Ile Ser Cys Ser Gly Ser Ser Ser Asn Ile Gly Ser Asn Ser Val
                165                 170                 175

aac tgg tac cag cac ctc cca gga acg gcc ccc aaa ctc ctc atc tat      576
```

```
Asn Trp Tyr Gln His Leu Pro Gly Thr Ala Pro Lys Leu Leu Ile Tyr
            180                 185                 190

act aat gat cag cgg ccc tca ggg gtc cct gac cga ttc tct ggc tcc      624
Thr Asn Asp Gln Arg Pro Ser Gly Val Pro Asp Arg Phe Ser Gly Ser
        195                 200                 205

aag tct ggc acc tca gcc tcc ctg gcc atc agt ggg ctc cag tct gag      672
Lys Ser Gly Thr Ser Ala Ser Leu Ala Ile Ser Gly Leu Gln Ser Glu
    210                 215                 220

gat gag gct gat tat tac tgt gca gca tgg gat gac acc ctg act ggt      720
Asp Glu Ala Asp Tyr Tyr Cys Ala Ala Trp Asp Asp Thr Leu Thr Gly
225                 230                 235                 240

ccg gtc ttc ggc gga ggg acc aag ctg acc gtc cta ggt                  759
Pro Val Phe Gly Gly Gly Thr Lys Leu Thr Val Leu Gly
                245                 250


<210> SEQ ID NO 125
<211> LENGTH: 726
<212> TYPE: DNA
<213> ORGANISM: Artificial Sequence
<220> FEATURE:
<221> NAME/KEY: CDS
<222> LOCATION: (1)..(726)
<223> OTHER INFORMATION: Polynucleotide encoding RGD0145 scFv protein

<400> SEQUENCE: 125

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga aga tac cga tac ttt gac aac tgg ggc cag ggg aca atg gtc      336
Ala Arg Arg Tyr Arg Tyr Phe Asp Asn Trp Gly Gln Gly Thr Met Val
            100                 105                 110

acc gtc tcg agt gga ggc ggc ggt tca ggc gga ggt ggc tct ggc ggt      384
Thr Val Ser Ser Gly Gly Gly Gly Ser Gly Gly Gly Gly Ser Gly Gly
        115                 120                 125

ggc gga agt gca ctt tct tct gag ctg act cag gac cct gct gtg tct      432
Gly Gly Ser Ala Leu Ser Ser Glu Leu Thr Gln Asp Pro Ala Val Ser
    130                 135                 140

gtg gcc ttg gga cag aca gtc agg atc aca tgc caa gga gac agc ctc      480
Val Ala Leu Gly Gln Thr Val Arg Ile Thr Cys Gln Gly Asp Ser Leu
145                 150                 155                 160

aga acc tat tat gca agc tgg tac cag cag aag cca gga cag gcc cct      528
Arg Thr Tyr Tyr Ala Ser Trp Tyr Gln Gln Lys Pro Gly Gln Ala Pro
                165                 170                 175

gtt ctt gtc ttc tat ggt aaa aaa aat cgg ccc tca ggg atc cca gac      576
Val Leu Val Phe Tyr Gly Lys Lys Asn Arg Pro Ser Gly Ile Pro Asp
            180                 185                 190
```

```
cga ttc tct ggc tcc agc tca gga aac aca tct tcc ttg acc atc act      624
Arg Phe Ser Gly Ser Ser Ser Gly Asn Thr Ser Ser Leu Thr Ile Thr
        195                 200                 205

ggg gct cag gca gaa gat gac gct gac tat tac tgt aac tcc cgg gac      672
Gly Ala Gln Ala Glu Asp Asp Ala Asp Tyr Tyr Cys Asn Ser Arg Asp
    210                 215                 220

agc agt ggt aac cat ctg gta ttc ggc gga ggg acc aag ctg acc gtc      720
Ser Ser Gly Asn His Leu Val Phe Gly Gly Gly Thr Lys Leu Thr Val
225                 230                 235                 240

cta ggt                                                              726
Leu Gly
```

<210> SEQ ID NO 126
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGD0153 scFv protein

<400> SEQUENCE: 126

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt acc aca tac tac gca gac tcc gtg      192
Ser Ala Ile Ser Gly Ser Gly Gly Thr Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga ttg cgg ggt agt acc agg tgg gaa gac ttc tat tac ttt gac      336
Ala Arg Leu Arg Gly Ser Thr Arg Trp Glu Asp Phe Tyr Tyr Phe Asp
            100                 105                 110

tac tgg ggc aaa ggg aca atg gtc acc gtc tcg agt gga ggc ggc ggt      384
Tyr Trp Gly Lys Gly Thr Met Val Thr Val Ser Ser Gly Gly Gly Gly
        115                 120                 125

tca ggc gga ggt ggc tct ggc ggt ggc gga agt gca cag act gtg gtg      432
Ser Gly Gly Gly Gly Ser Gly Gly Gly Gly Ser Ala Gln Thr Val Val
    130                 135                 140

atc cag gag cca tct ttc tca gtg tcc cct gga ggg aca gtc aca ctc      480
Ile Gln Glu Pro Ser Phe Ser Val Ser Pro Gly Gly Thr Val Thr Leu
145                 150                 155                 160

act tgt ggc ctg agc tct ggc tca gtc tct act act tac tac ccc agc      528
Thr Cys Gly Leu Ser Ser Gly Ser Val Ser Thr Thr Tyr Tyr Pro Ser
                165                 170                 175

tgg tac cag cag acc cca ggc cag gct cca cgc acg ctc atc tac aac      576
Trp Tyr Gln Gln Thr Pro Gly Gln Ala Pro Arg Thr Leu Ile Tyr Asn
            180                 185                 190

aca aac act cgc tct tct ggg gtc cct gat cgc ttc tct ggc tcc atc      624
Thr Asn Thr Arg Ser Ser Gly Val Pro Asp Arg Phe Ser Gly Ser Ile
        195                 200                 205
```

-continued

```
ctt ggg aac aaa gct gcc ctc acc atc acg ggg gcc cag gca gat gat      672
Leu Gly Asn Lys Ala Ala Leu Thr Ile Thr Gly Ala Gln Ala Asp Asp
    210                 215                 220

gaa tct gat tat tac tgt gtg ctg tat ctg ggt agt ggc att tgg gtg      720
Glu Ser Asp Tyr Tyr Cys Val Leu Tyr Leu Gly Ser Gly Ile Trp Val
225                 230                 235                 240

ttc ggc gga ggg acc aag ctg acc gtc cta ggt                          753
Phe Gly Gly Gly Thr Lys Leu Thr Val Leu Gly
                245                 250


<210> SEQ ID NO 127
<211> LENGTH: 741
<212> TYPE: DNA
<213> ORGANISM: Artificial Sequence
<220> FEATURE:
<221> NAME/KEY: CDS
<222> LOCATION: (1)..(741)
<223> OTHER INFORMATION: Polynucleotide encoding RGD0154 scFv protein

<400> SEQUENCE: 127

gag gtg cag ctg ttg gag tct ggg gga ggc ttg gtg cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tcg gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aca gat cct tac tat gat agt agt ggt tat tac ccc ttt agc tac      336
Ala Thr Asp Pro Tyr Tyr Asp Ser Ser Gly Tyr Tyr Pro Phe Ser Tyr
            100                 105                 110

tgg ggc cgg ggg aca atg gtc acc gtc tcg agt gga ggc ggc ggt tca      384
Trp Gly Arg Gly Thr Met Val Thr Val Ser Ser Gly Gly Gly Gly Ser
        115                 120                 125

ggc gga ggt ggc tct ggc ggt ggc gga agt gca cag tct gtc gtg acg      432
Gly Gly Gly Gly Ser Gly Gly Gly Gly Ser Ala Gln Ser Val Val Thr
    130                 135                 140

cag ccg ccc tca gtg tca gtg gcc cca gga aag acg gcc acg att acc      480
Gln Pro Pro Ser Val Ser Val Ala Pro Gly Lys Thr Ala Thr Ile Thr
145                 150                 155                 160

tgt ggg gga gac ttt gca act aaa agt gtg aat tgg tac caa cgg aag      528
Cys Gly Gly Asp Phe Ala Thr Lys Ser Val Asn Trp Tyr Gln Arg Lys
                165                 170                 175

ccg ggc cag gcc cct gtg acg gtc atc tat tat aat acc gag cgg ccc      576
Pro Gly Gln Ala Pro Val Thr Val Ile Tyr Tyr Asn Thr Glu Arg Pro
            180                 185                 190

cca gcg atc cct gag cgc ttc tct ggc tcc aac act ggg tcc acg gcc      624
Pro Ala Ile Pro Glu Arg Phe Ser Gly Ser Asn Thr Gly Ser Thr Ala
        195                 200                 205

acc ctg acc atc agc agg gtc gaa gcc ggg gat gag gcc gac tat tat      672
Thr Leu Thr Ile Ser Arg Val Glu Ala Gly Asp Glu Ala Asp Tyr Tyr
    210                 215                 220
```

```
tgt cag gtg tgg gac agt ttt act gat cat cgg ctg ttc ggc gga ggg      720
Cys Gln Val Trp Asp Ser Phe Thr Asp His Arg Leu Phe Gly Gly Gly
225                 230                 235                 240

acc aag gtc acc gtc cta ggt                                          741
Thr Lys Val Thr Val Leu Gly
                245


<210> SEQ ID NO 128
<211> LENGTH: 753
<212> TYPE: DNA
<213> ORGANISM: Artificial Sequence
<220> FEATURE:
<221> NAME/KEY: CDS
<222> LOCATION: (1)..(753)
<223> OTHER INFORMATION: Polynucleotide encoding RGD0169 scFv protein

<400> SEQUENCE: 128

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga gat aga gtg agg cgc gtt ccc ttt ggt tcg ggg agc tat tta      336
Ala Arg Asp Arg Val Arg Arg Val Pro Phe Gly Ser Gly Ser Tyr Leu
            100                 105                 110

aac ccc ttt gac tgg ggc caa ggg aca atg gtc acc gtc tcg agt gga      384
Asn Pro Phe Asp Trp Gly Gln Gly Thr Met Val Thr Val Ser Ser Gly
        115                 120                 125

ggc ggc ggt tca ggc gga ggt ggc tct ggc ggt ggc gga agt gca ctt      432
Gly Gly Gly Ser Gly Gly Gly Gly Ser Gly Gly Gly Gly Ser Ala Leu
    130                 135                 140

tcc tat gag ctg act cag cca ccc tca gtg tcc gtg tcc cca gga caa      480
Ser Tyr Glu Leu Thr Gln Pro Pro Ser Val Ser Val Ser Pro Gly Gln
145                 150                 155                 160

aca gcc agc atc acc tgt act ggg gat aaa ttg gcg gag aaa tat gtt      528
Thr Ala Ser Ile Thr Cys Thr Gly Asp Lys Leu Ala Glu Lys Tyr Val
                165                 170                 175

tct tgg tat cag cag aag aca ggc cgg tcc cct gtg ttg gtc atc tat      576
Ser Trp Tyr Gln Gln Lys Thr Gly Arg Ser Pro Val Leu Val Ile Tyr
            180                 185                 190

caa gat gac agg cgg ccc tca gag atc cct gag cga ttc tct ggc tcc      624
Gln Asp Asp Arg Arg Pro Ser Glu Ile Pro Glu Arg Phe Ser Gly Ser
        195                 200                 205

aac tct ggg aac aca gcc act ttg acc gtc agc ggg gcc cag tct atg      672
Asn Ser Gly Asn Thr Ala Thr Leu Thr Val Ser Gly Ala Gln Ser Met
    210                 215                 220

gat gag gct gac tac tac tgt caa gta tgg gac agc aac act gtg ata      720
Asp Glu Ala Asp Tyr Tyr Cys Gln Val Trp Asp Ser Asn Thr Val Ile
```

-continued

```
225                 230                 235                 240

ttc ggc gga ggg acc aag gtc acc gtc cta ggt                         753
Phe Gly Gly Gly Thr Lys Val Thr Val Leu Gly
                245                 250


<210> SEQ ID NO 129
<211> LENGTH: 747
<212> TYPE: DNA
<213> ORGANISM: Artificial Sequence
<220> FEATURE:
<221> NAME/KEY: CDS
<222> LOCATION: (1)..(747)
<223> OTHER INFORMATION: Polynucleotide encoding RGD0170 scFv protein

<400> SEQUENCE: 129

gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80

ctg caa atg aac agc ctg aga acc gag gac acg gcc gtg tat tac tgt     288
Leu Gln Met Asn Ser Leu Arg Thr Glu Asp Thr Ala Val Tyr Tyr Cys
                85                  90                  95

gcg aga cag cag ccc ttc acc gac gcg ttc gac att tgg ggc caa ggg     336
Ala Arg Gln Gln Pro Phe Thr Asp Ala Phe Asp Ile Trp Gly Gln Gly
            100                 105                 110

aca atg gtc acc gtc tcg agt gga ggc ggc ggt tca ggc gga ggt ggc     384
Thr Met Val Thr Val Ser Ser Gly Gly Gly Gly Ser Gly Gly Gly Gly
        115                 120                 125

tct ggc ggt ggc gga agt gca ctt aat ttt atg ctg act cag ccc cac     432
Ser Gly Gly Gly Gly Ser Ala Leu Asn Phe Met Leu Thr Gln Pro His
    130                 135                 140

tct gtg tcg gag tct ccg ggg aag acg gta acc atc tcc tgc acc ggc     480
Ser Val Ser Glu Ser Pro Gly Lys Thr Val Thr Ile Ser Cys Thr Gly
145                 150                 155                 160

agc agt ggc aac att gcc aac aac tat gtg cag tgg ttc caa cag cgc     528
Ser Ser Gly Asn Ile Ala Asn Asn Tyr Val Gln Trp Phe Gln Gln Arg
                165                 170                 175

ccg ggc agt gcc ccc acc act gtg atc tat gag gat aac caa aga ccc     576
Pro Gly Ser Ala Pro Thr Thr Val Ile Tyr Glu Asp Asn Gln Arg Pro
            180                 185                 190

tct ggg gtc cct gat cgg ttc tct ggc tcc atc gac agc tcc tcc aac     624
Ser Gly Val Pro Asp Arg Phe Ser Gly Ser Ile Asp Ser Ser Ser Asn
        195                 200                 205

tct gcc tcc ctc acc atc tct gga ctg aag act gag gac gag gct gac     672
Ser Ala Ser Leu Thr Ile Ser Gly Leu Lys Thr Glu Asp Glu Ala Asp
    210                 215                 220

tac tac tgt cag tct tat gat agc agc aat ctt tat gtg gta ttc ggc     720
Tyr Tyr Cys Gln Ser Tyr Asp Ser Ser Asn Leu Tyr Val Val Phe Gly
225                 230                 235                 240

gga ggg acc aag gtc acc gtc cta ggt                                 747
```

```
Gly Gly Thr Lys Val Thr Val Leu Gly
                245


<210> SEQ ID NO 130
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0180 scFv protein

<400> SEQUENCE: 130

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc gga gac aat tcc aag aac acg ctg tat      240
Lys Gly Arg Phe Thr Ile Ser Gly Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga cta ggt aac tgg aac gac gtc ttt gac tac tgg ggc caa ggg      336
Ala Arg Leu Gly Asn Trp Asn Asp Val Phe Asp Tyr Trp Gly Gln Gly
            100                 105                 110

aca atg gtc acc gtc tcg agt gga ggc ggc ggt tca ggc gga ggt ggc      384
Thr Met Val Thr Val Ser Ser Gly Gly Gly Gly Ser Gly Gly Gly Gly
        115                 120                 125

tct ggc ggt ggc gga agt gca ctt aat ttt atg ctg act cag ccc cac      432
Ser Gly Gly Gly Gly Ser Ala Leu Asn Phe Met Leu Thr Gln Pro His
    130                 135                 140

tct gtg tcg gag tct ccg ggg aag acg gta acc atc tcc tgc acc cgc      480
Ser Val Ser Glu Ser Pro Gly Lys Thr Val Thr Ile Ser Cys Thr Arg
145                 150                 155                 160

agc agt ggc agc att gcc aac aac tat gtg cag tgg tac cag cag cgc      528
Ser Ser Gly Ser Ile Ala Asn Asn Tyr Val Gln Trp Tyr Gln Gln Arg
                165                 170                 175

ccg ggc agt gcc ccc acc act gtg atc ttt gag gat gac caa aga ccc      576
Pro Gly Ser Ala Pro Thr Thr Val Ile Phe Glu Asp Asp Gln Arg Pro
            180                 185                 190

tct ggg gtc cct gat cgg ttc tct ggc tcc atc gac cgc tcc tcc aac      624
Ser Gly Val Pro Asp Arg Phe Ser Gly Ser Ile Asp Arg Ser Ser Asn
        195                 200                 205

tct gcc tcc ctc acc atc tct gga ctg aag act gac gac gag gct gac      672
Ser Ala Ser Leu Thr Ile Ser Gly Leu Lys Thr Asp Asp Glu Ala Asp
    210                 215                 220

tac tac tgt cag tct aat gat ggc acc aat cct tgg gtg ttc ggc gga      720
Tyr Tyr Cys Gln Ser Asn Asp Gly Thr Asn Pro Trp Val Phe Gly Gly
225                 230                 235                 240

ggg acc aag ctg acc gtc cta ggt                                      744
Gly Thr Lys Leu Thr Val Leu Gly
                245
```

```
<210> SEQ ID NO 131
<211> LENGTH: 744
<212> TYPE: DNA
<213> ORGANISM: Artificial Sequence
<220> FEATURE:
<221> NAME/KEY: CDS
<222> LOCATION: (1)..(744)
<223> OTHER INFORMATION: Polynucleotide encoding RGD0182 scFv protein

<400> SEQUENCE: 131

gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95

gca aga gag gat cct tgg agt gac gct ttt gat ttg tgg ggc aaa ggg     336
Ala Arg Glu Asp Pro Trp Ser Asp Ala Phe Asp Leu Trp Gly Lys Gly
            100                 105                 110

aca atg gtc acc gtc tcg agt gga ggc ggc ggt tca ggc gga ggt ggc     384
Thr Met Val Thr Val Ser Ser Gly Gly Gly Gly Ser Gly Gly Gly Gly
        115                 120                 125

tct ggc ggt ggc gga agt gca ctt aat ttt atg ctg act cag ccc cac     432
Ser Gly Gly Gly Gly Ser Ala Leu Asn Phe Met Leu Thr Gln Pro His
    130                 135                 140

tct gtg tcg gag tct ccg ggg aag acg gtc acc atc tcc tgc acc ggc     480
Ser Val Ser Glu Ser Pro Gly Lys Thr Val Thr Ile Ser Cys Thr Gly
145                 150                 155                 160

agc agt ggc agc att gcc aac aac tat gtg cag tgg tac caa cag cgc     528
Ser Ser Gly Ser Ile Ala Asn Asn Tyr Val Gln Trp Tyr Gln Gln Arg
                165                 170                 175

ccg ggc agt gcc ccc acc act gtg att tat gag gat aac caa aga ccc     576
Pro Gly Ser Ala Pro Thr Thr Val Ile Tyr Glu Asp Asn Gln Arg Pro
            180                 185                 190

tct gga gtc cct gat cgg ttc tct gcc tcc atc gac agg tcc tcc aac     624
Ser Gly Val Pro Asp Arg Phe Ser Ala Ser Ile Asp Arg Ser Ser Asn
        195                 200                 205

tct gcc tcc ctc acc atc tct gga ctg atg act gag gac gag gct gac     672
Ser Ala Ser Leu Thr Ile Ser Gly Leu Met Thr Glu Asp Glu Ala Asp
    210                 215                 220

tac tac tgt cag tct tat gat agc aac aat cat tgg gtg ttc ggc gga     720
Tyr Tyr Cys Gln Ser Tyr Asp Ser Asn Asn His Trp Val Phe Gly Gly
225                 230                 235                 240

ggg acc aag ctg acc gtc cta ggt                                     744
Gly Thr Lys Leu Thr Val Leu Gly
                245


<210> SEQ ID NO 132
<211> LENGTH: 735
```

-continued

```
<212> TYPE: DNA
<213> ORGANISM: Artificial Sequence
<220> FEATURE:
<221> NAME/KEY: CDS
<222> LOCATION: (1)..(735)
<223> OTHER INFORMATION: Polynucleotide encoding RGD0183 scFv protein

<400> SEQUENCE: 132

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg agg gga tcc gat agc agc aac tgg ttc ttt gac tac tgg ggc cag      336
Ala Arg Gly Ser Asp Ser Ser Asn Trp Phe Phe Asp Tyr Trp Gly Gln
            100                 105                 110

ggg aca atg gtc acc gtc tcg agt gga ggc ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga agt gca ctt gat gtt gtg atg act cag tct      432
Gly Ser Gly Gly Gly Gly Ser Ala Leu Asp Val Val Met Thr Gln Ser
    130                 135                 140

cca gcc acc ctg tct ttg tct cca ggg gaa aga gcc acc ctc tcc tgc      480
Pro Ala Thr Leu Ser Leu Ser Pro Gly Glu Arg Ala Thr Leu Ser Cys
145                 150                 155                 160

agg gcc agt cag agt gtt agc agc ttc tta gcc tgg tac caa cag aaa      528
Arg Ala Ser Gln Ser Val Ser Ser Phe Leu Ala Trp Tyr Gln Gln Lys
                165                 170                 175

cct ggc cag gct ccc agg ctc ctc atg tat gat gca tcc aac agg gcc      576
Pro Gly Gln Ala Pro Arg Leu Leu Met Tyr Asp Ala Ser Asn Arg Ala
            180                 185                 190

act ggc atc cca gcc agg ttc agt ggc agt ggg tct ggg aca gac ttc      624
Thr Gly Ile Pro Ala Arg Phe Ser Gly Ser Gly Ser Gly Thr Asp Phe
        195                 200                 205

act ctc acc atc agc agc cta gag cct gaa gat ttt gca gtt tat tac      672
Thr Leu Thr Ile Ser Ser Leu Glu Pro Glu Asp Phe Ala Val Tyr Tyr
    210                 215                 220

tgt cag cag cgt agc aac tgg ccg atc acc ttc ggc caa ggg aca cga      720
Cys Gln Gln Arg Ser Asn Trp Pro Ile Thr Phe Gly Gln Gly Thr Arg
225                 230                 235                 240

ctg gag att aaa cgt                                                  735
Leu Glu Ile Lys Arg
                245


<210> SEQ ID NO 133
<211> LENGTH: 726
<212> TYPE: DNA
<213> ORGANISM: Artificial Sequence
<220> FEATURE:
```

```
<221> NAME/KEY: CDS
<222> LOCATION: (1)..(726)
<223> OTHER INFORMATION: Polynucleotide encoding RGD0193 scFv protein

<400> SEQUENCE: 133

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gca aga agg cgg tat gcg ttg gat tat tgg ggc cgg ggc acc ctg gtc      336
Ala Arg Arg Arg Tyr Ala Leu Asp Tyr Trp Gly Arg Gly Thr Leu Val
            100                 105                 110

acc gtc tcg agt gga ggc ggc ggt tca ggc gga ggt ggc tct ggc ggt      384
Thr Val Ser Ser Gly Gly Gly Gly Ser Gly Gly Gly Gly Ser Gly Gly
        115                 120                 125

ggc gga agt gca ctt tct tct gag ctg act cag gac cct gct gtg tct      432
Gly Gly Ser Ala Leu Ser Ser Glu Leu Thr Gln Asp Pro Ala Val Ser
    130                 135                 140

gtg gcc ttg gga cag aca gtc agg atc aca tgc cag gga gac agc ctc      480
Val Ala Leu Gly Gln Thr Val Arg Ile Thr Cys Gln Gly Asp Ser Leu
145                 150                 155                 160

aga aac tat tat cca agc tgg tac cag cag agc cca gga cag gcc cct      528
Arg Asn Tyr Tyr Pro Ser Trp Tyr Gln Gln Ser Pro Gly Gln Ala Pro
                165                 170                 175

gta ctt gtc atc tat ggt aaa aac aag cgg ccc tca ggg atc cca gac      576
Val Leu Val Ile Tyr Gly Lys Asn Lys Arg Pro Ser Gly Ile Pro Asp
            180                 185                 190

cga ttc tct ggc tcc agc tca gga aac aca gct tcc ttg acc atc act      624
Arg Phe Ser Gly Ser Ser Ser Gly Asn Thr Ala Ser Leu Thr Ile Thr
        195                 200                 205

ggg gct cag gcg gaa gat gag gct gac tat tac tgt aac tcc cgg gac      672
Gly Ala Gln Ala Glu Asp Glu Ala Asp Tyr Tyr Cys Asn Ser Arg Asp
    210                 215                 220

agc agt ggt aac cat cta cta ttc ggc gga ggg acc aag ctg acc gtc      720
Ser Ser Gly Asn His Leu Leu Phe Gly Gly Gly Thr Lys Leu Thr Val
225                 230                 235                 240

cta ggt                                                              726
Leu Gly


<210> SEQ ID NO 134
<211> LENGTH: 741
<212> TYPE: DNA
<213> ORGANISM: Artificial Sequence
<220> FEATURE:
<221> NAME/KEY: CDS
<222> LOCATION: (1)..(741)
<223> OTHER INFORMATION: Polynucleotide encoding RGD0195 scFv protein
```

<400> SEQUENCE: 134

```
gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aca gat cct tac tat gat agt agt ggt tat tac ccc ttt agc tac      336
Ala Thr Asp Pro Tyr Tyr Asp Ser Ser Gly Tyr Tyr Pro Phe Ser Tyr
            100                 105                 110

tgg ggc caa ggg aca atg gtc acc gtc tcg agt gga ggc ggc ggt tca      384
Trp Gly Gln Gly Thr Met Val Thr Val Ser Ser Gly Gly Gly Gly Ser
        115                 120                 125

ggc gga ggt ggc tct ggc ggt ggc gga agt gca cag tct gtg ctg act      432
Gly Gly Gly Gly Ser Gly Gly Gly Gly Ser Ala Gln Ser Val Leu Thr
    130                 135                 140

cag cca ccc tca gtg tca gtg gcc cca gga aag acg gcc aca att acc      480
Gln Pro Pro Ser Val Ser Val Ala Pro Gly Lys Thr Ala Thr Ile Thr
145                 150                 155                 160

tgt ggg gga gac ttt gca act aaa aat gtg aat tgg tac caa cgg aag      528
Cys Gly Gly Asp Phe Ala Thr Lys Asn Val Asn Trp Tyr Gln Arg Lys
                165                 170                 175

ccg ggc cag gcc cct gtg acg gtc atc tat tat aat acc gag cgg ccc      576
Pro Gly Gln Ala Pro Val Thr Val Ile Tyr Tyr Asn Thr Glu Arg Pro
            180                 185                 190

tca gcg atc cct gag cgc ttc tct ggc tcc aac act ggg tcc acg gcc      624
Ser Ala Ile Pro Glu Arg Phe Ser Gly Ser Asn Thr Gly Ser Thr Ala
        195                 200                 205

acc ctg acc atc agc agg gtc gaa gcc ggg gat gag gcc gac tat tat      672
Thr Leu Thr Ile Ser Arg Val Glu Ala Gly Asp Glu Ala Asp Tyr Tyr
    210                 215                 220

tgt cag gtg tgg gat agt ttt act gat cat cgg ctg ttc ggc gga ggg      720
Cys Gln Val Trp Asp Ser Phe Thr Asp His Arg Leu Phe Gly Gly Gly
225                 230                 235                 240

acc aag ctg act gtc cta ggt                                          741
Thr Lys Leu Thr Val Leu Gly
                245
```

<210> SEQ ID NO 135
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 135

```
caggtgcagc tggtgcagtc tgg                                             23
```

<210> SEQ ID NO 136
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 136
caggtcaact taagggagtc tgg 23

<210> SEQ ID NO 137
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 137
gaggtgcagc tggtggagtc tgg 23

<210> SEQ ID NO 138
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 138
caggtgcagc tgcaggagtc ggg 23

<210> SEQ ID NO 139
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 139
gaggtgcagc tgttgcagtc tgc 23

<210> SEQ ID NO 140
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 140
caggtacagc tgcagcagtc agg 23

<210> SEQ ID NO 141
<211> LENGTH: 24
<212> TYPE: DNA
<213> ORGANISM: Artificial sequence
<220> FEATURE:
<223> OTHER INFORMATION: PCR primer useful for amplifying VH and VL domains

<400> SEQUENCE: 141
tgaggagacg gtgaccaggg tgcc 24

```
<210> SEQ ID NO 142
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 142

tgaagagacg gtgaccattg tccc                                        24


<210> SEQ ID NO 143
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 143

tgaggagacg gtgaccaggg ttcc                                        24


<210> SEQ ID NO 144
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 144

tgaggagacg gtgaccgtgg tccc                                        24


<210> SEQ ID NO 145
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 145

gacatccaga tgacccagtc tcc                                         23


<210> SEQ ID NO 146
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 146

gatgttgtga tgactcagtc tcc                                         23


<210> SEQ ID NO 147
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 147

gatattgtga tgactcagtc tcc                                         23


<210> SEQ ID NO 148
```

<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 148
gaaattgtgt tgacgcagtc tcc 23

<210> SEQ ID NO 149
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 149
gacatcgtga tgacccagtc tcc 23

<210> SEQ ID NO 150
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 150
gaaacgacac tcacgcagtc tcc 23

<210> SEQ ID NO 151
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 151
gaaattgtgc tgactcagtc tcc 23

<210> SEQ ID NO 152
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 152
cagtctgtgt tgacgcagcc gcc 23

<210> SEQ ID NO 153
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 153
cagtctgccc tgactcagcc tgc 23

<210> SEQ ID NO 154
<211> LENGTH: 23

<212> TYPE: DNA
<213> ORGANISM: Artificial sequence
<220> FEATURE:
<223> OTHER INFORMATION: PCR primer useful for amplifying VH and VL domains

<400> SEQUENCE: 154
tcctatgtgc tgactcagcc acc 23

<210> SEQ ID NO 155
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 155
tcttctgagc tgactcagga ccc 23

<210> SEQ ID NO 156
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 156
cacgttatac tgactcaacc gcc 23

<210> SEQ ID NO 157
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 157
caggctgtgc tcactcagcc gtc 23

<210> SEQ ID NO 158
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 158
aattttatgc tgactcagcc cca 23

<210> SEQ ID NO 159
<211> LENGTH: 24
<212> TYPE: DNA
<213> ORGANISM: Artificial sequence
<220> FEATURE:
<223> OTHER INFORMATION: PCR primer useful for amplifying VH and VL domains

<400> SEQUENCE: 159
acgtttgatt tccaccttgg tccc 24

<210> SEQ ID NO 160
<211> LENGTH: 24
<212> TYPE: DNA

```
<213> ORGANISM: Artificial sequence
<220> FEATURE:
<223> OTHER INFORMATION: PCR primer useful for amplifying VH and VL
      domains

<400> SEQUENCE: 160

acgtttgatc tccagcttgg tccc                                           24


<210> SEQ ID NO 161
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 161

acgtttgata tccactttgg tccc                                           24


<210> SEQ ID NO 162
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 162

acgtttgatc tccaccttgg tccc                                           24


<210> SEQ ID NO 163
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 163

acgtttaatc tccagtcgtg tccc                                           24


<210> SEQ ID NO 164
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 164

cagtctgtgt tgacgcagcc gcc                                            23


<210> SEQ ID NO 165
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 165

cagtctgccc tgactcagcc tgc                                            23


<210> SEQ ID NO 166
<211> LENGTH: 23
<212> TYPE: DNA
<213> ORGANISM: Artificial sequence
```

<220> FEATURE:
<223> OTHER INFORMATION: PCR primer useful for amplifying VH and VL domains

<400> SEQUENCE: 166
tcctatgtgc tgactcagcc acc 23

<210> SEQ ID NO 167
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 167
tcttctgagc tgactcagga ccc 23

<210> SEQ ID NO 168
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 168
cacgttatac tgactcaacc gcc 23

<210> SEQ ID NO 169
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 169
caggctgtgc tcactcagcc gtc 23

<210> SEQ ID NO 170
<211> LENGTH: 23
<212> TYPE: DNA
<213> ORGANISM: Artificial sequence
<220> FEATURE:
<223> OTHER INFORMATION: PCR primer useful for amplifying VH and VL domains

<400> SEQUENCE: 170
aattttatgc tgactcagcc cca 23

<210> SEQ ID NO 171
<211> LENGTH: 1114
<212> TYPE: DNA
<213> ORGANISM: human

<400> SEQUENCE: 171
gcacgaggcc aaacagattt gcagatcaag gagaacccag gagtttcaaa gaagcgctag 60
taaggtctct gagatccttg cactagctac atcctcaggg taggaggaag atggcttcca 120
gaagcatgcg gctgctccta ttgctgagct gcctggccaa aacaggagtc ctgggtgata 180
tcatcatgag acccagctgt gctcctggat ggttttacca caagtccaat tgctatggtt 240
acttcaggaa gctgaggaac tggtctgatg ccgagctcga gtgtcagtct tacggaaacg 300
gagcccacct ggcatctatc ctgagtttaa aggaagccag caccatagca gagtacataa 360

```
gtggctatca gagaagccag ccgatatgga ttggcctgca cgacccacag aagaggcagc    420

agtggcagtg gattgatggg gccatgtatc tgtacagatc ctggtctggc aagtccatgg    480

gtgggaacaa gcactgtgct gagatgagct ccaataacaa ctttttaact tggagcagca    540

acgaatgcaa caagcgccaa cacttcctgt gcaagtaccg accatagagc aagaatcaag    600

attctgctaa ctcctgcaca gccccgtcct cttcctttct gctagcctgg ctaaatctgc    660

tcattatttc agaggggaaa cctagcaaac taagagtgat aagggcccta ctacactggc    720

ttttttaggc ttagagacag aaactttagc attggcccag tagtggcttc tagctctaaa    780

tgtttgcccc gccatccctt tccacagtat ccttcttccc tcctcccctg tctctggctg    840

tctcgagcag tctagaagag tgcatctcca gcctatgaaa cagctgggtc tttggccata    900

agaagtaaag atttgaagac agaaggaaga aactcaggag taagcttcta gaccccttca    960

gcttctacac ccttctgccc tctctccatt gcctgcaccc caccccagcc actcaactcc   1020

tgcttgtttt tcctttggcc ataggaaggt ttaccagtag aatccttgct aggttgatgt   1080

gggccataca ttcctttaat aaaccattgt gtac                                1114
```

```
<210> SEQ ID NO 172
<211> LENGTH: 158
<212> TYPE: PRT
<213> ORGANISM: human

<400> SEQUENCE: 172

Met Ala Ser Arg Ser Met Arg Leu Leu Leu Leu Leu Ser Cys Leu Ala
1               5                   10                  15

Lys Thr Gly Val Leu Gly Asp Ile Ile Met Arg Pro Ser Cys Ala Pro
            20                  25                  30

Gly Trp Phe Tyr His Lys Ser Asn Cys Tyr Gly Tyr Phe Arg Lys Leu
        35                  40                  45

Arg Asn Trp Ser Asp Ala Glu Leu Glu Cys Gln Ser Tyr Gly Asn Gly
    50                  55                  60

Ala His Leu Ala Ser Ile Leu Ser Leu Lys Glu Ala Ser Thr Ile Ala
65                  70                  75                  80

Glu Tyr Ile Ser Gly Tyr Gln Arg Ser Gln Pro Ile Trp Ile Gly Leu
                85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
        115                 120                 125

Cys Ala Glu Met Ser Ser Asn Asn Asn Phe Leu Thr Trp Ser Ser Asn
    130                 135                 140

Glu Cys Asn Lys Arg Gln His Phe Leu Cys Lys Tyr Arg Pro
145                 150                 155


<210> SEQ ID NO 173
<211> LENGTH: 137
<212> TYPE: PRT
<213> ORGANISM: Homo sapiens
<220> FEATURE:
<223> OTHER INFORMATION: human mature J chain

<400> SEQUENCE: 173

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
```

```
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135


<210> SEQ ID NO 174
<211> LENGTH: 137
<212> TYPE: PRT
<213> ORGANISM: Artificial sequence
<220> FEATURE:
<223> OTHER INFORMATION: Mutant form of human mature J chain with C134S
      mutation compared to wild type Mature form of human J chain (SEQ
      ID NO:173)

<400> SEQUENCE: 174

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Ser Tyr Pro Asp
    130                 135


<210> SEQ ID NO 175
<211> LENGTH: 112
<212> TYPE: PRT
<213> ORGANISM: Artificial sequence
<220> FEATURE:
<223> OTHER INFORMATION: Mutant form of human mature J chain with amino
      acids 113-137 deleted compared to wild type Mature form of human J
      chain (SEQ ID NO:173)

<400> SEQUENCE: 175

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30
```

-continued

```
Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110


<210> SEQ ID NO 176
<211> LENGTH: 137
<212> TYPE: PRT
<213> ORGANISM: Artificial sequence
<220> FEATURE:
<223> OTHER INFORMATION: Mutant form of human mature J chain with C109S
      and C134S mutation compared to wild type mature form of human J
      chain (SEQ ID NO:173)

<400> SEQUENCE: 176

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Ser Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Ser Tyr Pro Asp
    130                 135
```

ANTIBODIES THAT SPECIFICALLY BIND TO REG IV

CROSS-REFERENCE TO RELATED APPLICATIONS

This application is a continuation of U.S. application Ser. No. 11/017,030, filed Dec. 21, 2004, which is a continuation-in-part of International Patent Application PCT/US2003/019908, filed Jun. 26, 2003, which claims benefit under 35 U.S.C. §119(e) of U.S. Provisional Application No. 60/392,382, filed Jul. 1, 2002. Each of the above referenced patent applications is hereby incorporated by reference in its entirety.

STATEMENT UNDER 37 C.F.R. §1.77(b)(4)s

This application refers to a "Sequence Listing" listed below, which is provided as an electronic document on two identical compact discs (CD-R), labeled "Copy 1" and "Copy 2." These compact discs each contain the file "PF592P1C1 Sequence Listing.txt" (386,267 bytes, created on Oct. 17, 2006), which is hereby incorporated in its entirety herein. The Sequence Listing may be viewed on an IBM-PC machine running the MS-Windows operating system.

FIELD OF THE INVENTION

The present invention relates to antibodies and related molecules that specifically bind to Reg IV. Such antibodies have uses, for example, in the diagnosis, prevention, and treatment of gastrointestinal tract cancers, inflammatory bowel disorders, and diabetes. The invention also relates to nucleic acid molecules encoding anti-Reg IV antibodies, vectors and host cells containing these nucleic acids, and methods for producing the same. The present invention relates to methods and compositions for preventing, detecting, diagnosing, treating or ameliorating a disease or disorder including gastrointestinal tract cancers, inflammatory bowel disorders, and diabetes, comprising administering to an animal, preferably a human, an effective amount of one or more antibodies or fragments or variants thereof, or related molecules, that specifically bind to Reg IV.

BACKGROUND OF THE INVENTION

Reg (Regeneration gene) and Reg-related genes are members of a multi-gene family that is part of the calcium (C-type) dependent lectin superfamily. Members of the Reg family include: Reg I-alpha (REG1A), Reg I-beta (REG1B), REG-related sequence (RS), and pancreatitis associated protein (PAP; Miyashita et al., *FEBS Lett.* 377:429-433 (1995)). All of these genes are tandemly ordered in a 95-kb DNA region of 2p12. Recently, a new member of the Reg family, Reg IV, was isolated and characterized (Hartupee et al., *Biochim. Biophys. Acta.* 1518:287-293 (2001)). Reg IV is 30% identical and 50% homologous to Reg I and is mainly expressed in the pancreas, intestine, and colon. Studies have shown that Reg IV is significantly upregulated in a variety of disorders.

Reg IV MRNA, for instance, is significantly upregulated by mucosal injury from the inflammatory bowel diseases ulcerative colitis and Crohn's disease (Hartupee et al., *Biochim. Biophys. Acta.* 1518:287-293 (2001)). Inflammatory Bowel Disease (IBD) includes a number of chronic inflammatory disorders of the intestines. The two most common Inflammatory Bowel Diseases are ulcerative colitis and Crohn's disease. While both are inflammatory diseases of the bowel, there are several significant differences between ulcerative colitis and Crohn's disease. In ulcerative colitis, inflammation is confined to the inner lining (mucosa and/or submucosa) of the large intestine (colon and/or rectum), while in Crohn's disease inflammation extends beyond the inner lining and penetrates deeper layers of the intestinal wall of any part of the digestive system (esophagus, stomach, small intestine, large intestine, and/or anus). These disorders can cause painful, often life altering symptoms including, for example, diarrhea, cramping and rectal bleeding. Depending on the severity of these symptoms, patients may be unable to work or leave the home due to pain, fatigue, and the need for constant access to bathroom facilities. Accordingly, more effective treatments for inflammatory bowel disease would not only improve the health of vast numbers of people worldwide, but would also reduce the economic costs of these afflictions at the individual and societal level.

Reg proteins have also been shown to induce the proliferation of islet β-cells and to ameliorate the diabetes of 90% depancreatized rats and of non-obese diabetic mice (Watanabe, et al. *PNAS U.S.A.* 91:3589-3592 (1994); Gross et al., *Endocrinology* 139:2369-2374 (1998)). Over the past few decades, an increasing percentage of the population has become diabetic. Diabetes mellitus is categorized into two types: Type I, known as Insulin-Dependent Diabetes Mellitus (IDDM) or Type II, known as Non-Insulin-Dependent Diabetes Mellitus (NIDDM). IDDM is an autoimmune disorder in which the insulin-secreting pancreatic beta cells of the islets of Langerhans are destroyed. In these individuals, recombinant insulin therapy is employed to maintain glucose homeostasis and normal energy metabolism. NIDDM, on the other hand, is a polygenic disorder with no one gene responsible for the progression of the disease.

Insulin affects fat, muscle, and liver. Insulin is the major regulator of energy metabolism. Malfunctioning of any step(s) in insulin secretion and/or action can lead to many disorders, including for example the dysregulation of oxygen utilization, adipogenesis, glycogenesis, lipogenesis, glucose uptake, protein synthesis, thermogenesis, and maintenance of the basal metabolic rate. This malfunctioning results in diseases and/or disorders that include, but are not limited to, hyperinsulinemia, insulin resistance, insulin deficiency, hyperglycemia, hyperlipidemia, hyperketonemia, and diabetes. Numerous debilitating secondary effects include, but are not limited to, obesity, forms of blindness (cataracts and diabetic retinopathy), limb amputations, kidney failure, fatty liver, and coronary artery disease. Current drugs used to treat insulin resistance and/or diabetes (e.g., insulin secratogogues—sulfonylurea, insulin sensitizers—thiazolidenediones and metformin, and α-glucosidase and lipase inhibitors) are inadequate. Thus, more effective treatments for diabetes are needed.

PAP, REGIA, and REGIB are expressed in low levels in normal colonic epithelial cells, but elevated in 75% of tumors (Rechreche et al., *Int. J. Cancer* 81:688-694 (1999)). The most common gastrointestinal (GI) tract cancer in this country is cancer of the colon and rectum; followed by cancer of the pancreas. The most common tumor of the colon is adenomatous polyp. Primary lymphoma is rare in the colon and most common in the small intestine. Adenomatous polyps are the most common benign gastrointestinal tumors. They occur throughout the GI tract, most commonly in the colon and stomach, and are found more frequently in males than in females. They may be single, or more commonly, multiple, and sessile or pedunculated. They may be inherited, as in familial polyposis and Gardener's syndrome, which primarily involves the colon. Development of colon cancer is common in familial polyposis. Polyps often cause bleeding, which may occult or gross, but rarely cause pain unless complications ensue. Papillary adenoma, a less common form found only in the colon, may also cause electrolyte loss and mucoid discharge. A malignant tumor includes a carcinoma of the colon which may be infiltrating or exophytic and occurs most commonly in the rectosigmoid. Because the content of the ascending colon is liquid, a carcinoma in this area usually does not cause obstruction, but the patient tends to present late in the course of the disease with anemia, abdominal pain, or an abdominal mass or a palpable mass.

The prognosis with colonic tumors depends on the degree of bowel wall invasion and on the presence of regional lymph node involvement and distant metastases. The prognosis with carcinoma of the rectum and descending colon is quite unexpectedly good. Cure rates of 80 to 90% are possible with early resection before nodal invasion develops. For this reason, great care must be taken to exclude this disease when unexplained anemia, occult gastrointestinal bleeding, or change in bowel habits develop in a previously healthy patient. Complete removal of the lesion before it spreads to the lymph nodes provides the best chance of survival for a patient with cancer of the colon. Detection in an asymptomatic patient by occult-bleeding, blood screening results in the highest five year survival. Although colon and rectal cancers are currently treated with increasing rates of success, pancreatic cancer and other upper GI tract cancers (such as adenocarcinomas of the distal esophagus, stomach, bile ducts, liver, and duodenum) continue to induce high rates of mortality. The prognosis for persons with a GI tract adenocarcinoma, for example, is often very poor because these tumors are usually not detected early, grow aggressively, and are not particularly sensitive to chemotherapy. Hence, new and innovative treatments are urgently needed for both the most common, treatable GI tract cancers as well as the less common, usually fatal GI tract cancers.

Reg proteins have a variety of functions and are overexpressed in several disorders. There is a clear need, therefore, for identification and characterization of compositions, such as antibodies, that influence the biological activity of Reg proteins, both normally and in disease states. In particular, there is a need to isolate and characterize antibodies that modulate the biological activities of Reg IV for the treatment of gastrointestinal tract cancers, inflammatory bowel disease, and diabetes.

SUMMARY OF THE INVENTION

The present invention encompasses antibodies (including molecules comprising, or alternatively consisting of, antibody fragments or variants thereof) that specifically bind to a Reg IV polypeptide (International Publication Nos. WO 96/39541 and WO 2001/22920, which are hereby incorporated by reference in their entireties; GenBank ID: AAG02562; Hartupee et al., *Biochim. Biophys. Acta.* 1518: 287-293 (2001)) or a polypeptide fragment or variant of Reg IV. In particular, the invention encompasses antibodies (including molecules comprising, or alternatively consisting of, antibody fragments or variants thereof) that specifically bind to a Reg IV polypeptide or polypeptide fragment or variant of human Reg IV such as SEQ ID NO: 172.

The present invention relates to methods and compositions for preventing, treating or ameliorating a disease or disorder comprising administering to an animal, preferably a human, an effective amount of one or more antibodies or fragments or variants thereof, or related molecules, that specifically bind to Reg IV or a fragment or variant thereof. In specific embodiments, the present invention relates to methods and compositions for preventing, treating or ameliorating a disease or disorder associated with Reg IV function or aberrant Reg IV expression, comprising administering to an animal, preferably a human, an effective amount of one or more antibodies or fragments or variants thereof, or related molecules, that specifically bind to Reg IV or a fragment or variant thereof.

In highly preferred embodiments, the present invention encompasses methods for using antibodies of the invention to treat, prevent, diagnose and/or prognose cancer. In a specific embodiments, the antibodies of the present invention are used to treat, prevent, diagnose, and/or prognose gastrointestinal tract cancers (e.g., colon cancer, pancreatic cancer, rectal cancer, cancer of the gallbladder, cancer of the small intestine, cancer of the esophagus, cancer of the stomach, cancer of the bile ducts, cancer of the liver, cancer of the duodenum).

In highly preferred embodiments, the present invention encompasses methods for using antibodies of the invention to treat, prevent, diagnose and/or prognose colon cancer.

In other preferred embodiments, the present invention encompasses methods for using antibodies of the invention to treat, prevent, diagnose and/or prognose an inflammatory disorder. In a specific embodiment, the antibodies of the present invention are used to treat, prevent, diagnose, and/or prognose an inflammatory bowel disorder (e.g., Crohn's disease, ulcerative colitis).

In additional preferred embodiments, the present invention encompasses methods for using antibodies of the invention to treat, prevent, diagnose and/or prognose disorders of carbohydrate metabolism, including, but not limited to, diabetes mellitus, insulin-dependent diabetes mellitus, and/or non-insulin-dependent diabetes mellitus.

In a further preferred embodiment of the invention, antibodies of the present invention may be used to promote wound healing.

Another embodiment of the present invention includes the use of the antibodies of the invention as a diagnostic tool to monitor the expression of Reg IV.

The present invention encompasses single chain Fv's (scFvs) that specifically bind Reg IV polypeptides (e.g., SEQ ID NOs:1-67). Thus, the invention encompasses these scFvs, listed in Table 1. In addition, the invention encompasses cell lines engineered to express antibodies corresponding to these scFvs which have been deposited with the American Type Culture Collection ("ATCC™") as of the dates listed in Table 1 and given the ATCC™ Deposit Numbers identified in Table 1. The ATCC™ is located at 10801 University Boulevard, Manassas, Va. 20110-2209, USA. The ATCC™ deposit was made pursuant to the terms of the Budapest Treaty on the International Recognition of the Deposit of Microorganisms for Purposes of Patent Procedure.

Further, the present invention encompasses the polynucleotides encoding the scFvs, as well as the amino acid sequences of the scFvs. Molecules comprising, or alternatively consisting of, fragments or variants of these scFvs (e.g., VH domains, VH CDRs, VL domains, or VL CDRs having an amino acid sequence of the corresponding portion of any one of the scFvs referred to in Table 1), that specifically bind to Reg IV or fragments or variants thereof are also encompassed by the invention, as are nucleic acid molecules that encode these antibodies and/or molecules.

The present invention also provides anti-Reg IV antibodies that are coupled to a detectable label, such as an enzyme, a fluorescent label, a luminescent label, or a bioluminescent label. The present invention also provides anti-Reg IV antibodies that are coupled to a therapeutic or cytotoxic agent.

The present invention also provides anti-Reg IV antibodies that are coupled to a radioactive material, directly or indirectly.

The present invention also provides antibodies that bind Reg IV polypeptides and that act as either Reg IV agonists or Reg IV antagonists. In specific embodiments, the antibodies of the invention inhibit Reg IV binding to a Reg IV receptor (e.g., a member of the multiple exostoses family of receptors).

In specific embodiments, the antibodies of the invention inhibit proliferation of cells that express a Reg IV receptor. In specific embodiments, the antibodies of the invention inhibit proliferation of cancerous cells.

In specific embodiments, the antibodies of the invention stimulate proliferation of cells that express a Reg IV receptor. In specific embodiments, the antibodies of the invention stimulate- proliferation of pancreatic beta-cells.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, $F(ab')_2$ fragments, Fd fragments, disulfide-linked Fvs (sdFvs), anti-idiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, $F(ab')_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

The term "antibody," as used herein, refers to immunoglobulin molecules and immunologically active portions of immunoglobulin molecules, i.e., molecules that contain an antigen binding site that specifically binds an antigen. As such, the term antibody encompasses not only whole antibody molecules, but also antibody multimers, antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, $F(ab')_2$, disulfide linked Fvs (sdFvs), Fvs, and fragments comprising or alternatively consisting of, either a VL or a VH domain. The term "single chain Fv" or "scFv" as used herein refers to a polypeptide comprising a VH domain of antibody linked to a VL domain of an antibody. Antibodies that specifically bind to Reg IV may have cross-reactivity with other antigens. Preferably, antibodies that specifically bind to Reg IV do not cross-react with other antigens (e.g., other members of the Reg family). Antibodies that specifically bind to Reg IV can be identified, for example, by immunoassays or other techniques known to those of skill in the art.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$, and $IgA_2$) or subclass of mmunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms. Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers withon an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide (SEQ ID NO:173). Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31, and Frigerio et al., (2000) Plant Physiology 123:1483-94, both of which are hereby incorporated by reference in their entireties.) IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to to contain a J chain interaction domain) is not desired, it can be greatly reduced by expressing the antibody molecule in association with a mutant J chain that does not interact well with pIgR (e.g., SEQ ID NOS:174-176). Expression of an antibody with one of these mutant J chains will reduce its ability to bind to the polymeric IgA receptor on epithelial cells, thereby reducing transport of the antibody across the epithelial cell and its resultant secretion into the lumen of mucosa lined organs. ScFv dimers can also be formed through recombinant techniques known in the art; an example of the construction of scFv dimers is given in Goel et al., (2000) Cancer Research 60:6964-6971 which is hereby incorporated by reference in ts entirety. Antibody multimers may be purified using any suitable method known in the art, including, but not limited to, size exclusion chromatography.

By "isolated antibody" is intended an antibody removed from its native environment. Thus, an antibody produced by, purified from and/or contained within a hybridoma and/or a recombinant host cell is considered isolated for purposes of the present invention.

Unless otherwise defined in the specification, specific binding by an antibody to Reg IV means that an antibody binds Reg IV but does not significantly bind to (i.e., cross react with) proteins other than Reg IV, such as other proteins in the same family of proteins. An antibody that binds Reg IV protein and does not cross-react with other proteins is not necessarily an antibody that does not bind said other proteins in all conditions. Rather, the Reg IV-specific antibody of the invention preferentially binds Reg IV compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., consisting of sequential amino acids residues in a protein sequences) or conformational (i.e., consisting of one or more amino acid residues that are not contiguous in the primary structure of the protein but that are brought together by the secondary, tertiary or quaternary structure of a protein). Given that Reg IV-specific antibodies bind to epitopes of Reg IV, an antibody that specifically binds Reg IV may or may not bind fragments of Reg IV and/or variants of Reg IV (e.g., proteins that are at least 90% identical to Reg IV) depending on the presence, absence, or accessibility of the epitope bound by a given Reg IV-specific antibody in the Reg IV fragment or variant. Likewise, Reg IV-specific antibodies of the invention may bind species orthologues of Reg IV (including fragments thereof) depending on the presence, absence, or accessibility of the epitope recognized by the antibody in the orthologue. Additionally, Reg IV-specific antibodies of the invention may bind modified forms of Reg IV, for example, Reg IV fusion proteins. In such a case when antibodies of the invention bind Reg IV fusion proteins, the antibody must make binding contact with the Reg IV moiety of the fusion protein in order for the binding to be specific. Antibodies that specifically bind to Reg IV can be identified, for example, by immunoassays or other techniques known to those of skill in the art, e.g., the immunoassays described in the Examples below.

The term "variant" as used herein refers to a polypeptide that possesses a similar or identical amino acid sequence as a Reg IV polypeptide, a fragment of a Reg IV polypeptide, an anti-Reg IV antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a Reg IV polypeptide, a fragment thereof, an anti-Reg IV antibody or antibody fragment thereof (including a VH domain, VHCDR, VL domain, or VLCDR having an amino acid sequence of the corresponding portion of any one or more scFvs referred to in Table 1) described herein; (b) a polypeptide encoded by a nucleotide sequence, the complementary sequence of which hybridizes under stringent conditions to a nucleotide sequence encoding a Reg IV polypeptide (e.g., SEQ ID NO:172) or a fragment of a Reg IV polypeptide, an anti-Reg IV antibody or antibody fragment thereof (including a VH domain, VHCDR, VL domain, or VLCDR having an amino acid sequence of the corresponding portion of any one or more scFvs referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a Reg IV polypeptide, a fragment of a Reg IV polypeptide, an anti-Reg IV antibody or antibody fragment thereof (including a VH domain, VHCDR, VL domain, or VLCDR having an amino acid sequence of the corresponding portion of any one or more scFvs referred to in Table 1), described herein. A polypeptide with similar structure to a Reg IV polypeptide, a fragment of a Reg IV polypeptide, an anti-Reg IV antibody or antibody fragment thereof, described herein refers to a polypeptide that has a similar secondary, tertiary or quaternary structure of a Reg IV polypeptide, a fragment of a Reg IV polypeptide, an anti-Reg IV antibody, or antibody fragment thereof, described herein. The structure of a polypeptide can determined by methods known to those skilled in the art, including but not limited to, X-ray crystallography, nuclear magnetic resonance, and crystallographic electron microscopy. Preferably, a variant Reg IV polypeptide, a variant fragment of a Reg IV polypeptide, or a variant anti-Reg IV antibody and/or antibody fragment possesses similar or identical function and/or structure as the reference Reg IV polypeptide, the reference fragment of a Reg IV polypeptide, or the reference anti-Reg IV antibody and/or antibody fragment, respectively.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity =number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264-2268(1990), modified as in Karlin and Altschul *Proc. Natl. Acad. Sci. USA* 90:5873-5877(1993). The BLASTn and BLASTx programs of Altschul, et al. *J. Mol. Biol.* 215:403-410(1990) have incorporated such an algorithm. BLAST nucleotide searches can be performed with the BLASTn program (score=100, wordlength=12) to obtain nucleotide sequences homologous to a nucleic acid molecules of the invention. BLAST protein searches can be performed with the BLASTx program (score=50, wordlength=3) to obtain amino acid sequences homologous to a protein molecule of the invention. To obtain gapped alignments for comparison purposes, Gapped BLAST can be utilized as described in Altschul et al. *Nucleic Acids Res.* 25:3589-3402(1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti *Comput. Appl. Biosci.,* 10 :3-5(1994); and FASTA described in Pearson and Lipman *Proc. Natl. Acad. Sci.* 85:2444-8(1988). Within FASTA, ktup is a control option that sets the sensitivity and speed of the search.

The term “derivative” as used herein, refers to a variant polypeptide of the invention that comprises, or alternatively consists of, an amino acid sequence of a Reg IV polypeptide, a fragment of a Reg IV polypeptide, or an antibody of the invention that specifically binds to a Reg IV polypeptide, which has been altered by the introduction of amino acid residue substitutions, deletions or additions. The term “derivative” as used herein also refers to a Reg IV polypeptide, a fragment of a Reg IV polypeptide, an antibody that specifically binds to a Reg IV polypeptide which has been modified, e.g., by the covalent attachment of any type of molecule to the polypeptide. For example, but not by way of limitation, a Reg IV polypeptide, a fragment of a Reg IV polypeptide, or an anti-Reg IV antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a Reg IV polypeptide, a fragment of a Reg IV polypeptide, or an anti-Reg IV antibody, may be modified by chemical modifications using techniques known to those of skill in the art, including, but not limited to, specific chemical cleavage, acetylation, formylation, metabolic synthesis of tunicamycin, etc. Further, a derivative of a Reg IV polypeptide, a fragment of a Reg IV polypeptide, or an anti-Reg IV antibody, may contain one or more non-classical amino acids. A polypeptide derivative possesses a similar or identical function as a Reg IV polypeptide, a fragment of a Reg IV polypeptide, or an anti-Reg IV antibody, described herein.

The term “fragment” as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 110 amino acid residues, at least 120 amino acid residues, at least 130 amino acid residues, at least 140 amino acid residues, or at least 150 amino acid residues, of the amino acid sequence of Reg IV, or an anti-Reg IV antibody (including molecules such as scFv’s, that comprise, or alternatively consist of, antibody fragments or variants thereof) that specifically binds to Reg IV.

The term “host cell” as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

By “isolated antibody” is intended an antibody removed from its native environment. Thus, an antibody produced and/or contained within a recombinant host cell is considered isolated for purposes of the present invention.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, lgG, 1gA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hypervariable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk. *J, Mol. Biol.* 196:901-917 (1987); Chothia et al., *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J Immunol.* 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int. J. Cancer Suppl.* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-Reg IV Antibodies

Using phage display technology, single chain antibody molecules ("scFvs") have been identified that specifically bind to Reg IV (or fragments or variants thereof). Molecules comprising, or alternatively consisting of, fragments or variants of these scFvs (e.g., including a VH domain, VHCDR, VL domain, or VLCDR having an amino acid sequence of the corresponding portion of any one or more scFvs referred to in Table 1), that specifically bind to Reg IV (or fragments or variants thereof) are also encompassed by the invention, as are nucleic acid molecules that encode these scFvs, and/or molecules.

In particular, the invention relates to scFvs comprising, or alternatively consisting of the amino acid sequence of any one of SEQ ID NOs:1-67, referred to in Table I below. Molecules comprising, or alternatively consisting of, fragments or variants (e.g., including VH domains, VH CDRs, VL domains, or VL CDRs identified in Table 1) of the scFvs referred to in Table 1, that specifically bind to Reg IV are also encompassed by the invention, as are nucleic acid molecules that encode these scFvs, and/or molecules (e.g., SEQ ID NOs:68-134).

The present invention provides antibodies (including molecules comprising, or alternatively consisting of, antibody fragments or variants thereof) that specifically bind to a polypeptide or a polypeptide fragment of Reg IV. In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Cell lines that express IgG1 antibodies that comprise the VH and VL domains of scFvs of the invention have been deposited with the American Type Culture Collection ("ATCC™") on the dates listed in Table 1 and given the ATCC™ Deposit Numbers identified in Table 1. The ATCC™ is located at 10801 University Boulevard, Manassas, Va. 20110-2209, USA. The ATCC™ deposit was made pursuant to the terms of the Budapest Treaty on the International Recognition of the Deposit of Microorganisms for Purposes of Patent Procedure.

Accordingly, in one embodiment, the invention provides antibodies that comprise the VH and VL domains of scFvs of the invention.

In a preferred embodiment, an antibody of the invention is an antibody expressed by any one of the cell lines disclosed in Table 1.

TABLE 1 scFvs that Specifically bind to Reg IV

| scFv | scFv Protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 |
|---|---|---|---|---|---|---|---|---|---|---|
| RGB0101 | 1 | 68 | 1-131 | 31-35 | 50-66 | 99-120 | 147-254 | 168-178 | 194-200 | 233-243 |
| RGB0102 | 2 | 69 | 1-128 | 31-35 | 50-66 | 99-117 | 144-251 | 167-177 | 193-199 | 232-240 |
| RGB0103 | 3 | 70 | 1-127 | 31-35 | 50-66 | 99-116 | 145-255 | 167-179 | 195-201 | 236-244 |
| RGB0104 | 4 | 71 | 1-119 | 31-35 | 50-66 | 99-108 | 136-248 | 158-171 | 187-193 | 226-237 |
| RGB0106 | 5 | 72 | 1-125 | 31-35 | 50-66 | 99-114 | 141-248 | 162-172 | 188-194 | 227-237 |
| RGB0110 | 6 | 73 | 1-120 | 31-35 | 50-66 | 99-109 | 136-243 | 159-169 | 185-191 | 224-232 |
| RGB0113 | 7 | 74 | 1-125 | 31-35 | 50-66 | 99-114 | 141-248 | 162-172 | 188-194 | 227-237 |

TABLE 1-continued scFvs that Specifically bind to Reg IV

| scFv | scFv Protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 |
|---|---|---|---|---|---|---|---|---|---|---|
| RGB0114 | 8 | 75 | | | | | | | | |
| RGB0115 | 9 | 76 | 1-121 | 31-36 | 51-66 | 99-110 | 138-249 | 160-173 | 189-195 | 228-238 |
| RGB0118 | 10 | 77 | 1-124 | 31-35 | 50-66 | 99-113 | 140-247 | 161-171 | 187-193 | 226-236 |
| RGB0128 | 11 | 78 | 1-119 | 31-35 | 50-66 | 99-108 | 137-248 | 159-171 | 187-193 | 228-237 |
| RGB0129 | 12 | 79 | 1-124 | 31-35 | 50-66 | 99-113 | 142-252 | 164-176 | 192-198 | 233-241 |
| RGB0137 | 13 | 80 | 1-120 | 31-35 | 50-66 | 99-109 | 136-246 | 158-171 | 187-193 | 226-235 |
| RGB0146 | 14 | 81 | 1-123 | 31-37 | 52-67 | 100-112 | 139-249 | 161-173 | 189-195 | 228-238 |
| RGB0153 | 15 | 82 | 1-121 | 31-35 | 50-66 | 99-110 | 139-249 | 161-173 | 189-195 | 230-238 |
| RGB0163 | 16 | 83 | 1-123 | 31-35 | 50-66 | 99-112 | 140-247 | 162-171 | 187-193 | 226-236 |
| RGB0165 | 17 | 84 | 1-125 | 31-35 | 50-66 | 99-114 | 143-253 | 165-177 | 193-199 | 234-242 |
| RGB0174 | 18 | 85 | 1-121 | 31-35 | 50-66 | 99-110 | 138-248 | 160-172 | 188-194 | 227-237 |
| RGB0185 | 19 | 86 | 1-128 | 31-35 | 50-66 | 99-117 | 144-251 | 167-177 | 193-199 | 232-240 |
| RGB0187 | 20 | 87 | 1-124 | 31-35 | 50-66 | 99-113 | 142-253 | 164-176 | 192-198 | 233-242 |
| RGB0194 | 21 | 88 | 1-125 | 31-35 | 50-66 | 99-114 | 141-248 | 162-172 | 188-194 | 227-237 |
| RGC0102 | 22 | 89 | 1-122 | 31-36 | 51-66 | 99-111 | 139-250 | 161-173 | 189-195 | 228-239 |
| RGC0104 | 23 | 90 | 1-120 | 31-35 | 50-66 | 99-109 | 137-242 | 159-169 | 185-191 | 224-231 |
| RGC0107 | 24 | 91 | 1-118 | 31-37 | 52-67 | 100-107 | 136-246 | 158-170 | 186-192 | 225-235 |
| RGC0108 | 25 | 92 | 1-118 | 31-37 | 52-67 | 100-107 | 136-246 | 158-170 | 186-192 | 225-235 |
| RGC0110 | 26 | 93 | 1-118 | 31-35 | 50-66 | 99-107 | 136-246 | 158-170 | 186-192 | 227-235 |
| RGC0114 | 27 | 94 | 1-119 | 31-35 | 50-66 | 99-108 | 136-246 | 158-170 | 186-192 | 225-235 |
| RGC0115 | 28 | 95 | 1-116 | 31-35 | 50-66 | 99-105 | 134-242 | 156-166 | 182-188 | 221-231 |
| RGC0128 | 29 | 96 | 1-124 | 31-35 | 50-68 | 101-113 | 142-252 | 164-176 | 192-198 | 233-241 |
| RGC0130 | 30 | 97 | 1-124 | 31-35 | 50-66 | 99-113 | 140-249 | 162-174 | 190-196 | 229-238 |
| RGC0131 | 31 | 98 | 1-129 | 31-35 | 50-66 | 99-118 | 147-257 | 169-181 | 197-203 | 238-246 |
| RGC0137 | 32 | 99 | 1-120 | 31-35 | 50-66 | 99-109 | 137-244 | 159-169 | 185-191 | 224-233 |
| RGC0139 | 33 | 100 | 1-123 | 31-35 | 50-66 | 99-112 | 140-248 | 162-172 | 188-194 | 227-237 |
| RGC0142 | 34 | 101 | 1-120 | 31-35 | 50-66 | 99-109 | 137-243 | 159-171 | 187-189 | 222-232 |
| RGC0145 | 35 | 102 | 1-120 | 31-35 | 50-66 | 99-109 | 137-243 | 159-171 | 187-189 | 222-232 |
| RGC0150 | 36 | 103 | 1-122 | 31-36 | 51-66 | 99-111 | 139-249 | 161-173 | 189-195 | 228-238 |
| RGC0153 | 37 | 104 | 1-123 | 31-35 | 50-66 | 99-112 | 141-251 | 163-175 | 191-197 | 232-240 |
| RGC0154 | 38 | 105 | 1-120 | 31-35 | 50-66 | 99-109 | 138-245 | 160-170 | 186-192 | 225-234 |
| RGC0157 | 39 | 106 | 1-125 | 31-35 | 50-66 | 99-114 | 143-253 | 165-177 | 193-199 | 234-242 |
| RGC0162 | 40 | 107 | 1-119 | 31-35 | 50-66 | 99-108 | 137-247 | 159-171 | 187-193 | 228-236 |
| RGC0164 | 41 | 108 | 1-118 | 31-35 | 50-66 | 99-107 | 135-245 | 157-170 | 186-192 | 225-234 |
| RGC0169 | 42 | 109 | 1-121 | 31-35 | 50-66 | 99-110 | 139-246 | 162-172 | 188-194 | 227-235 |
| RGC0175 | 43 | 110 | 1-120 | 31-35 | 50-66 | 99-109 | 138-248 | 160-172 | 188-194 | 229-237 |
| RGD0102 | 44 | 111 | 1-120 | 31-35 | 50-66 | 99-109 | 136-243 | 159-169 | 185-191 | 224-232 |
| RGD0108 | 45 | 112 | 1-127 | 31-35 | 50-66 | 99-116 | 144-254 | 166-178 | 194-200 | 233-243 |
| RGD0112 | 46 | 113 | 1-119 | 31-35 | 50-66 | 99-108 | 137-248 | 159-171 | 187-193 | 228-237 |
| RGD0117 | 47 | 114 | 1-119 | 31-35 | 50-66 | 99-108 | 137-248 | 159-171 | 187-193 | 228-237 |
| RGD0119 | 48 | 115 | 1-120 | 31-35 | 50-66 | 99-109 | 138-245 | 161-171 | 187-193 | 226-234 |
| RGD0121 | 49 | 116 | 1-119 | 31-35 | 50-66 | 99-108 | 137-244 | 160-170 | 186-192 | 225-233 |
| RGD0122 | 50 | 117 | 1-123 | 31-35 | 50-66 | 99-112 | 140-247 | 162-171 | 187-193 | 226-236 |
| RGD0123 | 51 | 118 | 1-120 | 31-35 | 50-66 | 99-109 | 137-248 | 159-172 | 188-194 | 227-237 |
| RGD0124 | 52 | 119 | 1-127 | 31-35 | 50-66 | 99-116 | 144-254 | 166-178 | 194-200 | 233-243 |
| RGD0130 | 53 | 120 | 1-120 | 31-35 | 50-66 | 99-109 | 138-245 | 161-171 | 187-193 | 226-234 |
| RGD0135 | 54 | 121 | 1-120 | 31-35 | 50-66 | 99-109 | 137-249 | 159-172 | 188-194 | 227-238 |
| RGD0136 | 55 | 122 | 1-123 | 31-35 | 50-66 | 99-112 | 141-251 | 163-175 | 191-197 | 232-240 |
| RGD0141 | 56 | 123 | 1-121 | 31-35 | 50-66 | 99-110 | 138-248 | 160-172 | 188-194 | 227-237 |
| RGD0143 | 57 | 124 | 1-126 | 31-35 | 50-66 | 99-115 | 143-253 | 165-177 | 193-199 | 232-242 |
| RGD0145 | 58 | 125 | 1-116 | 31-35 | 50-66 | 99-105 | 134-242 | 156-166 | 182-188 | 221-231 |
| RGD0153 | 59 | 126 | 1-124 | 31-35 | 50-66 | 99-113 | 141-251 | 163-176 | 192-198 | 231-240 |
| RGD0154 | 60 | 127 | 1-123 | 31-35 | 50-66 | 99-112 | 140-247 | 162-171 | 187-193 | 226-236 |
| RGD0169 | 61 | 128 | 1-127 | 31-35 | 50-66 | 99-116 | 145-251 | 167-177 | 193-199 | 232-240 |
| RGD0170 | 62 | 129 | 1-119 | 31-35 | 50-66 | 99-108 | 137-249 | 159-171 | 187-193 | 228-238 |
| RGD0180 | 63 | 130 | 1-119 | 31-35 | 50-66 | 99-108 | 137-248 | 159-171 | 187-193 | 228-237 |
| RGD0182 | 64 | 131 | 1-119 | 31-35 | 50-66 | 99-108 | 137-248 | 159-171 | 187-193 | 228-237 |
| RGD0183 | 65 | 132 | 1-120 | 31-35 | 50-66 | 99-109 | 138-245 | 161-171 | 187-193 | 226-234 |
| RGD0193 | 66 | 133 | 1-116 | 31-35 | 50-66 | 99-105 | 134-242 | 156-166 | 182-188 | 221-231 |
| RGD0195 | 67 | 134 | 1-123 | 31-35 | 50-66 | 99-112 | 140-247 | 162-171 | 187-193 | 226-236 |

The present invention encompasses antibodies (including molecules comprising, or alternatively consisting of, antibody fragments or variants thereof) that specifically bind to a Reg IV polypeptide or a fragment, variant, or fusion protein thereof. A Reg IV polypeptide includes, but is not limited to, Reg IV (SEQ ID NO:172) or the polypeptide encoded by the cDNA contained in ATCC™ Deposit No. 97129 on Apr. 28, 1995. Reg IV may be produced through recombinant expression of nucleic acids encoding the polypeptides of SEQ ID NO:172 (e.g., the cDNA in ATCC™ Deposit Number 97129). Antibodies of the invention may specifically bind Reg IV as well as fragments and variants thereof, and are described in more detail below.

Reg IV Polypeptides

In certain embodiments of the present invention, the antibodies of the present invention bind Reg IV polypeptide, or fragments or variants thereof. The following section describes the Reg IV polypeptides, fragments and variants that may be bound by the antibodies of the invention in more detail.

In certain embodiments, the antibodies of the present invention specifically bind Reg IV polypeptide. An antibody that specifically binds Reg IV may, in some embodiments, bind fragments, variants (including species orthologs and allelic variants of Reg IV), multimers or modified forms of Reg IV. For example, an antibody specific for Reg IV may bind the Reg IV moiety of a fusion protein comprising all or a portion of Reg IV.

Reg IV proteins may be found as monomers or multimers (i.e., dimers, trimers, tetramers, and higher multimers). Accordingly, the present invention relates to antibodies that bind Reg IV proteins found as monomers or as part of multimers. In specific embodiments, antibodies of the invention bind Reg IV monomers, dimers, trimers or tetramers. In additional embodiments, antibodies of the invention bind at least dimers, at least trimers, or at least tetramers containing one or more Reg IV polypeptides.

Antibodies of the invention may bind Reg IV homomers or heteromers. As used herein, the term homomer, refers to a multimer containing only Reg IV proteins of the invention (including Reg IV fragments, variants, and fusion proteins, as described herein). These homomers may contain Reg IV proteins having identical or different polypeptide sequences. In a specific embodiment, a homomer of the invention is a multimer containing only Reg IV proteins having an identical polypeptide sequence. In another specific embodiment, antibodies of the invention bind Reg IV homomers containing Reg IV proteins having different polypeptide sequences. In specific embodiments, antibodies of the invention bind a Reg IV homodimer (e.g., containing Reg IV proteins having identical or different polypeptide sequences) or a homotrimer (e.g., containing Reg IV proteins having identical or different polypeptide sequences). In additional embodiments, antibodies of the invention bind at least a homodimer, at least a homotrimer, or at least a homotetramer of Reg IV.

As used herein, the term heteromer refers to a multimer containing heterologous proteins (i.e., proteins containing polypeptide sequences that do not correspond to a polypeptide sequences encoded by a gene encoding Reg IV) in addition to the Reg IV proteins of the invention. In a specific embodiment, antibodies of the invention bind a heterodimer, a heterotrimer, or a heterotetramer. In additional embodiments, the antibodies of the invention bind at least a heterodimer, at least a heterotrimer, or at least a heterotetramer containing one or more Reg IV polypeptides.

Antibodies of the invention may bind Reg IV multimers that are the result of hydrophobic, hydrophilic, ionic and/or covalent associations and/or may be indirectly linked, by for example, liposome formation. Thus, in one embodiment, antibodies of the invention may bind multimers, such as, for example, homodimers or homotrimers, that are formed when Reg IV proteins contact one another in solution. In another embodiment, antibodies of the invention may bind heteromultimers, such as, for example, heterotrimers or heterotetramers, that are formed when proteins of the invention contact antibodies to the Reg IV polypeptides (including antibodies to the heterologous polypeptide sequence in a fusion protein) in solution. In other embodiments, antibodies of the invention may bind multimers that are formed by covalent associations with and/or between the Reg IV proteins. Such covalent associations may involve one or more amino acid residues contained in the polypeptide sequence of the protein (e.g., the polypeptide sequence recited in SEQ ID NO:172 or the polypeptide encoded by the deposited cDNA clone of ATCC™ Deposit 97129). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a Reg IV fusion protein. In one example, covalent associations are between the heterologous sequence contained in a fusion protein (see, e.g., U.S. Pat. No. 5,478,925). In a specific example, the covalent associations are between the heterologous sequence contained in a Reg IV-Fc fusion protein (as described herein). In another specific example, covalent associations of fusion proteins are between heterologous polypeptide sequences from another Reg family ligand/receptor member that is capable of forming covalently associated multimers.

Antibodies of the invention can bind multimers that were generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C-terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that antibodies of the invention may bind (see, e.g., U.S. Pat. No. 5,478,925, which is herein incorporated by reference in its entirety).

Alternatively, antibodies of the invention may bind multimers that were generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a Reg IV polypeptide to a sequence encoding a linker polypeptide and then further to a synthetic polynucleotide encoding the translated product of the polypeptide in the reverse orientation from the original C-terminus to the N-terminus (see, e.g., U.S. Pat. No. 5,478,925, which is herein incorporated by reference in its entirety). In another embodiment, recombinant techniques described herein or otherwise known in the art are applied to generate recombinant Reg IV polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more Reg IV polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple Reg IV polypeptides separated by peptide linkers may be produced using conventional recombinant DNA technology. In specific embodiments, antibodies of the invention bind proteins comprising multiple Reg IV polypeptides separated by peptide linkers.

Another method for preparing multimer Reg IV polypeptides involves use of Reg IV polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric Reg IV proteins are those described in PCT application WO 94/10308, hereby incorporated by reference. Recombinant fusion proteins comprising a soluble Reg IV polypeptide fused to a peptide that dimerizes or trimerizes in solution are expressed in suitable host cells, and the resulting soluble multimeric Reg IV is recovered from the culture supernatant using techniques known in the art. In specific embodiments, antibodies of the invention bind Reg IV-leucine zipper fusion protein monomers and/or Reg IV-leucine zipper fusion protein multimers.

Other peptides derived from naturally occurring dimeric proteins may be employed in preparing dimeric Reg IV. In specific embodiments, antibodies of the invention bind Reg IV-fusion protein monomers and/or Reg IV fusion protein dimers.

Antibodies that bind Reg IV receptor polypeptides may bind them as isolated polypeptides, in their naturally occurring state and/or their native conformation. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. Thus, antibodies of the present invention may bind recombinantly produced Reg IV polypeptides.

Antibodies of the present invention may also bind Reg IV purified from a cell culture, wherein the cells in said cell culture comprise a polynucleotide encoding amino acids 1 to 158 of SEQ ID NO:172 operably associated with a regulatory sequence that controls expression of said polynucleotide. Antibodies of the present invention may also bind Reg IV purified from a cell culture, said Reg IV is encoded by a polynucleotide encoding amino acids 1 to 158 of SEQ ID NO:172 operably associated with a regulatory sequence that controls expression of said polynucleotide.

Antibodies of the present invention may bind Reg IV polypeptide fragments comprising or alternatively, consisting of, an amino acid sequence contained in SEQ ID NO:172, encoded by the cDNA contained in ATCC™ deposit Number 97129, or encoded by nucleic acids which hybridize (e.g., under stringent hybridization conditions) to the nucleotide sequence contained in ATCC™ deposit Number 97129, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 22, 23 to 43, 44 to 63, 64 to 83, 84 to 103, 104 to 123, 124 to 143, and/or 144 to 158 of SEQ ID NO:172. In this context "about" includes the particularly recited value, larger or smaller by several (5, 4, 3, 2, or 1) amino acids, at either extreme or at both extremes. Moreover, polypeptide fragments that antibodies of the invention may bind can be at least about 10, 20, 30, 40, 50, 60, 70, 80, 90, 100, 110, 120, 130, 140, or 150 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising, or alternatively consisting of, a fragment of the predicted mature Reg IV polypeptide (predicted to constitute amino acid residues from about 23 to about 158 in SEQ ID NO:172), wherein the fragment has a Reg IV functional activity (e.g., antigenic activity or biological activity); and/or a polypeptide comprising, or alternatively, consisting of, one, two, three, four or more, epitope bearing portions of the Reg IV protein.

In highly preferred embodiments, the antibodies of the invention that bind Reg IV prevent a Reg IV from binding to a Reg IV receptor. In other highly preferred embodiments, the antibodies of the invention that bind Reg IV antagonize or neutralize Reg IV. In other highly preferred embodiments, the antibodies of the invention that bind Reg IV inhibit proliferation of the cells expressing a Reg IV receptor (e.g., colon cancer cells). In other highly preferred embodiments, the antibodies of the invention are agonistic that bind Reg IV enhance Reg IV's biological activity, e.g., the ability to stimulate proliferation of the cells expressing a Reg IV receptor (e.g., pancreatic beta-cells). This enhancement of Reg IV activity may be the result of crosslinking of Reg IV molecules bound to their receptors.

Antibodies of the invention may also bind fragments comprising, or alternatively, consisting of structural or functional attributes of Reg IV. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) Reg IV. Certain preferred regions are those set out in Table 2 and include, but are not limited to, regions of the aforementioned types identified by analysis of the amino acid sequence depicted in (SEQ ID NO:172), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of Reg IV set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column; Column IX represents a Hopp-Woods hydrophobicity plot; Column X represents the results of an Eisenberg analysis of alpha amphipathic regions; Column XI represents the results of an Eisenberg analysis of beta amphipathic regions; Column XII represents the results of a Karplus-Schultz analysis of flexible regions; Column XIII represents the Jameson-Wolf antigenic index score; and Column XIV represents the Emini surface probability plot.

In a preferred embodiment, the data presented in columns VIII, XIII, and XIV of Table 2 can be used to determine regions of Reg IV which exhibit a high degree of potential for antigenicity. Regions of high antigenicity are determined from the data presented in columns VIII, XIII, and/or XIV by choosing values which represent regions of the polypeptide which are likely to be exposed on the surface of the polypeptide in an environment in which antigen recognition may occur in the process of initiation of an mmune response.

The above-mentioned preferred regions set out in Table 2 include, but are not limited to, regions of the aforementioned types identified by analysis of the amino acid sequence set out in SEQ ID NO:172. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments bound by one or more antibodies of the invention are those that comprise regions of Reg IV that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 0.27 | −0.21 | * | . | . | 0.50 | 0.98 |
| Ala | 2 | A | . | . | . | . | T | . | 0.06 | −0.26 | * | . | . | 0.85 | 1.03 |
| Ser | 3 | A | . | . | . | . | T | . | 0.56 | −0.07 | * | * | . | 0.70 | 0.80 |
| Arg | 4 | A | . | . | . | . | T | . | 0.13 | −0.50 | * | . | . | 0.85 | 1.58 |
| Ser | 5 | A | . | . | . | . | T | . | −0.29 | −0.43 | * | * | . | 0.85 | 1.29 |
| Met | 6 | A | A | . | . | . | . | . | −0.50 | −0.24 | * | . | . | 0.30 | 0.79 |
| Arg | 7 | A | A | . | . | . | . | . | −0.72 | 0.06 | * | * | . | −0.30 | 0.33 |
| Leu | 8 | A | A | . | . | . | . | . | −1.23 | 0.74 | * | * | . | −0.60 | 0.21 |
| Leu | 9 | A | A | . | . | . | . | . | −1.64 | 1.04 | * | * | . | −0.60 | 0.17 |
| Leu | 10 | A | A | . | . | . | . | . | −2.01 | 0.81 | * | * | . | −0.60 | 0.12 |
| Leu | 11 | A | A | . | . | . | . | . | −2.22 | 1.39 | * | * | . | −0.60 | 0.08 |
| Leu | 12 | A | A | . | . | . | . | . | −2.92 | 1.39 | * | * | . | −0.60 | 0.08 |
| Ser | 13 | A | A | . | . | . | . | . | −2.07 | 1.20 | * | . | . | −0.60 | 0.09 |
| Cys | 14 | A | A | . | . | . | . | . | −1.57 | 0.51 | * | . | . | −0.60 | 0.23 |
| Leu | 15 | A | A | . | . | . | . | . | −1.10 | 0.31 | * | * | . | −0.30 | 0.40 |
| Ala | 16 | A | A | . | . | . | . | . | −1.14 | 0.06 | * | . | . | −0.30 | 0.29 |
| Lys | 17 | A | A | . | . | . | . | . | −1.14 | 0.31 | * | . | F | −0.15 | 0.40 |
| Thr | 18 | . | A | B | . | . | . | . | −1.19 | 0.43 | . | . | F | −0.45 | 0.40 |
| Gly | 19 | . | A | B | . | . | . | . | −0.52 | 0.17 | . | * | F | −0.15 | 0.40 |
| Val | 20 | . | . | B | B | . | . | . | −0.60 | −0.33 | . | . | F | 0.45 | 0.33 |
| Leu | 21 | . | . | B | B | . | . | . | −0.90 | 0.36 | . | * | . | −0.30 | 0.16 |
| Gly | 22 | . | . | B | B | . | . | . | −1.54 | 0.56 | * | * | . | −0.60 | 0.11 |
| Asp | 23 | . | . | B | B | . | . | . | −1.12 | 0.74 | * | * | . | −0.60 | 0.15 |
| Ile | 24 | . | . | B | B | . | . | . | −0.99 | 0.10 | * | * | . | −0.30 | 0.36 |
| Ile | 25 | . | . | B | B | . | . | . | −0.43 | −0.16 | * | * | . | 0.30 | 0.56 |
| Met | 26 | . | . | B | B | . | . | . | −0.29 | −0.20 | * | * | . | 0.52 | 0.45 |
| Arg | 27 | . | . | B | . | . | T | . | −0.53 | 0.37 | * | * | . | 0.54 | 0.35 |
| Pro | 28 | . | . | B | . | . | T | . | −0.74 | 0.19 | * | * | . | 0.76 | 0.50 |
| Ser | 29 | . | . | . | . | T | T | . | −0.20 | −0.07 | . | * | . | 1.98 | 0.78 |
| Cys | 30 | . | . | . | . | T | T | . | 0.40 | −0.26 | . | . | . | 2.20 | 0.39 |
| Ala | 31 | . | . | . | . | . | T | C | 0.30 | 0.66 | . | * | . | 0.88 | 0.27 |
| Pro | 32 | . | . | . | . | T | T | . | −0.06 | 1.01 | . | . | . | 0.86 | 0.17 |
| Gly | 33 | . | . | . | . | T | T | . | 0.12 | 1.39 | . | . | . | 0.64 | 0.51 |
| Trp | 34 | . | . | B | . | . | T | . | 0.47 | 1.31 | . | . | . | 0.02 | 0.68 |
| Phe | 35 | . | . | B | . | . | . | . | 0.83 | 0.81 | . | . | . | −0.40 | 0.88 |
| Tyr | 36 | . | . | B | . | . | . | . | 1.42 | 0.77 | . | * | . | −0.25 | 1.19 |
| His | 37 | . | . | . | . | T | T | . | 0.97 | 0.74 | . | . | . | 0.35 | 1.82 |
| Lys | 38 | . | . | . | . | T | T | . | 1.07 | 0.40 | . | * | F | 0.50 | 1.13 |
| Ser | 39 | . | . | . | . | T | T | . | 1.01 | 0.37 | . | . | F | 0.80 | 1.13 |
| Asn | 40 | . | . | . | . | T | T | . | 1.47 | 0.04 | . | * | F | 0.65 | 0.82 |
| Cys | 41 | . | . | . | . | T | T | . | 1.01 | 0.30 | . | * | . | 0.50 | 0.64 |
| Tyr | 42 | . | . | . | . | T | T | . | 1.16 | 1.09 | . | * | . | 0.20 | 0.42 |
| Gly | 43 | . | . | B | . | . | T | . | 1.16 | 0.70 | * | * | . | −0.20 | 0.51 |
| Tyr | 44 | . | . | B | . | . | T | . | 0.64 | 0.30 | * | * | . | 0.25 | 1.89 |
| Phe | 45 | . | A | B | . | . | . | . | 0.76 | 0.41 | * | . | . | −0.60 | 0.99 |
| Arg | 46 | . | A | B | . | . | . | . | 1.42 | −0.34 | * | . | . | 0.75 | 1.97 |
| Lys | 47 | . | A | B | . | . | . | . | 1.38 | −0.37 | * | . | F | 1.20 | 2.02 |
| Leu | 48 | . | A | B | . | . | . | . | 1.42 | −0.21 | * | . | F | 1.50 | 2.45 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 49 | . | A | . | . | T | . | . | 1.67 | −0.61 | * | . | F | 2.50 | 1.68 |
| Asn | 50 | . | . | . | . | T | . | . | 1.78 | −0.61 | * | * | F | 3.00 | 1.40 |
| Trp | 51 | . | . | . | . | . | T | C | 1.67 | −0.11 | * | * | F | 2.40 | 1.72 |
| Ser | 52 | . | . | . | . | . | T | C | 0.81 | −0.80 | * | * | F | 2.40 | 1.52 |
| Asp | 53 | A | . | . | . | . | T | . | 1.62 | −0.11 | * | * | F | 1.45 | 0.78 |
| Ala | 54 | A | . | . | . | . | T | . | 0.84 | −0.51 | * | * | F | 1.60 | 1.28 |
| Glu | 55 | A | . | . | . | . | . | . | 0.84 | −0.86 | . | * | . | 0.80 | 0.51 |
| Leu | 56 | A | . | . | . | . | . | . | 0.83 | −0.84 | . | * | . | 0.80 | 0.53 |
| Glu | 57 | A | . | . | . | . | . | . | 0.89 | −0.46 | . | * | . | 0.66 | 0.71 |
| Cys | 58 | A | . | . | . | . | T | . | 0.54 | −0.20 | . | * | . | 1.02 | 0.64 |
| Gln | 59 | A | . | . | . | . | T | . | 1.13 | 0.23 | . | * | . | 0.58 | 0.77 |
| Ser | 60 | . | . | . | . | T | T | . | 0.79 | −0.06 | . | * | F | 1.89 | 0.71 |
| Tyr | 61 | . | . | . | . | T | T | . | 1.01 | 0.37 | . | * | F | 1.60 | 1.31 |
| Gly | 62 | . | . | . | . | T | T | . | 0.98 | 0.30 | . | . | F | 1.29 | 0.77 |
| Asn | 63 | . | . | . | . | T | T | . | 0.83 | 0.40 | * | . | F | 0.83 | 0.78 |
| Gly | 64 | . | . | . | . | . | T | C | 0.24 | 0.70 | * | . | F | 0.47 | 0.41 |
| Ala | 65 | . | . | . | . | . | T | C | 0.24 | 0.44 | . | . | . | 0.16 | 0.42 |
| His | 66 | . | A | B | . | . | . | . | −0.40 | 0.40 | . | . | . | −0.60 | 0.35 |
| Leu | 67 | . | A | B | . | . | . | . | −0.87 | 0.69 | . | . | . | −0.60 | 0.25 |
| Ala | 68 | A | A | . | . | . | . | . | −1.17 | 0.94 | . | . | . | −0.60 | 0.20 |
| Ser | 69 | A | A | . | . | . | . | . | −1.63 | 0.83 | . | * | . | −0.60 | 0.20 |
| Ile | 70 | A | A | . | . | . | . | . | −1.00 | 1.01 | . | . | . | −0.60 | 0.20 |
| Leu | 71 | A | A | . | . | . | . | . | −0.97 | 0.33 | . | . | . | −0.30 | 0.39 |
| Ser | 72 | A | A | . | . | . | . | . | −0.74 | −0.17 | . | . | . | 0.30 | 0.51 |
| Leu | 73 | A | A | . | . | . | . | . | −0.46 | −0.06 | . | . | . | 0.30 | 0.73 |
| Lys | 74 | A | A | . | . | . | . | . | −0.47 | −0.36 | . | . | F | 0.60 | 1.19 |
| Glu | 75 | A | A | . | . | . | . | . | −0.47 | −0.56 | . | . | F | 0.90 | 1.28 |
| Ala | 76 | A | A | . | . | . | . | . | −0.24 | −0.26 | * | * | F | 0.60 | 1.09 |
| Ser | 77 | A | A | . | . | . | . | . | 0.06 | −0.44 | * | . | F | 0.45 | 0.55 |
| Thr | 78 | A | . | . | B | . | . | . | 0.62 | −0.44 | * | . | . | 0.30 | 0.55 |
| Ile | 79 | A | . | . | B | . | . | . | −0.31 | 0.31 | * | . | . | −0.30 | 0.85 |
| Ala | 80 | A | . | . | B | . | . | . | −0.61 | 0.50 | * | . | . | −0.60 | 0.45 |
| Glu | 81 | . | . | B | B | . | . | . | −0.37 | 0.50 | * | . | . | −0.60 | 0.41 |
| Tyr | 82 | . | . | B | B | . | . | . | −0.31 | 0.44 | * | . | . | −0.60 | 0.58 |
| Ile | 83 | . | . | B | B | . | . | . | 0.00 | 0.51 | * | * | . | −0.60 | 0.91 |
| Ser | 84 | . | . | . | . | T | T | . | 1.00 | 0.41 | * | . | . | 0.40 | 0.91 |
| Gly | 85 | . | . | . | . | T | T | . | 1.29 | 0.41 | * | * | F | 0.90 | 1.13 |
| Tyr | 86 | . | . | . | . | T | T | . | 1.29 | 0.04 | * | * | F | 1.40 | 2.17 |
| Gln | 87 | . | . | . | . | T | T | . | 1.32 | −0.24 | . | * | F | 2.20 | 2.80 |
| Arg | 88 | . | . | . | B | T | . | . | 1.32 | −0.20 | * | * | F | 2.00 | 4.37 |
| Ser | 89 | . | . | B | B | . | . | . | 1.33 | 0.06 | . | . | F | 0.80 | 1.96 |
| Gln | 90 | . | . | B | B | . | . | . | 0.79 | 0.21 | . | . | F | 0.60 | 1.19 |
| Pro | 91 | . | . | B | B | . | . | . | 0.69 | 0.50 | . | . | F | −0.05 | 0.43 |
| Ile | 92 | . | . | B | B | . | . | . | −0.12 | 0.93 | . | . | . | −0.40 | 0.31 |
| Trp | 93 | . | . | B | B | . | . | . | −0.27 | 1.23 | . | . | . | −0.60 | 0.15 |
| Ile | 94 | . | . | B | B | . | . | . | 0.03 | 1.33 | . | . | . | −0.60 | 0.13 |
| Gly | 95 | . | . | B | . | . | . | . | −0.18 | 0.90 | . | . | . | −0.40 | 0.31 |
| Leu | 96 | . | . | . | . | . | . | C | 0.03 | 0.64 | * | . | . | 0.14 | 0.46 |
| His | 97 | . | . | . | . | . | . | C | 0.97 | 0.13 | * | * | . | 0.93 | 1.14 |
| Asp | 98 | . | . | . | . | . | T | C | 1.37 | −0.56 | . | . | F | 2.52 | 2.30 |
| Pro | 99 | . | . | . | . | . | T | C | 2.26 | −0.99 | . | . | F | 2.86 | 5.46 |
| Gln | 100 | . | . | . | . | T | T | . | 2.60 | −1.27 | . | * | F | 3.40 | 6.95 |
| Lys | 101 | . | . | . | . | T | T | . | 3.12 | −1.37 | . | * | F | 3.06 | 7.21 |
| Arg | 102 | . | . | . | B | T | . | . | 3.16 | −0.46 | . | * | F | 2.02 | 4.90 |
| Gln | 103 | . | . | . | B | T | . | . | 2.87 | −0.49 | . | * | F | 1.68 | 4.90 |
| Gln | 104 | . | . | B | B | . | . | . | 2.19 | 0.03 | * | * | F | 0.34 | 2.58 |
| Trp | 105 | . | . | B | B | . | . | . | 2.19 | 0.71 | * | * | . | −0.60 | 0.92 |
| Gln | 106 | . | . | B | B | . | . | . | 1.80 | 0.71 | * | . | . | −0.60 | 0.89 |
| Trp | 107 | . | . | B | B | . | . | . | 1.10 | 0.74 | * | * | . | −0.60 | 0.51 |
| Ile | 108 | . | . | B | B | . | . | . | 0.50 | 0.84 | . | . | . | −0.60 | 0.49 |
| Asp | 109 | . | . | . | B | T | . | . | 0.26 | 0.54 | . | * | . | −0.20 | 0.28 |
| Gly | 110 | . | . | . | . | T | . | . | −0.27 | 0.90 | * | . | . | 0.00 | 0.42 |
| Ala | 111 | . | . | B | B | T | . | . | −0.51 | 0.67 | * | . | . | −0.20 | 0.49 |
| Met | 112 | . | . | B | B | . | . | . | −0.11 | 0.74 | * | . | . | −0.60 | 0.46 |
| Tyr | 113 | . | . | B | B | . | . | . | 0.48 | 0.74 | * | . | . | −0.60 | 0.91 |
| Leu | 114 | . | . | B | B | . | . | . | 0.19 | 0.70 | * | . | . | −0.45 | 1.21 |
| Tyr | 115 | . | . | B | B | . | . | . | 0.23 | 1.11 | * | . | . | −0.45 | 1.28 |
| Arg | 116 | . | . | B | B | . | . | . | 0.48 | 0.89 | * | . | . | −0.45 | 1.10 |
| Ser | 117 | . | . | . | . | T | . | . | 1.12 | 0.56 | . | . | F | 0.30 | 1.31 |
| Trp | 118 | . | . | . | . | T | T | . | 1.07 | −0.13 | . | . | F | 1.40 | 1.68 |
| Ser | 119 | . | . | . | . | . | T | C | 1.28 | −0.50 | . | . | F | 1.20 | 1.15 |
| Gly | 120 | . | . | . | . | T | T | . | 1.18 | 0.11 | . | . | F | 0.96 | 0.85 |
| Lys | 121 | . | . | . | . | T | T | . | 0.72 | 0.16 | . | . | F | 1.27 | 0.80 |
| Ser | 122 | . | . | . | . | . | T | C | 1.02 | −0.33 | . | * | F | 1.98 | 0.59 |
| Met | 123 | . | . | . | . | T | T | . | 1.36 | −0.31 | . | . | F | 2.49 | 0.96 |
| Gly | 124 | . | . | . | . | T | T | . | 1.62 | −0.74 | . | . | F | 3.10 | 0.96 |
| Gly | 125 | . | . | . | . | T | T | . | 1.30 | −0.24 | . | . | F | 2.49 | 0.97 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 126 | . | . | . | . | . | T | C | 0.67 | −0.06 | . | . | F | 1.98 | 0.53 |
| Lys | 127 | A | . | . | . | . | T | . | 0.97 | −0.17 | . | . | F | 1.47 | 0.54 |
| His | 128 | A | . | . | . | . | T | . | 0.97 | −0.60 | . | . | F | 1.46 | 0.94 |
| Cys | 129 | . | . | B | . | . | T | . | 1.01 | −0.41 | . | . | . | 0.70 | 0.58 |
| Ala | 130 | . | . | B | . | . | . | . | 1.06 | −0.43 | * | * | . | 0.78 | 0.39 |
| Glu | 131 | . | . | B | . | . | . | . | 1.06 | −0.04 | . | . | . | 1.06 | 0.38 |
| Met | 132 | A | . | . | . | . | . | . | 1.01 | −0.14 | . | * | F | 1.64 | 1.15 |
| Ser | 133 | . | . | . | . | T | T | . | 1.04 | −0.31 | . | * | F | 2.52 | 1.82 |
| Ser | 134 | . | . | . | . | T | T | . | 1.01 | −0.41 | . | * | F | 2.80 | 1.69 |
| Asn | 135 | . | . | . | . | T | T | . | 0.79 | 0.37 | . | * | F | 1.92 | 1.48 |
| Asn | 136 | . | . | . | . | . | T | C | 0.48 | 0.44 | . | . | F | 0.99 | 0.91 |
| Asn | 137 | . | . | . | B | . | . | C | 0.79 | 0.54 | . | . | F | 0.31 | 0.98 |
| Phe | 138 | . | . | B | B | . | . | . | 0.79 | 1.07 | . | . | . | −0.32 | 0.64 |
| Leu | 139 | . | . | B | B | . | . | . | 0.79 | 1.06 | . | . | . | −0.60 | 0.54 |
| Thr | 140 | . | . | . | B | T | . | . | 0.79 | 1.04 | . | . | . | −0.20 | 0.45 |
| Trp | 141 | . | . | . | B | T | . | . | 0.79 | 1.04 | . | . | . | −0.20 | 0.83 |
| Ser | 142 | . | . | . | . | . | T | C | 0.12 | 0.26 | * | . | F | 0.60 | 1.74 |
| Ser | 143 | . | . | . | . | . | T | C | 0.82 | 0.14 | * | . | F | 0.79 | 0.65 |
| Asn | 144 | . | . | . | . | T | T | . | 1.68 | 0.06 | . | * | F | 1.33 | 0.99 |
| Glu | 145 | . | . | . | . | T | T | . | 2.10 | −0.86 | . | . | F | 2.72 | 1.47 |
| Cys | 146 | . | . | . | . | T | . | . | 2.39 | −1.24 | . | . | F | 2.86 | 2.16 |
| Asn | 147 | . | . | . | . | T | T | . | 2.66 | −1.23 | . | * | F | 3.40 | 2.32 |
| Lys | 148 | A | . | . | . | . | T | . | 2.26 | −1.13 | . | . | F | 2.66 | 1.82 |
| Arg | 149 | A | . | . | . | . | T | . | 1.44 | −0.34 | . | . | F | 2.02 | 2.95 |
| Gln | 150 | A | . | . | . | . | T | . | 0.78 | −0.23 | . | * | F | 1.68 | 1.51 |
| His | 151 | A | . | . | . | . | . | . | 1.49 | −0.06 | . | * | . | 0.84 | 0.41 |
| Phe | 152 | . | . | B | . | . | . | . | 1.24 | −0.06 | . | * | . | 0.50 | 0.41 |
| Leu | 153 | . | . | B | . | . | . | . | 1.31 | 0.70 | . | * | . | −0.40 | 0.37 |
| Cys | 154 | . | . | B | . | . | T | . | 0.99 | 0.30 | . | * | . | 0.37 | 0.54 |
| Lys | 155 | . | . | . | . | T | T | . | 0.60 | 0.23 | * | * | . | 1.04 | 0.96 |
| Tyr | 156 | . | . | . | . | T | T | . | 0.24 | −0.13 | . | * | . | 2.06 | 1.49 |
| Arg | 157 | . | . | . | . | . | T | C | 0.56 | −0.39 | . | * | . | 2.13 | 3.55 |
| Pro | 158 | . | . | . | . | T | . | . | 0.98 | −0.53 | . | * | . | 2.70 | 2.27 |

In another aspect, the invention provides an antibody that binds a peptide or polypeptide comprising an epitope-bearing portion of a polypeptide described herein. An epitope may either be linear (i.e., consisting of sequential amino acids residues in a protein sequences) or conformational (i.e., consisting of one or more amino acid residues that are not contiguous in the primary structure of the protein but that are brought together by the secondary, tertiary or quaternary structure of a protein). An epitope may an immunogenic and/or an antigenic epitope. An "immunogenic epitope" is defined as a part of a protein that elicits an antibody response. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides are therefore useful to raise antibodies, including monoclonal antibodies, that bind to a Reg IV polypeptide of the invention. See, for instance, Wilson et al., *Cell* 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:172.

Antibodies of the invention may bind one or more antigenic Reg IV polypeptides or peptides including, but not limited to: a polypeptide comprising amino acid residues from about 48 to about 52 of SEQ ID NO:172;.a polypeptide comprising amino acid residues from about 98 to about 103 of SEQ ID NO:172; a polypeptide comprising amino acid residues from about 122 to about 126 of SEQ ID NO:172; a polypeptide comprising amino acid residues from about 132 to about 135 of SEQ ID NO:172; and/or a polypeptide comprising amino acid residues from about 145 to about 150 of SEQ ID NO:172. In this context "about" includes the particularly recited range, larger or smaller by several (5, 4, 3, 2, or 1) amino acids, at either terminus or at both termini. As indicated above, the inventors have determined that the above polypeptide fragments are antigenic regions of the Reg IV protein. Epitope-bearing Reg IV peptides and polypeptides may be produced by any conventional means. Houghten, R. A., "General method for the rapid solid-phase synthesis of large numbers of peptides: specificity of antigen-antibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, Reg IV polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric Reg IV protein or protein fragment alone (Fountoulakis et al., *J Biochem* 270:3958-3964 (1995)). Thus, antibodies of the invention may bind fusion proteins that comprise all or a portion of a Reg IV polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified Reg IV polypeptides or Reg IV polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., *J. Biol. Chem.,* 268:2984-2988 (1993) reported modified KGF proteins that had heparin binding activity even if 3, 8, or 27 amino-terminal amino acid residues were missing However, even if deletion of one or more amino acids from the N-terminus of a protein results in modification or loss of one or more biological functions of the protein, other functional activities (e.g., biological activities, ability to multimerize, and/or ability to bind a Reg IV receptor may still be retained. For example, the ability of shortened Reg IV polypeptides to induce and/or bind to antibodies which recognize the complete or mature forms of the Reg IV polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a Reg IV polypeptide with a large number of deleted N-terminal amino acid residues may retain some biological or immunogenic activities. In fact, peptides composed of as few as six amino acid residues of Reg IV may evoke an immune response.

Accordingly, the present invention further provides antibodies that bind polypeptides having one or more residues deleted from the amino terminus of the Reg IV amino acid sequence of SEQ ID NO:172 up to the leucine residue at position number 153 and polynucleotides encoding such polypeptides. In particular, the present invention provides antibodies that bind polypeptides comprising the amino acid sequence of residues $n^1$-158 of SEQ ID NO:172, where $n^1$ is an integer from 2 to 153 corresponding to the position of the amino acid residue in SEQ ID NO:172

More in particular, the invention provides antibodies that bind polypeptides comprising, or alternatively consisting of, the amino acid sequence of residues of A-2 to P-158; S-3 to P-158; R-4 to P-158; S-5 to P-158; M-6 to P-158; R-7 to P-158; L-8 to P-158; L-9 to P-158; L-10 to P-158; L-11 to P-158; L-12 to P-158; S-13 to P-158; C-14 to P-158; L-15 to P-158; A-16 to P-158; K-17 to P-158; T-18 to P-158; G-19 to P-158; V-20 to P-158; L-21 to P-158; G-22 to P-158; D-23 to P-158; I-24 to P-158; I-25 to P-158; M-26 to P-158; R-27 to P-158; P-28 to P-158; S-29 to P-158; C-30 to P-158; A-31 to P-158; P-32 to P-158; G-33 to P-158; W-34 to P-158; F-35 to P-158; Y-36 to P-158; H-37 to P-158; K-38 to P-158; S-39 to P-158; N-40 to P-158; C-41 to P-158; Y-42 to P-158; G-43 to P-158; Y-44 to P-158; F-45 to P-158; R-46 to P-158; K-47 to P-158; L-48 to P-158; R-49 to P-158; N-50 to P-158; W-51 to P-158; S-52 to P-158; D-53 to P-158; A-54 to P-158; E-55 to P-158; L-56 to P-158; E-57 to P-158; C-58 to P-158; Q-59 to P-158; S-60 to P-158; Y-61 to P-158; G-62 to P-158; N-63 to P-158; G-64 to P-158; A-65 to P-158; H-66 to P-158; L-67 to P-158; A-68 to P-158; S-69 to P-158; I-70 to P-158; L-71 to P-158; S-72 to P-158; L-73 to P-158; K-74 to P-158; E-75 to P-158; A-76 to P-158; S-77 to P-158; T-78 to P-158; I-79 to P-158; A-80 to P-158; E-81 to P-158; Y-82 to P-158; I-83 to P-158; S-84 to P-158; G-85 to P-158; Y-86 to P-158; Q-87 to P-158; R-88 to P-158; S-89 to P-158; Q-90 to P-158; P-91 to P-158; I-92 to P-158; W-93 to P-158; I-94 to P-158; G-95 to P-158; L-96 to P-158; H-97 to P-158; D-98 to P-158; P-99 to P-158; Q-100 to P-158; K-101 to P-158; R-102 to P-158; Q-103 to P-158; Q-104 to P-158; W-105 to P-158; Q-106 to P-158; W-107 to P-158; I-108 to P-158; D-109 to P-158; G-110 to P-158; A-111 to P-158; M-112 to P-158; Y-113 to P-158; L-114 to P-158; Y-115 to P-158; R-116 to P-158; S-117 to P-158; W-118 to P-158; S-119 to P-158; G-120 to P-158; K-121 to P-158; S-122 to P-158; M-123 to P-158; G-124 to P-158; G-125 to P-158; N-126 to P-158; K-127 to P-158; H-128 to P-158; C-129 to P-158; A-130 to P-158; E-131 to P-158; M-132 to P-158; S-133 to P-158; S-134 to P-158; N-135 to P-158; N-136 to P-158; N-137 to P-158; F-138 to P-158; L-139 to P-158; T-140 to P-158; W-141 to P-158; S-142 to P-158; S-143 to P-158; N-144 to P-158; E-145 to P-158; C-146 to P-158; N-147 to P-158; K-148 to P-158; R-149 to P-158; Q-150 to P-158; H-151 to P-158; F-152 to P-158; L-153 to P-158 of the Reg IV sequence of SEQ ID NO:172.

As mentioned above, even if deletion of one or more amino acids from the C-terminus of a protein results in modification of loss of one or more biological functions of the protein, other functional activities (e.g., biological activities, ability to multimerize, and/or ability to bind a Reg IV receptor may still be retained. For example the ability of the shortened Reg IV polypeptide to induce and/or bind to antibodies which recognize the complete or mature forms of the Reg IV polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a Reg IV polypeptide with a large number of deleted C-terminal amino acid residues may retain some biological or immunogenic activities. In fact, peptides composed of as few as six amino acid residues of Reg IV may evoke an immune response.

In another embodiment, antibodies of the invention bind C-terminal deletions of the Reg IV polypeptide that can be described by the general formula 1-$m^1$ where $m^1$ is a number from 6 to 157 corresponding to the amino acid sequence identified of SEQ ID NO:172. In specific embodiments, the invention provides antibodies that bind Reg IV polypeptides comprising, or alternatively consisting of, the amino acid sequence of residues: M-1 to R-157; M-1 to Y-156; M-1 to K-155; M-1 to C-154; M-1 to L-153; M-1 to F-152; M-1 to H-151; M-1 to Q-150; M-1 to R-149; M-1 to K-148; M-1 to N-147; M-1 to C-146; M-1 to E-145; M-1 to N-144; M-1 to S-143; M-1 to S-142; M-1 to W-141; M-1 to T-140; M-1 to L-139; M-1 to F-138; M-1 to N-137; M-1 to N-136; M-1 to N-135; M-1 to S-134; M-1 to S-133; M-1 to M-132; M-1 to E-131; M-1 to A-130; M-1 to C-129; M-1 to H-128; M-1 to K-127; M-1 to N-126; M-1 to G-125; M-1 to G-124; M-1 to M-123; M-1 to S-122; M-1 to K-121; M-1 to G-120; M-1 to S-119; M-1 to W-118; M-1 to S-117; M-1 to R-116; M-1 to Y-115; M-1 to L-114; M-1 to Y-113; M-1 to M-112; M-1 to A-111; M-1 to G-110; M-1 to D-109; M-1 to 1-108; M-1 to W-107; M-1 to Q-106; M-1 to W-105; M-1 to Q-104; M-1 to Q-103; M-1 to R-102; M-1 to K-101; M-1 to Q-100; M-1 to P-99; M-1 to D-98; M-1 to H-97; M-1 to L-96; M-1 to G-95; M-1 to I-94; M-1 to W-93; M-1 to I-92; M-1 to P-91; M-1 to Q-90; M-1 to S-89; M-1 to R-88; M-1 to Q-87; M-1 to Y-86; M-1 to G-85; M-1 to S-84; M-1 to 1-83; M-1 to Y-82; M-1 to E-81; M-1 to A-80; M-1 to I-79; M-1 to T-78; M-1 to S-77; M-1 to A-76; M-1 to E-75; M-1 to K-74; M-1 to L-73; M-1 to S-72; M-1 to L-71; M-1 to 1-70; M-1 to S-69; M-1 to A-68; M-1 to L-67; M-1 to H-66; M-1 to A-65; M-1 to G-64; M-1 to N-63; M-1 to G-62; M-1 to Y-61; M-1 to S-60; M-1 to Q-59; M-1 to C-58; M-1 to E-57; M-1 to L-56; M-1 to E-55; M-1 to A-54; M-1 to D-53; M-1 to S-52; M-1 to W-51; M-1 to N-50; M-1 to R-49; M-1 to L-48; M-1 to K-47; M-1 to R-46; M-1 to F45; M-1 to Y-44; M-1 to G43; M-1 to Y42; M-1 to C41; M-1 to N40; M-1 to S-39; M-1 to K-38; M-1 to H-37; M-1 to Y-36; M-1 to F-35; M-1 to W-34; M-1 to G-33; M-1 to P-32; M-1 to A-31; M-1 to C-30; M-1 to S-29; M-1 to P-28; M-1 to R-27; M-1 to M-26; M-1 to I-25; M-1 to I-24; M-1 to D-23; M-1 to G-22; M-1 to L-21; M-1 to V-20; M-1 to G-19; M-1 to T-18; M-1 to K-17; M-1 to A-16; M-1 to L-15; M-1 to C-14; M-1 to S-13; M-1 to L-12; M-1 to L-11; M-1 to L-10; M-1 to L-9; M-1 to L-8; M-1 to R-7; M-1 to M-6 of the Reg IV sequence of SEQ ID NO:172.

In another embodiment, antibodies of the invention bind C-terminal deletions of the Reg IV polypeptide that can be described by the general formula 23-$m^2$ where $m^2$ is a number from 28 to 157 corresponding to the amino acid sequence identified of SEQ ID NO:172. In specific embodiments, the invention provides antibodies that bind Reg IV polypeptides comprising, or alternatively consisting of, the amino acid sequence of residues: D-23 to R-157; D-23 to Y-156; D-23 to K-155; D-23 to C-154; D-23 to L-153; D-23 to F-152; D-23 to H-151; D-23 to Q-150; D-23 to R-149; D-23 to K-148; D-23 to N-147; D-23 to C-146; D-23 to E-145; D-23 to N-144; D-23 to S-143; D-23 to S-142; D-23 to W-141; D-23 to T-140; D-23 to L-139; D-23 to F-138; D-23 to N-137; D-23 to N-136; D-23 to N-135; D-23 to S-134; D-23 to S-133; D-23 to M-132; D-23 to E-131; D-23 to A-130; D-23 to C-129; D-23 to H-128; D-23 to K-127; D-23 to N-126; D-23 to G-125; D-23 to G-124; D-23 to M-123; D-23 to S-122; D-23 to K-121; D-23 to G-120; D-23 to S-119; D-23 to W-118; D-23 to S-117; D-23 to R-116; D-23 to Y-115; D-23 to L-114; D-23 to Y-113; D-23 to M-112; D-23 to A-111; D-23 to G-110; D-23 to D-109; D-23 to I-108; D-23 to W-107; D-23 to Q-106; D-23 to W-105; D-23 to Q-104; D-23 to Q-103; D-23 to R-102; D-23 to K-101; D-23 to Q-100; D-23 to P-99; D-23 to D-98; D-23 to H-97; D-23 to L-96; D-23 to G-95; D-23 to I-94; D-23 to W-93; D-23 to I-92; D-23 to P-91; D-23 to Q-90; D-23 to S-89; D-23 to R-88; D-23 to Q-87; D-23 to Y-86; D-23 to G-85; D-23 to S-84; D-23 to I-83; D-23 to Y-82; D-23 to E-81; D-23 to A-80; D-23 to I-79; D-23 to T-78; D-23 to S-77; D-23 to A-76; D-23 to E-75; D-23 to K-74; D-23 to L-73; D-23 to S-72; D-23 to L-71; D-23 to I-70; D-23 to S-69; D-23 to A-68; D-23 to L-67; D-23 to H-66; D-23 to A-65; D-23 to G-64; D-23 to N-63; D-23 to G-62; D-23 to Y-61; D-23 to S-60; D-23 to Q-59; D-23 to C-58; D-23 to E-57; D-23 to L-56; D-23 to E-55; D-23 to A-54; D-23 to D-53; D-23 to S-52; D-23 to W-51; D-23 to N-50; D-23 to R-49; D-23 to L-48; D-23 to K47; D-23 to R46; D-23 to F45; D-23 to Y-44; D-23 to G-43; D-23 to Y-42; D-23 to C-41; D-23 to N-40; D-23 to S-39; D-23 to K-38; D-23 to H-37; D-23 to Y-36; D-23 to F-35; D-23 to W-34; D-23 to G-33; D-23 to P-32; D-23 to A-31; D-23 to C-30; D-23 to S-29; D-23 to P-28 of the Reg IV sequence of SEQ ID NO:172.

Antibodies o f the invention may bind polypeptides having one or more amino acids deleted from both the amino and the carboxyl termini of a Reg IV polypeptide, which may be described generally as having residues $n^1$-$m^1$ and/or $n^1$-$m^2$ of SEQ ID NO:172, where $n^1$, $m^1$, and $m^2$ are integers as described above.

Preferably, antibodies of the present invention bind fragments of Reg IV comprising a portion of the mature protein; i.e., within residues 23-158 of SEQ ID NO:172.

It will be recognized in the art that some amino acid sequence of Reg IV can be varied without significant effect of the structure or function of the protein. If such differences in sequence are contemplated, it should be remembered that there will be critical areas on the protein which determine activity. Such areas will usually comprise residues which make up the ligand binding site or which form tertiary structures which affect these domains.

Thus, antibodies of the invention may bind variations of the Reg IV protein which show substantial Reg IV protein activity or which include regions of Reg IV such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:172, or that encoded by the cDNA in ATCC™ deposit 97129. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the Reg IV protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a Reg IV that contains one or more amino acid substitutions, deletions or additions, either from natural mutations or human manipulation.

As indicated, changes are preferably of a minor nature, such as conservative amino acid substitutions (see Table 3) that do not significantly affect the folding or activity of the protein.

TABLE 3

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:172 and/or any of the polypeptide fragments described herein is 75, 70, 60, 50, 40, 35, 30, 25, 20, 15, 10, 9, 8, 7, 6, 5, 4, 3, 2, 1 or 30-20,20-15,20-10, 15-10, 10-1, 5-10, 1-5, 1-3or 1-2.

In specific embodiments, the antibodies of the invention bind Reg IV polypeptides or fragments or variants thereof (especially a fragment comprising or alternatively consisting of, the mature form of Reg IV), that contains any one or more of the following conservative mutations in Reg IV: M1 replaced with A, G, I, L, S, T, or V; A2 replaced with G, I, L, S, T, M, or V; S3 replaced with A, G, I, L, T, M, or V; R4 replaced with H, or K; S5 replaced with A, G, I, L, T, M, or V; M6 replaced with A, G, I, L, S, T, or V; R7 replaced with H, or K; L8 replaced with A, G, I, S, T, M, or V; L9 replaced with A, G, I, S, T, M, or V; L10 replaced with A, G, I, S, T, M, or V; L11 replaced with A, G, I, S, T, M, or V; L12 replaced with A, G, I, S, T, M, or V; S13 replaced with A, G, I, L, T, M, or V; L15 replaced with A, G, I, S, T, M, or V; A16 replaced with G, I, L, S, T, M, or V; K17 replaced with H, or R; T18 replaced with A, G, I, L, S, M, or V; G19 replaced with A, I, L, S, T, M, or V; V20 replaced with A, G, I, L, S, T, or M; L21 replaced with A, G, I, S, T, M, or V; G22 replaced with A, I, L, S, T, M, or V; D23 replaced with E; I24 replaced with A, G, L, S, T, M, or V; I25 replaced with A, G, L, S, T, M, or V; M26 replaced with A, G, I, L, S, T, or V; R27 replaced with H, or K; S29 replaced with A, G, I, L, T, M, or V; A31 replaced with G, I, L, S, T, M, or V; G33 replaced with A, I, L, S, T, M, or V; W34 replaced with F, or Y; F35 replaced with W, or Y; Y36 replaced with F, or W; H37 replaced with K, or R; K38 replaced with H, or R; S39 replaced with A, G, I, L, T, M, or V; N40 replaced with Q; Y42 replaced with F, or W; G43 replaced with A, I, L, S, T, M, or V; Y44 replaced with F, or W; F45 replaced with W, or Y; R46 replaced with H, or K; K47 replaced with H, or R; L48 replaced with A, G, I, S, T, M, or V; R49 replaced with H, or K; N50 replaced with Q; W51 replaced with F, or Y; S52 replaced with A, G, I, L, T, M, or V; D53 replaced with E; A54 replaced with G, I, L, S, T, M, or V; E55 replaced with D; L56 replaced with A, G, I, S, T, M, or V; E57 replaced with D; Q59 replaced with N; S60 replaced with A, G, I, L, T, M, or V; Y61 replaced with F, or W; G62 replaced with A, I, L, S, T, M, or V; N63 replaced with Q; G64 replaced with A, I, L, S, T, M, or V; A65 replaced with G, I, L, S, T, M, or V; H66 replaced with K, or R; L67 replaced with A, G, I, S, T, M, or V; A68 replaced with G, I, L, S, T, M, or V; S69 replaced with A, G, I, L, T, M, or V; I70 replaced with A, G, L, S, T, M, or V; L71 replaced with A, G, I, S, T, M, or V; S72 replaced with A, G, I, L, T, M, or V; L73 replaced with A, G, I, S, T, M, or V; K74 replaced with H, or R; E75 replaced with D; A76 replaced with G, I, L, S, T, M, or V; S77 replaced with A, G, I, L, T, M, or V; T78 replaced with A, G, I, L, S, M, or V; I79 replaced with A, G, L, S, T, M, or V; A80 replaced with G, I, L, S, T, M, or V; E81 replaced with D; Y82 replaced with F, or W; I83 replaced with A, G, L, S, T, M, or V; S84 replaced with A, G, I, L, T, M, or V; G85 replaced with A, I, L, S, T, M, or V; Y86 replaced with F, or W; Q87 replaced with N; R88 replaced with H, or K; S89 replaced with A, G, I, L, T, M, or V; Q90 replaced with N; 192 replaced with A, G, L, S, T, M, or V; W93 replaced with F, or Y; I94 replaced with A, G, L, S, T, M, or V; G95 replaced with A, I, L, S, T, M, or V; L96 replaced with A, G, I, S, T, M, or V; H97 replaced with K, or R; D98 replaced with E; Q100 replaced with N; K101 replaced with H, or R; R102 replaced with H, or K; Q103 replaced with N; Q104 replaced with N; W105 replaced with F, or Y; Q106 replaced with N; W107 replaced with F, or Y; I108 replaced with A, G, L, S, T, M, or V; D109 replaced with E; G110 replaced with A, I, L, S, T, M, or V; A111 replaced with G, I, L, S, T, M, or V; M 212 replaced with A, G, I, L, S, T, or V; Y113 replaced with F, or W; L114 replaced with A, G, I, S, T, M, or V; Y115 replaced with F, or W; R116 replaced with H, or K; S117 replaced with A, G, I, L, T, M, or V; W 118 replaced with F, or Y; S119 replaced with A, G, I, L, T, M, or V; G120 replaced with A, I, L, S, T, M, or V; K121 replaced with H, or R; S122 replaced with A, G, I, L, T, M, or V; M123 replaced with A, G, I, L, S, T, or V; G124 replaced with A, I, L, S, T, M, or V; G125 replaced with A, I, L, S, T, M, or V; N126 replaced with Q; K127 replaced with H, or R; H128 replaced with K, or R; A130 replaced with G, I, L, S, T, M, or V; E131 replaced with D; M132 replaced with A, G, I, L, S, T, or V; S133 replaced with A, G, I, L, T, M, or V; S134 replaced with A, G, I, L, T, M, or V; N135 replaced with Q; N136 replaced with Q; N137 replaced with Q; F138 replaced with W, or Y; L139 replaced with A, G, I, S, T, M, or V; T140 replaced with A, G, I, L, S, M, or V; W141 replaced with F, or Y; S142 replaced with A, G, I, L, T, M, or V; S143 replaced with A, G, I, L, T, M, or V; N144 replaced with Q; E145 replaced with D; N147 replaced with Q; K148 replaced with H, or R; R149 replaced with H, or K; Q150 replaced with N; H151 replaced with K, or R; F152 replaced with W, or Y; L153 replaced with A, G, I, S, T, M, or V; K155 replaced with H, or R; Y156 replaced with F, or W; and/or R157 replaced with H, or K of SEQ ID NO:172.

In specific embodiments, the antibodies of the invention bind Reg IV polypeptides or fragments or variants thereof (especially a fragment comprising or alternatively consisting of, the extracellular soluble domain of Reg IV), that contains any one or more of the following non-conservative mutations in Reg IV: M1 replaced with D, E, H, K, R, N, Q, F, W, Y, P, or C; A2 replaced with D, E, H, K, R, N, Q, F, W, Y, P, or C; S3 replaced with D, E, H, K, R, N, Q, F, W, Y, P, or C; R4 replaced with D, E, A, G, I, L, S, T, M, V, N, Q, F, W, Y, P, or C; S5 replaced with D, E, H, K, R, N, Q, F, W, Y, P, or C; M6 replaced with D, E, H, K, R, N, Q, F, W, Y, P, or C; R7 replaced with D, E, A, G, I, L, S, T, M, V, N, Q, F, W, Y, P, or C; L8 replaced with D, E, H, K, R, N, Q, F, W, Y, P, or C; L9 replaced with D, E, H, K, R, N, Q, F, W, Y, P, or C; L10 replaced with D, E, H, K, R, N, Q, F, W, Y, P, or C; L11 replaced with D, E, H, K, R, N, Q, F, W, Y, P, or C; L12 replaced with D, E, H, K, R, N, Q, F, W, Y, P, or C; S13 replaced with D, E, H, K, R, N, Q, F, W, Y, P, or C; C14 replaced with D, E, H, K, R, A, G, I, L, S, T, M, V, N, Q, F, W, Y, or P; L15 replaced with D, E, H, K, R, N, Q, F, W, Y, P, or C; A16 replaced with D, E, H, K, R, N, Q, F, W, Y, P, or C; K17 replaced with D, E, A, G, I, L, S, T, M, V, N, Q, F, W, Y, P, or C; T18 replaced with D, E, H, K, R, N, Q, F, W, Y, P, or C; G19 replaced with D, E, H, K, R, N, Q, F, W, Y, P, or C; V20 replaced with D, E, H, K, R, N, Q, F, W, Y, P, or C; L21 replaced with D, E, H, K, R, N, Q, F, W, Y, P, or C; G22 replaced with D, E, H, K, R, N, Q, F, W, Y, P, or C; D23 replaced with H, K, R, A, G, I, L, S, T, M, V, N, Q, F, W, Y, P, or C; I24 replaced with D, E, H, K, R, N, Q, F, W, Y, P, or C; I25 replaced with D, E, H, K, R, N, Q, F, W, Y, P, or C; M26 replaced with D, E, H, K, R, N, Q, F, W, Y, P, or C; R27 replaced with D, E, A, G, I, L, S, T, M, V, N, Q, F, W, Y, P, or C; P28 replaced with D, E, H, K, R, A, G, I, L, S, T, M, V, N, Q, F, W, Y, or C; S29 replaced with D, E, H, K, R, N, Q, F, W, Y, P, or C; C30 replaced with D, E, H, K, R, A, G, I, L, S, T, M, V, N, Q, F, W, Y, or P; A31 replaced with D, E, H, K, R, N, Q, F, W, Y, P, or C; P32 replaced with D, E, H, K, R, A, G, I, L, S, T, M, V, N, Q, F, W, Y, or C; G33 replaced with D, E, H, K, R, N, Q, F, W, Y, P, or C; W34 replaced with D, E, H, K, R, N, Q, A, G, I, L, S, T, M, V, P, or C; F35 replaced with D, E, H, K, R, N, Q, A, G, I, L, S, T, M, V, P, or C; Y36 replaced with D, E, H, K, R, N, Q, A, G, I, L, S, T, M, V, P, or C; H37replaced with D, E, A, G, I, L, S, T, M, V, N, Q, F, W, Y, P, or C; K38 replaced with D, E, A, G, I, L, S, T, M, V, N, Q, F, W, Y, P, or C; S39 replaced with D, E, H, K, R, N, Q, F, W, Y, P, or C; N40 replaced with D, E, H, K, R, A, G, I, L, S, T, M, V, F, W, Y, P, or C; C41 replaced with D, E, H, K, R, A, G, I, L, S, T, M, V, N, Q, F, W, Y, or P; Y42 replaced with D, E, H, K, R, N, Q, A, G, I, L, S, T, M, V, P, or C; G43 replaced with D, E, H, K, R, N, Q, F, W, Y, P, or C; Y44 replaced with D, E, H, K, R, N, Q, A, G, I, L, S, T, M, V, P, or C; F45 replaced with D, E, H, K, R, N, Q, A, G, I, L, S, T, M, V, P, or C; R46 replaced with D, E, A, G, I, L, S, T, M, V, N, Q, F, W, Y, P, or C; K47 replaced with D, E, A, G, I, L, S, T, M, V, N, Q, F, W, Y, P, or C; L48 replaced with D, E, H, K, R, N, Q, F, W, Y, P, or C; R49 replaced with D, E, A, G, I, L, S, T, M, V, N, Q, F, W, Y, P, or C; N50 replaced with D, E, H, K, R, A, G, I, L, S, T, M, V, F, W, Y, P, or C; W51 replaced with D, E, H, K, R, N, Q, A, G, I, L, S, T, M, V, P, or C; S52 replaced with D, E, H, K, R, N, Q, F, W, Y, P, or C; D53 replaced with H, K, R, A, G, I, L, S, T, M, V, N, Q, F, W, Y, P, or C; A54 replaced with D, E, H, K, R, N, Q, F, W, Y, P, or C; E55 replaced with H, K, R, A, G, I, L, S, T, M, V, N, Q, F, W, Y, P, or C; L56 replaced with D, E, H, K, R, N, Q, F, W, Y, P, or C; E57 replaced with H, K, R, A, G, I, L, S, T, M, V, N, Q, F, W, Y, P, or C; C58 replaced with D, E, H, K, R, A, G, I, L, S, T, M, V, N, Q, F, W, Y, or P; Q59 replaced with D, E, H, K, R, A, G, I, L, S, T, M, V, F, W, Y, P, or C; S60 replaced with D, E, H, K, R, N, Q, F, W, Y, P, or C; Y61 replaced with D, E, H, K, R, N, Q, A, G, I, L, S, T, M, V, P, or C; G62 replaced with D, E, H, K, R, N, Q, F, W, Y, P, or C; N63 replaced with D, E, H, K, R, A, G, I, L, S, T, M, V, F, W, Y, P, or C; G64 replaced with D, E, H, K, R, N, Q, F, W, Y, P, or C; A65 replaced with D, E, H, K, R, N, Q, F, W, Y, P, or C; H66 replaced with D, E, A, G, I, L, S, T, M, V, N, Q, F, W, Y, P, or C; L67 replaced with D, E, H, K, R, N, Q, F, W, Y, P, or C; A68 replaced with D, E, H, K, R, N, Q, F, W, Y, P, or C; S69 replaced with D, E, H, K, R, N, Q, F, W, Y, P, or C; I70 replaced with D, E, H, K, R, N, Q, F, W, Y, P, or C; L71 replaced with D, E, H, K, R, N, Q, F, W, Y, P, or C; S72 replaced with D, E, H, K, R, N, Q, F, W, Y, P, or C; L73 replaced with D, E, H, K, R, N, Q, F, W, Y, P, or C; K74 replaced with D, E, A, G, I, L, S, T, M, V, N, Q, F, W, Y, P, or C; E75 replaced with H, K, R, A, G, I, L, S, T, M, V, N, Q, F, W, Y, P, or C; A76 replaced with D, E, H, K, R, N, Q, F, W, Y, P, or C; S77 replaced with D, E, H, K, R, N, Q, F, W, Y, P, or C; T78 replaced with D, E, H, K, R, N, Q, F, W, Y, P, or C; I79 replaced with D, E, H, K, R, N, Q, F, W, Y, P, or C; A80 replaced with D, E, H, K, R, N, Q, F, W, Y, P, or C; E81 replaced with H, K, R, A, G, I, L, S, T, M, V, N, Q, F, W, Y, P, or C; Y82 replaced with D, E, H, K, R, N, Q, A, G, I, L, S, T, M, V, P, or C; I83 replaced with D, E, H, K, R, N, Q, F, W, Y, P, or C; S84 replaced with D, E, H, K, R, N, Q, F, W, Y, P, or C; G85 replaced with D, E, H, K, R, N, Q, F, W, Y, P, or C; Y86 replaced with D, E, H, K, R, N, Q, A, G, I, L, S, T, M, V, P, or C; Q87 replaced with D, E, H, K, R, A, G, I, L, S, T, M, V, F, W, Y, P, or C; R88replaced with D, E, A, G, I, L, S, T, M, V, N, Q, F, W, Y, P, or C; S89 replaced with D, E, H, K, R, N, Q, F, W, Y, P, or C; Q90 replaced with D, E, H, K, R, A, G, I, L, S, T, M, V, F, W, Y, P, or C; P91 replaced with D, E, H, K, R, A, G, I, L, S, T, M, V, N, Q, F, W, Y, or C; I92 replaced with D, E, H, K, R, N, Q, F, W, Y, P, or C; W93 replaced with D, E, H, K, R, N, Q, A, G, I, L, S, T, M, V, P, or C; I94 replaced with D, E, H, K, R, N, Q, F, W, Y, P, or C; G95 replaced with D, E, H, K, R, N, Q, F, W, Y, P, or C; L96 replaced with D, E, H, K, R, N, Q, F, W, Y, P, or C; H97 replaced with D, E, A, G, I, L, S, T, M, V, N, Q, F, W, Y, P, or C; D98 replaced with H, K, R, A, G, I, L, S, T, M, V, N, Q, F, W, Y, P, or C; P99 replaced with D, E, H, K, R, A, G, I, L, S, T, M, V, N, Q, F, W, Y, or C; Q100 replaced with D, E, H, K, R, A, G, I, L, S, T, M, V, F, W, Y, P, or C; K101 replaced with D, E, A, G, I, L, S, T, M, V, N, Q, F, W, Y, P, or C; R102 replaced with D, E, A, G, I, L, S, T, M, V, N, Q, F, W, Y, P, or C; Q103 replaced with D, E, H, K, R, A, G, I, L, S, T, M, V, F, W, Y, P, or C; Q104 replaced with D, E, H, K, R, A, G, I, L, S, T, M, V, F, W, Y, P, or C; W105 replaced with D, E, H, K, R, N, Q, A, G, I, L, S, T, M, V, P, or C; Q106 replaced with D, E, H, K, R, A, G, I, L, S, T, M, V, F, W, Y, P, or C; W107 replaced with D, E, H, K, R, N, Q, A, G, I, L, S, T, M, V, P, or C; I108 replaced with D, E, H, K, R, N, Q, F, W, Y, P, or C; D109 replaced with H, K, R, A, G, I, L, S, T, M, V, N, Q, F, W, Y, P, or C; G110 replaced with D, E, H, K, R, N, Q, F, W, Y, P, or C; A111 replaced with D, E, H, K, R, N, Q, F, W, Y, P, or C; M112 replaced with D, E, H, K, R, N, Q, F, W, Y, P, or C; Y113 replaced with D, E, H, K, R, N, Q, A, G, I, L, S, T, M, V, P, or C; L114 replaced with D, E, H, K, R, N, Q, F, W, Y, P, or C; Y115 replaced with D, E, H, K, R, N, Q, A, G, I, L, S, T, M, V, P, or C; R 16 replaced with D, E, A, G, I, L, S, T, M, V, N, Q, F, W, Y, P, or C; S117 replaced with D, E, H, K, R, N, Q, F, W, Y, P, or C; W118 replaced with D, E, H, K, R, N, Q, A, G, I, L, S, T, M, V, P, or C; S119 replaced with D, E, H, K, R, N, Q, F, W, Y, P, or C; G120 replaced with D, E, H, K, R, N, Q, F, W, Y, P, or C; K121 replaced with D, E, A, G, I, L, S, T, M, V, N, Q, F, W, Y, P, or C; S122 replaced with D, E, H, K, R, N, Q, F, W, Y, P, or C; M123 replaced with D, E, H, K, R, N, Q, F, W, Y, P, or C; G124 replaced with D, E, H, K, R, N, Q, F, W, Y, P, or C; G125 replaced with D, E, H, K, R, N, Q, F, W, Y, P, or C; N126 replaced with D, E, H, K, R, A, G, I, L, S, T, M, V, F, W, Y, P, or C; K127 replaced with D, E, A, G, I, L, S, T, M, V, N, Q, F, W, Y, P, or C; H128 replaced with D, E, A, G, I, L, S, T, M, V, N, Q, F, W, Y, P, or C; C129 replaced with D, E, H, K, R, A, G, I, L, S, T, M, V, N, Q, F, W, Y, or P; A130 replaced with D, E, H, K, R, N, Q, F, W, Y, P, or C; E131 replaced with H, K, R, A, G, I, L, S, T, M, V, N, Q, F, W, Y, P, or C; M132 replaced with D, E, H, K, R, N, Q, F, W, Y, P, or C; S133 replaced with D, E, H, K, R, N, Q, F, W, Y, P, or C; S134 replaced with D, E, H, K, R, N, Q, F, W, Y, P, or C; N135 replaced with D, E, H, K, R, A, G, I, L, S, T, M, V, F, W, Y, P, or C; N136 replaced with D, E, H, K, R, A, G, I, L, S, T, M, V, F, W, Y, P, or C; N137 replaced with D, E, H, K, R, A, G, I, L, S, T, M, V, F, W, Y, P, or C; F138 replaced with D, E, H, K, R, N, Q, A, G, I, L, S, T, M, V, P, or C; L139 replaced with D, E, H, K, R, N, Q, F, W, Y, P, or C; T140 replaced with D, E, H, K, R, N, Q, F, W, Y, P, or C; W141 replaced with D, E, H, K, R, N, Q, A, G, I, L, S, T, M, V, P, or C; S142 replaced with D, E, H, K, R, N, Q, F, W, Y, P, or C; S143 replaced with D, E, H, K, R, N, Q, F, W, Y, P, or C; N144 replaced with D, E, H, K, R, A, G, I, L, S, T, M, V, F, W, Y, P, or C; E145 replaced with H, K, R, A, G, I, L, S, T, M, V, N, Q, F, W, Y, P, or C; C146 replaced with D, E, H, K, R, A, G, I, L, S, T, M, V, N, Q, F, W, Y, or P; N147 replaced with D, E, H, K, R, A, G, I, L, S, T, M, V, F, W, Y, P, or C; K148 replaced with D, E, A, G, I, L, S, T, M, V, N, Q, F, W, Y, P, or C; R149 replaced with D, E, A, G, I, L, S, T, M, V, N, Q, F, W, Y, P, or C; Q150 replaced with D, E, H, K, R, A, G, I, L, S, T, M, V, F, W, Y, P, or C; H151 replaced with D, E, A, G, I, L, S, T, M, V, N, Q, F, W, Y, P, or C; F152 replaced with D, E, H, K, R, N, Q, A, G, I, L, S, T, M, V, P, or C; L153 replaced with D, E, H, K, R, N, Q, F, W, Y, P, or C; C154 replaced with D, E, H, K, R, A, G, I, L, S, T, M, V, N, Q, F, W, Y, or P; K155 replaced with D, E, A, G, I, L, S, T, M, V, N, Q, F, W, Y, P, or C; Y156 replaced with D, E, H, K, R, N, Q, A, G, I, L, S, T, M, V, P, or C; R157 replaced with D, E, A, G, I, L, S, T, M, V, N, Q, F, W, Y, P, or C; P158 replaced with D, E, H, K, R, A, G, I, L, S, T, M, V, N, Q, F, W, Y, or C of SEQ ID NO:172.

Amino acids in the Reg IV protein of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of Reg IV that are essential for Reg IV function. In other preferred embodiments, antibodies of the present invention bind regions of Reg IV that are essential for Reg IV function and inhibit or abolish Reg IV function. In other preferred embodiments, antibodies of the present invention bind Reg IV enhance Reg IV function.

Additionally, protein engineering may be employed to improve or alter the characteristics of Reg IV polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified Reg IV polypeptides.

Non-naturally occurring variants of Reg IV may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses antibodies that bind Reg IV derivatives and analogs that have one or more amino acid residues deleted, added, and/or substituted to generate Reg IV polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the Reg IV polypeptides and/or an amino acid deletion at the second position of any one or more such recognition sequences will prevent glycosylation of the Reg IV at the modified tripeptide sequence (see, e.g., Miyajimo et al., EMBO J 5(6):1193-1197). Additionally, one or more of the amino acid residues of Reg IV polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of the polypeptide encoded by the deposited cDNAs (the deposit having ATCC™ Accession Number 97129); a polypeptide comprising, or alternatively, consisting of the polypeptide of SEQ ID NO:172 minus the amino terminal methionine; as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clones (the deposit having ATCC™ Accession Number 97129), the polypeptide of SEQ ID NO:172, and portions of such polypeptides with at least 30 amino acids and more preferably at least 50 amino acids.

By a polypeptide having an amino acid sequence at least, for example, 95% "identical" to a reference amino acid sequence of a Reg IV polypeptide is intended that the amino acid sequence of the polypeptide is identical to the reference sequence except that the polypeptide sequence may include up to one amino acid alterations per each 20 amino acids of the reference amino acid of the Reg IV polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:172 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty-5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the Reg IV polypeptide sequence set forth herein as $n^1$-$m^1$, and/or $n^1$-$m^2$. In preferred embodiments, the present invention encompasses antibodies that bind proteins containing polypeptides at least 90%, 95%, 96%, 97%, 98% or 99% identical to polypeptides having the amino acid sequence of the specific Reg IV N- and C-terminal deletions recited herein.

In certain preferred embodiments, antibodies of the invention bind Reg IV fusion proteins as described above wherein the Reg IV portion of the fusion protein are those described as $n^1$-$m^1$, and/or $n^1$-$m^2$ herein.

Antibodies of the Invention May Bind Modified Reg IV Polypeptides

It is specifically contemplated that antibodies of the present invention may bind modified forms of Reg IV protein.

In specific embodiments, antibodies of the present invention bind Reg IV polypeptides (such as those described above) including, but not limited to naturally purified Reg IV polypeptides, Reg IV polypeptides produced by chemical synthetic procedures, and Reg IV polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, Reg IV polypeptides may also include an initial modified methionine residue, in some cases as a result of host-mediated processes.

In addition, Reg IV proteins that antibodies of the present invention may bind can be chemically synthesized using techniques known in the art (e.g., see Creighton, Proteins: Structures and Molecular Principles, W. H. Freeman & Co., N.Y. (1983), and Hunkapiller, et al., *Nature* 310:105-111 (1984)). For example, a peptide corresponding to a fragment of a Reg IV polypeptide can be synthesized by use of a peptide synthesizer. Furthermore, if desired, nonclassical amino acids or chemical amino acid analogs can be introduced as a substitution or addition into the Reg IV polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses antibodies that bind Reg IV polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications to Reg IV polypeptides include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of Reg IV polypeptide which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties, attached to each Reg IV polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the antibodies of the present invention may bind Reg IV polypeptides that are modified by either natural processes, such as posttranslational processing, or by chemical modification techniques which are well known in the art. It will be appreciated that the same type of modification may be present in the same or varying degrees at several sites in a given Reg IV polypeptide. Reg IV polypeptides may be branched, for example, as a result of ubiquitination, and they may be cyclic, with or without branching. Cyclic, branched, and branched cyclic Reg IV polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Antibodies that Specifically Bind Reg IV

In one embodiment, the invention provides antibodies (e.g., anti-Reg IV antibodies comprising two heavy chains and two light chains linked together by disulfide bridges) that specifically bind a Reg IV polypeptide (e.g., SEQ ID NO:172) or fragments or variants thereof, wherein the amino acid sequence of the heavy chain and the amino acid sequence of the light chain are the same as the amino acid sequence of a heavy chain and a light chain of an antibody expressed by one or more cell lines referred to in Table 1. In another embodiment, the invention provides antibodies (each consisting of two heavy chains and two light chains linked together by disulfide bridges to form an antibody) that specifically bind a Reg IV polypeptide (e.g., SEQ ID NO:172) or fragments or variants thereof, wherein the amino acid sequence of the heavy chain or the amino acid sequence of the light chain are the same as the amino acid sequence of a heavy chain or a light chain of an antibody expressed by one or more cell lines referred to in Table 1. Specific binding to Reg IV polypeptides may be determined by immunoassays known in the art or described herein for assaying specific antibody-antigen binding. Molecules comprising, or alternatively consisting of, fragments or variants of these antibodies that specifically bind to Reg IV are also encompassed by the invention, as are nucleic acid molecules encoding these antibodies molecules, fragments and/or variants (e.g., SEQ ID NOs:68-134).

In one embodiment of the present invention, antibodies that specifically bind to Reg IV or a fragment or variant thereof, comprise a polypeptide having the amino acid sequence of a heavy chain of an antibody expressed by at least one of the cell lines referred to in Table 1 and/or a light chain of an antibody expressed by at least one of the cell lines referred to in Table 1.

In another embodiment of the present invention, antibodies that specifically bind to Reg IV or a fragment or variant thereof, comprise a polypeptide having the amino acid sequence of any one of the VH domains of at least one of the scFvs referred to in Table 1 and/or any one of the VL domains of at least one of the scFvs referred to in Table 1. In preferred embodiments, antibodies of the present invention comprise the amino acid sequence of a VH domain and VL domain of the scFvs referred to in Table 1. Molecules comprising, or alternatively consisting of, antibody fragments or variants of the VH and/or VL domains of at least one of the scFvs referred to in Table 1 that specifically bind to Reg IV are also encompassed by the invention, as are nucleic acid molecules encoding these VH and VL domains, molecules, fragments and/or variants.

The present invention also provides antibodies that specifically bind to a polypeptide, or polypeptide fragment or variant of Reg IV, wherein said antibodies comprise, or alternatively consist of, a polypeptide having an amino acid sequence of any one, two, three, or more of the VH CDRs contained in a VH domain of one or more scFvs referred to in Table 1. In particular, the invention provides antibodies that specifically bind Reg IV, comprising, or alternatively consisting of, a polypeptide having the amino acid sequence of a VH CDR1 contained in a VH domain of one or more scFvs referred to in Table 1. In another embodiment, antibodies that specifically bind Reg IV, comprise, or alternatively consist of, a polypeptide having the amino acid sequence of a VH CDR2 contained in a VH domain of one or more scFvs referred to in Table 1. In a preferred embodiment, antibodies that specifically bind Reg IV comprise, or alternatively consist of, a polypeptide having the amino acid sequence of a VH CDR3 contained in a VH domain of one or more scFvs referred to in Table 1. Molecules comprising, or alternatively consisting of, these antibodies or antibody fragments or variants thereof, that specifically bind to Reg IV or a Reg IV fragment or variant thereof are also encompassed by the invention, as are nucleic acid molecules encoding these antibodies, molecules, fragments and/or variants (e.g., SEQ ID NOs:68-134).

The present invention also provides antibodies that specifically bind to a polypeptide, or polypeptide fragment or variant of Reg IV, wherein said antibodies comprise, or alternatively consist of, a polypeptide having an amino acid sequence of any one, two, three, or more of the VL CDRs contained in a VL domain of one or more scFvs referred to in Table 1. In particular, the invention provides antibodies that specifically bind Reg IV, comprising, or alternatively consisting of, a polypeptide having the amino acid sequence of a VL CDR1 contained in a VL domain of one or more scFvs referred to in Table 1. In another embodiment, antibodies that specifically bind Reg IV, comprise, or alternatively consist of, a polypeptide having the amino acid sequence of a VL CDR2 contained in a VL domain of one or more scFvs referred to in Table 1. In a preferred embodiment, antibodies that specifically bind Reg IV comprise, or alternatively consist of, a polypeptide having the amino acid sequence of a VL CDR3 contained in a VL domain of one or more scFvs referred to in Table 1. Molecules comprising, or alternatively consisting of, these antibodies or antibody fragments or variants thereof, that specifically bind to Reg IV or a Reg IV fragment or variant thereof are also encompassed by the invention, as are nucleic acid molecules encoding these antibodies, molecules, fragments and/or variants (e.g., SEQ ID NOs:68-134).

The present invention also provides antibodies (including molecules comprising, or altematively consisting of, antibody fragments or variants) that specifically bind to a Reg IV polypeptide or polypeptide fragment or variant of Reg IV, wherein said antibodies comprise, or alternatively consist of, one, two, three, or more VH CDRs and one, two, three or more VL CDRs, as contained in a VH domain or VL domain of one or more scFvs referred to in Table 1. In particular, the invention provides for antibodies that specifically bind to a polypeptide or polypeptide fragment or variant of Reg IV, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VIH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1. In a preferred embodiment, one or more of these combinations are from the same scFv as disclosed in Table 1. Molecules comprising, or alternatively consisting of, fragments or variants of these antibodies, that specifically bind to Reg IV are also encompassed by the invention, as are nucleic acid molecules encoding these antibodies, molecules, fragments or variants (e.g., SEQ ID NOs:68-134).

Nucleic Acid Molecules Encoding Anti-Reg IV Antibodies

The present invention also provides for nucleic acid molecules, generally isolated, encoding an antibody of the invention (including molecules comprising, or alternatively consisting of, antibody fragments or variants thereof). In specific embodiments, the nucleic acid molecules encoding an antibody of the invention comprise, or alternatively consist of SEQ ID NOs:68-134 or fragments or variants thereof.

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 and a VL domain having an amino acid sequence of VL domain of at least one of the scFvs referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or a VL domain having an amino acid sequence of a VL domain of at least one of the scFvs referred to in Table 1.

The present invention also provides antibodies that comprise, or alternatively consist of, variants (including derivatives) of the antibody molecules (e.g., the VH domains and/or VL domains) described herein, which antibodies specifically bind to Reg IV or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randonly along all or part of the coding sequence, such as by saturation mutagenesis, and the resultant mutants can be screened for biological activity to identify mutants that retain activity (e.g., the ability to bind a Reg IV receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or mprove a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to specifically bind Reg IV) can be determined using techniques described herein or by routinely modifying techniques known in the art.

In a specific embodiment, an antibody of the invention (including a molecule comprising, or alternatively consisting of, an antibody fragment or variant thereof), that specifically binds Reg IV polypeptides or fragments or variants thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1. under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds. , 1989, *Current Protocols in Molecular Biology, Vol. I, Green Publishing Associates, Inc. and John Wiley & Sons, Inc., New York at pages* 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to a Reg IV polypeptide or fragments or variants of a Reg IV polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1.

In another embodiment, an antibody (including a molecule comprising, or alternatively consisting of, an antibody fragment or variant thereof), that specifically binds to a Reg IV polypeptide or fragments or variants of a Reg IV polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1.

Methods of Producing Antibodies

Antibodies in accordance with the invention are preferably prepared utilizing a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a Reg IV polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/O1 134; PCT publications WO 90/02809; WO 91/10737; WO 92/01047; WO 92/18719; WO 93/1 1236; WO 95/15982; WO 95/20401; W097/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single chain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind Reg IV polypeptides with preferred binding characteristics such as improved affinity or improved off rates. Additionally, VH and VL domains—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind Reg IV polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including, but not limited to, myeloma cell lines hybridoma cell lines. Sequences encoding the cDNAs or genomic clones for the particular antibodies can be used for transformation of a suitable mammalian or non-mammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 2), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH or VL domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the mmunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, .e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, NY and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of one or more scFvs referred to in Table 1, or fragments or variants thereof, are inserted within antibody framework regions using recombinant DNA techniques known in the art. In a specific embodiment, one, two, three, four, five, six, or more of the CDRs of VH and/or VL domains of one or more scFvs referred to in Table 1, or fragments or variants thereof, are inserted within antibody framework regions using recombinant DNA techniques known in the art. The antibody framework regions may be naturally occurring or consensus antibody framework regions, and preferably human antibody framework regions (see, e.g., Chothia et al., J. Mol. Biol. 278: 457-479 (1998) for a listing of human antibody framework regions, the contents of which are hereby incorporated by reference in its entirety). Preferably, the polynucleotides generated by the combination of the antibody framework regions and CDRs encode an antibody (including molecules comprising, or alternatively consisting of, antibody fragments or variants thereof) that specifically binds to Reg IV. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

XENOMOUSE™ Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral mmune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (mAbs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XENOMOUSE™ strains as published in 1994. See Green et al. *Nature Genetics* 7:13-21 (1994). The XENOMOUSE™ strains were engineered with yeast artificial chromosomes (YACS) containing germline configuration fragments of the human heavy chain locus and kappa light chain locus, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XENOMOUSE™ mice. See Mendez et al. *Nature Genetics* 15:146-156 (1997), Green and Jakobovits *J Exp. Med.* 188:483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, Ser. No. 07/710,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/471,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J Exp. Med.* 188:483 495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against Reg IV polypeptides in order to vitiate concerns and/or effects of HAMA or HACA responses.

Monoclonal antibodies specific for Reg IV polypeptides may also be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XENOMOUSE™ mice may be immunized with Reg IV polypeptides. After immunization, the splenocytes of such mice may be extracted and fused with a suitable myeloma cell line. Any suitable myeloma cell line may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the Reg IV polypeptides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, W098/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another mmunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1, or fragments or variants thereof, and framework regions (and, optionally one or more CDRs not present in the scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s of a VH or VL domain of one or more of the scFvs referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants thereof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entireties by reference herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa califomica nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, HeLa, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O30 and HsS78Bst.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloning, Vol.* 3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: W087/04462; W086/05807; W089/01036; W089/10404; and W091/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, t may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310: 105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal on, e.g., alpha-emitters such as, for example, 213Bi, or other radioisotopes such as, for example, iodine (131I, 125I, 123I, 121I ), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin.

In specific embodiments, antibodies of the invention may be labeled with Europium. For example, antibodies of the invention may be labelled with Europium using the DELFIA Eu-labeling kit (catalog# 1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N",N"'-tetraacetic acid (DOTA). In specific embodiments, the macrocyclic chelator is α-(5-isothiocyanato-2-methoxyphenyl)-1,4,7,10-tetraaza-cyclododecane-1,4,7,10-tetraacetic acid. In other specific embodiments, the DOTA is attached to the antibody of the invention via a linker molecule. Examples of linker molecules useful for conjugatinga macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus -may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intenn. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (ClSO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-Reg IV Antibodies

Antibodies of the present invention (including molecules comprising, or alternatively consisting of, antibody fragments or variants thereof) may also be described or specified in terms of their binding to Reg IV polypeptides or fragments or variants of Reg IV polypeptides. In specific embodiments, antibodies of the invention bind Reg IV polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind Reg IV polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind Reg IV polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times^{13}$ M, $10^{-13}$ M, $5\times10^{-14}$ M, $10^{-14}$ M, $5\times10^{-15}$ M, or $10^{-15}$ M. The invention encompasses antibodies that bind Reg IV polypeptides with a dissociation constant or $K_D$ that is within any one of the ranges that are between each of the individual recited values.

In specific embodiments, antibodies of the invention bind Reg IV polypeptides or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, antibodies of the invention bind Reg IV polypeptides or fragments or variants thereof with an off rate ($k_{off}$) less than or equal to $5\times10^{-4}$ sec$^{-1}$, $10^{-4}$sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$. The invention encompasses antibodies that bind Reg IV polypeptides with an off rate ($k_{off}$) that is within any one of the ranges that are between each of the individual recited values.

In other embodiments, antibodies of the invention bind Reg IV polypeptides or fragments or variants thereof with an on rate ($k_{on}$) of greater than or equal to $10^3$ M$^{-1}$ sec$^{-1}$, $5\times10^3$ M$^{-1}$ sec$^{-}$, $10^4$ M$^{-1}$ sec$^{-1}$ or $5\times10^4$ M$^{-1}$ sec$^{-1}$. More preferably, antibodies of the invention bind Reg IV polypeptides or fragments or variants thereof with an on rate ($k_{on}$) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$. The invention encompasses antibodies that bind Reg IV polypeptides with on rate ($k_{on}$) that is within any one of the ranges that are between each of the individual recited values.

The antibodies of the invention (including molecules comprising, or alternatively consisting of, antibody fragments or variants thereof) specifically bind to a polypeptide or polypeptide fragment or variant of human Reg IV (e.g., SEQ ID NO:172). In another embodiment, the antibodies of the invention specifically bind to a polypeptide or polypeptide fragment or variant of simian Reg IV polypeptides. In yet another embodiment, the antibodies of the invention specifically bind to a polypeptide or polypeptide fragment or variant of murine Reg IV polypeptides. In one embodiment, the antibodies of the invention bind specifically to human and simian Reg IV polypeptides. In another embodiment, the antibodies of the invention bind specifically to human Reg IV polypeptides and murine Reg IV polypeptides. More preferably, antibodies of the invention, preferentially bind to human Reg IV polypeptides compared to murine Reg IV polypeptides.

In preferred embodiments, the antibodies of the present invention (including molecules comprising, or alternatively consisting of, antibody fragments or variants thereof), specifically bind to Reg IV polypeptides and do not cross-react with any other antigens. In preferred embodiments, the antibodies of the invention specifically bind to Reg IV polypeptides (e.g., SEQ ID NO:172 or fragments or variants thereof) and do not cross-react with one or more additional members of the Reg Family (e.g., Reg I-alpha (REG1A), Reg I-beta (REG1B), REG-related sequence (RS), and/or pancreatitis associated protein (PAP)).

In another embodiment, the antibodies of the present invention (including molecules comprising, or alternatively consisting of, antibody fragments or variants thereof), specifically bind to Reg IV polypeptides and cross-react with other antigens. In other embodiments, the antibodies of the invention specifically bind to Reg IV polypeptides (e.g., SEQ ID NO:172, or fragments or variants thereof) and cross-react with one or more additional members of the Reg Family (e.g., Reg I-alpha (REG1A), Reg I-beta (REG1B), REG-related sequence (RS), and/or pancreatitis associated protein (PAP)).

By way of non-limiting example, an antibody may be considered to bind a first antigen preferentially f it binds said first antigen with a dissociation constant ($K_D$) that is less than the antibody's $K_D$ for the second antigen. In another non-limiting embodiment, an antibody may be considered to bind a first antigen preferentially if t binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affmity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if t binds said first antigen with a $k_{off}$ that is at least one order of magnitude less than the antibody's $k_{off}$ for the second antigen. In another non-limiting embodiment, an antibody may be considered to bind a first antigen preferentially if t binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to Reg IV polypeptides, the ability to inhibit Reg IV mediated biological activity (e.g., the ability to inhibit proliferation of cancerous cells, see Example 3, or the ability to inhibit proliferation of Reg IV receptor expressing cells); or the ability to substantially block binding of Reg IV, or a fragment, variant or fusion protein thereof, to its receptor. Other biological activities that antibodies against Reg IV polypeptides may have, include, but are not limited to, the ability to stimulate Reg IV mediated biological activity (e.g., to stimulate proliferation of pancreatic beta-cells or the ability to stimulate proliferation of Reg IV receptor expressing cells). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that inhibit one or more Reg IV polypeptide mediated biological activities. In one embodiment, an antibody that inhibits one or more Reg IV polypeptide mediated biological activities comprises, or alternatively consists of a VH and/or a VL domain of at least one of the scFvs referred to in Table 1, or fragment or variant thereof. In a specific embodiment, an antibody that inhibits one or more Reg IV polypeptide mediated biological activities comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that inhibit proliferation of cells (e.g., cancerous cells). In one embodiment, an antibody that inhibits proliferation of cells (e.g., cancerous cells) comprises, or alternatively consists of a VH and/or a VL domain of at least one of the scFvs referred to in Table 1, or fragment or variant thereof. In a specific embodiment, an antibody that inhibits proliferation of cells (e.g., cancerous cells) comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the binding of Reg IV to a Reg IV receptor. In one embodiment, an antibody that blocks or inhibits the binding of Reg IV to a Reg IV receptor comprises, or alternatively consists of a VH and/or a VL domain of at least one of the scFvs referred to in Table 1, or fragment or variant thereof. In a specific embodiment, an antibody that blocks or inhibits the binding of Reg IV to a Reg IV receptor comprises, or alternatively consists of a VH and a VL domain of any one of the scFvs referred to in Table 1, or fragment or variant thereof. In a specific embodiment, the Reg IV receptor is a member of the multiple exostoses family. Nucleic acid molecules encoding these antibodies are also encompassed by the invention.

The present invention also provides for antibodies (including molecules comprising, or alternatively consisting of, antibody fragments or variants thereof), that stimulate proliferation of cells (e.g., pancreatic beta-cells). In one embodiment, an antibody that stimulates proliferation of cells (e.g., pancreatic beta-cells) comprises, or alternatively consists of a VH and/or a VL domain of at least one of the scFvs referred to in Table 1, or fragment or variant thereof. In a specific embodiment, an antibody that stimulates proliferation of cells (e.g., pancreatic beta-cells) comprises, or alternatively consists of a VH and a VL domain of any one of the scFvs referred to in Table 1, or fragment or variant thereof. Nucleic acid molecules encoding these antibodies are also encompassed by the invention.

Antibodies of the present invention (including antibody fragments or variants thereof) may be characterized in a variety of ways. In particular, antibodies and related molecules of the invention may be assayed for the ability to specifically bind to Reg IV polypeptides or a fragment or variant of Reg IV polypeptides using techniques described herein or routinely modifying techniques known in the art. Assays for the ability of the antibodies of the invention to specifically bind Reg IV polypeptides or a fragment of Reg IV polypeptides may be performed in solution (e.g., Houghten, Bio/Techniques 13:412-421(1992)), on beads (e.g., Lam, Nature 354: 82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Antibodies that have been identified to specifically bind to Reg IV polypeptides or a fragment or variant of Reg IV polypeptides can then be assayed for their specificity and affinity for Reg IV polypeptides or fragments or variants of Reg IV polypeptides using or routinely modifying techniques described herein or otherwise known in the art.

The antibodies of the invention may be assayed for specific binding to Reg IV polypeptides and cross-reactivity with other antigens by any method known in the art. Immunoassays which can be used to analyze specific binding and cross-reactivity include, but are not limited to, competitive and non-competitive assay systems using techniques such as BIACORE™ analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen in the form of a Reg IV-Fc fusion protein, may be bound to the anti-Ig Fc coated to the plate. This may be desirable so as to maintain the antigen protein (e.g., the Reg IV polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for Reg IV and the binding off-rates can be determined from the data by Scatchard plot analysis. Competition with a second antibody can also be determined using radioimmunoassays. In this case, Reg IV polypeptide is incubated with an antibody of the present invention conjugated to a labeled compound (e.g., compound labeled with $^3$H or $^{125}$I) in the presence of increasing amounts of an unlabeled second anti-Reg IV antibody. This kind of competitive assay between two antibodies, may also be used to determine if two antibodies bind the same, closely associated (e.g., overlapping) or different epitopes.

In a preferred embodiment, BIACORE™ kinetic analysis is used to determine the binding on and off rates of antibodies (including antibody fragments or variants thereof) to Reg IV, or fragments of Reg IV. BIACORE™ kinetic analysis comprises analyzing the binding and dissociation of antibodies from chips with immobilized Reg IV on their surface.

Immunoprecipitation protocols generally comprise lysing a population of cells in a lysis buffer such as RIPA buffer (1% NP-40 or Triton X-100, 1% sodium deoxycholate, 0.1% SDS, 0.15M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of.the polypeptide) to generate fusion proteins. The fusion does not necessarily need to be direct, but may occur through linker sequences. For example, antibodies of the invention may be used to target heterologous polypeptides to particular cell types (e.g., pancreatic beta-cells and/or colon cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/2 1232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, $F(ab)_2$ fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 9 1/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357-11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287: 265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to Reg IV may be recombined with one or more components, motifs, sections, parts, domains, fragments, etc. of one or more heterologous molecules.

Moreover, the antibodies of the present invention (including antibody fragments or variants thereof), can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{135}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}y$, $^{47}Sc$, $^{186}Re$, $^{188}Re$, $^{142}Pr$, $^{105}Rh$, and $^{97}Ru$.

Further, an antibody of the invention (including an scFv or other molecule comprising, or alternatively consisting of, antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$p, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), Fas Ligand (Takahashi et al., *Int. Immunol.,* 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et aL (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of Reg IV polypeptides in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types, such as pancreatic beta-cells. In other embodiments, the antibodies of the invention may be useful as tumors and/or cancer cell markers (e.g., colon cancer cells). Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

Epitope Mapping

The present invention provides antibodies (including antibody fragments or variants thereof), that can be used to identify epitopes of a Reg IV polypeptide. In particular, the antibodies of the present invention can be used to identify epitopes of a human Reg IV polypeptide (e.g., SEQ ID NO:172); a murine Reg IV; a rat Reg IV polypeptide; or a monkey Reg IV polypeptide, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occurring forms of Reg IV polypeptides.

Diagnostic Uses of Antibodies

Labeled antibodies of the invention (including molecules comprising, or alternatively consisting of, antibody fragments or variants thereof) which specifically bind to a Reg IV polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) which specifically bind to a Reg IV polypeptide can be used for diagnostic purposes to detect, diagnose, prognose, or monitor diseases and/or disorders associated with the aberrant expression and/or activity of a Reg IV polypeptide.

The invention provides for the detection of expression of a Reg IV polypeptide comprising: (a) assaying the expression of a Reg IV polypeptide in a biological sample from an individual using one or more antibodies of the invention that specifically binds to a Reg IV polypeptide; and (b) comparing the level of a Reg IV polypeptide with a standard level of a Reg IV polypeptide, (e.g., the level in normal biological samples).

The invention provides for the detection of aberrant expression of a Reg IV polypeptide comprising: (a) assaying the expression of a Reg IV polypeptide in a biological sample from an individual using one or more antibodies of the invention that specifically binds to a Reg IV polypeptide; and (b) comparing the level of a Reg IV polypeptide with a standard level of a Reg IV polypeptide, e.g., in normal biological samples, whereby an increase or decrease in the assayed level of a Reg IV polypeptide compared to the standard level of a Reg IV polypeptide is indicative of aberrant expression.

By "biological sample" is intended any fluids and/or cells obtained from an individual, body fluid, body tissue, body cell, cell line, tissue culture, or other source which may contain a Reg IV polypeptide protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with aberrant expression of a Reg IV polypeptide or a Reg IV polypeptide receptor in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that specifically binds to a Reg IV polypeptide; b) waiting for a time interval following the administering for permitting the labeled antibody to preferentially concentrate at sites in the subject where Reg IV polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of a Reg IV polypeptide or a Reg IV polypeptide receptor. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 milliCuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In specific embodiments, antibodies of the present invention may be used in the diagnosis, prevention, and treatment of gastrointestinal tract cancers, inflammatory bowel diseases, and/or diabetes, particularly those diseases and/or disorders described in the "Therapeutic Uses of Antibodies" sections below.

Therapeutic Uses of Antibodies

One or more antibodies of the present invention (including molecules comprising, or alternatively consisting of, antibody fragments or variants thereof) that specifically bind to Reg IV may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein.

Therapeutic Uses of Antibodies for Treating Cancers

In highly preferred embodiments, antibodies of the invention that bind a Reg IV polypeptide and inhibit proliferation of Reg IV receptor expressing cells are used to diagnose, treat, prevent or ameliorate cancer. In specific embodiments, antibodies of the invention are used to inhibit the progression or metastasis of colon cancer.

In other preferred embodiments, antibodies of the invention that bind a Reg IV polypeptide and inhibit proliferation of Reg IV receptor expressing cells are used to diagnose, treat, prevent or ameliorate cancers and related disorders including, but not limited to, cervical cancer, leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In specific embodiments, antibodies of the invention used to treat the aforementioned cancers are administered with or conjugated to a cytotoxic and/or chemotherapeutic agent.

Therapeutic Uses of Antibodies for Treating Inflammatory Disorders and Wound Healing In highly preferred embodiments, antibodies and antibody compositions of the invention may be useful for treating, diagnosing, preventing, and/or detecting inflammatory diseases. In a specific embodiment, antibodies and antibody compositions of the invention are useful in the diagnosis, treatment, detection, and/or prevention of Crohn's disease, ulcerative colitis, and other inflammatory bowel diseases.

In other preferred embodiments, antibodies and antibody compositions of the invention are useful in the diagnosis and treatment or prevention of immune diseases and disorders including, but not limited to, inflammation associated with infection (e.g., septic shock, sepsis, or systemic inflammatory response syndrome), schemia-reperfusion injury, endotoxin lethality, complement-mediated hyperacute rejection, nephritis, cytokine or chemokine induced lung injury, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can affect virtually any tissue of the body. Accordingly, antibodies of the invention have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In other preferred embodiments, antibodies of the present invention are useful to diagnose, prognose, prevent, and/or treat immune complex diseases, including, but not limited to, serum sickness, post streptococcal glomerulonephritis, polyarteritis nodosa, and immune complex-induced vasculitis.

Antibodies and antibody compositions of the invention are also useful in promoting angiogenesis and/or wound healing (e.g., wounds, burns, ulcers, and bone fractures).

In a highly preferred embodiment, antibodies and antibody compositions of the invention may be used to stimulate epithelial cell proliferation and basal keratinocytes for the purpose of wound healing, and to stimulate hair follicle production and healing of dermal wounds. Antibodies and antibody compositions of the invention may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Antibodies and antibody compositions of the invention could be used to promote dermal reestablishment subsequent to dermal loss In another highly preferred embodiment, antibodies and antibody compositions of the invention may be used as an adjuvant to enhance immune responsiveness to specific antigen, such as in anti-viral immune responses.

More generally, antibodies and antibody compositions of the invention are useful in regulating (i.e., elevating or reducing) immune response. For example, antibodies and antibody compositions of the invention may be useful in preparation or recovery from surgery, trauma, radiation therapy, chemotherapy, and transplantation, or may be used to boost immune response and/or recovery in the elderly and immunocompromised individuals. Alternatively, antibodies and antibody compositions of the invention are useful as immunosuppressive agents, for example in the treatment or prevention of autoimmune disorders. In specific embodiments, antibodies and antibody compositions of the invention are used to treat or prevent chronic inflammatory, allergic or autoimmune conditions, such as those described herein or are otherwise known in the art.

Therapeutic and Diagnostic Uses of Antibodies for Treating Diabetes Mellitus

In highly preferred embodiments, antibodies and antibody compositions of the invention are used to diagnose, treat, prevent or ameliorate disorders of carbohydrate metabolism including, but not limited to, Insulin-Dependent Diabetes Mellitus and/or Non-Insulin-Dependent Diabetes Mellitus.

In other preferred embodiments, antibodies and antibody compositions of the invention are used to diagnose, treat, prevent or ameliorate disorders of insulin secretion and/or action including, but not limited to, hyperinsulinemia, insulin resistance, insulin deficiency, hyperglycemia, hypoglycemia, hyperlipidemia, and hyperketonemia.

Additional Therapeutic Uses of Antibodies

The antibodies of the invention can be used to diagnose, treat, ameliorate or prevent diseases, disorders or conditions associated with aberrant expression and/or activity of Reg IV, including, but not limited to, any one or more of the diseases, disorders, or conditions described herein. The treatment and/or prevention of diseases, disorders, or conditions associated with aberrant Reg IV expression and/or activity includes, but is not limited to, alleviating symptoms associated with those diseases, disorders or conditions. Antibodies of the invention may be provided in pharmaceutically acceptable compositions as known in the art or as described herein.

Further, antibodies of the present invention (including molecules comprising, or alternatively consisting of, antibody fragments or variants thereof) which activate Reg IV-mediated biological activities (e.g., proliferation of pancreatic beta-cells)) can be administered to an animal to diagnose, treat, prevent or ameliorate a disease or disorder described herein, particularly diabetes mellitus. These antibodies may potentiate or activate either all or a subset of the biological activities of Reg IV, for example, by inducing a conformational change in Reg IV. In a specific embodiment, an antibody of the present invention that increases Reg IV activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to Reg IV activity in absence of the antibody is administered to an animal to diagnose, treat, prevent or ameliorate a disease or disorder. In another embodiment, a combination of antibodies, a combination of antibody fragments, a combination of antibody variants, or a combination of antibodies, antibody fragments and/or antibody variants that increase Reg IV activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to Reg IV activity in absence of the said antibodies or antibody fragments and/or antibody variants is administered to an animal to diagnose, treat, prevent or ameliorate a disease or disorder.

Further, antibodies of the present invention (including molecules comprising, or alternatively consisting of, antibody fragments or variants thereof) which activate Reg IV-mediated biological activities (e.g., the inhibition of inflammation) can be administered to an animal to diagnose, treat, prevent or ameliorate a disease or disorder associated with aberrant Reg IV expression and/or function or aberrant Reg IV receptor expression and/or function, especially inflammatory bowel disorders (e.g., Crohn's disease and ulcerative colitis). These antibodies may potentiate or activate either all or a subset of the biological activities of Reg IV, for example, by inducing a conformational change in Reg IV. In a specific embodiment, an antibody of the present invention that increases Reg IV activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to Reg IV activity in absence of the antibody is administered to an animal to diagnose, treat, prevent or ameliorate a disease or disorder associated with aberrant Reg IV expression and/or function or aberrant Reg IV receptor expression and/or function. In another embodiment, a combination of antibodies, a combination of antibody fragments, a combination of antibody variants, or a combination of antibodies, antibody fragments and/or antibody variants that increase Reg IV activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to Reg IV activity in absence of the said antibodies or antibody fragments and/or antibody variants is administered to an animal to diagnose, treat, prevent or ameliorate a disease or disorder associated with aberrant Reg IV expression and/or function or aberrant Reg IV receptor expression and/or function.

Antibodies of the present invention (including molecules comprising, or alternatively consisting of, antibody fragments or variants thereof) that function as agonists or antagonists of a Reg IV, preferably of Reg IV signal transduction, can be administered to an animal to diagnose, treat, prevent or ameliorate a disease or disorder associated with aberrant Reg IV expression and/or function or aberrant Reg IV receptor expression and/or function. For example, antibodies of the invention which mimic the action of Reg IV binding to the Reg IV receptor, in full or in part, (e.g. antibodies that act as Reg IV agonists), may be administered to an animal to diagnose, treat, prevent or ameliorate a disease or disorder associated aberrant Reg IV expression, function, or aberrant Reg IV receptor expression or function. As an alternative example, antibodies of the invention which disrupt or prevent the interaction between Reg IV and its receptor or inhibit, reduce, or prevent signal transduction through one or more Reg IVs, may be administered to an animal to diagnose, treat, prevent or ameliorate a disease or disorder associated with aberrant Reg IV expression and/or function or aberrant Reg IV receptor expression and/or function. Antibodies of the invention which do not prevent Reg IV from binding its ligand but inhibit or downregulate Reg IV signal transduction can be administered to an animal to diagnose, treat, prevent or ameliorate a disease or disorder associated with aberrant Reg IV expression, aberrant Reg IV function, aberrant Reg IV receptor expression, or aberrant Reg IV receptor function. The ability of an antibody of the invention to enhance, inhibit, upregulate or downregulate Reg IV signal transduction may be determined by techniques described herein or otherwise known in the art. For example, Reg IV-induced receptor activation and the activation of signaling molecules can be determined by detecting the association of adaptor proteins with the Reg IV receptors, by mmunoprecipitation followed by western blot analysis (for example, as described herein).

In a specific embodiment, an antibody of the present invention (including molecules comprising, or alternatively consisting of, antibody fragments or variants thereof) that inhibits or downregulates, in full or in part, Reg IV activity (e.g., the proliferation of Reg IV receptor expressing cells) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Reg IV activity in absence of the antibody is administered to an animal to diagnose, treat, prevent or ameliorate a disease or disorder associated with aberrant Reg IV expression and/or function or aberrant Reg IV receptor expression and/or function, especially colon cancer and other proliferative disorders. In another embodiment, a combination of antibodies, a combination of antibody fragments, a combination of antibody variants, or a combination of antibodies, antibody fragments, and/or variants that inhibit or downregulate Reg IV activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to Reg IV activity in absence of said antibodies, antibody fragments, and/or antibody variants are administered to an animal to diagnose, treat, prevent or ameliorate a disease or disorder associated with aberrant Reg IV expression and/or function or aberrant Reg IV receptor expression and/or function.

Suitable agents, which also block binding of Reg IV to a Reg IV receptor that may be administered with the antibodies of the present invention include, but are not limited to, soluble Reg IV receptor polypeptides; multimeric forms of soluble Reg IV receptor polypeptides; anti-Reg IV antibodies that block binding of Reg IV to one or more Reg IV receptors; and muteins of Reg IV that bind Reg IV receptors but do not transduce a biological signal.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or inebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:71 (1983); see also Levy et al., Science 228:190 (1985); During et al., Ann. Neurol. 25:35 1 (1989); Howard et al., J.Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; BIOLISTIC™, DUPONT™), or coating with lipids or cell-surface receptors or transfecting agents, or by administering it in linkage to a homeobox—like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that specifically bind to one or more Reg IV polypeptides, or polynucleotides encoding antibodies that specifically bind to one or more Reg IV polypeptides, for both immunoassays and therapy of disorders related to Reg IV polynucleotides or polypeptides, including fragments thereof. Such antibodies will preferably have an affinity for Reg IV polypeptides and/or Reg IV polypeptide fragments. Preferred binding affinities include those with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M; or $10^{-5}$ M. More preferably, antibodies of the invention bind Reg IV polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind Reg IV polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, 10 −12 M, $5\times^{-13}$ M, $10^{-13}$ M, $5\times10^{-14}$ M, $10^{-14}$ M, $5\times10^{-15}$ M, or $10^{-15}$ M. In a preferred embodiment, antibodies of the invention inhibit proliferation of Reg IV receptor expressing cells. In an additional preferred embodiment, antibodies of the invention induce proliferation and/or anti-inflamrnmatory activities of Reg IV receptor expressing cells.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to chemotherapeutic agents, anti-inflammatories, mmunomodulatory agents, and agents used to treat diabetes. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Combination Therapies with Anti-Reg IV Antibodies, Immunomodulatory Agents, and/or Chemotherapeutic Agents Anti-Reg IV antibodies may be administered in combination with other anti-Reg IV antibodies, mmunomodulatory agents, and/or chemotherapeutics.

In specific embodiments, an antibody of the invention that specifically binds Reg IV is used or administered in combination with a second antibody that specifically binds Reg IV. In another embodiment, the antibodies specific for Reg IV are antagonistic antibodies that inhibit proliferation of Reg IV expressing cells. In a specific embodiment, the combination of anti-Reg IV treatment inhibits more proliferation of Reg IV expressing cells than either anti-Reg IV antibody treatment alone. The anti-Reg IV antibodies can be administered either simultaneously, sequentially, or a combination of simultaneous or sequential administration throughout the dosage regimen. In another specific embodiment anti-Reg IV antibodies are used or administered in combination with a chemotherapeutic drug, and/or immunomodulatory drug. In a particular embodiment, the synergistic inhibition of proliferation resulting from anti-Reg IV antibody treatment, is more evident or more pronounced when the anti-Reg IV antibodies are used or administered in combination with a chemotherapeutic agent, immunomodulatory drug, and/or a cross-linking reagent.

In specific embodiments, an antibody of the invention that specifically binds Reg IV is used or administered in combination with a second antibody that specifically binds Reg IV. In another embodiment, the antibodies specific for Reg IV are agonistic antibodies that stimulate proliferation of Reg IV expressing cells. In a specific embodiment, the combination of anti-Reg IV treatment stimulates more proliferation of Reg IV expressing cells than either anti-Reg IV antibody treatment alone. The anti-Reg IV antibodies can be administered either simultaneously, sequentially, or a combination of simultaneous or sequential administration throughout the dosage regimen. In another specific embodiment anti-Reg IV antibodies are used or administered in combination with an agent used to treat diabetes, and/or immunomodulatory drug. In a particular embodiment, the synergistic stimulation of proliferation resulting from anti-Reg IV antibody treatment, is more evident or more pronounced when the anti-Reg IV antibodies are used or administered in combination with an agent used to treat diabetes, an mmunomodulatory drug, and/or a cross-linking reagent.

In additional embodiments, anti-Reg IV antibodies of the present invention may be administered in combination with a soluble form of other Reg proteins which include, but are not limited to, Reg I-alpha (REG1A), Reg I-beta (REG1B), REG-related sequence (RS), and pancreatitis associated protein (PAP).

In a highly preferred embodiment, compositions of the invention are administered in combination with a chemotherapeutic agent. Chemotherapeutic agents that may be administered with the compositions of the invention include, but are not limited to, antibiotic derivatives (e.g., doxorubicin (adriamycin), bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, etoposide, Topotecan, 5-Fluorouracil, paclitaxel (TAXOL™), Cisplatin, Cytarabine, and IFN-gamma, irinotecan (CAMPTOSAR™, CPT-11), and gemcitabine (GEMZAR™)).

In an additional highly preferred embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another preferred embodiment, antibody and antibody compositions of the invention are administered in combination with steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685), ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucocorticosteroids, adrenocortical steroids such as DELTASONE™ (prednisone) and HYDELTRASOL™ (prednisolone), FOLEX™ and MEXATE™ (methotrexate), OXSORALEN-ULTRA™ (methoxsalen) and RAPAMUNE™ (sirolimus). In a specific embodiment, immunosuppressants may be used to prevent rejection of organ or bone marrow transplantation.

In other embodiments, the compositions of the invention are administered in combination with mmunostimulants including, but not limited to, levamisole (e.g., ERGAMISOL™), isoprinosine (e.g. INOSIPLEX™), interferons (e.g. interferon alpha), and interleukins (e.g., IL-2).

In other embodiments, antibody compositions of the invention may be administered in combination with anti-opportunistic infection agents. Anti-opportunistic agents that may be administered in combination with the albumin fusion proteins and/or polynucleotides of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF).

In other preferred embodiments, antibody compositions of the invention are administered in combination with alpha-glucosidase inhibitors. Alpha-Glucosidase inhibitors that may be administered in combination with the Therapeutics of the invention include, but are not limited to, miglitol (Glyset), acarbose (Precose), voglibose (Basen; Glustat). In a specific embodiment, alpha-glucosidase inhibitors may be used to delay the absorption of carbohydrates after meals to prevent blood glucose levels from rising too much in diabetics.

In other preferred embodiments, antibody compositions of the invention are administered in combination with Insulin and Related Agents. Insulin and Related Agents that may be administered in combination with the antibody compositions of the invention include, but are not limited to, Insulin Mixtures (Humulin 50/50, Humulin 70/30, Novolin 70/30), intermediate acting insulin (Humulin L, Humulin N, Iletin II Lente, Iletin II NPH, Novolin L, Novolin N), long acting insulin (Humulin U, Lantus), rapid acting insulin (Humalog, Insulin lispro, Insulin Aspart), short acting insulin (Humulin R, Iletin II Regular, Novolin R, Novolin BR), AERx Insulin Inhaler, Basulin (Insulin Flamel), Inhaled Insulin, Insulin detemir (long-acting insulin, NN-304), Macrulin (oral insulin), Mecasermin (Somazon), Oral Insulin, Oralin (Oralgen, RapidMist), and Transfersulin (insulin, Transfersome).

In other preferred embodiments, antibody compositions of the invention are administered in combination with Hormone Inhibitors. Hormone Inhibitors that may be administered in combination with the antibody compositions of the invention include, but are not limited to, BAY-27-9955 and pegvisomant (Somavert, Trovert). In a specific embodiment, BAY-27-9955 acts to minimize the action of glucagons by complexing with glucagon. In another specific embodiment, pegvisomant acts to block the effect of human Growth Hormone by binding the human Growth Hormone receptor.

In other preferred embodiments, antibody compositions of the invention are administered in combination with Sulfonylureas. Sulfonylureas that may be administered in combination with the antibody compositions of the invention include, but are not limited to, glimepiride (Amaryl), glyburide-(DiaBeta, Glynase PresTab, Micronase), chlorpropamide (Diabinese), acetohexamide (Dymelor), glipizide (Glucotrol, Glucotrol XL), tolbutamide (Orinase), tolazamide (Tolinase), gliclazide (Adianor), and glipentide (Staticum). In a specific embodiment, Sulfonylureas may be used to increase the release of insulin from the pancreas.

In other preferred embodiments, antibody compositions of the invention are administered in combination with Biguanides. Biguanides that may be administered in combination with the antibody compositions of the invention include, but are not limited to, metformin (Glucophage) and a combination of metformin with glibenclamide (Glucovance, Glucophage+Glyburide). In a specific embodiment, Biguanides act as insulin sensitizers to enhance the effect of insulin but also cause a loss of appetite in the treatment of diabetes mellitus.

In other preferred embodiments, antibody compositions of the invention are administered in combination with Thiazolidinediones. Thiazolidinediones that may be administered in combination with the antibody compositions of the invention include, but are not limited to, rosiglitazone maleate (Avandia), pioglitazone hydrochloride (Actos), isaglitazone (MCC-555,RWJ241947), and troglitazone (Rezulin, Romozin, Prelay, Noscal). In a specific embodiment, Thiazolidinediones act as insulin sensitizers to enhance the effect of insulin.

In other preferred embodiments, antibody compositions of the invention are administered in combination with other Insulin Sensitizers. Other Insulin Sensitizers that may be administered in combination with the antibody compositions of the invention include, but are not limited to, Bexarotene (Targretin), Chiro inositol (INS-1), Chromium picolinate (Chromax Plus; Chromax), Vanadium (KP-102, LP-100), and PPAR-gamma Activators which include, but are not limited to, GI-262570 (GW-2570), GW-409544 (GW-544), and KRP-297.

In other preferred embodiments, antibody compositions of the invention are administered in combination with Non-Sulfonylureas including Meglitinides. Non-Sulfonylureas that may be administered in combination with the antibody compositions of the invention include, but are not limited to, repaglinide (Prandin, Aculin), rateglinide (Starlix), BTS 67582, Mitiglinide (KAD-1229), and ProBeta. In a specific embodiment, Non-Sulfonylureas act to increase insulin secretion from the pancreas.

In other preferred embodiments, antibody compositions of the invention are administered in combination with Glucagon-Like Peptide 1. Glucagon-Like Peptide 1 that may be administered in combination with the Therapeutics of the invention include, but are not limited to, AC-2993 (Exendin-4), insulinotropin (GLP-1-(7-37)), and NNC 90-1170. In a specific embodiment, Glucagon-Like Peptide 1 act as insulin releasers, insulin sensitizers, appetite suppressors and glucagon secretion blockers among other things.

In other preferred embodiments, antibody compositions of the invention are administered in combination with Beta-cell Growth Factors. Beta-cell Growth Factors (Stewart, et al., March 2001, Journal of Clinical Endocrinology & Metabolism 86(3): 984-988) that may be administered in combination with the Therapeutics of the invention include, but are not limited to, betacellulin, exendin-4, glucagons-like peptide-1, hepatocyte growth factors, insulin-like growth factor-I, insulin-like growth factor-II, islet neogenesis-associated protein, placental lactogen, PTH-related protein, and cytokeratin 20 (Anastasi, et al., December 1999, Eur J Endocrinol 141(6): 644-52). In a specific embodiment, Beta-cell Growth Factors may act to prevent rejection of the pancreas transplantation or islet allotransplants.

In still other preferred embodiments, antibody compositions of the invention are administered in combination with one or more of the following: bromocriptine (Ergoset), etomoxir, iloprost (Endoprost), acetylcholine, ascorbic acid (Vitamin C), and antagonists of resistin (Steppan et al., January 2001, Nature 409(6818):307-12) and is contemplated for the treatment, prevention, and/or amelioration of diabetes mellitus, i.e. both IDDM and/or NIDDM.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce tumor formation in in vitro, ex vivo and in vivo assays. Antibodies or compositions of the invention can also be tested for their ability to stimulate pancreatic beta-cell proliferation in in vitro and in vivo assays. Antibodies or compositions of the invention can also be tested for their ability to reduce inflammation in in vitro and in vivo assays known to those of skill in the art. Antibodies or compositions of the invention can also be tested for their ability to alleviate of one or more symptoms associated with colon cancer, an inflammatory bowel disease, and/or diabetes. Further, antibodies or compositions of the invention can be tested for their ability to increase the survival period of animals suffering from disease or disorder, including colon cancer, an inflammatory bowel disorder, and/or diabetes. Techniques known to those of skill in the art can be used to analyze the function of the antibodies or compositions of the invention in vivo.

Antibodies or compositions of the invention can be tested for their ability to modulate the proliferation of cells (i.e., pancreatic beta-cell or colon cancer cell proliferation). Techniques known to those of skill in the art can be used for measuring these activities. For example, cellular proliferation can be assayed by $^{3}$H-thymidine incorporation assays and trypan blue cell counts. In a preferred embodiment, the ability of an antibody or composition of the invention to inhibit cell proliferation is measured. In another preferred embodiment, the ability of an antibody or composition of the invention to induce cell proliferation is measured.

Panels/Mixtures

The present invention also provides for mixtures of antibodies (including scFvs and other molecules comprising, or alternatively consisting of, antibody fragments or variants thereof) that specifically bind to Reg IV or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to Reg IV or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to Reg IV or a fragment or variant thereof, wherein the panel has at least one, two, three, four, five or more different antibodies of the invention. In specific embodiments, the invention provides for panels of antibodies that have different affinities for Reg IV, different specificities for Reg IV, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a VH domain of one or more of the scFvs referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a VH domain of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a VH domain of one or more of the scFvs referred to in Table 1, or a variant thereof.

Other embodiments of the present invention providing for compositions comprising, one or more antibodies (including molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of one or more of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that specifically binds to Reg IV polypeptides or fragments or variants thereof. In a specific embodiment, the kits of the present invention contain a substantially isolated Reg IV polypeptide or fragment or variant thereof as a control. Preferably, the kits of the present invention further comprise a control antibody which does not react with any, some or all Reg IV. In another specific embodiment, the kits of the present invention contain a means for detecting the binding of an antibody to Reg IV polypeptides (eg., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized Reg IV. The Reg IV provided in the kit may also be attached to a solid support. In a more specific embodiment the detecting means of the above-described kit includes a solid support to which Reg IV is attached. Such a kit may also include a non-attached reporter-labeled anti-human antibody. In this embodiment, binding of the antibody to Reg IV can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with Reg IV, and means for detecting the binding of Reg IV polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound Reg IV obtained by the methods of the present invention. After Reg IV polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-Reg IV antibody on the solid support. Typically, the reporter is an enzyme which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant Reg IV, and a reporter-labeled anti-human antibody for detecting surface-bound anti-Reg IV antibody.

Gene Therapy

In a specific embodiment, nucleic acids comprising sequences encoding antibodies or functional derivatives thereof, are administered to diagnose, treat, inhibit or prevent a disease or disorder associated with aberrant expression and/or activity of Reg IV and/or its receptors, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev.

Pharmacol. Toxicol. 32:573-596 (1993); Mulligan, Science 260:926-932 (1993); and Morgan and Anderson, Ann. Rev. Biochem. 62:191-217 (1993); May, TIBTECH 11 (5).155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; BIOLISTIC™, DUPONT™), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be faulted in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22715; W092/203 16; W093/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651(1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication W094/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Having generally described the invention, the same will be more readily understood by reference to the following examples, which are provided by way of illustration and are not intended as limiting.

EXAMPLES

Example 1

Generation of Anti-Reg IV Antibodies

General Methods—Rescue of the Library.

A library of scFvs is constructed from the RNA of human PBLs as described in WO92/01047 (which is hereby incorporated by reference in its entirety). To rescue phage displaying antibody fragments, approximately 109 *E. coli* harboring the phagemid are used to inoculate 50 ml of 2× TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC 19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2× TY broth containing 100 micrograms ampicillin/ml and 25 micrograms kanamycin/ml (2× TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a Reg IV polypeptide. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCI, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 micrograms/ml ampicillin. The resulting bacterial library is then rescued with delta gene 3 helper phage as described above to prepare phage for a subsequent round of selection. This process is usually repeated for a total of 2-4 rounds of affinity purification.

Characterization of Binders.

Eluted phage from the final rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 2

Identification and Cloning of VH and VL Domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may lysed in the TRIZOL™ reagent (LIFE TECHNOLOGIES™, Rockville, Md) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Altematively, DNA encoding an scFv, e.g. a vector containing the scFv expression construct, may be used as template material for the following PCR reaction. Primers used to amplify VH and VL genes are shown in Table 4. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 micro-liter volume containing 1×PCR buffer, 2 mM of each DNTP, 0.7 units of High Fidelity Taq polymerase, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 4

Primer Sequences Used to Amplify VH and VL domains.

| Primer name | SEQ ID SEQ | Primer Sequence (5'-3') |
|---|---|---|
| VH Primers | | |
| Hu VH1-5' | 135 | CAGGTGCAGCTGGTGCAGTCTGG |
| Hu VH2-5' | 136 | CAGGTCAACTTAAGGGAGTCTGG |
| Hu VH3-5' | 137 | GAGGTGCAGCTGGTGGAGTCTGG |
| Hu VH4-5' | 138 | CAGGTGCAGCTGCAGGAGTCGGG |
| Hu VH5-5' | 139 | GAGGTGCAGCTGTTGCAGTCTGC |
| Hu VH6-5' | 140 | CAGGTACAGCTGCAGCAGTCAGG |
| Hu JH1,2-5' | 141 | TGAGGAGACGGTGACCAGGGTGCC |
| Hu JH3-5' | 142 | TGAAGAGACGGTGACCATTGTCCC |
| Hu JH4,5-5' | 143 | TGAGGAGACGGTGACCAGGGTTCC |
| Hu JH6-5' | 144 | TGAGGAGACGGTGACCGTGGTCCC |
| VL Primers | | |
| Hu Vkappa1-5' | 145 | GAGATCCAGATGACCCAGTCTCC |
| Hu Vkappa2a-5' | 146 | GATGTTGTGATGACTCAGTCTCC |
| Hu Vkappa2b-5' | 147 | GATATTGTGATGACTCAGTCTCC |
| Hu Vkappa3-5' | 148 | GAAATTGTGTTGACGCAGTCTCC |

TABLE 4-continued

Primer Sequences Used to Amplify VH and VL domains.

| Primer name | SEQ ID SEQ | Primer Sequence (5'-3') |
|---|---|---|
| Hu Vkappa4-5' | 149 | GAGATCGTGATGACCCAGTCTCC |
| Hu Vkappa5-5' | 150 | GAAACGACACTCACGCAGTCTCC |
| Hu Vkappa6-5' | 151 | GAAATTGTGCTGACTCAGTCTCG |
| Hu Vlambda1-5' | 152 | CAGTCTGTGTTGACGCAGCCGCC |
| Hu Vlambda2-5' | 153 | CAGTCTGCCCTGACTCAGCCTGC |
| Hu Vlambda3-5' | 154 | TCCTATGTGCTGACTCAGCCACC |
| Hu Vlambda3b-5' | 155 | TCTTCTGAGCTGACTCAGGACCC |
| Hu Vlambda4-5' | 156 | CACGTTATACTGACTCAACCGCC |
| Hu Vlambda5-5' | 157 | CAGGCTGTGCTCACTCAGCCGTC |
| Hu Vlambda6-5' | 158 | AATTTTATGCTGACTCAGCCCCA |
| Hu Jkappa1-3' | 159 | ACGTTTGATTTCCACCTTGGTCCC |
| Hu Jkappa2-3' | 160 | ACGTTTGATCTCCAGCTTGGTCCC |
| Hu Jkappa3-3' | 161 | ACGTTTGATATCCACTTTGGTCCC |
| Hu Jkappa4-3' | 162 | ACGTTTGATCTCCACCTTGGTCCC |
| Hu Jkappa5-3' | 163 | ACGTTTAATCTCCAGTCGTGTCCC |
| Hu Jlambda1-3' | 164 | CAGTCTGTGTTGACGCAGCCGCC |
| Hu Jlambda2-3' | 165 | CAGTCTGCCCTGACTCAGCCTGC |
| Hu Jlambda3--3' | 166 | TCCTATGTGCTGACTCAGCCACC |
| Hu Jlambda3b-3' | 167 | TCTTCTGAGCTGACTCAGGACCC |
| Hu Jlambda4-3' | 168 | CACGTTATACTGACTCAACCGCC |
| Hu Jlambda5-3' | 169 | CAGGCTGTGCTCACTCAGCCGTC |
| Hu Jlambda6-3' | 170 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art.

Example 3

Modulation of Reg IV-Mediated Cell Proliferation using Reg IV Antibodies

General Methods

Representative Cell Types that may be used in this Assay

RIN-M cells: These cells are available from the American Type Tissue Culture Collection (ATCC™ Cell Line Number CRL-2057 ). The RIN-M cell line was derived from a radiation induced transplantable rat islet cell tumor. The line was established from a nude mouse xenograft of the tumor. The cells produce and secrete islet polypeptide hormones, and produce L-dopa decarboxylase (a marker for cells having amine precursor uptake and decarboxylation, or APUD, activity).

ARIP cells: These are pancreatic exocrine cells of epithelial morphology available from the American Type Tissue Culture Collection (ATCC™ Cell Line Number CRL-1674). See also, references: Jessop, N. W. and Hay, R. J., "Characteristics of two rat pancreatic exocrine cell lines derived from transplantable tumors," In Vitro 16: 212, (1980); Cockell, M. et al., "Identification of a cell-specific DNA-binding activity that interacts with a transcriptional activator of genes expressed in the acinar pancreas," *Mol. Cell. Biol.* 9: 2464-2476, (1989); Roux, E., et al. "The cell-specific transcription factor PTFI contains two different subunits that interact with the DNA" *Genes Dev.* 3: 1613-1624, (1989); and, Hui, H., et al., "Glucagon-like peptide 1 induces differentiation of islet duodenal homeobox-1-positive pancreatic ductal cells into insulin-secreting cells," Diabetes 50: 785-796 (2001).

Adenocarcinoma cells: These are cells from a colon adenocarcinoma cell line available from the American Type Culture Collection (ATCC™).

Cell Preparation

The RIN-M cell-line is grown in RPMI 1640 medium (Hyclone, #SH300027.01) with 10% fetal bovine serum (HyClone, #SH30088.03) and is subcultured every 6 to 8 days at a ratio of 1:3 to 1:6. The medium is changed every 3 to 4 days.

The ARIP (ATCC™ #CRL-1674) cell-line is grown in Ham's F12K medium (ATCC™, #30-2004) with 2 mM L-glutamine adjusted to contain 1.5 g/L sodium bicarbonate and 10% fetal bovine serum. The ARIP cell-line is subcultured at a ratio of 1:3 to 1:6 twice per week. The medium is changed every 3 to 4 days.

Assay Protocol

The cells are seeded at 4000 cells/well in 96-well plates and cultured for 48 to 72 hours to 50% confluence. The cells are switched to serum-free media at 100 μL/well. After incubation for 48-72 hours, Reg IV and/or the antibody compositions of the subject invention are added to the well at varying concentrations. Incubation persists for an additional 36 hours. [$^3$H]-Thymidine (5-20 Ci/mmol) (Amersham Pharmacia, #TRK120) is diluted to 1 microCurie/5 microliters. After the 36 hour incubation, 5 microliters is added per well for a further 24 hours. The reaction is terminated by washing the cells gently with cold Phosphate-Buffered Saline, "PBS", once. The cells are then fixed with 100 microliters of 10% ice cold TCA for 15 min at 4° C. The PBS is removed and 200 microliters of 0.2 N NaOH is added. The plates are incubated for 1 hour at room temperature with shaking. The solution is transferred to a scintillation vial and 5 mL of scintillation fluid compatible with aqueous solutions is added and mixed vigorously. The vials are counted in a beta scintillation counter.

Exemplary Embodiments of the Invention

Some exemplary embodiments of the invention include, but are not limited to, the following:

A. An isolated antibody that specifically binds Reg IV comprising:
   (a) an amino acid sequence that is at least 80% identical to a VH domain of any one of the scFvs of SEQ ID NOS: 1-67;
   (b) an amino acid sequence that is at least 80% identical to a VL domain of any one of the scFvs of SEQ ID NOS: 1-67; or
   (c) both (a) and (b).

B. The antibody of embodiment A comprising:
   (a) the amino acid sequence of a VH domain of any one of the scFvs of SEQ ID NOS: 1-67;
   (b) the amino acid sequence of a VL domain of any one of the scFvs of SEQ ID NOS: 1-67; or
   (c) both (a) and (b).

C. The antibody of embodiment B comprising the amino acid sequence of a VH domain of any one of the scFvs of SEQ ID NOS: 1-67 and the amino acid sequence of a VL domain of any one of the scFVs of SEQ ID NOS: 1-67.

D. The antibody of embodiment C wherein the VH domain and the VL domain are from the same scFv.

E. The isolated antibody or fragment thereof of embodiment A that specifically binds Reg IV purified from a cell culture, wherein Reg IV is encoded by a polynucleotide encoding amino acids 1 to 158 of SEQ ID NO:172 operably associated with a regulatory sequence that controls expression of said polynucleotide.

F. The antibody of embodiment A wherein the antibody is selected from the group consisting of:
   (a) a whole immunoglobulin molecule;
   (b) an scFv;
   (c) a monoclonal antibody;
   (d) a human antibody;
   (e) a chimeric antibody;
   (f) a Fab fragment;
   (g) an F(ab')2;
   (h) an Fv; and
   (i) a disulfide linked Fv.

G. The antibody of embodiment A which also comprises a heavy chain immunoglobulin constant domain selected from the group consisting of:
   (a) a human IgM constant domain;
   (b) a human IgG 1 constant domain;
   (c) a human IgG2 constant domain;
   (d) a human IgG3 constant domain;
   (e) a human IgG4 constant domain; and
   (f) a human IgA constant domain.

H. The antibody of embodiment A which also comprises a light chain immunoglobulin constant domain selected from the group consisting of:
   (a) a human Ig kappa constant domain; and
   (b) a human Ig lambda constant domain.

I. The antibody of embodiment A wherein the antibody has a dissociation constant (KD) less than or equal to 10-9M.

J. The antibody of embodiment A wherein the antibody is conjugated to a detectable label.

K. The antibody of embodiment J, wherein the detectable label is a radiolabel.

L. The antibody of embodiment K, wherein the radiolabel is 125I, 131I, 111In, 90Y, 99Tc, 177Lu, 166Ho, or 153Sm.

M. The antibody of embodiment J, wherein the detectable label is an enzyme, a fluorescent label, a luminescent label, or a bioluminescent label.

N. The antibody of embodiment A wherein the antibody is biotinylated.

O. The antibody of embodiment A wherein the antibody is conjugated to a therapeutic or cytotoxic agent.

P. The antibody of any one of embodiment A which is attached to a solid support.

Q. The antibody or portion thereof of embodiment A wherein said antibody specifically binds to Reg IV in a Western blot.

R. The antibody or portion thereof of embodiment A wherein said antibody specifically binds to Reg IV in an ELISA.

S. An isolated cell that produces the antibody of embodiment A.

T. The antibody of embodiment A wherein the antibody inhibits proliferation of Reg IV receptor expressing cells.

U. The antibody of embodiment T wherein the cells expressing a Reg IV receptor are colon cancer cells.

V. The antibody of embodiment A wherein the antibody downregulates Reg IV expression.

W. The antibody of embodiment A wherein the antibody inhibits Reg IV binding to a Reg IV receptor.

X. The antibody of embodiment A wherein the antibody stimulates proliferation of cells expressing a Reg IV receptor.

Y. The antibody of embodiment A wherein the antibody upregulates Reg IV expression.

Z. An antibody that competitively inhibts the binding of an antibody of embodiment C to a Reg IV polypeptide.

AA. A method of treating, preventing or ameliorating a inflammatory bowel disorder, a cancer of the gastrointestinal tract or diabetes comprising administering the antibody of embodiment A to an animal.

AB. The method of embodiment AA, wherein the animal is a human.

AC. The method of embodiment AA, wherein the inflammatory bowel disorder is ulcerative colitis.

AD. The method of embodiment AA, wherein the inflammatory bowel disorder is Crohn's disease.

AE. The method of embodiment AA, wherein the antibody is administered in combination with an mmunomodulatory agent.

AF. The method of embodiment AA, wherein the cancer of the gastrointestinal tract is selected from the group consisting of:

(a) colon cancer;

(b) pancreatic cancer;

(c) rectal cancer;

(d) gallbladder cancer;

(e) cancer of the small intestine;

(f) cancer of the esophagus;

(g) cancer of the stomach;

(h) cancer of the bile ducts;

(i) cancer of the liver; and (j) cancer of the duodenum.

AG. The method of embodiment AF, wherein the cancer is colon cancer.

AH. The method of embodiment AA, wherein the antibody is administered in combination with a chemotherapeutic agent.

AI. The method of embodiment AA, wherein the disease or disorder is non-insulin dependent diabetes.

AJ. The method of embodiment AA, wherein the disease or disorder is insulin dependent diabetes.

AK. A method of detecting expression of a Reg IV polypeptide comprising:

(a) assaying the expression of a Reg IV polypeptide in a biological sample from an individual using the antibody of embodiment 1; and (b) comparing the level of a Reg IV polypeptide with a standard level of a Reg IV polypeptide.

AL. A kit comprising the antibody of embodiment A.

AM. The kit of embodiment AL comprising a control antibody.

AN. The kit of embodiment AL, wherein the antibody is coupled or conjugated to a detectable label.

AO. An isolated antibody that specifically binds Reg IV comprising a first amino acid sequence at least 95% identical to a second amino acid sequence selected from the group consisting of:

(a) the amino acid sequence of either VHCDR1, VHCDR2, or VHCDR3 of any one of the scFvs of SEQ ID NOS: 1-67.

(b) the amino acid sequence of either VLCDR1, VLCDR2, or VLCDR3 of any one of the scFvs of SEQ ID NOS:1-67.

AP. The antibody of embodiment AO, wherein the second amino acid sequence consists of the amino acid sequence of a VHCDR3 of any one of the scFvs of SEQ ID NOS: 1-67.

AQ. The isolated antibody or fragment thereof of embodiment AO that specifically binds Reg IV purified from a cell culture, wherein Reg IV is encoded by a polynucleotide encoding amino acids 1 to 158 of SEQ ID NO:172 operably associated with a regulatory sequence that controls expression of said polynucleotide.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosure (including the specification, sequence listing, and drawings) of Provisional Application No. 60/392,382 filed Jul. 1, 2002 is herein incorporated by reference in its entirety.

What is claimed is:

1. An isolated antibody or fragment thereof that specifically binds Reg IV comprising an amino acid sequence selected from the group consisting of:

(a) the amino acid sequence of the VH and VL domains of the scFv of SEQ ID NO: 1;

(b) the amino acid sequence of the VH and VL domains of the scFv of SEQ ID NO: 2;

(c) the amino acid sequence of the VH and VL domains of the scFv of SEQ ID NO: 3;

(d) the amino acid sequence of the VH and VL domains of the scFv of SEQ ID NO: 4;

(e) the amino acid sequence of the VH and VL domains of the scFv of SEQ ID NO: 5;

(f) the amino acid sequence of the VH and VL domains of the scFv of SEQ ID NO: 6;

(g) the amino acid sequence of the VH and VL domains of the scFv of SEQ ID NO: 7;

(h) the amino acid sequence of the VH and VL domains of the scFv of SEQ ID NO: 9;

(i) the amino acid sequence of the VH and VL domains of the scFv of SEQ ID NO: 10;

(j) the amino acid sequence of the VH and VL domains of the scFv of SEQ ID NO: 11;

(k) the amino acid sequence of the VH and VL domains of the scFv of SEQ ID NO: 12;

(I) the amino acid sequence of the VH and VL domains of the scFv of SEQ ID NO: 15;

(m) the amino acid sequence of the VH and VL domains of the scFv of SEQ ID NO: 17;

(n) the amino acid sequence of the VH and VL domains of the scFv of SEQ ID NO: 20;

(o) the amino acid sequence of the VH and VL domains of the scFv of SEQ ID NO: 46;

(p) the amino acid sequence of the VH and VL domains of the scFv of SEQ ID NO: 47;

(q) the amino acid sequence of the VH and VL domains of the scFv of SEQ ID NO: 55;

(r) the amino acid sequence of the VH and VL domains of the scFv of SEQ ID NO: 63; and (s) the amino acid sequence of the VH and VL domains of the scFv of SEQ ID NO: 64.

2. The isolated antibody or fragment thereof of claim 1 that specifically binds Reg IV purified from a cell culture, wherein Reg IV is encoded by a polynucleotide encoding amino acids 1 to 158 of SEQ ID NO:172 operably associated with a regulatory sequence that controls expression of said polynucleotide.

3. The isolated antibody or fragment thereof of claim 1 wherein the antibody or fragment thereof is selected from the group consisting of:

(a) a whole immunoglobulin molecule;

(b) an scFv;

(c) a monoclonal antibody;

(d) a human antibody;

(e) a chimeric antibody;

(f) a Fab fragment;

(g) an F(ab')2;

(h) an Fv; and (i) a disulfide linked Fv.

4. The isolated antibody or fragment thereof of claim 1 which also comprises a heavy chain immunoglobulin constant domain selected from the group consisting of:

(a) a human IgM constant domain;

(b) a human IgG1 constant domain;

(c) a human IgG2 constant domain;

(d) a human IgG3 constant domain;

(e) a human IgG4 constant domain; and (f) a human IgA constant domain.

5. The isolated antibody or fragment thereof of claim 1 which also comprises a light chain immunoglobulin constant domain selected from the group consisting of:

(a) a human Ig kappa constant domain; and (b) a human Ig lambda constant domain.

6. The isolated antibody or fragment thereof of claim 1 wherein the antibody or fragment thereof has a dissociation constant ($K_D$) less than or equal to $10^{-9}$M.

7. The isolated antibody or fragment thereof of claim 1 wherein the antibody or fragment thereof is conjugated to a detectable label.

8. The isolated antibody or fragment thereof of claim 1 wherein the antibody or fragment thereof specifically binds to Reg IV in a Western blot or ELISA.

9. The isolated antibody or fragment thereof of claim 1 wherein the antibody or fragment thereof inhibits proliferation of Reg IV receptor expressing cells.

10. The isolated antibody or fragment thereof of claim 1 wherein the antibody or fragment thereof inhibits Reg IV binding to a Reg IV receptor.

11. The isolated antibody or fragment thereof of claim 1 wherein the antibody or fragment thereof stimulates proliferation of cells expressing a Reg IV receptor.

12. An isolated antibody or fragment thereof that specifically binds Reg IV comprising an amino acid sequence selected from the group consisting of:

(a) the amino acid sequence of the VHCDR1, VHCDR2, VHCDR3, VLCDR1, VLCDR2, and VLCDR3 of SEQ ID NO: 1;

(b) the amino acid sequence of the VHCDR1, VHCDR2, VHCDR3, VLCDR1, VLCDR2, and VLCDR3 of SEQ ID NO: 2;

(c) the amino acid sequence of the VHCDR1, VHCDR2, VHCDR3, VLCDR1, VLCDR2, and VLCDR3 of SEQ ID NO: 3;

(d) the amino acid sequence of the VHCDR1, VHCDR2, VHCDR3, VLCDR1, VLCDR2, and VLCDR3 of SEQ ID NO: 4;

(e) the amino acid sequence of the VHCDR1, VHCDR2, VHCDR3, VLCDR1, VLCDR2, and VLCDR3 of SEQ ID NO: 5;

(f) the amino acid sequence of the VHCDR1, VHCDR2, VHCDR3, VLCDR1, VLCDR2, and VLCDR3 of SEQ ID NO: 6;

(g) the amino acid sequence of the VHCDR1, VHCDR2, VHCDR3, VLCDR1, VLCDR2, and VLCDR3 of SEQ ID NO: 7;

(h) the amino acid sequence of the VHCDR1, VHCDR2, VHCDR3, VLCDR1, VLCDR2, and VLCDR3 of SEQ ID NO: 9;

(i) the amino acid sequence of the VHCDR1, VHCDR2, VHCDR3, VLCDR1, VLCDR2, and VLCDR3 of SEQ ID NO: 10;

(j) the amino acid sequence of the VHCDR1, VHCDR2, VHCDR3, VLCDR1, VLCDR2, and VLCDR3 of SEQ ID NO: 11;

(k) the amino acid sequence of the VHCDR1, VHCDR2, VHCDR3, VLCDR1, VLCDR2, and VLCDR3 of SEQ ID NO: 12;

(1) the amino acid sequence of the VHCDR1, VHCDR2, VHCDR3, VLCDR1, VLCDR2, and VLCDR3 of SEQ ID NO: 15;

(m) the amino acid sequence of the VHCDR1, VHCDR2, VHCDR3, VLCDR1, VLCDR2, and VLCDR3 of SEQ ID NO: 17;

(n) the amino acid sequence of the VHCDR1, VHCDR2, VHCDR3, VLCDR1, VLCDR2, and VLCDR3 of SEQ ID NO: 20;

(o) the amino acid sequence of the VHCDR1, VHCDR2, VHCDR3, VLCDR1, VLCDR2, and VLCDR3 of SEQ ID NO: 46;

(p) the amino acid sequence of the VHCDR1, VHCDR2, VHCDR3, VLCDR1, VLCDR2, and VLCDR3 of SEQ ID NO: 47;

(q) the amino acid sequence of the VHCDR1, VHCDR2, VHCDR3, VLCDR1, VLCDR2, and VLCDR3 of SEQ ID NO: 55;

(r) the amino acid sequence of the VHCDR1, VHCDR2, VHCDR3, VLCDR1, VLCDR2, and VLCDR3 of SEQ ID NO: 63; and (s) the amino acid sequence of the VHCDR1, VHCDR2, VHCDR3, VLCDR1, VLCDR2, and VLCDR3 of SEQ ID NO: 64.

13. The isolated antibody or fragment thereof of claim 12 that specifically binds Reg IV purified from a cell culture, wherein Reg IV is encoded by a polynucleotide encoding amino acids 1 to 158 of SEQ ID NO:172 operably associated with a regulatory sequence that controls expression of said polynucleotide.

14. The isolated antibody or fragment thereof of claim 12 wherein the antibody or fragment thereof is selected from the group consisting of:

(a) a whole immunoglobulin molecule;

(b) an scFv;

(c) a monoclonal antibody;

(d) a human antibody;

(e) a chimeric antibody;

(f) a Fab fragment;

(g) an F(ab')2;

(h) an Fv; and (i) a disulfide linked Fv.

15. The isolated antibody or fragment thereof of claim 12 wherein the antibody or fragment thereof is conjugated to a detectable label.

16. The isolated antibody or fragment thereof of claim 12 wherein the antibody or fragment thereof specifically binds to Reg IV in a Western blot or ELISA.

17. The isolated antibody or fragment thereof of claim 12 wherein the antibody or fragment thereof inhibits proliferation of Reg IV receptor expressing cells.

18. The isolated antibody or fragment thereof of claim 12 wherein the antibody or fragment thereof inhibits Reg IV binding to a Reg IV receptor.

19. The isolated antibody or fragment thereof of claim 12 wherein the antibody or fragment thereof stimulates proliferation of cells expressing a Reg IV receptor.

* * * * *